US012624050B2

(12) United States Patent
Zhan et al.

(10) Patent No.: US 12,624,050 B2
(45) Date of Patent: May 12, 2026

(54) THREE FUSED RING DERIVATIVE-CONTAINING SALT OR CRYSTAL FORM AND PHARMACEUTICAL COMPOSITION THEREOF

(71) Applicants: Shanghai Hansoh Biomedical Co., Ltd., Shanghai (CN); Jiangsu Hansoh Pharmaceutical Group Co., Ltd., Lianyungang (CN)

(72) Inventors: Xiaolan Zhan, Shanghai (CN); Linsong Guo, Shanghai (CN)

(73) Assignees: Shanghai Hansoh Biomedical Co., Ltd., Shanghai (CN); Jiangsu Hansoh Pharmaceutical Group Co., Ltd., Jiangsu (CN)

( * ) Notice: Subject to any disclaimer, the term of this patent is extended or adjusted under 35 U.S.C. 154(b) by 969 days.

(21) Appl. No.: 17/777,966

(22) PCT Filed: Nov. 19, 2020

(86) PCT No.: PCT/CN2020/130035

§ 371 (c)(1),
(2) Date: May 18, 2022

(87) PCT Pub. No.: WO2021/104146

PCT Pub. Date: Jun. 3, 2021

(65) Prior Publication Data

US 2023/0014383 A1 Jan. 19, 2023

(30) Foreign Application Priority Data

Nov. 25, 2019 (CN) ......................... 201911168310.3

(51) Int. Cl.
*C07D 498/04* (2006.01)
*C07D 498/14* (2006.01)

(52) U.S. Cl.
CPC ......... *C07D 498/04* (2013.01); *C07D 498/14* (2013.01); *C07B 2200/13* (2013.01)

(58) Field of Classification Search
CPC .. C07D 498/04; C07D 498/14; C07B 2200/13
USPC ...................................................... 514/211.1
See application file for complete search history.

(56) References Cited

FOREIGN PATENT DOCUMENTS

| | | | |
|---|---|---|---|
| CN | 102762576 | A | 10/2012 |
| CN | 103562210 | A | 2/2014 |
| CN | 107873032 | A | 4/2018 |
| CN | 107995911 | A | 5/2018 |
| CN | 110088111 | A | 8/2019 |
| WO | 2010029028 | A1 | 3/2010 |
| WO | 2011022439 | A1 | 2/2011 |
| WO | 2018197653 | A1 | 11/2018 |
| WO | 2019228341 | A1 | 12/2019 |
| WO | 2020020385 | A1 | 1/2020 |

OTHER PUBLICATIONS

Byrn et al., Solid-State Chemistry of Drugs, 1999, SSCI, Inc., Second Edition, pp. 62-63 (Year: 1999).*

Newman et al., Solid-state analysis of the active pharmaceutical ingredient in drug products, DDT, vol. 8, No. 19, Oct. 2003, pp. 898-905 (Year: 2003).*

Chawla et al., Challenges in Polymorphism of Pharmaceuticals, CRIPS, vol. 5, No. 1, Jan.-Mar. 2004, pp. 9-12 (Year: 2004).*

Brittain et al., Polymorphism in Pharmaceutical Solids, 1995, vol. 95, p. 228-229 (Year: 1995).*

Vippagunta et al., Advanced Drug Reviews, 48 (2001), pp. 3-26 (Year: 2001).*

Written Opinion of the International Searching Authority: China National Intellectual Property Administration; International Application No. PCT/CN2020/130035; Feb. 19, 2021; 9 pages.

International Preliminary Report on Patentability; The International Bureau of WIPO; International Application No. PCT/CN2020/130035; Jun. 9, 2022; 11 pages.

(Continued)

*Primary Examiner* — Kristin A Vajda

(74) *Attorney, Agent, or Firm* — Taft Stettinius & Hollister LLP

(57) ABSTRACT

A three fused ring derivative-containing salt and a crystal form thereof. In particular, the present invention relates to a compound having general formula (I), a crystal form thereof, a preparation method therefor, a pharmaceutical composition containing a therapeutically effective amount of the compound and the crystal form thereof, and use thereof in the preparation of a medicament for treating PI3K-mediated related diseases.

(I)

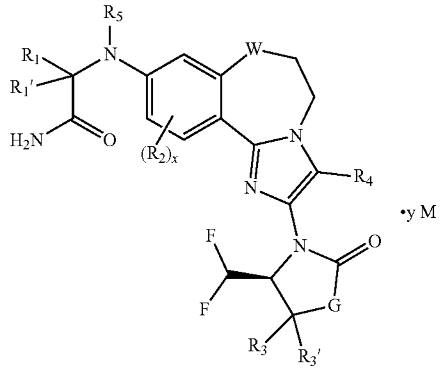

22 Claims, 6 Drawing Sheets

(56) References Cited

OTHER PUBLICATIONS

International Search Report; China National Intellectual Property Administration; International Application No. PCT/CN2020/130035; Feb. 19, 2021; 12 pages.

Han, Chong et al.; Synthesis of PI3K inhibitor GDC-0077 via a stereocontrolled N-arylation of α-amino acids; Tetrahedron; 2019; pp. 4351-4357; vol. 75.

Heffron, Timothy P et al.; The Rational Design of Selective Benzoxazepin Inhibitors of the #-Isoform of Phosphoinositide 3-Kinase Culminating in the Identification of (S)-2-((2-(1-isopropyl-1H-1,2,4-triazol-5-yl)-5,6-dihydrobenzo[f]imidazo[1,2-d][1,4]oxazepin-9-yl)oxy)propanamide (GDC-0326); Journal of Medicinal Chemistry; Jan. 7, 2016; 58 pages.

* cited by examiner

THREE FUSED RING DERIVATIVE-CONTAINING SALT OR CRYSTAL FORM AND PHARMACEUTICAL COMPOSITION THEREOF

CROSS-REFERENCE TO RELATED APPLICATIONS

This application is a U.S. National Phase of International PCT Application No. PCT/CN2020/130035 filed Nov. 19, 2020, which claims priority to Chinese Patent Application Serial No. 201911168310.3 filed Nov. 25, 2019, the contents of each application are incorporated herein by reference in their entireties.

FIELD OF THE INVENTION

The present invention belongs to the field of drug synthesis, and specifically relates to a salt of three ring fused derivative salt and a crystal form thereof, a preparation method and use thereof.

BACKGROUND OF THE INVENTION

The phosphatidylinositol 3-kinase (PI3K) protein family is classified into four major classes: I, II, III and IV, and is involved in the regulation of various cellular functions such as cell growth, proliferation, differentiation, survival, glucose metabolism and the like. The four classes of PI3K proteins have different structures and functions, among which the most widely studied is the Class I PI3K, which is further classified into four subtypes: PI3Kα, PI3Kβ, PI3Kδ and PI3Kγ. Among them, PI3Kα is activating mutated and amplified in a variety of tumors, and is closely related to the onset and development of tumors. It has been reported that PI3Kβ can activate platelets and plays an important role in the onset and development of thrombosis and other diseases. PI3Kδ and PI3Kγ are mainly expressed in the blood system and are closely related to the immune system and the onset of inflammation. In addition, PI3Kγ is closely related to blood pressure stability and smooth muscle contraction.

PI3Kα is activating mutated and amplified in a variety of tumors and is a driver of tumorigenesis. PI3Kα is a heterodimer consisting of a p110 catalytic subunit and a p85 regulatory subunit. PI3Kα is activated by receptor tyrosine kinases (RTKs) and G protein-coupled receptors (GPCRs). After activation, it catalyzes the production of phosphatidylinositol 3 phosphate (PIP3) from phosphatidylinositol 2 phosphate (PIP2), and PIP3 can further activate protein kinase B (PKB, also known as AKT) and its downstream signaling pathways. A variety of cell growth factors, such as epidermal growth factor (EGF), fibroblast growth factor (FGF), vascular endothelial growth factor (VEGF), hepatocyte growth factor (HGF) and insulin, can all activate PI3Kα, thereby activating downstream proliferation signaling pathways in cells. Abnormal activation of PI3Kα can lead to rapid cell proliferation, thereby causing tumorigenesis.

PI3Kα has been an important target for tumor drug research and development, but most compounds are broad-spectrum inhibitors of PI3Ks, resulting in serious side effects in clinical research, which severely limits the development of PI3Ks inhibitors. Current studies have determined that most of the side effects of broad-spectrum PI3Ks inhibitors are caused by the inhibition of PI3Kβ, PI3Kδ and PI3Kγ subtypes. Among them, PI3Kβ plays an important role in the mechanism of the side effects of thrombocytopenia and thrombosis. Inhibition of PI3Kδ can lead to immune system abnormalities. Autoimmune and infectious toxicities such as pneumonia, hepatitis and diarrhea/enteritis are closely related to the inhibition of PI3Kδ targets. PI3Kγ is closely related to blood pressure stability and smooth muscle contraction, and is a major target that causes the side effect of hypertension. Therefore, the development of highly active and selective PI3Kα inhibitors can further improve the anti-tumor effect of PI3Kα inhibitors and reduce or eliminate the various serious side effects such as inflammation, thrombocytopenia, hypertension and the like, which are caused by inhibition of other subtypes.

The PI3Kα selective inhibitor BYL-719 developed by Novartis is currently in the phase III clinical study, the PI3Kα selective inhibitor MLN1117 developed by Takeda has entered the phase II clinical study, and the selective inhibitor GDC-0077 developed by Genentech has also been in phase I clinical study.

International applications WO2010029082A1 and WO2011022439A1 have reported compounds related to PI3Kα selective inhibitors, but later studies have shown that none of the compounds have high cellular activity, which affects their clinical anti-tumor effects. Therefore, there is an urgent need to develop PI3Kα selective inhibitors with high activity and high selectivity. PI3Kα selective inhibitors can be used to treat a variety of multiple tumors with PI3Kα activating mutations or amplifications, and have great value of clinical application.

The PCT patent applications (application numbers: PCT/CN2019/088788 and PCT/CN2019/104558) of Jiangsu Hansoh Pharmaceutical Group Co., Ltd. disclose a series of structures of three ring fused derivative inhibitors. In subsequent research and development, in order to make the products easy to handle, filter and dry and to improve the solubility of the products, and to seek for suitable features of easy storage, long-term stability of the product, high bioavailability and the like, the present invention has carried out comprehensive study on the salts of the above substances, and is committed to obtaining the most suitable salts and crystal forms.

SUMMARY OF THE INVENTION

All contents involved in the patent applications PCT/CN2019/088788 and PCT/CN2019/104558 can be cited in the present invention.

The object of the present invention is to provide an acid addition salt of formula (I), having the following structure:

(I)

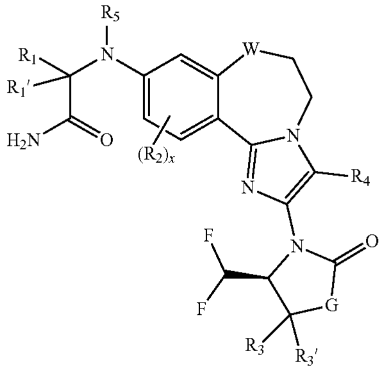

•y M wherein:

W is selected from the group consisting of —O—, —S— and —$NR_{aa}$—;

G is selected from the group consisting of —O—, —S—, —$CR_{aa}R_{bb}$— and —$NR_{aa}$—;

$R_1$ and $R_1$' are each selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, cyano-substituted $C_{1-6}$ alkyl, $C_{3-8}$ cycloalkyl, 3 to 8 membered heterocyclyl, $C_{6-10}$ aryl, 5 to 10 membered heteroaryl, —$(CH_2)_nR_{cc}$, —$(CH_2)_nOR_{cc}$ and —$CR_{aa}R_{bb}OR_{cc}$;

or, $R_1$ and $R_1$' are attached together to form a $C_{3-8}$ cycloalkyl or 3 to 8 membered heterocyclyl, wherein the $C_{3-8}$ cycloalkyl or 3 to 8 membered heterocyclyl is optionally further substituted by one or more substituents selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_2$ is selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl, 5 to 10 membered heteroaryl and —$(CH_2)_nOR_{cc}$;

or, any two $R_2$ are attached together to form a $C_{3-8}$ cycloalkyl or 3 to 8 membered heterocyclyl, wherein the $C_{3-8}$ cycloalkyl or 3 to 8 membered heterocyclyl is optionally further substituted by one or more substituents selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_3$ and $R_3$' are each selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

or, $R_3$ and $R_3$' are attached together to form an oxo, $C_{3-8}$ cycloalkyl or 3 to 8 membered heterocyclyl, wherein the $C_{3-8}$ cycloalkyl or 3 to 8 membered heterocyclyl is optionally further substituted by one or more substituents selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_4$ is selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_5$ is selected from the group consisting of hydrogen, deuterium, $C_{1-6}$ alkyl and $C_{1-6}$ haloalkyl;

or, $R_1$ or $R_1$' is attached with $R_5$ to form a 3 to 8 membered heterocyclyl, wherein the 3 to 8 membered heterocyclyl is optionally further substituted by one or more substituents selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_{aa}$, $R_{bb}$ and $R_{cc}$ are each independently selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

M is an inorganic acid or an organic acid, wherein the inorganic acid is selected from the group consisting of hydrochloric acid, sulfuric acid, nitric acid, hydrobromic acid, hydrofluoric acid, hydroiodic acid and phosphoric acid; the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid;

n is an integer from 0 to 3;

x is an integer from 0 to 3; and y is an integer from 1 to 5, preferably an integer from 1 to 3, and more preferably 1.

In preferred embodiments of the present invention, in the acid addition salt of formula (I), $R_1$ and $R_1$' are each selected from the group consisting of hydrogen, $C_{1-6}$ alkyl, $C_{1-6}$ hydroxyalkyl, $C_{1-6}$ haloalkyl, $C_{1-6}$ alkoxy, 3 to 8 membered heterocyclyl, —$(CH_2)_nOR_{cc}$ and —$CR_{aa}R_{bb}OR_{cc}$, preferably hydrogen, $C_{1-3}$ alkyl, $C_{1-3}$ hydroxyalkyl, $C_{1-3}$ haloalkyl, $C_{1-3}$ alkoxy, 3 to 6 membered heterocyclyl, —$(CH_2)_nOR_{cc}$ and —$CR_{aa}R_{bb}OR_{cc}$, more preferably hydrogen, methyl, ethyl, propyl, isopropyl, methoxy, ethoxy, propoxy, fluoromethyl, fluoroethyl, fluoropropyl, chloromethyl, chloroethyl, chloropropyl, hydroxymethyl, hydroxyethyl, hydroxypropyl, oxacyclopropyl, oxacyclobutyl, oxacyclopentyl, oxacyclohexyl, azacyclopropyl, azacyclobutyl, azacyclopentyl, azacyclohexyl, —$(CH_2)OCH_3$, —$(CH_2)_2OCH_3$, —$CH(CH_3)OCH_3$ and —$C(CH_3)_2OCH_3$, and further preferably hydrogen, methyl, methoxy, isopropyl, fluorine-containing methyl, hydroxymethyl, oxacyclobutyl, —$(CH_2)OCH_3$ and —$CH(CH_3)OCH_3$.

In more preferred embodiments of the present invention, in the acid addition salt of formula (I), $R_2$ is selected from the group consisting of hydrogen, $C_{1-6}$ alkyl, halogen, cyano and —$(CH_2)_nOR_{cc}$, preferably hydrogen, $C_{1-3}$ alkyl, halogen, cyano and —$(CH_2)_nOR_{cc}$, more preferably hydrogen, methyl, ethyl, propyl, methoxy, ethoxy, propoxy, fluorine, chlorine, bromine and cyano, and further preferably hydrogen, fluorine, methyl, methoxy and cyano;

or, any two $R_2$ are attached together to form a substituted or unsubstituted $C_{3-6}$ cycloalkyl or a substituted or unsubstituted 3 to 6 membered heterocyclyl, preferably a substituted or unsubstituted $C_{3-6}$ cycloalkyl or substituted or unsubstituted 3 to 6 membered heterocyclyl containing 1 to 3 atoms selected from the group consisting of N, O and S, more preferably cyclopropyl, cyclobutyl, cyclopentyl, cyclohexyl, oxacyclopropyl, oxacyclobutyl, oxacyclopentyl, oxacyclohexyl, azacyclopropyl, azacyclobutyl, azacyclopentyl or azacyclohexyl, and further preferably cyclobutyl, cyclopentyl, 1,3-dioxocyclopentyl or 1,3-dioxocyclohexyl.

In further preferred embodiments of the present invention, in the acid addition salt of formula (I), $R_3$ and $R_3$' are each selected from the group consisting of hydrogen, $C_{1-6}$ alkyl, halogen, cyano and $C_{1-6}$ alkoxy, preferably hydrogen, $C_{1-3}$ alkyl, halogen, cyano and $C_{1-3}$ alkoxy, more preferably hydrogen, methyl, ethyl, propyl, fluorine, chlorine, bromine, cyano, methoxy, ethoxy and propoxy, and more preferably hydrogen, fluorine, methyl, methoxy and cyano;

or, $R_3$ and $R_3$' are attached together to form an oxo, $C_{3-6}$ cycloalkyl or 3 to 6 membered heterocyclyl, preferably oxo, $C_{3-6}$ cycloalkyl or 3 to 6 membered heterocyclyl containing 1 to 3 N, O or S atoms, more preferably oxo, cyclopropyl, cyclobutyl, cyclopentyl, cyclohexyl, oxacyclopropyl, oxacyclobutyl, oxacyclopentyl, oxacyclohexyl, azacyclopropyl, azacyclobutyl, azacyclopentyl or azacyclohexyl, and further preferably oxo, cyclopropyl or oxacyclobutyl.

In still further preferred embodiments of the present invention, in the acid addition salt of formula (I), $R_4$ is selected from the group consisting of hydrogen, $C_{1-6}$ alkyl, halogen, cyano, $C_{1-6}$ haloalkyl and $C_{3-8}$ cycloalkyl, preferably hydrogen, $C_{1-3}$ alkyl, halogen, cyano, $C_{1-3}$ haloalkyl and $C_{3-6}$ cycloalkyl, more preferably hydrogen, methyl, ethyl, propyl, fluorine, chlorine, bromine, cyano, fluoromethyl, fluoroethyl, chloromethyl, chloroethyl, trifluoromethyl, trifluoroethyl, trichloromethyl, trichloroethyl, cyclopropyl, cyclobutyl, cyclopentyl and cyclohexyl, and further preferably hydrogen, fluorine, chlorine, methyl, trifluoromethyl, cyano and cyclopropyl.

In preferred embodiments of the present invention, in the acid addition salt of formula (I), $R_5$ is selected from the group consisting of hydrogen, $C_{1-6}$ alkyl and $C_{1-6}$ haloalkyl, preferably hydrogen, $C_{1-3}$ alkyl and $C_{1-3}$ haloalkyl, more preferably hydrogen, methyl, ethyl, propyl, fluorine-containing methyl, fluorine-containing ethyl, fluorine-containing propyl, chlorine-containing methyl, chlorine-containing ethyl and chlorine-containing propyl, and further preferably hydrogen and methyl;

or, $R_1$ or $R_1$' is attached with $R_5$ to form a 3 to 6 membered heterocyclyl, optionally substituted by one or more substituents selected from the group consisting of fluorine, chlorine, bromine, methyl, ethyl and propyl, preferably azacyclopropyl, azacyclobutyl, azacyclopentyl, azacyclohexyl, fluorine-substituted azacyclopropyl, fluorine-substituted azacyclobutyl, fluorine-substituted azacyclopentyl, fluorine-substituted azacyclohexyl, methyl-substituted azacyclopropyl, methyl-substituted azacyclobutyl, methyl pyrrolidinyl or methyl-substituted azacylcohexyl, and further preferably azacyclobutyl, azacyclopentyl or methyl pyrrolidinyl.

In preferred embodiments of the present invention, in the acid addition salt of formula (I), $R_{aa}$, $R_{bb}$ and $R_{cc}$ are each independently selected from the group consisting of hydrogen, $C_{1-6}$ alkyl, $C_{1-6}$ alkoxy, $C_{3-8}$ cycloalkyl and 3 to 8 membered heterocyclyl, preferably hydrogen, $C_{1-3}$ alkyl, $C_{1-3}$ alkoxy, $C_{3-6}$ cycloalkyl or 3 to 6 membered heterocyclyl containing 1-3 N, O or S atoms, more preferably hydrogen, methyl, ethyl, propyl, methoxy, ethoxy, propoxy, cyclopropyl, cyclobutyl, cyclopentyl, cyclohexyl, oxacyclopropyl, oxacyclobutyl, oxacyclopentyl and oxacyclobutyl, and further preferably hydrogen, methyl, ethyl, isopropyl, methoxy, cyclopropyl and oxacyclobutyl.

In preferred embodiments of the present invention, in the acid addition salt of formula (I), M is selected from the group consisting of sulfuric acid, phosphoric acid, benzenesulfonic acid, cinnamic acid, tartaric acid, ethane-1,2-disulfonic acid, ethanesulfonic acid, fumaric acid and methanesulfonic acid, preferably sulfuric acid, tartaric acid, ethane-1, 2-disulfonic acid, ethanesulfonic acid, fumaric acid and methanesulfonic acid, more preferably sulfuric acid, ethane-1,2-disulfonic acid, ethanesulfonic acid and methanesulfonic acid, and further preferably ethanesulfonic acid.

In further preferred embodiments of the present invention, in the acid addition salt of formula (I), the W is O.

In further preferred embodiments of the present invention, in the acid addition salt of formula (I), the G is O or S.

In further preferred embodiments of the present invention, in the acid addition salt of formula (I), the $R_5$ is hydrogen.

In further preferred embodiments of the present invention, in the acid addition salt of formula (I), the $R_1$' and $R_3$' are hydrogen.

In further preferred embodiments of the present invention, in the acid addition salt of formula (I), W is selected from the group consisting of —O—, —S— and —$NR_{aa}$—;

G is selected from the group consisting of —O— and —S—;

$R_1$ and $R_1$' are each selected from the group consisting of hydrogen, methyl, methoxy, isopropyl, fluorine-containing methyl, hydroxymethyl, oxacyclobutyl, —$CH_2OCH_3$ and —$CH(CH_3)OCH_3$;

$R_2$ is selected from the group consisting of hydrogen, fluorine, methyl, methoxy and cyano;

$R_3$ and $R_3$' are each selected from the group consisting of hydrogen, fluorine, methyl, methoxy and cyano;

$R_4$ is selected from the group consisting of hydrogen, fluorine, chlorine, methyl, trifluoromethyl, cyano and cyclopropyl;

$R_5$ is selected from the group consisting of hydrogen and methyl;

$R_{aa}$, $R_{bb}$ and $R_{cc}$ are each independently selected from the group consisting of hydrogen, methyl, ethyl, isopropyl, methoxy, cyclopropyl and oxacyclobutyl.

In further preferred embodiments of the present invention, when W is —O—, $R_5$ is hydrogen, $R_1$ is methyl, $R_1$' is hydrogen, $R_2$ is hydrogen, $R_3$ and $R_3$' are hydrogen and $R_4$ is hydrogen, G is not —O—.

In further preferred embodiments of the present invention, the structure of the acid addition salt of formula (I) is as shown in formula (II-A) or (II-B):

(II-A)

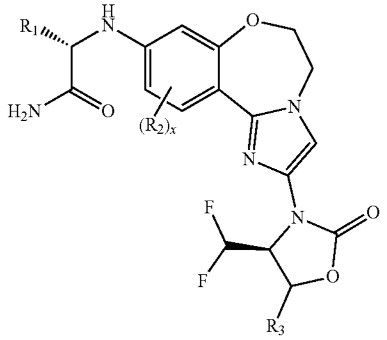

•y M (II-B)

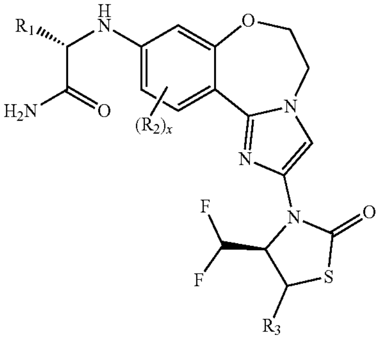

•y M.

In further preferred embodiments of the present invention, the acid addition salt of formula (I) is in crystal form or amorphous form.

In further preferred embodiments of the present invention, the acid addition salt of formula (I) includes both crystal form and amorphous form, wherein, the acid addition salt of formula (I) is a hydrate or an anhydrate, preferably an anhydrate.

The present invention further provides a method for preparing the acid addition salt of formula (I), specifically comprising the following steps of:

1) preparing the stock solution: weighing free base of the compound and adding an organic solvent to obtain a clear or suspended stock solution;
2) preparing the counter ion acid solution: adding counter ion acid M into an organic solvent or water to obtain a clear counter ion acid solution;
3) preparing the salt of the compound: adding the counter ion acid solution to the stock solution to obtain a clear salt solution, stirring the salt solution to precipitate a solid, and drying the solid;

wherein:

the organic solvent is one or more selected from the group consisting of alcohols, esters, hydrocarbons, ketones, ethers, benzenes, amides and nitriles, preferably one or more of methanol, ethanol, isopropanol, tert-butanol, ethyl acetate, n-hexane, heptane, dichloromethane, chloroform, carbon tetrachloride, dichloroethane, acetone, 2-butanone, 3-pentanone, isopropyl ether, petroleum ether, methyl tert-butyl ether, tetrahydrofuran, 1,4-dioxane, benzene, toluene, N,N-dimethylformamide and acetonitrile, more preferably one or more of methanol, ethanol, isopropanol, ethyl acetate, acetone, dichloromethane and acetonitrile, and further preferably one or more of methanol, ethanol, isopropanol, acetone and acetonitrile;

the counter ion acid is selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, D-tartaric acid, pamoic acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid, preferably sulfuric acid, phosphoric acid, benzenesulfonic acid, cinnamic acid, tartaric acid, ethane-1,2-disulfonic acid, ethanesulfonic acid, fumaric acid and methanesulfonic acid, more preferably sulfuric acid, tartaric acid, ethane-1,2-disulfonic acid, ethanesulfonic acid, fumaric acid and methanesulfonic acid, further preferably sulfuric acid, ethane-1,2-disulfonic acid, ethanesulfonic acid and methanesulfonic acid, and still further preferably ethanesulfonic acid.

The concentration of the organic solvent in step 2) is 0.8 to 3.0 mol/L, preferably 1.0 to 2.5 mol/L, and more preferably 1.2 to 2.2 mol/L.

Preferably, the vacuum temperature in step 3) is 30 to 60° C., preferably 35 to 50° C., and more preferably 40° C.

More preferably, the amount of the counter ion acid in step 3) is 0.4 to 2.0 equivalents, preferably 0.5 to 1.5 equivalents, and more preferably 0.6 to 1.2 equivalents.

The present invention further provides a method for preparing the compound of formula (I) and crystal form thereof, specifically comprising the following steps of:

1) weighing an appropriate amount of free base and suspending it with a poor solvent;
2) optionally, weighing an appropriate amount of counter ion acid M and dissolving it with an organic solvent;
3) optionally, adding the solution in step 2) to the suspension in step 1), and stirring the resulting mixture to precipitate a solid;
4) optionally, adding an organic solvent to the solid obtained in step 3), and stirring the resulting mixture to precipitate a crystal;
5) stirring and cooling the mixture, followed by precipitating a crystal to obtain the target product;

wherein:

the poor solvent is one or more selected from the group consisting of alcohols, esters, ketones, ethers, benzenes, amides and nitriles, preferably one or more of methanol, ethanol, n-propanol, isopropanol, n-butanol, isobutanol, tert-butanol, ethyl acetate, acetone, 2-butanone, tetrahydrofuran, 1,4-dioxane, benzene, toluene, N,N-dimethylformamide, N,N-dimethylacetamide and acetonitrile, more preferably one or more of methanol, ethanol, isopropanol, tetrahydrofuran, ethyl acetate, acetonitrile and acetone, and further preferably one or more of methanol, ethanol, isopropanol, tetrahydrofuran, ethyl acetate, acetonitrile or 88% acetone;

the organic solvent in the step 2) is one or more selected from the group consisting of alcohols, esters, hydrocarbons, ketones, ethers, benzenes, amides and nitriles, preferably one or more of methanol, ethanol, isopropanol, tert-butanol, ethyl acetate, dichloromethane, chloroform, carbon tetrachloride, dichloroethane, n-hexane, heptane, acetone, 2-butanone, 3-pentanone, petroleum ether, tetrahydrofuran, methyl tert-butyl ether, isopropyl ether, 1,4-dioxane, benzene, toluene, N,N-dimethylformamide and acetonitrile, more preferably one or more of methanol, ethanol, isopropanol, tert-butanol, acetone, tetrahydrofuran, toluene, N,N-dimethylformamide and acetonitrile, and more preferably one or more of methanol, ethanol, isopropanol, acetone and acetonitrile;

the above-mentioned good solvents and organic solutions need to be miscible when used;

the counter ion acid is selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid, preferably sulfuric acid, phosphoric acid, benzenesulfonic acid, cinnamic acid, tartaric acid, ethane-1,2-disulfonic acid, ethanesulfonic acid, fumaric acid and methanesulfonic acid, more preferably sulfuric acid, tartaric acid, ethane-1,2-disulfonic acid, ethanesulfonic acid, fumaric acid and methanesulfonic acid, further preferably sulfuric acid, ethane-1,2-disulfonic acid, ethanesulfonic acid and methanesulfonic acid, and still further preferably ethanesulfonic acid.

the organic solvent in step 4) is one or more selected from the group consisting of alcohols, esters and ethers, preferably one or more of methanol, ethanol, n-propanol, isopropanol, ethyl acetate, petroleum ether, methyl tert-butyl ether, tetrahydrofuran and 1,4-dioxane, more preferably one or more of methanol, ethanol, n-propanol, isopropanol, ethyl acetate, methyl tert-butyl ether and tetrahydrofuran, and further preferably one or more of methanol, ethanol, isopropanol, ethyl acetate and methyl tert-butyl ether.

The present invention further provides a method for preparing the compound of formula (I) and crystal form thereof, specifically comprising the following steps of:

1) weighing an appropriate amount of salt of the compound and suspending it with a poor solvent;
2) shaking the suspension obtained above;
3) centrifuging the above suspension, removing the supernatant, and vacuum-drying the remaining solid to obtain the target product;

wherein:

the poor solvent is one or more selected from the group consisting of alcohols, ketones, esters, ethers, benzenes, amides and nitriles, preferably one or more of methanol, ethanol, n-propanol, isopropanol, n-butanol, isobutanol, tert-butanol, acetone, 2-butanone, ethyl acetate, tetrahydrofuran, 1,4-dioxane, benzene, toluene, N,N-dimethylformamide, N,N-dimethylacetamide and acetonitrile, and further preferably one or more of methanol, ethanol, n-propanol, isopropanol, 88% acetone and acetonitrile.

The suspension density in step 1) is 20 to 200 mg/mL, preferably 30 to 150 mg/mL, and more preferably 50 to 100 mg/mL;

preferably, the temperature in step 2) is 20 to 80° C., preferably 25 to 60° C., and more preferably 25 to 40° C.; the time is 1 to 15 days, and preferably 1 to 10 days;

more preferably, the temperature of vacuum drying is 20 to 60° C., preferably 20 to 50° C., and more preferably 40° C.

The present invention further provides a method for preparing the compound of formula (I) and crystal form thereof, specifically comprising the following steps of:

1) weighing an appropriate amount of salt of the compound, and exposing the salt of the compound to a certain humidity for a certain period of time, wherein:

the humidity is RH=70% to 95%, preferably RH=75% to 95%, more preferably RH=80% to 95%, and further preferably RH=92.5%; the time is 1 h to 3 days, preferably 1 h to 2 days, more preferably 1 h to 1 day, and further preferably 3 h.

The present invention still further provides a method for preparing the compound of formula (I) and crystal form thereof, specifically comprising the following steps of:

1) weighing an appropriate amount of free base and suspending it with a poor solvent;
2) weighing an appropriate amount of counter ion acid M and dissolving it with an organic solvent;
3) adding the solution in step 2) to the suspension in step 1), and heating the reaction;
4) optionally, adding an organic solvent to the solution in step 3);
5) optionally, adding a salt of the compound to the solution in step 4);
6) cooling the mixture to precipitate a crystal;

preferably, the poor solvent is one or more selected from the group consisting of alcohols, ketones, esters, ethers, benzenes, amides and acetonitrile, preferably one or more of methanol, ethanol, n-propanol, isopropanol, n-butanol, isobutanol, tert-butanol, acetone, 2-butanone, ethyl acetate, tetrahydrofuran, 1,4-dioxane, benzene, toluene, N,N-dimethylformamide, N,N-dimethylacetamide and acetonitrile, and more preferably one or more of methanol, ethanol, n-propanol, isopropanol, acetone and acetonitrile;

preferably, the counter ion acid is selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid, preferably sulfuric acid, phosphoric acid, benzenesulfonic acid, cinnamic acid, tartaric acid, ethane-1,2-disulfonic acid, ethanesulfonic acid, fumaric acid and methanesulfonic acid, more preferably sulfuric acid, tartaric acid, ethane-1,2-disulfonic acid, ethanesulfonic acid, fumaric acid and methanesulfonic acid, further preferably sulfuric acid, ethane-1,2-disulfonic acid, ethanesulfonic acid and methanesulfonic acid, and still further preferably ethanesulfonic acid and methanesulfonic acid;

preferably, the organic solvent in step 2) is selected from alcoholic solvents, preferably one or more of methanol, ethanol, n-propanol, isopropanol, n-butanol, isobutanol and tert-butanol, and preferably one or more of methanol, ethanol, isopropanol and tert-butanol;

preferably, the heating temperature in step 3) is 30 to 80° C., preferably 40 to 60° C., and more preferably 50° C.;

preferably, the organic solvent in step 4) is one or more selected from the group consisting of alcohols, esters and ethers, preferably one or more of methanol, ethanol, n-propanol, isopropanol, ethyl acetate, petroleum ether, methyl tert-butyl ether, tetrahydrofuran and 1,4-dioxane, more preferably one or more of methanol, ethanol, n-propanol, isopropanol, ethyl acetate, methyl tert-butyl ether and tetrahydrofuran, and further preferably one or more of methanol, ethanol, isopropanol, ethyl acetate and methyl tert-butyl ether.

The present invention further provides a method for preparing the compound of formula (I) and crystal form thereof, specifically comprising the following steps of:

1) weighing an appropriate amount of free base and suspending it with a poor solvent;
2) weighing an appropriate amount of counter ion acid M and dissolving it with an organic solvent;
3) adding the solution in step 2) to the suspension in step 1), and adding an organic solvent after dissolution;
4) optionally, adding an appropriate amount of salt of the compound to the solution in step 3), and stirring the resulting mixture to precipitate a crystal;

preferably, the poor solvent is one or more selected from the group consisting of alcohols, ketones, esters, ethers, benzenes, amides and acetonitrile, preferably one or more of methanol, ethanol, n-propanol, isopropanol, n-butanol, isobutanol, tert-butanol, acetone, 2-butanone, ethyl acetate, tetrahydrofuran, 1,4-dioxane, benzene, toluene, N,N-dimethylformamide, N,N-dimethylacetamide and acetonitrile, and more preferably one or more of methanol, ethanol, n-propanol, isopropanol, acetone and acetonitrile;

preferably, the counter ion acid is selected from the group consisting of hydrochloric acid, sulfuric acid, nitric acid, hydrobromic acid, hydrofluoric acid, hydroiodic acid, phosphoric acid, 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid, preferably sulfuric acid, phosphoric acid, benzenesulfonic acid, cinnamic acid, tartaric acid, ethane-1,2-disulfonic acid, ethanesulfonic acid, fumaric acid and methanesulfonic acid, more preferably sulfuric acid, tartaric acid, ethane-1,2-disulfonic acid, ethanesulfonic acid, fumaric acid and methanesulfonic acid, further preferably sulfuric acid, ethane-1,2-disulfonic acid, ethanesulfonic acid and methanesulfonic acid, and still further preferably ethanesulfonic acid and methanesulfonic acid;

preferably, the organic solvent in step 2) is selected from alcoholic solvents, preferably one or more of methanol, ethanol, n-propanol, isopropanol, n-butanol, isobutanol and tert-butanol, and preferably one or more of methanol, ethanol, isopropanol and tert-butanol;

preferably, the organic solvent in step 3) is one or more selected from the group consisting of alcohols, esters and ethers, preferably one or more of methanol, ethanol, n-propanol, isopropanol, ethyl acetate, petroleum ether, methyl tert-butyl ether, tetrahydrofuran and 1,4-dioxane, more preferably one or more of methanol, ethanol, n-propanol, isopropanol, ethyl acetate, methyl tert-butyl ether and tetrahydrofuran, and further preferably one or more of methanol, ethanol, isopropanol, ethyl acetate and methyl tert-butyl ether.

In preferred embodiments of the present invention, the compound of formula (I) is an ethanesulfonate, mesylate or sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is ethanesulfonic acid, and y is 1, i.e., crystal form A of ethanesulfonate salt, having a structure as follows:

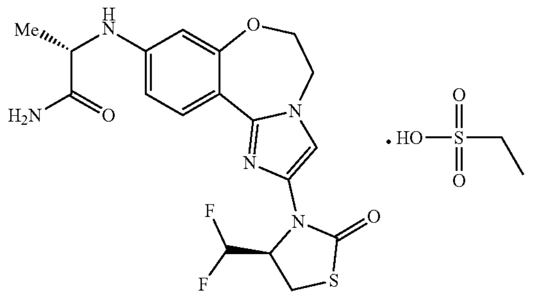

wherein, the X-ray powder diffraction pattern thereof comprises one or more diffraction peaks at 2θ of 6.8±0.2° and 13.4±0.2°, 14.7±0.2° and 19.5±0.2°, 20.1±0.2°, 23.9±0.2°, 24.4±0.2°, 25.0±0.2°, 23±0.2°, 23.6±0.2°, 9.3±0.2° and 17.3±0.2°; and preferably comprises optional 2, 4, 6, 8 or 10 of the above diffraction peaks;

or, the X-ray powder diffraction pattern thereof comprises two or three diffraction peaks at 2θ of 6.8±0.2°, 13.4±0.2°, 14.7±0.2° and 19.5±0.2°, optionally further comprising one or more diffraction peaks at 2θ of 20.1±0.2°, 23.9±0.2°, 24.4±0.2°, 25.0±0.2°, 23±0.2° and 23.6±0.2°; and preferably comprising 2, 3, 4, 5 or 6 of the above diffraction peaks;

for example, the X-ray powder diffraction pattern thereof has characteristic peaks at 13.4±0.2°, 14.7±0.2°, 19.5±0.2°, 20.1±0.2°, 23±0.2°, 23.9±0.2°, 24.4±0.2° and 25.0±0.2;

the X-ray powder diffraction pattern thereof has characteristic peaks at 6.8±0.2°, 13.4±0.2°, 14.7±0.2°, 19.5±0.2°, 20.1±0.2°, 23.9±0.2°, 23±0.2° and 23.6±0.2°;

the X-ray powder diffraction pattern thereof has characteristic peaks at 6.8±0.2°, 13.4±0.2°, 14.7±0.2°, 19.5±0.2°, 20.1±0.2°, 23.9±0.2°, 24.4±0.2° and 25.0±0.2°;

the X-ray powder diffraction pattern thereof has characteristic peaks at 6.8±0.2°, 13.4±0.2°, 14.7±0.2°, 19.5±0.2°, 20.1±0.2°, 23.9±0.2°, 24.4±0.2°, 25.0±0.2°, 23±0.2° and 23.6±0.2°.

In preferred embodiments of the present invention, the X-ray powder diffraction pattern has diffraction peaks at 2θ of 6.8±0.2°, 9.3±0.2°, 13.4±0.2° and 14.7±0.2°; further has diffraction peaks at 2θ of 17.3±0.2°, 19.5±0.2°, 20.8±0.2°, 23.9±0.2° and 25.0±0.2°; still further has diffraction peaks at 2θ of 9.8±0.2°, 18.4±0.2°, 19.1±0.2°, 20.1±0.2°, 23.0±0.2°, 23.6±0.2°, 24.4±0.2°, 27.3±0.2° and 30.7±0.2°; and still further has diffraction peaks at 2θ of 10.5±0.2°, 17.5±0.2°, 26.9±0.2°, 27.7±0.2°, 28.6±0.2°, 29.6±0.2°, 35.7±0.2° and 37.6±0.2°;

or, the X-ray powder diffraction pattern has diffraction peaks at 2θ of 6.8±0.2° and 13.4±0.2°; preferably also has diffraction peaks at 2θ of 14.7±0.2° and 19.5±0.2°; more preferably also has diffraction peaks at 2θ (+0.2°) of 20.1±0.2°, 23.9±0.2°, 24.4±0.2° and 25.0±0.2°; further preferably also has diffraction peaks at 23±0.2° and 23.6±0.2°; further preferably also has diffraction peaks at 9.3±0.2° and 17.3±0.2°; still further preferably also has diffraction peaks at 2θ of 9.8±0.2°, 18.4±0.2°, 19.1±0.2°, 23.6±0.2°, 27.3±0.2° and 30.7±0.2°; and even further preferably also has diffraction peaks at 2θ of 10.5±0.2°, 17.5±0.2°, 26.9±0.2°, 27.7±0.2°, 28.6±0.2°, 29.6±0.2°, 35.7±0.2° and 37.6±0.2°.

Using Cu-Kα radiation, the characteristic X-ray diffraction peaks represented by 2θ angle and interplanar spacing d value are shown in Table 1.

TABLE 1

XRPD diffraction data of crystal form A of ethanesulfonate salt

| No. | 2θ (±0.2°) | d value | Peak height | Proportion (I %) | Area | Proportion (I %) |
|---|---|---|---|---|---|---|
| 1 | 6.772 | 13.0423 | 318 | 13.4 | 2483 | 10.2 |
| 2 | 9.254 | 9.5482 | 1050 | 44.2 | 9001 | 36.9 |
| 3 | 9.791 | 9.0264 | 268 | 11.3 | 2130 | 8.7 |
| 4 | 10.468 | 8.4442 | 141 | 5.9 | 1695 | 7 |
| 5 | 13.423 | 6.591 | 1528 | 64.3 | 14395 | 59.1 |
| 6 | 14.651 | 6.0413 | 655 | 27.6 | 6256 | 25.7 |
| 7 | 17.287 | 5.1254 | 727 | 30.6 | 7700 | 31.6 |
| 8 | 17.543 | 5.0513 | 236 | 9.9 | 2847 | 11.7 |
| 9 | 18.398 | 4.8184 | 239 | 10.1 | 2270 | 9.3 |
| 10 | 19.052 | 4.6543 | 348 | 14.6 | 4583 | 18.8 |
| 11 | 19.526 | 4.5424 | 644 | 27.1 | 6761 | 27.8 |
| 12 | 20.136 | 4.4063 | 494 | 20.8 | 4093 | 16.8 |
| 13 | 20.826 | 4.2617 | 736 | 31 | 7572 | 31.1 |
| 14 | 23.048 | 3.8556 | 330 | 13.9 | 2614 | 10.7 |
| 15 | 23.57 | 3.7714 | 452 | 19 | 4735 | 19.4 |
| 16 | 23.917 | 3.7175 | 1559 | 65.6 | 13823 | 56.7 |
| 17 | 24.43 | 3.6405 | 495 | 20.8 | 4147 | 17 |
| 18 | 25.023 | 3.5557 | 2377 | 100 | 24362 | 100 |
| 19 | 26.886 | 3.3134 | 275 | 11.6 | 2719 | 11.2 |
| 20 | 27.341 | 3.2592 | 516 | 21.7 | 5645 | 23.2 |
| 21 | 27.688 | 3.2191 | 316 | 13.3 | 2948 | 12.1 |
| 22 | 28.625 | 3.1158 | 289 | 12.2 | 3580 | 14.7 |
| 23 | 29.628 | 3.0126 | 125 | 5.3 | 2041 | 8.4 |
| 24 | 30.703 | 2.9096 | 373 | 15.7 | 4548 | 18.7 |
| 25 | 35.667 | 2.5152 | 153 | 6.4 | 1822 | 7.5 |
| 26 | 37.556 | 2.3929 | 295 | 12.4 | 3545 | 14.6 |

The compound of formula (I) according to the present invention is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 1; the TGA spectrum thereof is substantially as shown in FIG. 2; and the DSC spectrum thereof is substantially as shown in FIG. 3.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is mesylate salt, and y is 1, i.e., crystal form A of mesylate salt, having a structure as follows:

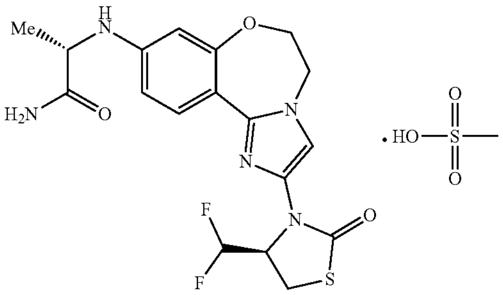

wherein, the X-ray powder diffraction pattern thereof comprises one or more diffraction peaks at 2θ of 6.1±0.20, 7.5±0.2°, 8.0±0.2°, 14.9±0.20, 23.8±0.20, 8.4±0.2°, 18.8±0.20, 20.7±0.20, 22.3±0.20 and 22.8±0.2°; and preferably comprises optional 2, 4, 6, 8 or 10 of the above diffraction peaks;

or, the X-ray powder diffraction pattern thereof comprises two or three diffraction peaks at 2θ of 6.1±0.2°, 7.5±0.2° and 8.0±0.2°, optionally further comprises one or more diffraction peaks at 2θ of 14.9±0.20, 18.8±0.20, 20.7±0.20, 22.3±0.20, 22.8±0.20 and 23.8±0.2°; and preferably comprises 2, 3, 4, 5 or 6 of the above diffraction peaks;

for example, the X-ray powder diffraction pattern thereof has characteristic peaks at 6.1±0.2°, 7.5±0.2°, 8.0±0.2°, 14.9±0.20, 18.8±0.20, 22.3±0.20, 22.8±0.20 and 23.8±0.2.

Or, the X-ray powder diffraction pattern thereof has diffraction peaks at 2θ of 6.1±0.2°, 7.5±0.2°, 8.0±0.2°, 14.9±0.20 and 23.8±0.2°; further has diffraction peaks at 2θ of 8.4±0.2°, 18.8±0.20, 20.7±0.20, 22.3±0.20 and 22.8±0.2°; and still further has diffraction peaks at 2θ of 13.5±0.20 and 25.2±0.20.

Using Cu-Kα radiation, the characteristic X-ray diffraction peaks represented by 2θ angle and interplanar spacing d value are shown in Table 2.

TABLE 2

XRPD diffraction data of crystal form A of mesylate salt

| No. | 2θ (±0.2°) | d value | Peak height | Proportion (I %) | Area | Proportion (I %) |
|---|---|---|---|---|---|---|
| 1 | 6.114 | 14.4436 | 2388 | 100 | 31283 | 100 |
| 2 | 7.463 | 11.836 | 981 | 41.1 | 12556 | 40.1 |
| 3 | 7.971 | 11.0829 | 1983 | 83 | 25000 | 79.9 |
| 4 | 8.361 | 10.5665 | 304 | 12.7 | 5284 | 16.9 |
| 5 | 12.079 | 7.3209 | 240 | 10.1 | 5032 | 16.1 |
| 6 | 13.456 | 6.5746 | 334 | 14 | 4384 | 14 |
| 7 | 14.897 | 5.9418 | 787 | 33 | 14734 | 47.1 |
| 8 | 15.808 | 5.6013 | 155 | 6.5 | 3629 | 11.6 |
| 9 | 18.764 | 4.7251 | 510 | 21.4 | 9923 | 31.7 |
| 10 | 20.653 | 4.2971 | 404 | 16.9 | 8160 | 26.1 |
| 11 | 20.969 | 4.2331 | 166 | 7 | 4591 | 14.7 |
| 12 | 21.276 | 4.1727 | 175 | 7.3 | 2114 | 6.8 |
| 13 | 22.251 | 3.9919 | 610 | 25.5 | 10644 | 34 |
| 14 | 22.765 | 3.9029 | 436 | 18.3 | 7415 | 23.7 |
| 15 | 23.779 | 3.7387 | 918 | 38.4 | 16253 | 52 |
| 16 | 24.233 | 3.6698 | 218 | 9.1 | 7603 | 24.3 |
| 17 | 25.16 | 3.5366 | 324 | 13.6 | 4660 | 14.9 |
| 18 | 26.435 | 3.3688 | 136 | 5.7 | 4032 | 12.9 |
| 19 | 26.904 | 3.3111 | 245 | 10.3 | 4392 | 14 |
| 20 | 27.799 | 3.2066 | 195 | 8.2 | 2889 | 9.2 |
| 21 | 29.066 | 3.0696 | 124 | 5.2 | 2110 | 6.7 |
| 22 | 29.756 | 3 | 104 | 4.4 | 2408 | 7.7 |

The compound of formula (I) according to the present invention is crystal form A of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 4.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is mesylate salt, and y is 1, i.e., crystal form B of mesylate salt, having a structure as follows:

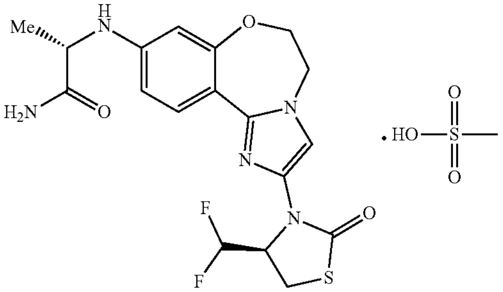

wherein, the X-ray powder diffraction pattern thereof comprises one or more diffraction peaks at 2θ of 24.4±0.2°, 13.3±0.2°, 23.8±0.2°, 20.3±0.2°, 19.7±0.2°, 17.2±0.2°, 26.7±0.2°, 9.0±0.2°, 23.1±0.2°, 9.9±0.2°, 14.3±0.2° and 21.6±0.2°; and preferably comprises optional 2, 4, 6, 8 or 10 of the above diffraction peaks;

or, the X-ray powder diffraction pattern thereof comprises two or three diffraction peaks at 24.4±0.2°, 13.3±0.2° and 23.8±0.2°, optionally further comprises one or more diffraction peaks at 2θ of 9.0±0.2°, 9.9±0.2°, 26.7±0.2°, 17.2±0.2° and 23.1±0.2°; and preferably comprises 2, 3, 4 or 5 of the above diffraction peaks;

for example, the X-ray powder diffraction pattern thereof has characteristic peaks at 24.4±0.2°, 13.3±0.2°, 23.8±0.2°, 9.0±0.2°, 9.9±0.2°, 26.7±0.2°, 17.2±0.2° and 23.1±0.2°.

Or, the X-ray powder diffraction pattern thereof has diffraction peaks at 2θ of 9.0±0.2°, 13.3±0.2°, 19.7±0.2° and 23.1±0.2°; further has diffraction peaks at 2θ of 9.9±0.2°, 17.2±0.2°, 20.3±0.2° and 26.7±0.2°; still further has diffraction peaks at 2θ of 14.3±0.2°, 21.6±0.2°, 23.8±0.2° and 28.4±0.2°; and even further comprises diffraction peaks at 2θ of 24.4±0.2°, 30.5±0.2° and 32.6±0.2°.

Using Cu-Kα radiation, the characteristic X-ray diffraction peaks represented by 20 angle and interplanar spacing d value are shown in Table 3.

TABLE 3

XRPD diffraction data of crystal form B of mesylate salt

| No. | 2θ (±0.2°) | d value | Peak height | Proportion (I %) | Area | Proportion (I %) |
|---|---|---|---|---|---|---|
| 1 | 6.086 | 14.5108 | 141 | 8.4 | 2348 | 8.8 |
| 2 | 8.954 | 9.8675 | 373 | 22.1 | 4510 | 16.9 |
| 3 | 9.882 | 8.9429 | 234 | 13.9 | 3979 | 14.9 |
| 4 | 13.298 | 6.6528 | 1064 | 63 | 15436 | 57.8 |
| 5 | 14.254 | 6.2083 | 224 | 13.3 | 3110 | 11.6 |
| 6 | 17.237 | 5.1402 | 461 | 27.3 | 7332 | 27.5 |
| 7 | 18.513 | 4.7886 | 110 | 6.5 | 2860 | 10.7 |
| 8 | 19.691 | 4.5049 | 472 | 28 | 11335 | 42.5 |
| 9 | 20.315 | 4.3678 | 494 | 29.3 | 10915 | 40.9 |
| 10 | 21.6 | 4.1108 | 210 | 12.4 | 2505 | 9.4 |
| 11 | 22.793 | 3.8982 | 117 | 6.9 | 3014 | 11.3 |

TABLE 3-continued

| XRPD diffraction data of crystal form B of mesylate salt | | | | | | |
|---|---|---|---|---|---|---|
| No. | 2θ (±0.2°) | d value | Peak height | Proportion (I %) | Area | Proportion (I %) |
| 12 | 23.14 | 3.8405 | 373 | 22.1 | 6610 | 24.8 |
| 13 | 23.805 | 3.7347 | 701 | 41.5 | 10440 | 39.1 |
| 14 | 24.378 | 3.6482 | 1688 | 100 | 26701 | 100 |
| 15 | 26.717 | 3.3339 | 439 | 26 | 9180 | 34.4 |
| 16 | 28.38 | 3.1422 | 162 | 9.6 | 2719 | 10.2 |
| 17 | 30.46 | 2.9323 | 153 | 9.1 | 2883 | 10.8 |
| 18 | 32.572 | 2.7467 | 136 | 8.1 | 2416 | 9 |
| 19 | 37.279 | 2.4101 | 110 | 6.5 | 2856 | 10.7 |

The compound of formula (Ia) according to the present invention is crystal form B of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 5.

In further preferred embodiments of the present invention, the compound of formula (I) is a crystal form (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is mesylate salt, and y is 1, i.e., crystal form C of mesylate salt, having a structure as follows:

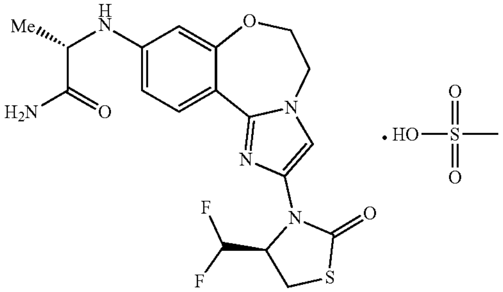

wherein, the X-ray powder diffraction pattern thereof comprises one or more diffraction peaks at 2θ of 22.5±0.20, 8.5±0.2°, 7.2±0.2°, 14.4±0.20, 26.7±0.20, 25.3±0.20, 12.8±0.20, 16.7±0.20, 6.1±0.2°, 12.1±0.20, 15.2±0.20 and 22.0±0.2°; and preferably comprises optional 2, 4, 6, 8 or 10 of the above diffraction peaks;

or, the X-ray powder diffraction pattern thereof comprises two or three diffraction peaks at 2θ of 22.5±0.20, 8.5±0.2° and 7.2±0.2°, optionally further comprises one or more diffraction peaks at 2θ of 14.4±0.2, 26.7±0.20, 12.8±0.2, 16.7±0.2 and 6.1±0.2°; and preferably comprises 2, 3, 4 or 5 of the above diffraction peaks;

for example, the X-ray powder diffraction pattern thereof has characteristic peaks at 2θ of 22.5±0.2, 8.5±0.2°, 7.2±0.2°, 14.4±0.2, 26.7±0.2, 12.8±0.2, 16.7±0.20 and 6.1±0.2°.

Or, the X-ray powder diffraction pattern thereof has diffraction peaks at 2θ of 7.2±0.2°, 14.4±0.20, 22.5±0.20 and 26.7±0.2°; further has diffraction peaks at 2θ of 6.1±0.2°, 12.8±0.2, 16.7±0.25 and 20.8±0.2°; still further has diffraction peaks at 2θ of 8.5±0.2°, 15.2±0.2, 22.0±0.24 and 25.3±0.2°; and even further has diffraction peaks at 2θ of 12.1±0.20, 19.1±0.26 and 23.8±0.29.

Using Cu-Kα radiation, the characteristic X-ray diffraction peaks represented by 2θ angle and interplanar spacing d value are shown in Table 4.

TABLE 4

| XRPD diffraction data of crystal form C of mesylate salt | | | | | | |
|---|---|---|---|---|---|---|
| No. | 2θ (±0.2°) | d value | Peak height | Proportion (I %) | Area | Proportion (I %) |
| 1 | 6.096 | 14.4855 | 308 | 13.7 | 4444 | 15 |
| 2 | 7.248 | 12.1865 | 850 | 37.9 | 10712 | 36.2 |
| 3 | 8.468 | 10.4337 | 1932 | 86.1 | 25054 | 84.7 |
| 4 | 12.079 | 7.3209 | 231 | 10.3 | 3017 | 10.2 |
| 5 | 12.775 | 6.9237 | 468 | 20.9 | 5782 | 19.5 |
| 6 | 14.432 | 6.1321 | 832 | 37.1 | 12024 | 40.6 |
| 7 | 15.224 | 5.8152 | 228 | 10.2 | 3634 | 12.3 |
| 8 | 16.705 | 5.3026 | 348 | 15.5 | 5347 | 18.1 |
| 9 | 19.088 | 4.6456 | 189 | 8.4 | 2805 | 9.5 |
| 10 | 20.304 | 4.37 | 198 | 8.8 | 2443 | 8.3 |
| 11 | 20.766 | 4.2739 | 278 | 12.4 | 8588 | 29 |
| 12 | 22.026 | 4.0323 | 211 | 9.4 | 3878 | 13.1 |
| 13 | 22.538 | 3.9418 | 2243 | 100 | 29581 | 100 |
| 14 | 23.812 | 3.7337 | 237 | 10.6 | 5155 | 17.4 |
| 15 | 24.103 | 3.6893 | 151 | 6.7 | 3911 | 13.2 |
| 16 | 25.252 | 3.5239 | 577 | 25.7 | 11692 | 39.5 |
| 17 | 25.859 | 3.4425 | 157 | 7 | 3224 | 10.9 |
| 18 | 26.66 | 3.3409 | 650 | 29 | 8158 | 27.6 |
| 19 | 28.989 | 3.0775 | 109 | 4.9 | 2239 | 7.6 |
| 20 | 30.248 | 2.9523 | 79 | 3.5 | 2604 | 8.8 |
| 21 | 30.863 | 2.8949 | 151 | 6.7 | 2655 | 9 |
| 22 | 36.55 | 2.4564 | 109 | 4.9 | 2929 | 9.9 |

The compound of formula (Ia) according to the present invention is crystal form C of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 6.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is sulfate salt, and y is 1, i.e., crystal form A of sulfate salt, having a structure as follows:

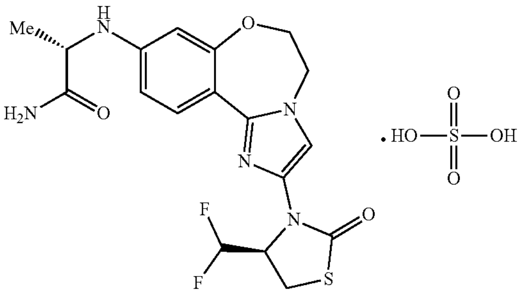

wherein, the X-ray powder diffraction pattern thereof comprises one or more diffraction peaks at 2θ of 8.4±0.2°, 7.2±0.2°, 20.1±0.2°, 22.7±0.2°, 24.5±0.2°, 25.7±0.2°, 18.9±0.2°, 26.7±0.2°, 16.4±0.2°, 18.2±0.2°, 22.0±0.2° and 12.6±0.2°; and preferably comprises optional 2, 4, 6, 8 or 10 of the above diffraction peaks;

or, the X-ray powder diffraction pattern thereof comprises two or three diffraction peaks at 2θ of 8.4±0.2°, 7.2±0.2° and 20.1±0.2°, optionally further comprises one or more diffraction peaks at 2θ of 22.7±0.2°, 24.5±0.2°, 25.7±0.2°, 18.9±0.2° and 16.4±0.2°; and preferably comprises 2, 3, 4 or 5 of the above diffraction peaks;

for example, the X-ray powder diffraction pattern thereof has diffraction peaks at 2θ of 8.4±0.2°, 7.2±0.2°, 20.1±0.2°, 22.7±0.2°, 24.5±0.2°, 25.7±0.2°, 18.9±0.2° and 16.4±0.2°.

Or, the X-ray powder diffraction pattern thereof has diffraction peaks at 2θ of 7.2±0.2°, 8.4±0.2°, 20.1±0.2° and 22.7±0.2°; further has diffraction peaks at 2θ of 5.8±0.2°, 16.4±0.2°, 18.9±0.2° and 26.7±0.2°; still further has diffraction peaks at 2θ of 12.6±0.2°, 14.7±0.2°, 17.2±0.2° and 25.1±0.2°; and even further has diffraction peaks at 2θ of 14.4±0.2°, 18.2±0.2°, 24.5±0.2° and 25.7±0.2°.

Using Cu-Kα radiation, the characteristic X-ray diffraction peaks represented by 2θ angle and interplanar spacing d value are shown in Table 5.

TABLE 5

XRPD diffraction data of crystal form A of sulfate salt

| No. | 2θ (±0.2°) | d value | Peak height | Proportion (I %) | Area | Proportion (I %) |
|---|---|---|---|---|---|---|
| 1 | 5.819 | 15.1744 | 197 | 41.3 | 1231 | 23.6 |
| 2 | 7.154 | 12.346 | 398 | 83.4 | 2966 | 56.8 |
| 3 | 8.435 | 10.4736 | 477 | 100 | 3545 | 67.9 |
| 4 | 9.95 | 8.8823 | 73 | 15.3 | 968 | 18.5 |
| 5 | 11.7 | 7.5571 | 80 | 16.8 | 494 | 9.5 |
| 6 | 12.648 | 6.9931 | 135 | 28.3 | 1020 | 19.5 |
| 7 | 14.38 | 6.1542 | 96 | 20.1 | 577 | 11 |
| 8 | 14.704 | 6.0196 | 91 | 19.1 | 686 | 13.1 |
| 9 | 15.711 | 5.6359 | 36 | 7.5 | 351 | 6.7 |
| 10 | 16.372 | 5.4097 | 234 | 49.1 | 1926 | 36.9 |
| 11 | 17.165 | 5.1615 | 92 | 19.3 | 622 | 11.9 |
| 12 | 18.243 | 4.859 | 204 | 42.8 | 1354 | 25.9 |
| 13 | 18.852 | 4.7034 | 261 | 54.7 | 1992 | 38.1 |
| 14 | 20.075 | 4.4195 | 369 | 77.4 | 5224 | 100 |
| 15 | 21.486 | 4.1324 | 90 | 18.9 | 1180 | 22.6 |
| 16 | 21.962 | 4.0438 | 171 | 35.8 | 1111 | 21.3 |
| 17 | 22.691 | 3.9156 | 326 | 68.3 | 3512 | 67.2 |
| 18 | 23.337 | 3.8085 | 58 | 12.2 | 702 | 13.4 |
| 19 | 24.475 | 3.634 | 300 | 62.9 | 2718 | 52 |
| 20 | 25.055 | 3.5512 | 95 | 19.9 | 573 | 11 |
| 21 | 25.687 | 3.4652 | 264 | 55.3 | 3811 | 73 |
| 22 | 26.728 | 3.3326 | 256 | 53.7 | 2547 | 48.8 |
| 23 | 28.789 | 3.0985 | 35 | 7.3 | 416 | 8 |
| 24 | 29.408 | 3.0347 | 52 | 10.9 | 576 | 11 |
| 25 | 32.549 | 2.7486 | 37 | 7.8 | 687 | 13.2 |
| 26 | 33.434 | 2.6779 | 38 | 8 | 519 | 9.9 |

The compound of formula (Ia) according to the present invention is crystal form A of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 7.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is sulfate salt, and y is 1, i.e., crystal form B of sulfate salt, having a structure as follows:

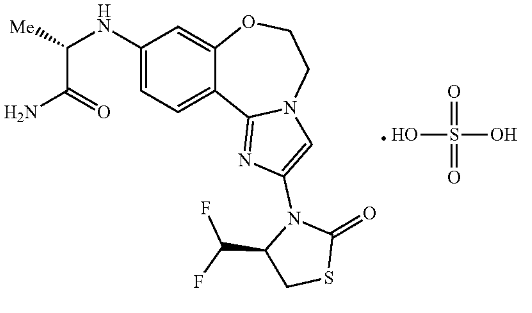

wherein, the X-ray powder diffraction pattern thereof comprises one or more diffraction peaks at 2θ of 4.8±0.2°, 7.6±0.2°, 12.2±0.2°, 14.0±0.2°, 18.5±0.2°, 22.9±0.2°, 23.8±0.2° and 24.9±0.2°; and preferably comprises optional 2, 4, 6 or 8 of the above diffraction peaks;

for example, the X-ray powder diffraction pattern thereof has diffraction peaks at 2θ of 4.8±0.2°, 7.6±0.2°, 12.2±0.2°, 14.0±0.2°, 18.5±0.2°, 22.9±0.2°, 23.8±0.2° and 24.9±0.2°.

Or, the X-ray powder diffraction pattern thereof has diffraction peaks at 2θ of 4.8±0.2° and 7.6±0.2°; and further has diffraction peaks at 2θ of 12.2±0.2°, 14.0±0.2°, 18.5±0.2°, 22.9±0.2° and 23.8±0.2°.

Using Cu-Kα radiation, the characteristic X-ray diffraction peaks represented by 2θ angle and interplanar spacing d value are shown in Table 6.

TABLE 6

XRPD diffraction data of crystal form B of sulfate salt

| No. | 2θ (±0.2°) | d value | Peak height | Proportion (I %) | Area | Proportion (I %) |
|---|---|---|---|---|---|---|
| 1 | 4.793 | 18.4195 | 2141 | 100 | 26152 | 100 |
| 2 | 7.619 | 11.5939 | 566 | 26.4 | 6134 | 23.5 |
| 3 | 9.564 | 9.2402 | 134 | 6.3 | 1181 | 4.5 |
| 4 | 12.213 | 7.2412 | 199 | 9.3 | 2627 | 10 |
| 5 | 13.978 | 6.3306 | 193 | 9 | 3116 | 11.9 |
| 6 | 18.47 | 4.7998 | 159 | 7.4 | 2240 | 8.6 |
| 7 | 20.412 | 4.3472 | 80 | 3.7 | 1381 | 5.3 |
| 8 | 20.725 | 4.2822 | 67 | 3.1 | 1183 | 4.5 |
| 9 | 22.9 | 3.8802 | 233 | 10.9 | 3517 | 13.4 |
| 10 | 23.802 | 3.7352 | 181 | 8.5 | 2582 | 9.9 |
| 11 | 24.874 | 3.5766 | 147 | 6.9 | 2784 | 10.6 |
| 12 | 26.918 | 3.3095 | 70 | 3.3 | 1118 | 4.3 |

The compound of formula (I) according to the present invention is crystal form B of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 8.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is sulfate salt, and y is 1, i.e., crystal form C of sulfate salt, having a structure as follows:

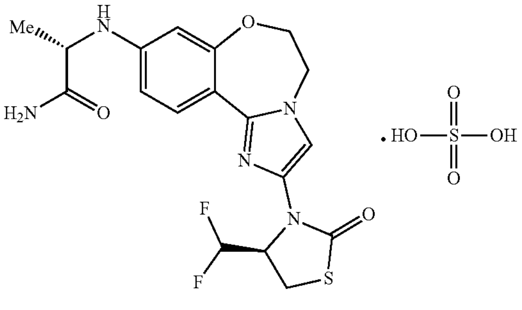

wherein, the X-ray powder diffraction pattern thereof comprises one or more diffraction peaks at 2θ of 24.5±0.2°, 13.3±0.2°, 23.9±0.2°, 9.0±0.2°, 17.3±0.2°, 19.4±0.2°, 26.9±0.2°, 20.4±0.2°, 17.7±0.2°, 9.9±0.2°, 20.0±0.2° and 28.3±0.2°; and preferably comprises optional 2, 4, 6, 8 or 10 of the above diffraction peaks;

or, the X-ray powder diffraction pattern thereof comprises two or three diffraction peaks at 2θ of 24.5±0.2°, 13.3±0.2° and 23.9±0.2°, optionally further comprises one or more diffraction peaks at 2θ of 9.0±0.2°, 17.3±0.2°, 19.4±0.2°, 17.7±0.2° and 9.9±0.2°; and preferably comprises 2, 3, 4 or 5 of the above diffraction peaks;

for example, the X-ray powder diffraction pattern thereof has diffraction peaks at 2θ of 24.5±0.2°, 13.3±0.2°, 23.9±0.2°, 9.0±0.2°, 17.3±0.2°, 19.4±0.2°, 17.7±0.2° and 9.9±0.2°.

Or, the X-ray powder diffraction pattern thereof has diffraction peaks at 2θ of 9.0±0.2°, 13.3±0.2°, 17.3±0.2° and 24.5±0.2°; further has diffraction peaks at 2θ of 9.9±0.2°, 17.7±0.2°, 19.4±0.2° and 26.9±0.2°; still further has diffraction peaks at 2θ of 14.3±0.2°, 18.6±0.2°, 28.3±0.2° and 37.5±0.2°; and even further has diffraction peaks at 2θ of 16.7±0.2°, 20.0±0.2°, 20.4±0.2°, 24.0±0.2° and 30.4±0.2°.

Using Cu-Kα radiation, the characteristic X-ray diffraction peaks represented by 2θ angle and interplanar spacing d value are shown in Table 7.

TABLE 7

XRPD diffraction data of crystal form C of sulfate salt

| No. | 2θ (±0.2°) | d value | Peak height | Proportion (I %) | Area | Proportion (I %) |
|---|---|---|---|---|---|---|
| 1 | 8.983 | 9.8364 | 731 | 41.3 | 9478 | 34.4 |
| 2 | 9.944 | 8.8879 | 256 | 14.5 | 3701 | 13.4 |
| 3 | 13.349 | 6.6272 | 1172 | 66.3 | 14529 | 52.7 |
| 4 | 14.301 | 6.1884 | 214 | 12.1 | 2375 | 8.6 |
| 5 | 16.692 | 5.3068 | 123 | 7 | 1204 | 4.4 |
| 6 | 17.314 | 5.1176 | 558 | 31.5 | 6283 | 22.8 |
| 7 | 17.746 | 4.9939 | 263 | 14.9 | 2392 | 8.7 |
| 8 | 18.55 | 4.7792 | 163 | 9.2 | 2551 | 9.3 |
| 9 | 19.431 | 4.5644 | 492 | 27.8 | 5623 | 20.4 |
| 10 | 20.014 | 4.4328 | 243 | 13.7 | 3004 | 10.9 |
| 11 | 20.413 | 4.347 | 307 | 17.4 | 3358 | 12.2 |
| 12 | 22.825 | 3.8928 | 113 | 6.4 | 1277 | 4.6 |
| 13 | 23.932 | 3.7152 | 831 | 47 | 11080 | 40.2 |
| 14 | 24.462 | 3.636 | 1769 | 100 | 27578 | 100 |
| 15 | 26.876 | 3.3146 | 394 | 22.3 | 6361 | 23.1 |
| 16 | 28.29 | 3.1521 | 224 | 12.7 | 2894 | 10.5 |
| 17 | 30.42 | 2.936 | 166 | 9.4 | 1830 | 6.6 |
| 18 | 37.534 | 2.3942 | 125 | 7.1 | 1808 | 6.6 |

The compound of formula (Ia) according to the present invention is crystal form C of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 9.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, wherein M is sulfate salt, and y is 1, i.e., crystal form D of sulfate salt, having a structure as follows:

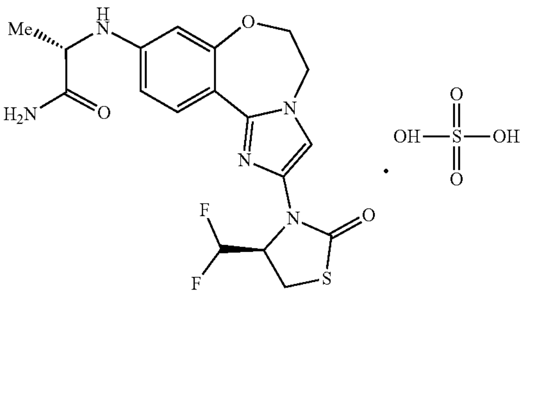

wherein, the X-ray powder diffraction pattern thereof comprises one or more diffraction peaks at 2θ of 7.6±0.2°, 22.5±0.2°, 8.9±0.2°, 15.0±0.2°, 23.9±0.2°, 26.6±0.2°, 24.6±0.2°, 5.8±0.2°, 12.9±0.2°, 19.9±0.2°, 20.7±0.2° and 11.6±0.2°; and preferably comprises optional 2, 4, 6, 8 or 10 of the above diffraction peaks;

or, the X-ray powder diffraction pattern thereof comprises two or three diffraction peaks at 2θ of 7.6±0.2°, 22.5±0.2° and 8.9±0.2°, optionally further comprises one or more diffraction peaks at 2θ of 15.0±0.2°, 26.6±0.2°, 5.8±0.2°, 12.9±0.2° and 11.6±0.2°; and preferably comprises 2, 3, 4 or 5 of the above diffraction peaks;

for example, the X-ray powder diffraction pattern thereof has diffraction peaks at 2θ of 7.6±0.2°, 22.5±0.2°, 8.9±0.2°, 15.0±0.2°, 26.6±0.2°, 5.8±0.2°, 12.9±0.2° and 11.6±0.2°.

Or, the X-ray powder diffraction pattern thereof has diffraction peaks at 2θ of 7.6±0.2°, 15.0±0.20, 22.5±0.20 and 23.9±0.2°; further has diffraction peaks at 2θ of 5.8±0.2°, 12.9±0.20, 19.9±0.20 and 26.6±0.2°; still further has diffraction peaks at 2θ of 8.9±0.2°, 16.8±0.20, 20.7±0.2° and 24.6±0.2°; and still further has diffraction peaks at 2θ of 10.1±0.20, 11.6±0.20, 17.4±0.20, 18.2±0.20, 19.1±0.20, 21.9±0.20, 25.4±0.20 and 27.7±0.20.

Using Cu-Kα radiation, the characteristic X-ray diffraction peaks represented by 2θ angle and interplanar spacing d value are shown in Table 8.

TABLE 8

XRPD diffraction data of crystal form D of sulfate salt

| No. | 2θ (±0.2°) | d value | Peak height | Proportion (I %) | Area | Proportion (I %) |
|---|---|---|---|---|---|---|
| 1 | 5.836 | 15.13 | 219 | 33.8 | 2547 | 28.5 |
| 2 | 7.561 | 11.6828 | 647 | 100 | 8944 | 100 |
| 3 | 8.868 | 9.9638 | 557 | 86.1 | 7281 | 81.4 |
| 4 | 10.11 | 8.7424 | 118 | 18.2 | 1493 | 16.7 |
| 5 | 11.06 | 7.9936 | 70 | 10.8 | 897 | 10 |
| 6 | 11.631 | 7.6022 | 193 | 29.8 | 2145 | 24 |
| 7 | 12.928 | 6.8423 | 205 | 31.7 | 2367 | 26.5 |
| 8 | 15.018 | 5.8945 | 489 | 75.6 | 6851 | 76.6 |
| 9 | 16.802 | 5.2723 | 179 | 27.7 | 3029 | 33.9 |
| 10 | 17.362 | 5.1034 | 122 | 18.9 | 1466 | 16.4 |
| 11 | 18.185 | 4.8744 | 151 | 23.3 | 1867 | 20.9 |
| 12 | 19.064 | 4.6515 | 119 | 18.4 | 1132 | 12.7 |
| 13 | 19.905 | 4.4568 | 201 | 31.1 | 2842 | 31.8 |
| 14 | 20.733 | 4.2806 | 198 | 30.6 | 3700 | 41.4 |
| 15 | 21.906 | 4.0541 | 132 | 20.4 | 1222 | 13.7 |
| 16 | 22.484 | 3.9511 | 568 | 87.8 | 8083 | 90.4 |
| 17 | 23.899 | 3.7203 | 370 | 57.2 | 5064 | 56.6 |
| 18 | 24.561 | 3.6215 | 268 | 41.4 | 5498 | 61.5 |
| 19 | 25.418 | 3.5012 | 134 | 20.7 | 2057 | 23 |
| 20 | 26.564 | 3.3528 | 271 | 41.9 | 4124 | 46.1 |
| 21 | 27.723 | 3.2152 | 130 | 20.1 | 1281 | 14.3 |
| 22 | 29.159 | 3.06 | 53 | 8.2 | 917 | 10.3 |

The compound of formula (Ia) according to the present invention is crystal form D of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 10.

In further preferred embodiments of the present invention, the compound of formula (I) is a crystal form of (S)-2-((2-((R)-4-(difluoromethyl)-2-oxothiazolidin-3-yl)-5,6-dihydrobenzo[f]imidazo[1,2-d ][1,4]oxazepin-9-yl)amino)propionamide, wherein M is sulfate salt, and y is 1, i.e., crystal form E of sulfate salt, having a structure as follows:

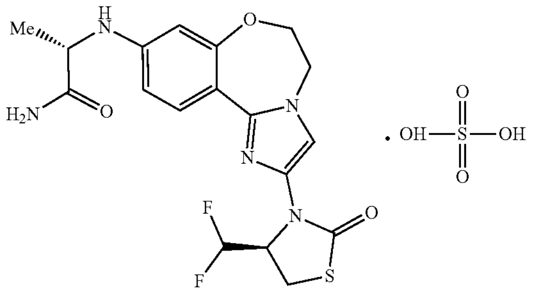 [SMILES: C[C@H](Nc1ccc2c(c1)OCCn1cc(N3C(=O)SC[C@H]3C(F)F)nc1-2)C(N)=O ; O=S(=O)(O)O]

the X-ray powder diffraction pattern thereof comprises one or more diffraction peaks at 2θ of 17.7±0.2°, 23.5±0.2°, 24.8±0.2°, 9.9±0.2°, 22.6±0.2°, 21.2±0.2°, 19.1±0.2°, 29.4±0.2°, 16.9±0.2°, 28.4±0.2°, 17.3±0.2° and 24.5±0.2°; and preferably comprises optional 2, 4, 6, 8 or 10 of the above diffraction peaks;

or, the X-ray powder diffraction pattern thereof comprises two or three diffraction peaks at 2θ of 17.7±0.2°, 23.5±0.2° and 24.8±0.2°, optionally further comprises one or more diffraction peaks at 2θ of 9.9±0.2°, 22.6±0.2°, 21.2±0.2°, 19.1±0.2° and 29.4±0.2°; and preferably comprises 2, 3, 4 or 5 of the above diffraction peaks;

for example, the X-ray powder diffraction pattern thereof has diffraction peaks at 2θ of 17.7±0.2°, 23.5±0.2°, 24.8±0.2°, 9.9±0.2°, 22.6±0.2°, 21.2±0.2°, 19.1±0.2° and 29.4±0.2°.

Or, the X-ray powder diffraction pattern thereof has diffraction peaks at 2θ of 9.9±0.2°, 17.7±0.2°, 22.6±0.2° and 24.8±0.2°; further has diffraction peaks at 2θ of 16.9±0.2°, 21.2±0.2°, 23.5±0.2° and 29.4±0.2°; still further has diffraction peaks at 2θ of 17.3±0.2°, 19.1±0.2°, 28.4±0.2° and 30.5±0.2°; and even further has diffraction peaks at 2θ of 14.1±0.2°, 16.2±0.2°, 19.6±0.2°, 20.7±0.2°, 24.5±0.2° and 26.5±0.2°.

Using Cu-Kα radiation, the characteristic X-ray diffraction peaks represented by 2θ angle and interplanar spacing d value are shown in Table 9.

TABLE 9

XRPD diffraction data of crystal form E of sulfate salt

| No. | 2θ (±0.2°) | d value | Peak height | Proportion (I %) | Area | Proportion (I %) |
|---|---|---|---|---|---|---|
| 1 | 9.866 | 8.9575 | 811 | 68.4 | 6544 | 60.6 |
| 2 | 14.073 | 6.2879 | 313 | 26.4 | 2485 | 23 |
| 3 | 14.629 | 6.0501 | 96 | 8.1 | 765 | 7.1 |
| 4 | 15.874 | 5.5785 | 63 | 5.3 | 636 | 5.9 |
| 5 | 16.15 | 5.4838 | 162 | 13.7 | 1879 | 17.4 |
| 6 | 16.891 | 5.2447 | 460 | 38.8 | 3654 | 33.8 |
| 7 | 17.263 | 5.1326 | 336 | 28.4 | 2523 | 23.4 |
| 8 | 17.657 | 5.0188 | 1185 | 100 | 10484 | 97.1 |
| 9 | 19.058 | 4.6528 | 549 | 46.3 | 6097 | 56.5 |
| 10 | 19.638 | 4.5169 | 316 | 26.7 | 2927 | 27.1 |
| 11 | 20.739 | 4.2794 | 127 | 10.7 | 1078 | 10 |
| 12 | 21.168 | 4.1937 | 618 | 52.2 | 5983 | 55.4 |
| 13 | 22.586 | 3.9335 | 732 | 61.8 | 10267 | 95.1 |
| 14 | 23.516 | 3.78 | 910 | 76.8 | 10796 | 100 |
| 15 | 24.517 | 3.6279 | 330 | 27.8 | 5160 | 47.8 |
| 16 | 24.796 | 3.5876 | 849 | 71.6 | 10165 | 94.2 |
| 17 | 26.511 | 3.3594 | 170 | 14.3 | 1966 | 18.2 |
| 18 | 27.028 | 3.2963 | 78 | 6.6 | 682 | 6.3 |
| 19 | 28.402 | 3.1399 | 413 | 34.9 | 5194 | 48.1 |
| 20 | 29.381 | 3.0374 | 461 | 38.9 | 6136 | 56.8 |
| 21 | 30.452 | 2.933 | 133 | 11.2 | 1497 | 13.9 |
| 22 | 31.884 | 2.8044 | 97 | 8.2 | 973 | 9 |

TABLE 9-continued

XRPD diffraction data of crystal form E of sulfate salt

| No. | 2θ (±0.2°) | d value | Peak height | Proportion (I %) | Area | Proportion (I %) |
|---|---|---|---|---|---|---|
| 23 | 32.605 | 2.744 | 114 | 9.6 | 1542 | 14.3 |
| 24 | 33.523 | 2.671 | 103 | 8.7 | 1558 | 14.4 |
| 25 | 34.914 | 2.5677 | 84 | 7.1 | 1466 | 13.6 |
| 26 | 35.683 | 2.5141 | 82 | 6.9 | 1070 | 9.9 |
| 27 | 36.421 | 2.4648 | 79 | 6.7 | 1105 | 10.2 |
| 28 | 37.231 | 2.413 | 59 | 5 | 920 | 8.5 |

The compound of formula (Ia) according to the present invention is crystal form E of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and the X-ray powder diffraction pattern thereof is substantially as shown in FIG. 11.

Another object of the present invention is to provide a pharmaceutical composition, comprising a therapeutically effective amount of the compound of formula (I) and a crystal form thereof, and one or more pharmaceutically acceptable carriers, diluents or excipients, (I)

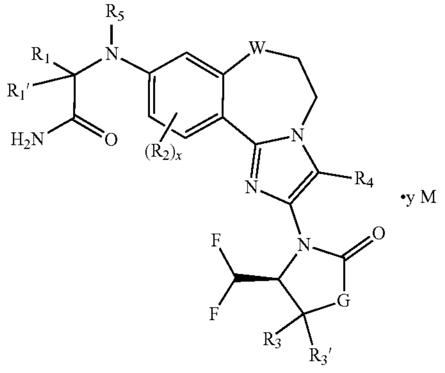

wherein:

W is selected from the group consisting of —O—, —S— and —$NR_{aa}$—;

G is selected from the group consisting of —O—, —S—, —$CR_{aa}R_{bb}$— and —$NR_{aa}$—;

$R_1$ and $R_1'$ are each selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, cyano-substituted $C_{1-6}$ alkyl, $C_{3-8}$ cycloalkyl, 3 to 8 membered heterocyclyl, $C_{6-10}$ aryl, 5 to membered heteroaryl, —$(CH_2)_nR_{cc}$, —$(CH_2)_nOR_{cc}$ and —$CR_{aa}R_{bb}OR_{cc}$;

or, $R_1$ and $R_1'$ are attached together to form a $C_{3-8}$ cycloalkyl or 3 to 8 membered heterocyclyl, wherein the $C_{3-8}$ cycloalkyl or 3 to 8 membered heterocyclyl is optionally further substituted by one or more substituents selected from the group consisting of deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_2$ is selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl, 5 to 10 membered heteroaryl and —$(CH_2)_nOR_{cc}$;

or, any two $R_2$ are attached together to form a $C_{3-8}$ cycloalkyl or 3 to 8 membered heterocyclyl, wherein the $C_{3-8}$ cycloalkyl or 3 to 8 membered heterocyclyl is optionally further substituted by one or more substituents selected from the group consisting of deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_3$ and $R_3'$ are each selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

or, $R_3$ and $R_3'$ are attached together to form an oxo, $C_{3-8}$ cycloalkyl or 3 to 8 membered heterocyclyl, wherein the $C_{3-8}$ cycloalkyl or 3 to 8 membered heterocyclyl is optionally further substituted by one or more substituents selected from the group consisting of deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_4$ is selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_5$ is selected from the group consisting of hydrogen, deuterium, $C_{1-6}$ alkyl and $C_{1-6}$ haloalkyl;

or, $R_1$ or $R_1'$ and $R_5$ are attached together to form a 3 to 8 membered heterocyclyl, wherein the 3 to 8 membered heterocyclyl is optionally further substituted by one or more substituents selected from the group consisting of deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

$R_{aa}$, $R_{bb}$ and $R_{cc}$ are each independently selected from the group consisting of hydrogen, deuterium, cyano, halogen, nitro, amino, $C_{1-6}$ alkyl, $C_{1-6}$ haloalkyl, $C_{1-6}$ alkoxy, $C_{1-6}$ hydroxyalkyl, $C_{3-8}$ cycloalkyl, 3 to 8 membered heterocyclyl, $C_{6-10}$ aryl and 5 to 10 membered heteroaryl;

M is an inorganic acid or an organic acid, wherein the inorganic acid is selected from the group consisting of hydrochloric acid, sulfuric acid, nitric acid, hydrobromic acid, hydrofluoric acid, hydroiodic acid and phosphoric acid; the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid;

n is an integer from 0 to 3;

x is an integer from 0 to 3; and y is an integer from 1 to 5, preferably an integer from 1 to 3, more preferably 1.

In preferred embodiments of the present invention, in the acid addition salt of formula (I), $R_1$ and $R_1'$ are each selected from the group consisting of hydrogen, $C_{1-6}$ alkyl, $C_{1-6}$ hydroxyalkyl, $C_{1-6}$ haloalkyl, $C_{1-6}$ alkoxy, 3 to 8 membered heterocyclyl, $-(CH_2)_nOR_{cc}$ and $-CR_{aa}R_{bb}OR_{cc}$, preferably hydrogen, $C_{1-3}$ alkyl, $C_{1-3}$ hydroxyalkyl, $C_{1-3}$ haloalkyl, $C_{1-3}$ alkoxy, 3 to 6 membered heterocyclyl, $-(CH_2)_nOR_{cc}$ and $-CR_{aa}R_{bb}OR_{cc}$, more preferably hydrogen, methyl, ethyl, propyl, isopropyl, methoxy, ethoxy, propoxy, fluoromethyl, fluoroethyl, fluoropropyl, chloromethyl, chloroethyl, chloropropyl, hydroxymethyl, hydroxyethyl, hydroxypropyl, oxacyclopropyl, oxacyclobutyl, oxacyclopentyl, oxacyclohexyl, azacyclopropyl, azacyclobutyl, azacyclopentyl, azacyclohexyl, $-CH_2OCH_3$, $-(CH_2)_2OCH_3$, $-CH(CH_3)OCH_3$ and $-C(CH_3)_2OCH_3$, more preferably hydrogen, methyl, methoxy, isopropyl, fluorine-containing methyl, hydroxymethyl, oxacyclobutyl, $-CH_2OCH_3$ and $-CH(CH_3)OCH_3$.

In preferred embodiments of the present invention, in the acid addition salt of formula (I), $R_2$ is selected from the group consisting of hydrogen, $C_{1-6}$ alkyl, halogen, cyano and $-(CH_2)_nOR_{cc}$, preferably hydrogen, $C_{1-3}$ alkyl, halogen, cyano and $-(CH_2)_nOR_{cc}$, more preferably hydrogen, methyl, ethyl, propyl, methoxy, ethoxy, propoxy, fluorine, chlorine, bromine and cyano, and further preferably hydrogen, fluorine, methyl, methoxy and cyano;

or, any two $R_2$ are attached together to form a substituted or unsubstituted $C_{3-6}$ cycloalkyl or a substituted or unsubstituted 3 to 6 membered heterocyclyl, preferably a substituted or unsubstituted $C_{3-6}$ cycloalkyl or substituted or unsubstituted 3 to 6 membered heterocyclyl containing 1 to 3 atoms selected from the group consisting of N, O and S, more preferably cyclopropyl, cyclobutyl, cyclopentyl, cyclohexyl, oxacyclopropyl, oxacyclobutyl, oxacyclopentyl, oxacyclohexyl, azacyclopropyl, azacyclobutyl, azacyclopentyl or azacyclohexyl, and further preferably cyclobutyl, cyclopentyl, 1,3-dioxocyclopentyl or 1,3-dioxocyclohexyl.

In preferred embodiments of the present invention, in the acid addition salt of formula (I), $R_3$ and $R_3'$ are each selected from the group consisting of hydrogen, $C_{1-6}$ alkyl, halogen, cyano and $C_{1-6}$ alkoxy, preferably hydrogen, $C_{1-3}$ alkyl, halogen, cyano and $C_{1-3}$ alkoxy, more preferably hydrogen, methyl, ethyl, propyl, fluorine, chlorine, bromine, cyano, methoxy, ethoxy and propoxy, more preferably hydrogen, fluorine, methyl, methoxy and cyano;

or, $R_3$ and $R_3'$ are attached together to form an oxo, $C_{3-6}$ cycloalkyl or 3 to 6 membered heterocyclyl, preferably oxo, $C_{3-6}$ cycloalkyl or 3 to 6 membered heterocyclyl containing 1 to 3 N, O or S atoms, more preferably oxo, cyclopropyl, cyclobutyl, cyclopentyl, cyclohexyl, oxacyclopropyl, oxacyclobutyl, oxacyclopentyl, oxacyclohexyl, azacyclopropyl, azacyclobutyl, azacyclopentyl or azacyclohexyl, and further preferably oxo, cyclopropyl or oxacyclobutyl.

In preferred embodiments of the present invention, in the acid addition salt of formula (I), $R_4$ is selected from the group consisting of hydrogen, $C_{1-6}$ alkyl, halogen, cyano, $C_{1-6}$ haloalkyl and $C_{3-8}$ cycloalkyl, preferably hydrogen, $C_{1-3}$ alkyl, halogen, cyano, $C_{1-3}$ haloalkyl and $C_{3-6}$ cycloalkyl, more preferably hydrogen, methyl, ethyl, propyl, fluorine, chlorine, bromine, cyano, fluoromethyl, fluoroethyl, chloromethyl, chloroethyl, trifluoromethyl, trifluoroethyl, trichloromethyl, trichloroethyl, cyclopropyl, cyclobutyl, cyclopentyl and cyclohexyl, and further preferably hydrogen, fluorine, chlorine, methyl, trifluoromethyl, cyano and cyclopropyl.

In preferred embodiments of the present invention, in the acid addition salt of formula (I), $R_5$ is selected from the group consisting of hydrogen, $C_{1-6}$ alkyl and $C_{1-6}$ haloalkyl, preferably hydrogen, $C_{1-3}$ alkyl and $C_{1-3}$ haloalkyl, more preferably hydrogen, methyl, ethyl, propyl, fluorine-containing methyl, fluorine-containing ethyl, fluorine-containing propyl, chlorine-containing methyl, chlorine-containing ethyl and chlorine-containing propyl, and further preferably hydrogen and methyl;

or, $R_1$ or $R_1'$ is attached with $R_5$ to form a 3 to 6 membered heterocyclyl, optionally substituted by one or more substituents selected from the group consisting of fluorine, chlorine, bromine, methyl, ethyl and propyl, preferably azacyclopropyl, azacyclobutyl, azacyclopentyl, azacyclohexyl, fluorine-substituted azacyclopropyl, fluorine-substituted azacyclobutyl, fluorine-substituted azacyclopentyl, fluorine-substituted azacyclohexyl, methyl-substituted azacyclopropyl, methyl-substituted azacyclobutyl, methyl pyrrolidinyl or methyl-substituted azacylcohexyl, and further preferably azacyclobutyl, azacyclopentyl or methyl pyrrolidinyl.

In preferred embodiments of the present invention, in the acid addition salt of formula (I), $R_{aa}$, $R_{bb}$ and $R_{cc}$ are each independently selected from the group consisting of hydrogen, $C_{1-6}$ alkyl, $C_{1-6}$ alkoxy, $C_{3-8}$ cycloalkyl or 3 to 8 membered heterocyclyl, preferably hydrogen, $C_{1-3}$ alkyl, $C_{1-3}$ alkoxy, $C_{3-6}$ cycloalkyl or 3 to 6 membered heterocyclyl containing 1-3 N, O or S atoms, more preferably hydrogen, methyl, ethyl, propyl, methoxy, ethoxy, propoxy, cyclopropyl, cyclobutyl, cyclopentyl, cyclohexyl, oxacyclopropyl, oxacyclobutyl, oxacyclopentyl and oxacyclobutyl, and further preferably hydrogen, methyl, ethyl, isopropyl, methoxy, cyclopropyl and oxacyclobutyl.

In preferred embodiments of the present invention, in the acid addition salt of formula (I), M is selected from the group consisting of sulfuric acid, phosphoric acid, benzenesulfonic acid, cinnamic acid, tartaric acid, ethane-1,2-disulfonic acid, ethanesulfonic acid, fumaric acid and methanesulfonic acid, preferably sulfuric acid, tartaric acid, ethane-1, 2-disulfonic acid, ethanesulfonic acid, fumaric acid and methanesulfonic acid, more preferably sulfuric acid, ethane-1,2-disulfonic acid, ethanesulfonic acid and methanesulfonic acid, and further preferably ethanesulfonic acid.

In preferred embodiments of the present invention, in the acid addition salt of formula (I), W is —O—.

In preferred embodiments of the present invention, in the acid addition salt of formula (I), G is —O— or —S—.

In preferred embodiments of the present invention, in the acid addition salt of formula (I), $R_5$ is hydrogen.

In preferred embodiments of the present invention, in the acid addition salt of formula (I), $R_1'$ and $R_3'$ are hydrogen.

In preferred embodiments of the present invention, the acid addition salt of formula (I) is further as shown in formula (II-A) or (II-B):

(II-A)

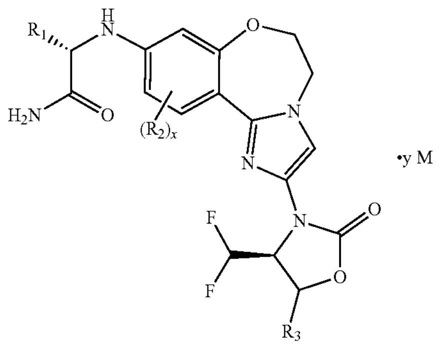

(II-B)

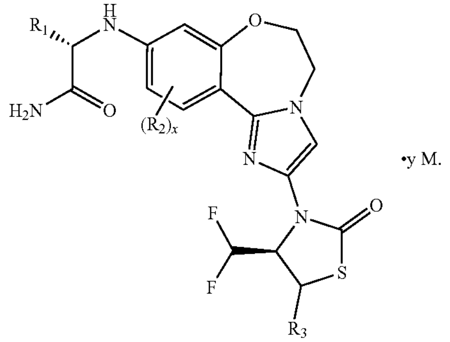

In preferred embodiments of the present invention, the specific structure of the acid addition salt of formula (I) is as follows:

1

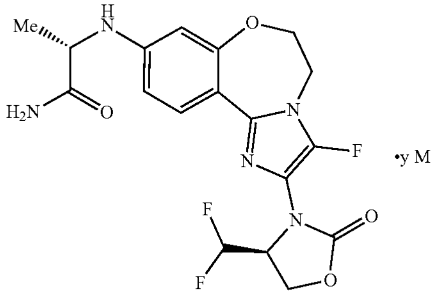

-continued
2
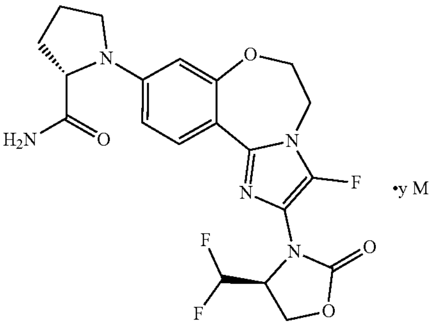
3
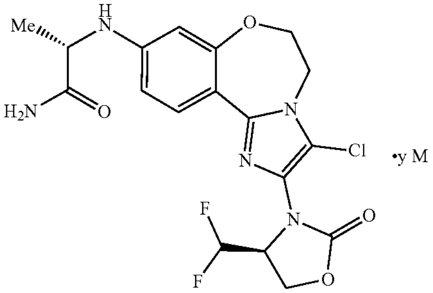
4
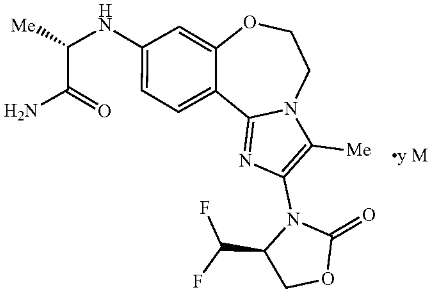
5
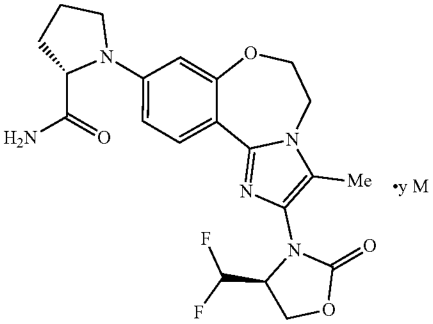
6
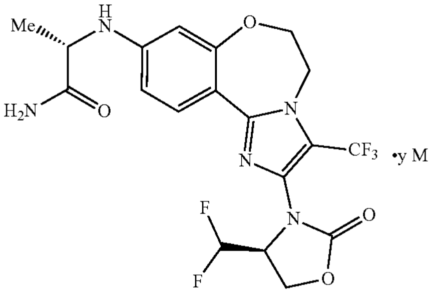
-continued
7
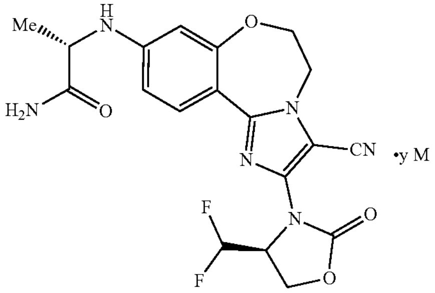
8
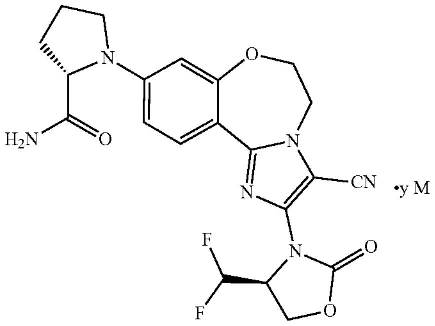
9
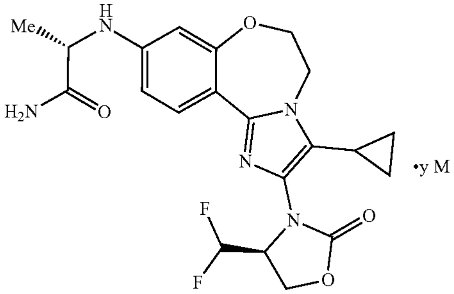
10
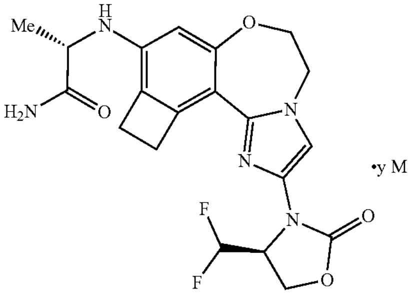
11
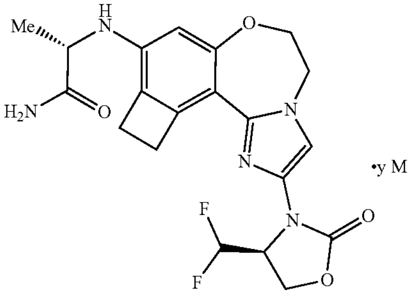

-continued
12
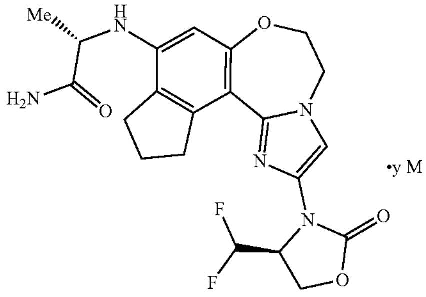
13
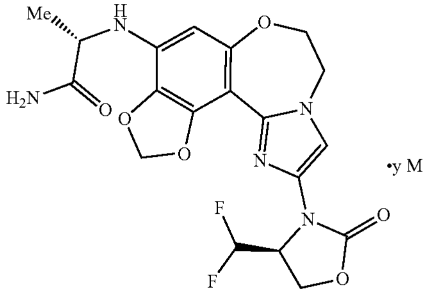
14
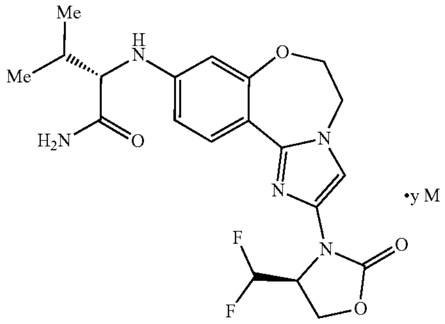
15
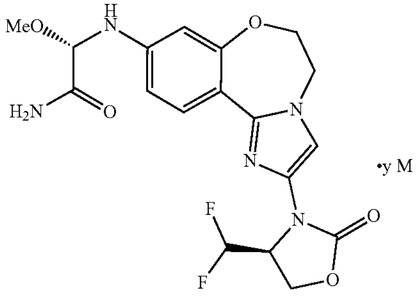
16
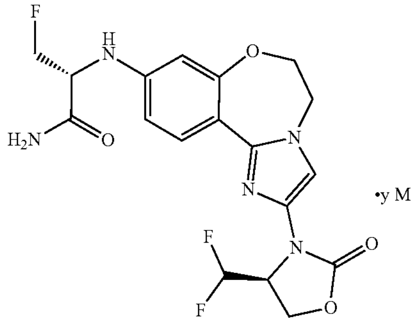
-continued
17
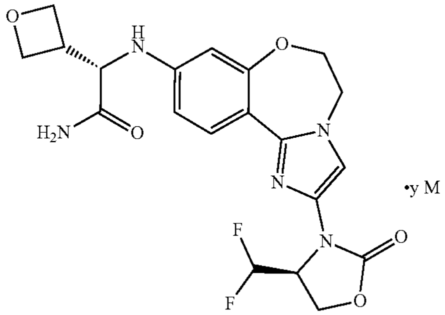
18
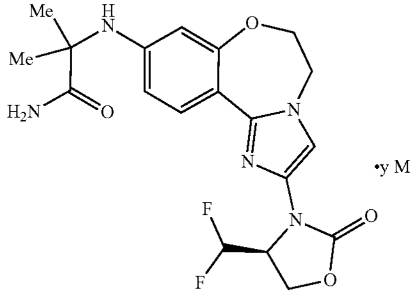
19
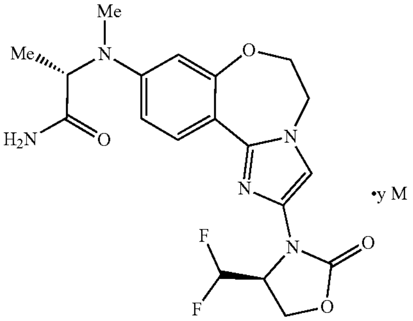
20
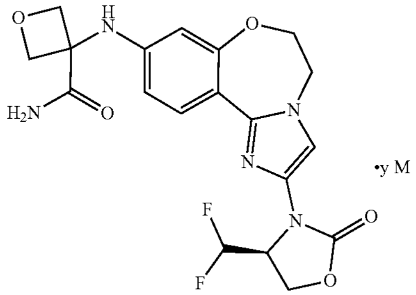
21
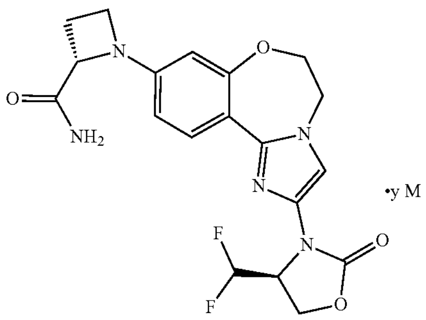

22
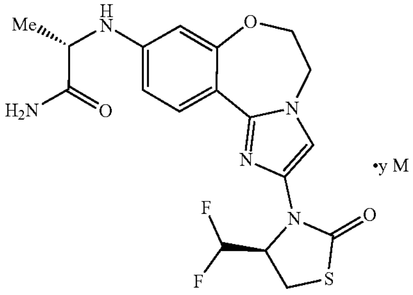
23
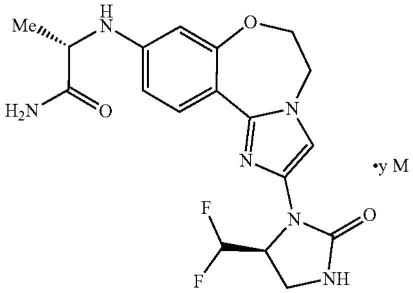
24
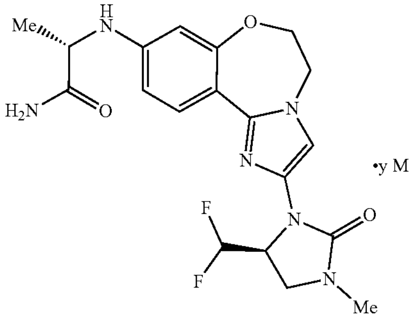
25
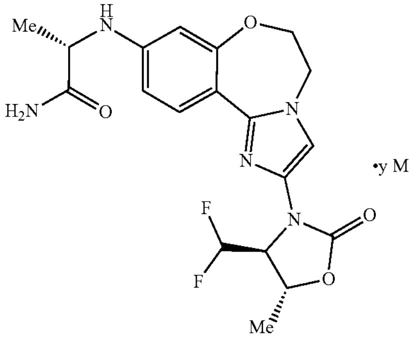
26
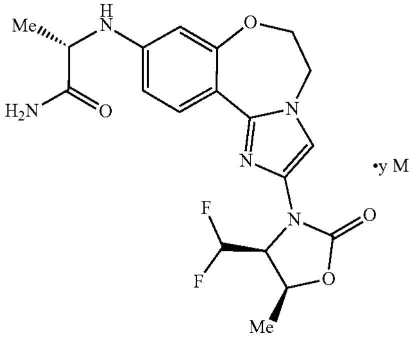
27
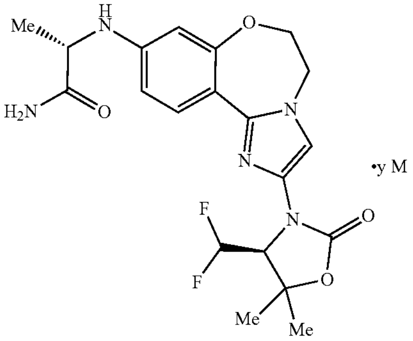
28
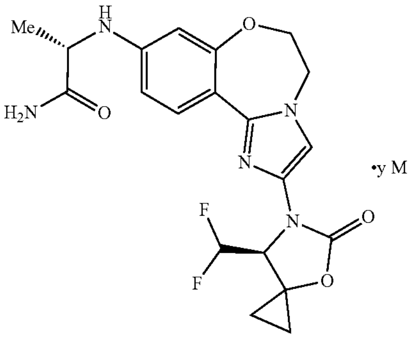
29
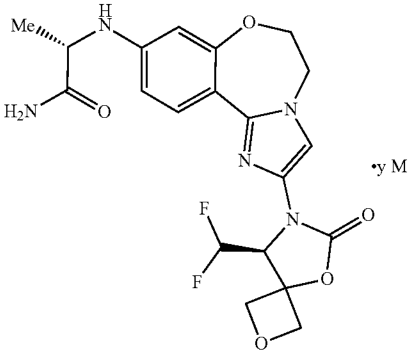
30
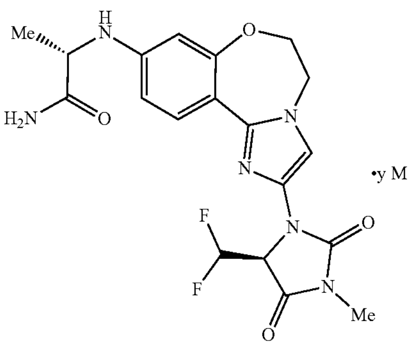

-continued
31
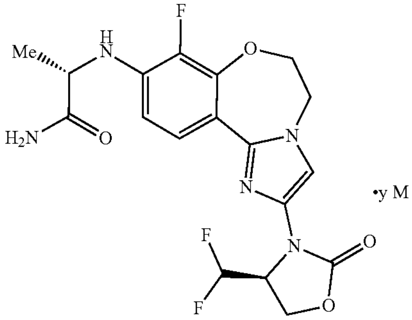
32
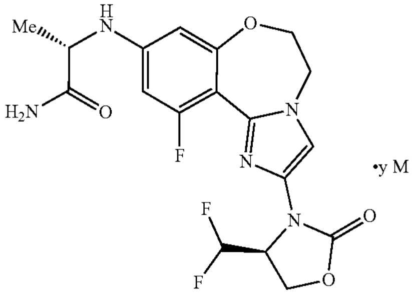
33
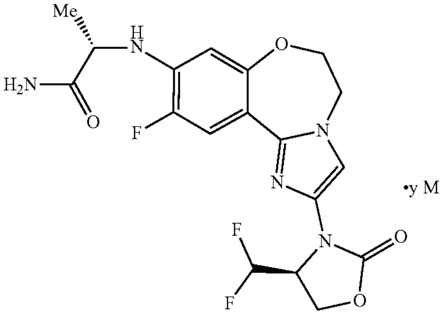
34
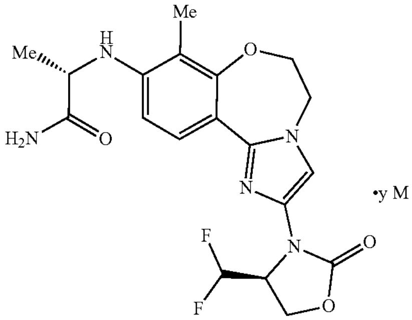
35
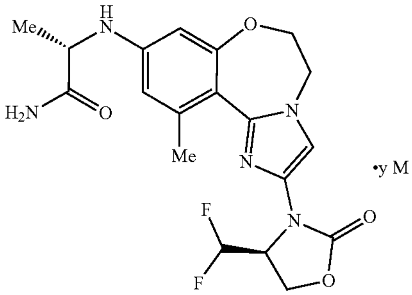
-continued
36
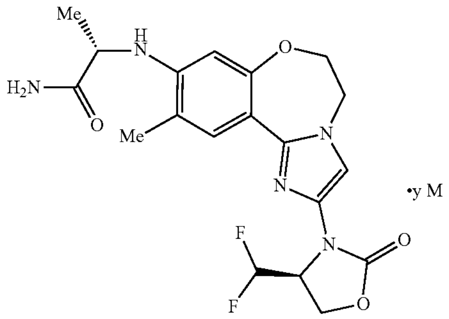
37
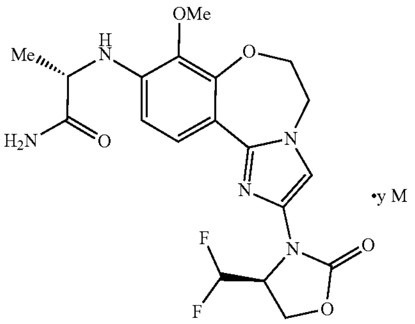
38
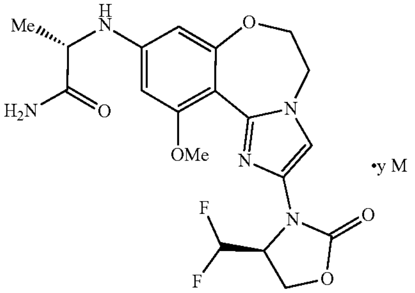
39
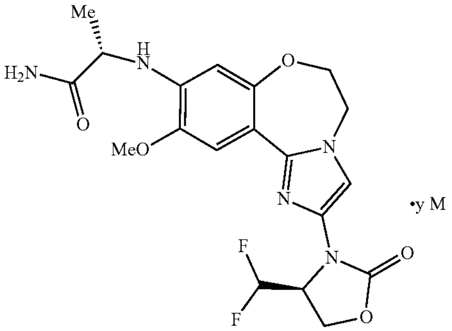
40
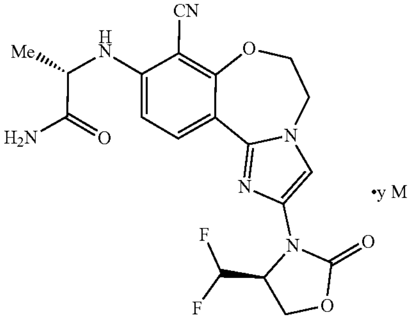

-continued
41
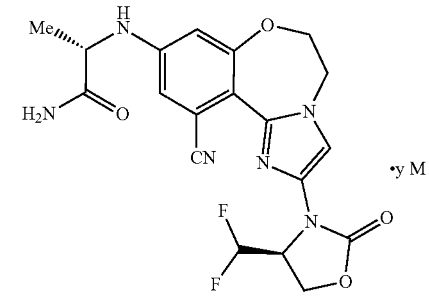
42
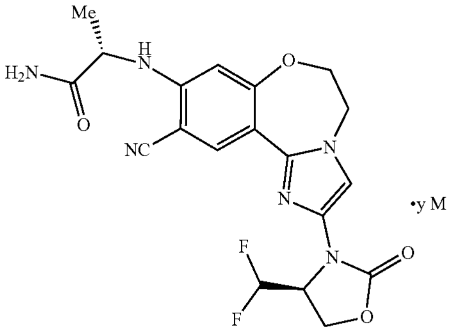
43
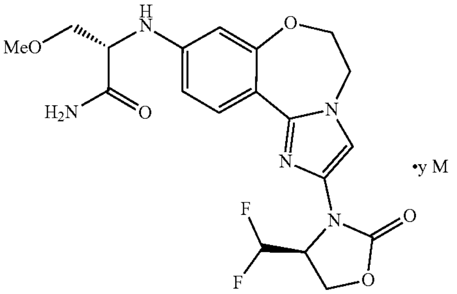
44
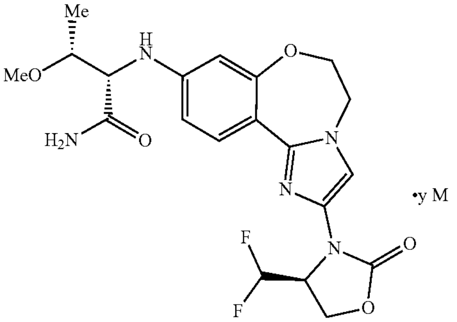
45
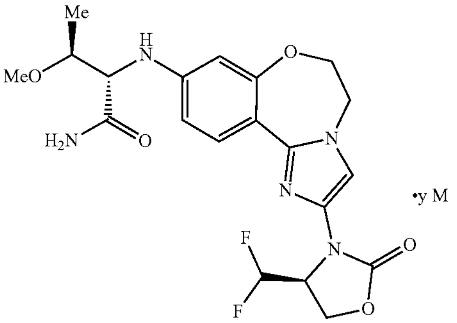
-continued
46
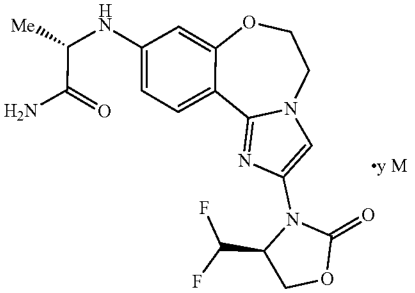
47
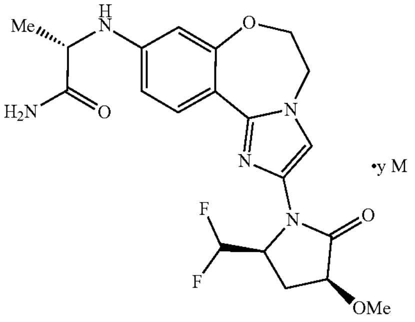
48
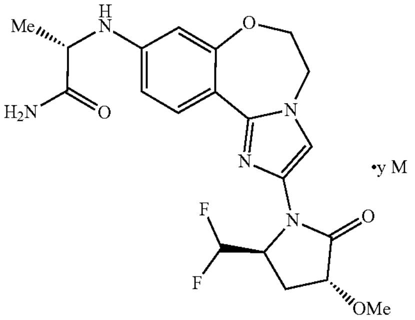
49
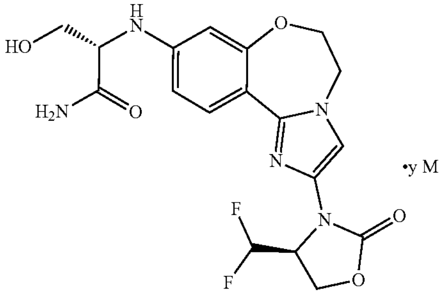
50
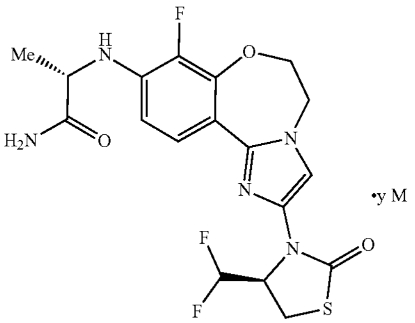

-continued
51
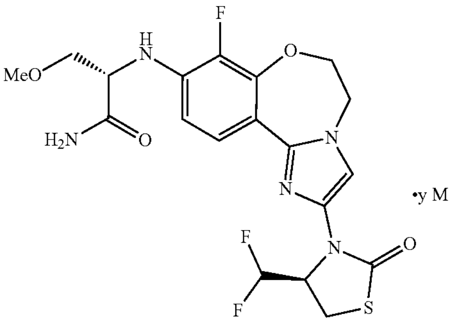
52
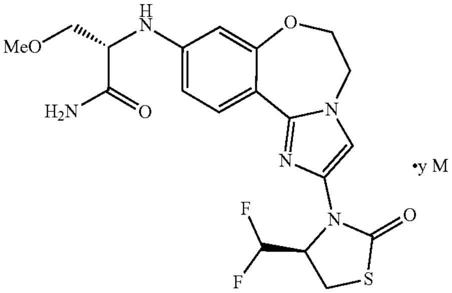
53
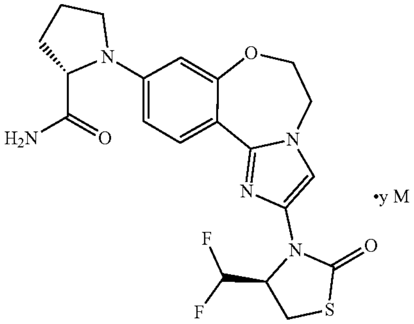
54
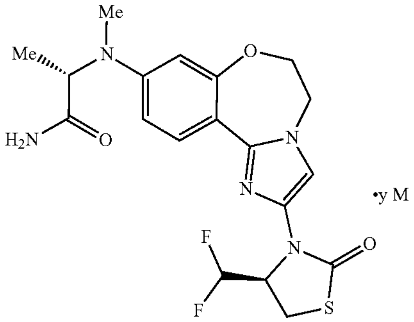
55
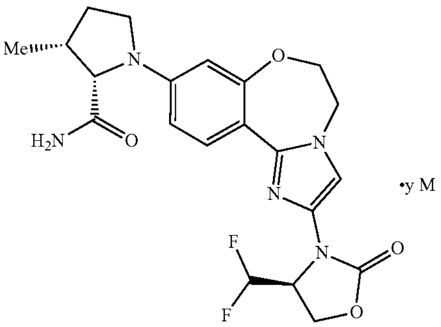
-continued
56
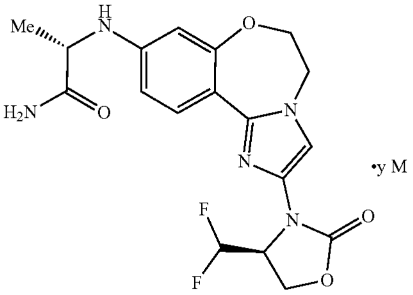
57
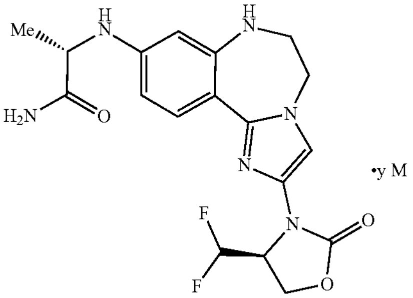
58
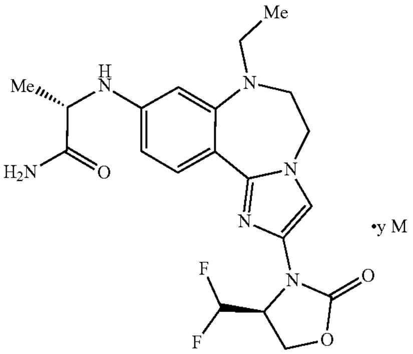
59
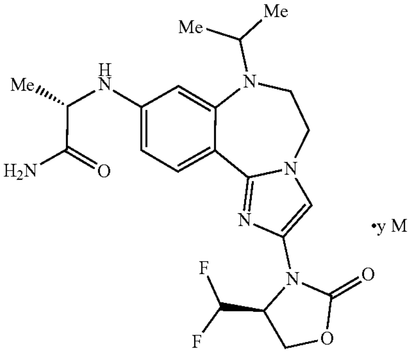

-continued

60

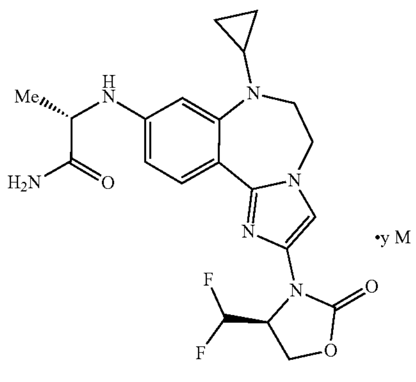

61

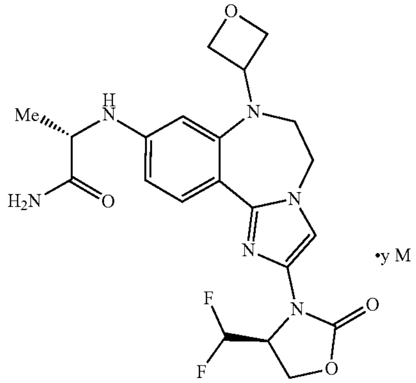

or

62

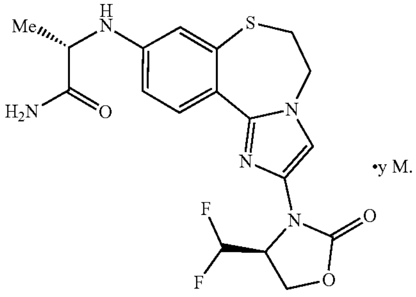

Another object of the present invention is to provide a use of the compound of formula (I) and a crystal form thereof and the pharmaceutical composition comprising the same in the preparation of a PI3K inhibitor medicament, and preferably a PI3Kα inhibitor medicament.

Another object of the present invention is to provide the compound of formula (I), a salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and a crystal form thereof, and one or more pharmaceutically acceptable carriers, diluents or excipients.

Another object of the present invention is to provide a use of the compound of formula (I), the salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, and a crystal form thereof, and the pharmaceutical composition comprising the same in the preparation of a PI3K inhibitor medicament, preferably a PI3Kα inhibitor medicament.

The use is a use in the preparation of a medicament for treating a cancer, bone disease, inflammatory disease, immune disease, nervous system disease, metabolic disease, respiratory disease and heart disease; wherein the cancer is a cancer selected from the group consisting of breast cancer, pancreatic cancer, non-small cell lung cancer (NSCLC), thyroid cancer, seminoma, melanoma, bladder cancer, liver cancer, kidney cancer, myelodysplastic syndrome (MDS), acute myeloid leukemia (AML) and colorectal cancer.

DETAILED DESCRIPTION OF THE INVENTION

Figure 1:
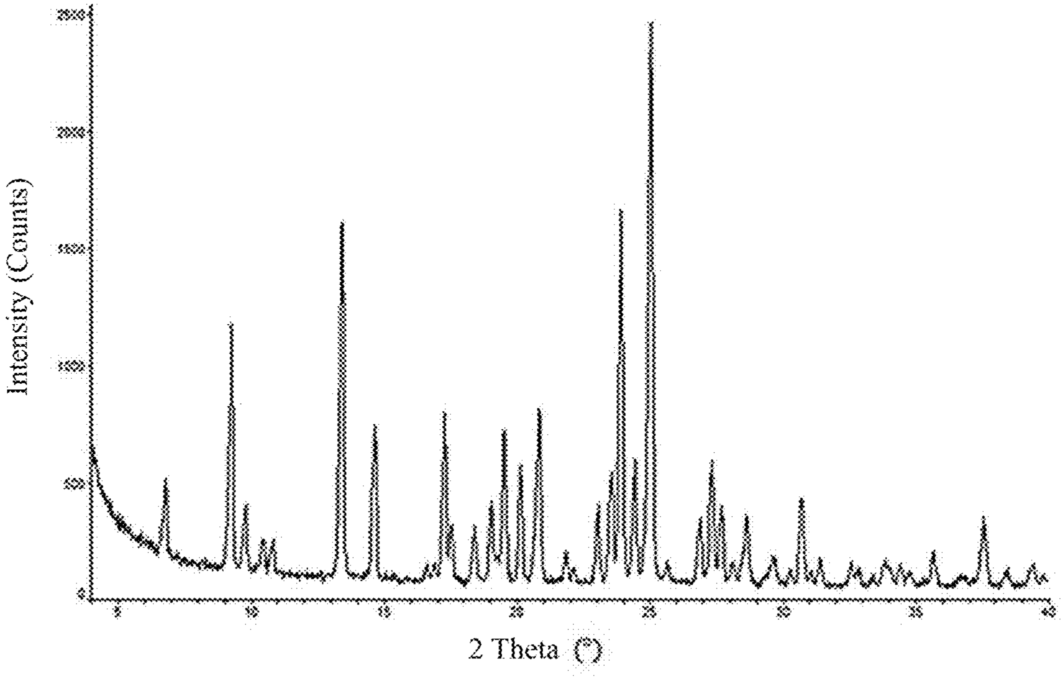
FIG. 1 is the XRPD pattern of crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

Unless otherwise stated, the terms used in the specification and claims have the following meanings.

The term "alkyl" refers to a saturated aliphatic hydrocarbon group, which is a straight or branched group comprising 1 to 20 carbon atoms, preferably an alkyl containing 1 to 8 carbon atoms, more preferably an alkyl with 1 to 6 carbon atoms, and most preferably an alkyl with 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-decyl, 2-methyl-2-ethylhexyl, 2-methyl-3-ethylhexyl, 2,2-diethylpentyl, n-decyl, 3,3-diethylhexyl, 2,2-diethylhexyl and various branched chain isomers thereof. The alkyl can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl. The alkyl of the present invention is preferably selected from the group consisting of methyl, ethyl, isopropyl, tert-butyl, haloalkyl, deuterated alkyl, alkoxy-substituted alkyl, hydroxy-substituted alkyl and cyano-substituted alkyl.

The term "alkylene" refers to an alkyl with one hydrogen atom being further substituted, for example, "methylene" refers to $—CH_2—$, "ethylene" refers to $—(CH_2)_2—$, "propylene" refers to $—(CH_2)_3—$, "butylene" refers to $—(CH_2)_4—$, and the like. The above substituent groups can be bonded to different carbon atoms to form a carbon chain, or can be bonded to one carbon atom to form a cycloalkyl. The term "alkenyl" refers to an alkyl as defined above that consists of at least two carbon atoms and at least one carbon-carbon double bond, for example ethenyl, 1-propenyl, 2-propenyl, 1-, 2- or 3-butenyl and the like. The alkenyl can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 8 carbon atoms, more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptantrienyl, cyclooctyl and the like. Polycyclic cycloalkyl includes a cycloalkyl having a spiro ring, fused ring or bridged ring. The cycloalkyl is preferably cyclopropyl, cyclobutyl, cyclohexyl, cyclopentyl and cycloheptyl.

The term "heterocyclyl" refers to a 3 to 20 membered saturated or partially unsaturated monocyclic or polycyclic hydrocarbon group, wherein one or more ring atoms are heteroatoms selected from the group consisting of nitrogen, oxygen and $S(O)_m$ (wherein m is an integer of 0 to 2), but excluding the ring moiety of —O—O—, —O—S— or —S—S—, with the remaining ring atoms being carbon atoms. Preferably, the heterocyclyl has 3 to 12 ring atoms wherein 1 to 4 atoms are heteroatoms; more preferably, 3 to 8 ring atoms; and most preferably 3 to 8 ring atoms. Non-limiting examples of monocyclic heterocyclyl include oxacyclobutyl, pyrrolidinyl, pyrrolidonyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, and preferably oxacyclobutyl, pyrrolidonyl, tetrahydrofuranyl, pyrazolidinyl, morpholinyl, piperazinyl and pyranyl. Polycyclic heterocyclyl includes a heterocyclyl having a spiro ring, fused ring or bridged ring. The heterocyclyl having a spiro ring, fused ring or bridged ring is optionally bonded to other groups via a single bond, or further fused to other cycloalkyl, heterocyclyl, aryl and heteroaryl via any two or more atoms in the ring.

The term "alkoxy" refers to —O-(alkyl) and —O-(unsubstituted cycloalkyl) group, wherein the alkyl is as defined above. The alkoxy is preferably is an alkoxy having 1 to 8 carbon atoms, more preferably an alkoxy having 1 to 6 carbon atoms, and most preferably an alkoxy having 1 to 3 carbon atoms. Non-limiting examples of alkoxy include methoxy, ethoxy, propoxy, butoxy, cyclopropoxy, cyclobutoxy, cyclopentyloxy and cyclohexyloxy. The alkoxy can be optionally substituted or unsubstituted. When substituted, the substituent group(s) are preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The "haloalkyl" refers to an alkyl substituted by one or more halogens, wherein the alkyl is as defined above.

The "haloalkoxy" refers to an alkoxy substituted by one or more halogens, wherein the alkoxy is as defined above.

The "hydroxyalkyl" refers to an alkyl substituted by hydroxy(s), wherein the alkyl is as defined above.

The "hydroxy" refers to an —OH group.

The "halogen" refers to fluorine, chlorine, bromine or iodine.

The "amino" refers to $—NH_2$ group.

The "cyano" refers to —CN group.

The "nitro" refers to $—NO_2$ group.

The "THF" refers to tetrahydrofuran.

The "EtOAc" refers to ethyl acetate.

The "DMSO" refers to dimethyl sulfoxide.

The "LDA" refers to lithium diisopropylamide.

The "DMAP" refers to 4-dimethylaminopyridine.

The "EtMgBr" refers to ethylmagnesium bromide.

The "HOSu" refers to N-hydroxysuccinimide.

The "EDCl" refers to 1-(3-dimethylaminopropyl)-3-ethylcarbodiimide hydrochloride.

The "IPA" refers to isopropanol.

The "MeOH" refers to methanol.

The "EtOH" refers to ethanol.

The "DMF" refers to N,N-dimethylformamide.

The "DIPEA" refers to N,N-diisopropylethylamine.

The "HEPES" refers to 4-hydroxyethylpiperazineethanesulfonic acid.

Different expressions such as "X is selected from the group consisting of A, B, or C", "X is selected from the group consisting of A, B and C", "X is A, B or C", "X is A, B and C" and the like express the same meaning, that is, X can be any one or more of A, B and C.

"Optional" or "optionally" means that the event or circumstance described subsequently can, but need not occur, and the description includes the situation in which the event or circumstance occurs or does not occur.

"Substituted" refers to one or more hydrogen atoms in a group, preferably up to 5, and more preferably 1 to 3 hydrogen atoms, independently substituted by the corresponding number of substituent group(s). It goes without saying that the substituent groups are only in their possible chemical positions. Those skilled in the art are able to determine whether the substitution is possible or impossible by experiments or theory without excessive effort. For example, the combination of amino or hydroxy having free hydrogen and carbon atoms having unsaturated bonds (such as olefinic) may be unstable.

The "stereoisomerism" includes geometric isomerism (cis-trans isomerism), optical isomerism and conformational isomerism.

The hydrogen atoms in the present invention can all be replaced by the isotope deuterium, and any hydrogen atom in the compounds involved in the examples of the present invention can also be replaced by a deuterium atom.

The "pharmaceutical composition" refers to a mixture containing one or more of the compounds described herein, or a physiologically/pharmaceutically acceptable salt or a prodrug thereof with other chemical components, and other components, for example a physiological/pharmaceutically acceptable carrier and excipient. The purpose of the pharmaceutical composition is to facilitate the drug administration to an organism and to benefit the absorption of the active ingredient, so as to exert the biological activity.

The "pharmaceutically acceptable salt" refers to a salt of the compound of the present invention, which is safe and effective for use in mammals and has the desired biological activity.

As described herein, new crystal forms can be identified by powder X-ray diffraction patterns. However, those skilled in the art know that the peak intensities and/or peak conditions of powder X-ray diffraction may vary due to different experimental conditions, such as different diffraction test conditions and/or preferred orientations. Meanwhile, due to the different accuracy of different instruments, the measured 2θ value will have an error of about ±0.2, and individual peaks may have an error of about ±0.3 or ±0.4. However, it is known that the relative intensity values of the peaks are more dependent on certain properties of the measured sample, such as the size of the crystals in the sample, the orientation of the crystals and the purity of the analyzed material, than the position of the peaks. Therefore, the shown peak intensity may have a deviation in the range of about +20% or more.

The "TGA" refers to a thermogravimetric analysis (TGA) experiment.

The "DSC" refers to a differential scanning calorimetry (DSC) experiment.

The "XRPD" refers to an X-ray powder diffraction (XRPD) experiment.

The "HPLC" refers to a high performance liquid chromatography (HPLC) experiment.

The "PK" refers to a pharmacokinetic (PK) experiment.

The present disclosure will be further described in accordance with the following examples, but these examples should not be considered as limiting the scope of the present disclosure.

I. Preparation of the Compounds

Examples The structures of the compounds of the present invention were determined by nuclear magnetic resonance (NMR) or/and liquid chromatography-mass spectrometry (LC-MS). The NMR chemical shift (δ) was given in the unit of parts per million (ppm). NMR was determined by a Bruker AVANCE-400 nuclear magnetic spectrometer. The solvents for measurement were deuterated dimethyl sulfoxide (DMSO-$d_6$), deuterated methanol ($CD_3OD$) and deuterated chloroform ($CDCl_3$). The internal standard was tetramethylsilane (TMS).

Liquid chromatography-mass spectrometry (LC-MS) was determined on an Agilent 1200 Infinity Series mass spectrometer. High performance liquid chromatography (HPLC) was determined on an Agilent 1200DAD high pressure liquid chromatograph (Sunfire C18 150×4.6 mm column) and Waters 2695-2996 high pressure liquid chromatograph (Gimini C18 150×4.6 mm column).

Yantai Huanghai HSGF254 or Qingdao GF254 silica gel plates were used as the silica gel plates for thin layer chromatography (TLC). The dimension of the silica gel plate used in TLC was 0.15 mm to 0.2 mm, and the dimension of the silica gel plate used in product purification was 0.4 mm to 0.5 mm. Yantai Huanghai 200 to 300 mesh silica gel were generally used as the carrier for column chromatography.

The starting materials in the examples of the present invention are known and commercially available, or can be synthesized by using methods known in the art.

Unless otherwise specified, all the reactions of the present invention are carried out under continuous magnetic stirring under a dry nitrogen or argon atmosphere, the solvent is a dry solvent, and the reaction temperature is given in the unit of degrees Celsius.

Intermediate 1

(S)-4-(Difluoromethyl)oxazolidin-2-one

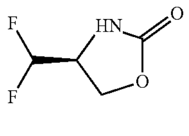

Step 1: Preparation of (R)-3-benzyl-4-(hydroxymethyl)oxazolidin-2-one

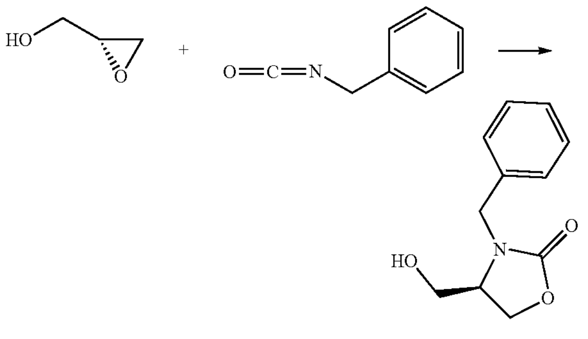

(R)-Oxapropan-2-ylmethanol (3.7 g, 50.0 mmol) and (isocyanatomethyl)benzene (6.66 g, 50.0 mmol) were mixed in dichloromethane (50 mL). The reaction solution was warmed up to 45° C. under a nitrogen atmosphere and stirred overnight. After cooling, 100 mL of saturated aqueous sodium bicarbonate solution was added, and the reaction solution was extracted with dichloromethane (100 mL×2). The organic phases were combined, washed with saturated brine, dried over anhydrous sodium sulfate, concentrated under reduced pressure, and subjected to column chromatography to obtain the title compound (R)-3-benzyl-4-(hydroxymethyl)oxazolidin-2-one (4.14 g, 40%).

MS m/z (ESI): 208.2 $[M+H]^+$.

Step 2: Preparation of (S)-3-benzyl-4-(dihydroxymethyl)oxazolidin-2-one

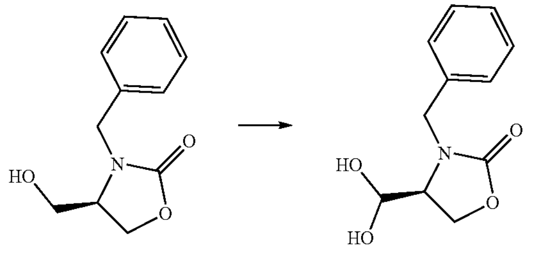 [SMILES: O=C1OC[C@@H](CO)N1Cc1ccccc1 ; O=C1OC[C@@H](C(O)O)N1Cc1ccccc1]

(R)-3-Benzyl-4-(hydroxymethyl)oxazolidin-2-one (4.14 g, 20.0 mmol) and IBX (16.8 g, 60.0 mmol) were mixed in ethyl acetate (100 mL), and the reaction solution was stirred under a nitrogen atmosphere at 85° C. for 3 h. After cooling, the reaction solution was filtered, and the filtrate was concentrated under reduced pressure to obtain 4.46 g of the crude product (S)-3-benzyl-4-(dihydroxymethyl)oxazolidin-2-one, which was directly used in the next step.

MS m/z (ESI): 224.2 $[M+H]^+$.

Step 3: Preparation of (S)-3-benzyl-4-(difluoromethyl)oxazolidin-2-one

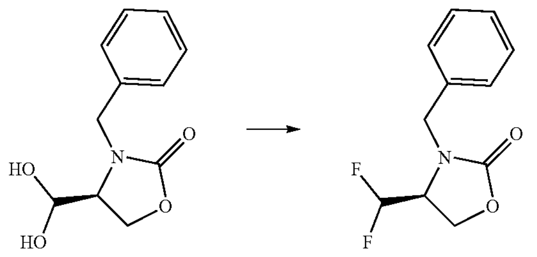 [SMILES: O=C1OC[C@@H](C(O)O)N1Cc1ccccc1 ; O=C1OC[C@@H](C(F)F)N1Cc1ccccc1]

(S)-3-Benzyl-4-(dihydroxymethyl)oxazolidin-2-one (4.46 g, 20.0 mmol) was dissolved in dichloromethane (100 mL). DAST (6.45 g, 40.0 mmol) was added dropwise under a nitrogen atmosphere in an ice bath, and the reaction solution was naturally warmed up to room temperature and reacted for 3 h. The reaction solution was slowly added dropwise to a pre-cooled saturated aqueous sodium bicarbonate solution. and extracted with dichloromethane (200 mL×2). The organic phases were combined, concentrated under reduced pressure and subjected to column chromatography to obtain the title compound (S)-3-benzyl-4-(difluoromethyl)oxazolidin-2-one (1.82 g, two-step yield: 40%).

MS m/z (ESI): 228.2 $[M+H]^+$.

Step 4: Preparation of (S)-4-(difluoromethyl)oxazolidin-2-one

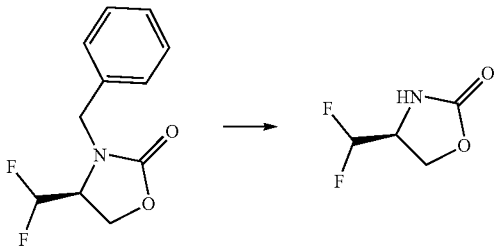 [SMILES: O=C1OC[C@@H](C(F)F)N1Cc1ccccc1 ; O=C1N[C@H](C(F)F)CO1]

(S)-3-Benzyl-4-(difluoromethyl)oxazolidin-2-one (1.82 g, 8 mmol) was dissolved in ethanol (100 mL). $Pd(OH)_2/C$ (300 mg) was added, and the reaction solution was stirred under a hydrogen atmosphere at 70° C. overnight. The reaction solution was cooled and filtered. The filtrate was concentrated under reduced pressure to obtain the title compound (S)-4-(difluoromethyl)oxazolidin-2-one (0.88 g, 80%).

$^1H$ NMR (400 MHz, $CDCl_3$) δ 4.05-4.18 (m, 1H), 4.39-4.45 (m, 1H), 4.54 (t, J=9.3 Hz, 1H), 5.78 (td, J=55.3, 4.7 Hz, 1H), 6.07 (s, 1H);

MS m/z (ESI): 138.1 $[M+H]^+$.

Intermediate 2

9-Bromo-2-iodo-5,6-dihydrobenzo[f]imidazo[1,2-d][1,4]oxazepine

Step 1: Preparation of 5-bromo-2-(1H-imidazol-2-yl)phenol

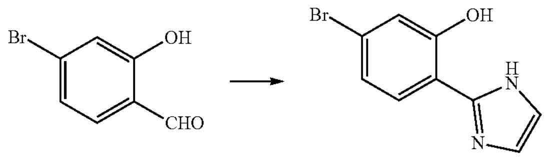 [SMILES: O=Cc1ccc(Br)cc1O ; Oc1cc(Br)ccc1-c1ncc[nH]1]

To a methanol solution (250 mL) of 4-bromo-2-hydroxybenzaldehyde (24.0 g, 119 mmol) was added an aqueous glyoxal solution (40 wt. %, 87 g, 597 mmol). Then aqueous ammonia (28 wt. %, 121 g, 860 mmol) was slowly added dropwise to the reaction solution in a water bath under stirring. The dropwise addition process lasted for 30 minutes, and the temperature of the reaction solution was controlled not to exceed 40° C. Then the mixture was stirred at 35° C. for two days, cooled, and concentrated under reduced pressure to remove the organic solvent and obtain the crude product 5-bromo-2-(1H-imidazol-2-yl)phenol, which was directly used in the next step.

MS m/z (ESI): 239.0 $[M+H]^+$.

Step 2: Preparation of 9-bromo-5,6-dihydrobenzo[f]imidazo[1,2-d][1,4]oxazepine

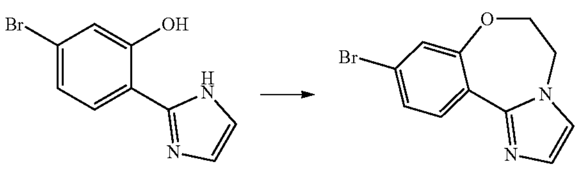 [SMILES: Oc1cc(Br)ccc1-c1ncc[nH]1 ; Brc1ccc2c(c1)OCCn1ccnc1-2]

The crude product 5-bromo-2-(1H-imidazol-2-yl)phenol (about 29 g, 119 mmol), cesium carbonate (158 g, 485 mmol) and 1,2-dibromoethane (42 mL, 485 mmol) were mixed in DMF (250 mL). The reaction solution was stirred at 85° C. overnight, cooled, and diluted with a large amount of ethyl acetate. The organic phase was washed with saturated brine several times, then dried over anhydrous sodium sulfate, concentrated, and subjected to column chromatography to obtain the title compound 9-bromo-5,6-dihydrobenzo[f]imidazo[1,2-d][1,4]oxazepine (12.5 g, two-step yield: 38%).

MS m/z (ESI): 265.0 $[M+H]^+$.

Step 3: Preparation of 9-bromo-2,3-diiodo-5,6-dihydrobenzo[f]imidazo[1,2-d][1,4]oxazepine

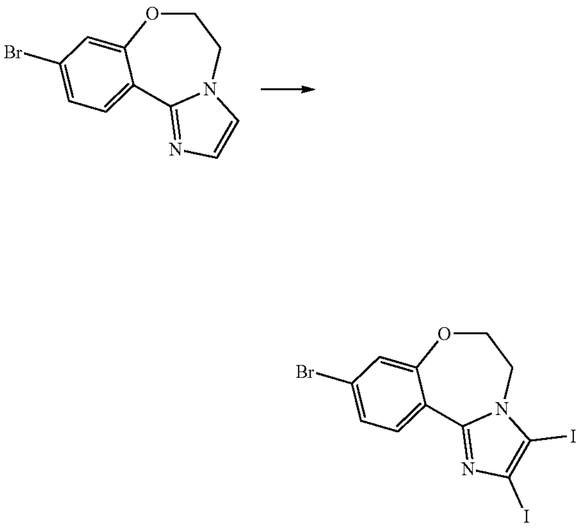 [SMILES: Brc1ccc2c(c1)OCCn1ccnc1-2 ; Brc1ccc2c(c1)OCCn1c-2nc(I)c1I]

To a solution of 9-bromo-5,6-dihydrobenzo[f]imidazo[1,2-d][1,4]oxazepine (11.7 g, 44.1 mmol) in DMF (150 mL) was added NIS (29.8 g, 132 mmol) in batches at room temperature. The reaction solution was stirred at 60° C. overnight, and cooled, then water was added to precipitate a solid. After filtration, the solid was dissolved in ethyl acetate, washed with 1 M aqueous NaOH solution and saturated brine successively, dried over anhydrous sodium sulfate, and concentrated to obtain the title compound 9-bromo-2,3-diiodo-5,6-dihydrobenzene[f]imidazo[1,2-d][1,4]oxazepine (22.5 g, yield: 98.7%).

MS m/z (ESI): 516.7 $[M+H]^+$.

Step 4: Preparation of 9-bromo-2-iodo-5,6-dihydrobenzo[f]imidazo[1,2-d][1,4]oxazepine

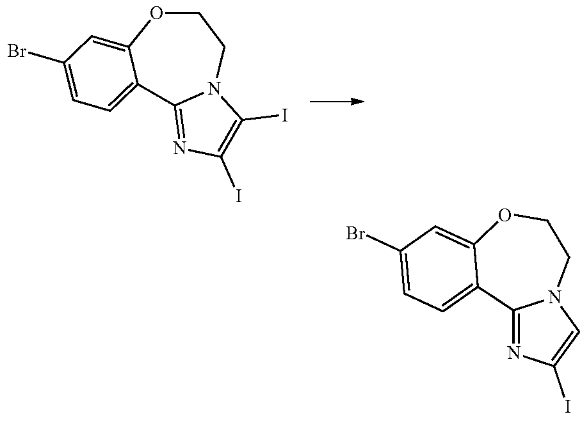

To a solution of 9-bromo-2,3-diiodo-5,6-dihydrobenzo[f]imidazo[1,2-d][1,4]oxazepine (21.0 g, 40.6 mmol) in THF (140 mL) was slowly added dropwise EtMgBr (1.0 M solution in THF, 60.9 mL, 60.9 mmol) at −20° C. After completion of the dropwise addition, the reaction solution was stirred at −15° C. for 3 hours. The reaction solution was slowly warmed up to room temperature, then a saturated aqueous ammonium chloride solution was added dropwise. The reaction solution was stirred for 15 minutes and extracted with ethyl acetate several times. The organic phases were combined, washed with saturated brine, dried over anhydrous sodium sulfate, concentrated, and subjected to column chromatography to obtain the title compound 9-bromo-2-iodo-5,6-dihydrobenzo[f]imidazo[1,2-d][1,4]oxazepine (12.5 g, yield: 79%).

MS m/z (ESI): 390.9 $[M+H]^+$.

Step 5: Preparation of (S)-3-(9-bromo-5,6-dihydrobenzo[f]imidazo[1,2-d][1,4]oxazepin-2-yl)-4-(difluoromethyl)oxazolidin-2-one

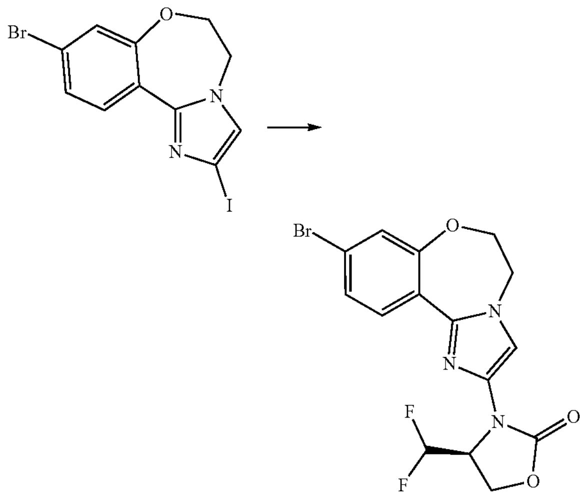

9-Bromo-2-iodo-5,6-dihydrobenzo[f]imidazo[1,2-d][1,4]oxazepine (300 mg, 0.77 mmol), (S)-4-(difluoromethyl)

oxazolidin-2-one (105 mg, 0.77 mmol), (1R,2R)—$N^1$,$N^2$-dimethylcyclohexane-1,2-diamine (43 mg, 0.30 mmol), copper acetate (27 mg, 0.15 mmol) and cesium carbonate (489 mg, 1.5 mmol) were mixed in 2-methyltetrahydrofuran (6 mL). The reaction system was purged with nitrogen three times, and the reaction was carried out at 78° C. for 22 hours. The reaction solution was cooled to room temperature, and 15% aqueous ammonia was added. The reaction solution was stirred for 5 minutes and extracted with EtOAc three times. The organic phases were combined and then washed with saturated aqueous sodium chloride solution. The filtrate was dried over anhydrous sodium sulfate, concentrated under reduced pressure to remove the organic solvent, and then subjected to column chromatography separation to obtain the title compound (S)-3-(9-bromo-5,6-dihydrobenzo[f]imidazo[1,2-d][1,4]oxazepin-2-yl)-4-(difluoromethyl)oxazolidin-2-one (186 mg, 61%).

$^1$H NMR (400 MHz, $CDCl_3$) δ 4.35-4.41 (m, 2H), 4.44-4.52 (m, 2H), 4.53-4.55 (m, 1H), 4.73-4.76 (m, 1H), 4.89-4.91 (m, 1H), 6.62-6.71 (m, 1H), 7.19-7.28 (m, 2H), 7.30 (s, 1H), 8.21 (d, J=8.6 Hz, 1H);

MS m/z (ESI): 400.1 $[M+H]^+$.

Example 1

Preparation of (S)-2-((2-((S)-4-(difluoromethyl)-2-oxooxazolidin-3-yl)-3-fluoro-5,6-dihydrobenzo[f]imidazo[1,2-d][1,4]oxazepin-9-yl)amino)propionamide

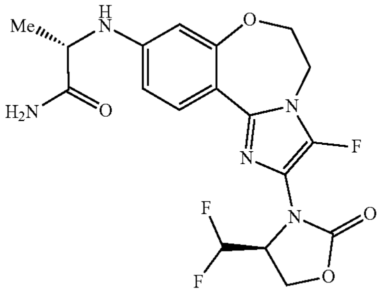 [SMILES: C[C@H](Nc1ccc2c(c1)OCCn1c-2nc(N2C(=O)OC[C@H]2C(F)F)c1F)C(N)=O]

Step 1: Preparation of 9-bromo-3-fluoro-2-iodo-5,6-dihydrobenzo[f]imidazo[1,2-d][1,4]oxazepine

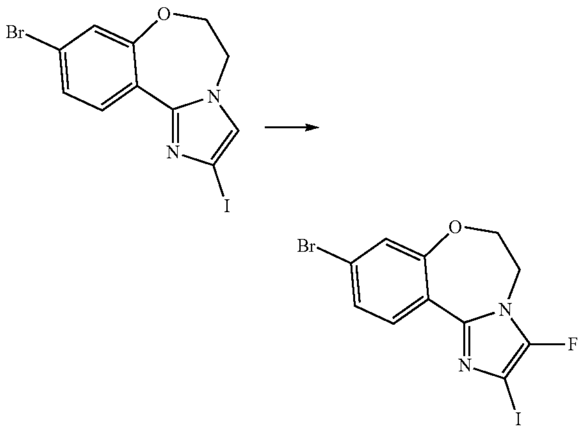

To a solution of LDA (1.28 mL, 2.56 mmol) in tetrahydrofuran (10 mL) was added dropwise a solution of 9-bromo-2-iodo-5,6-dihydrobenzo[f]imidazo[1,2-d][1,4]oxazepine (500 mg, 1.28 mmol) in tetrahydrofuran (10 mL) at −78° C. After completion of the dropwise addition, the reaction solution was stirred at −78° C. for 30 minutes. A solution of N-fluorobenzenesulfonamide (806 mg, 2.56 mmol) in tetrahydrofuran (9 mL) was added dropwise, and the reaction solution was stirred at this temperature for 30 minutes. The reaction was quenched with saturated aqueous ammonium chloride solution. The reaction solution was extracted with dichloromethane (100 mL×2). The organic phase was washed with saturated brine, dried over anhydrous sodium sulfate, concentrated and subjected to column chromatography to obtain the title compound 9-bromo-3-fluoro-2-iodo-5,6-dihydrobenzo[f]imidazo[1,2-d][1,4]oxazepine (150 mg, 29%).

$^1$H NMR (400 MHz, DMSO-$d_6$) δ 4.31-4.34 (m, 2H), 4.43-4.48 (m, 2H), 7.19-7.34 (m, 2H), 8.17 (d, J=8.6 Hz, 1H);

MS m/z (ESI): 408.9 $[M+H]^+$.

Step 2: Preparation of (S)-3-(9-bromo-3-fluoro-5,6-dihydrobenzo[f]imidazo[1,2-d][1,4]oxazepin-2-yl)-4-(difluoro methyl)oxazolidin-2-one

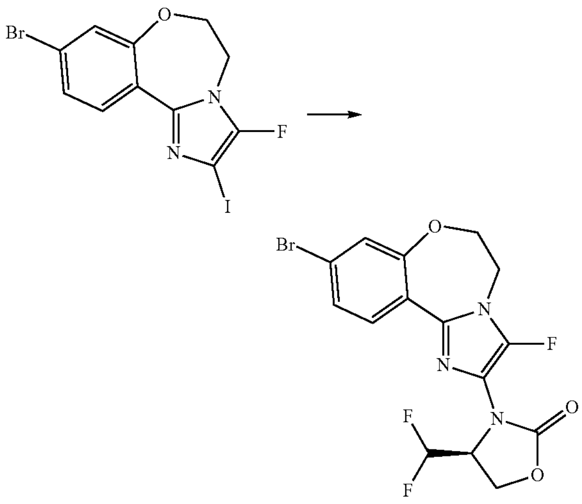

9-Bromo-3-fluoro-2-iodo-5,6-dihydrobenzo[f]imidazo[1,2-d][1,4]oxazepine (100 mg, 0.24 mmol), (S)-4-(difluoromethyl)oxazolidin-2-one (33.5 mg, 0.24 mmol), (1R,2R)—$N^1$,$N^2$-dimethylcyclohexane-1,2-diamine (35 mg, 0.24 mmol), cuprous iodide (46 mg, 0.24 mmol) and potassium phosphate (155 mg, 0.73 mmol) were mixed in dimethyl sulfoxide (10 mL), and the reaction was carried out at 130° C. for 3 hours. The reaction solution was cooled to room temperature, and 15% aqueous ammonia was added. The reaction solution was stirred for 5 minutes and extracted with EtOAc three times. The organic phases were combined, washed with saturated sodium chloride, dried over anhydrous sodium sulfate, concentrated under reduced pressure, and subjected to column chromatography to obtain the title compound (S)-3-(9-bromo-3-fluoro-5,6-dihydrobenzo[f]imidazo[1,2-d][1,4]oxazepin-2-yl)-4-(difluoro methyl)oxazolidin-2-one (21 mg, 20%).

$^1$H NMR (400 MHz, $CDCl_3$) δ 4.25-4.29 (m, 1H), 4.42-4.50 (m, 2H), 4.56-4.69 (m, 4H), 6.16-6.35 (m, 1H), 7.20-7.25 (m, 2H), 8.15 (d, J=8.4 Hz, 1H);

MS m/z (ESI): 417.9 $[M+H]^+$.

Step 3: Preparation of (2-((S)-4-(difluoromethyl)-2-oxooxazolidin-3-yl)-3-fluoro-5,6-dihydrobenzo[f]imidazo[1,2-d][1,4]oxazepin-9-yl)-L-alanine

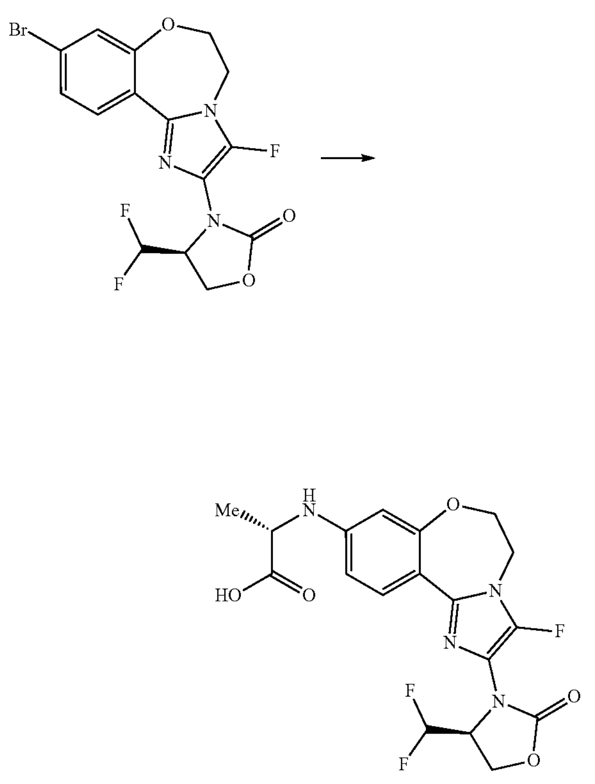

((S)-3-(9-bromo-3-fluoro-5,6-dihydrobenzo[f]imidazo[1,2-d][1,4]oxazepin-2-yl)-4-(di fluoromethyl)oxazolidin-2-one (21 mg, 0.05 mmol), L-alanine (13.5 mg, 0.15 mmol), cuprous iodide (4.8 mg, 0.025 mmol) and potassium phosphate (21 mg, 0.1 mmol) were mixed in dimethyl sulfoxide (3 mL). The reaction system was purged with nitrogen three times, and the reaction was carried out at 100° C. for 5 hours. The reaction solution was cooled to room temperature and directly used in the next step without treatment.

MS m/z (ESI): 427.1 $[M+H]^+$.

Step 4: Preparation of (S)-2-((2-((S)-4-(difluoromethyl)-2-oxooxazolidin-3-yl)-3-fluoro-5,6-dihydrobenzo[f]imidazo[1,2-d][1,4]oxazepin-9-yl)amino)propionamide

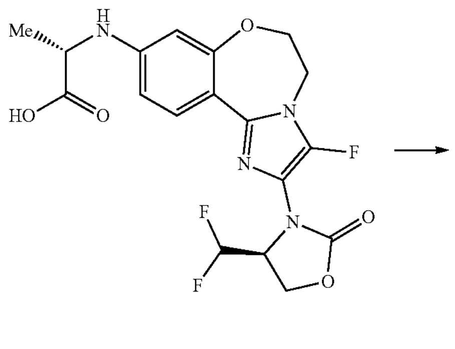

-continued

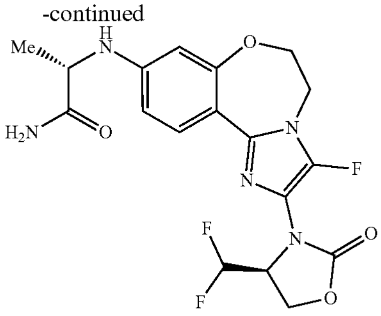

To the crude reaction solution of (2-((S)-4-(difluoromethyl)-2-oxooxazolidin-3-yl)-3-fluoro-5,6-dihydrobenzo[f]imidazo[1,2-d][1,4]oxazepin-9-yl)-L-alanine in the previous step was added ammonium chloride (16 mg, 0.29 mmol) and triethylamine (76 mg, 0.75 mmol). After stirring for 5 minutes, 0-(7-azabenzotriazol-1-yl)-N,N,N',N'-tetramethyluronium hexafluorophosphate (166 mg, 0.44 mmol) was added. The reaction solution was stirred at room temperature for 2 hours and filtered. To the filtrate was added a saturated aqueous sodium bicarbonate solution, followed by extraction with ethyl acetate three times. The organic phases were combined, dried over anhydrous sodium sulfate, concentrated under reduced pressure to remove the organic solvent, and then subjected to column chromatography separation to obtain the title compound (S)-2-((2-((S)-4-(difluoromethyl)-2-oxooxazolidin-3-yl)-3-fluoro-5,6-dihydrobenzo[f]imidazo[1,2-d][1,4]oxazepin-9-yl)amino)propionamide (8.5 mg, 39%).

$^1H$ NMR (400 MHz, $CDCl_3$) δ 1.55 (d, J=7.0 Hz, 3H), 3.70-3.87 (m, 1H), 4.21 (d, J=3.6 Hz, 2H), 4.43 (d, J=5.2 Hz, 2H), 4.57-4.66 (m, 2H), 5.35 (s, 1H), 6.10-6.27 (m, 2H), 6.37-6.50 (m, 2H), 8.07 (d, J=8.6 Hz, 1H).

MS m/z (ESI): 426.1 $[M+H]^+$.

Example 2

Preparation of (S)-1-(2-((S)-4-(difluoromethyl)-2-oxooxazolidin-3-yl)-3-fluoro-5,6-dihydrobenzo[f]imidazo[1,2-d][1,4]oxazepin-9-yl)pyrrolidine-2-carboxamide

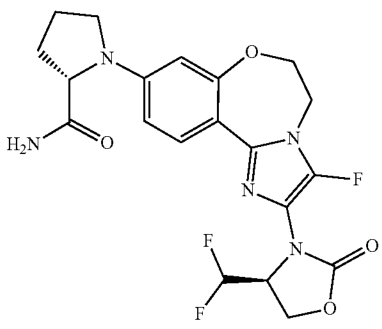

(S)-1-(2-((S)-4-(Difluoromethyl)-2-oxooxazolidin-3-yl)-3-fluoro-5,6-dihydrobenzo[f]imidazo[1,2-d][1,4]oxazepin-9-yl)pyrrolidine-2-carboxamide was prepared by referring to the method of Example 1.

MS m/z (ESI): 452.1 $[M+H]^+$.

Example 3

Preparation of (S)-2-((3-chloro-2-((S)-4-(difluoromethyl)-2-oxooxazolidin-3-yl)-5,6-dihydrobenzo[f]imidazo[1,2-d][1,4]oxazepin-9-yl)amino)propionamide

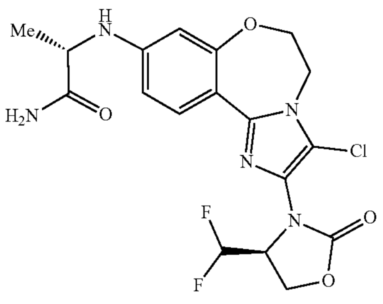 [SMILES: C[C@H](Nc1ccc2c(c1)OCCn1c-2nc(N2C(=O)OC[C@H]2C(F)F)c1Cl)C(N)=O]

(S)-2-((3-Chloro-2-((S)-4-(difluoromethyl)-2-oxooxazolidin-3-yl)-5,6-dihydrobenzo[f]imidazo[1,2-d][1,4]oxazepin-9-yl)amino)propionamide was prepared by referring to the method of Example 1.

$^1$H NMR (400 MHz, $CD_3OD$) δ 1.46 (d, J=7.0 Hz, 3H), 3.80-3.86 (m, 1H), 4.29-4.32 (m, 2H), 4.43-4.46 (m, 2H), 4.57-4.67 (m, 3H), 6.07-6.31 (m, 2H), 6.43-6.46 (m, 1H), 7.98 (d, J=8.8 Hz, 1H);

MS m/z (ESI): 442.1 $[M+H]^+$.

Example 4

Preparation of (S)-2-((2-((S)-4-(difluoromethyl)-2-oxooxazolidin-3-yl)-3-methyl-5,6-dihydrobenzo[f]imidazo[1,2-d][1,4]oxazepin-9-yl)amino)propionamide

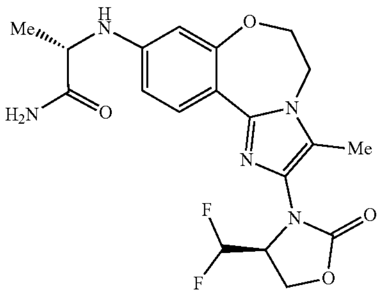 [SMILES: Cc1c(N2C(=O)OC[C@H]2C(F)F)nc2n1CCOc1cc(N[C@@H](C)C(N)=O)ccc1-2]

Step 1: Preparation of 5-bromo-2-(5-methyl-1H-imidazol-2-yl)phenol

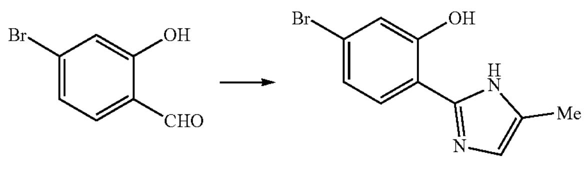 [SMILES: O=Cc1ccc(Br)cc1O ; Cc1cnc(-c2ccc(Br)cc2O)[nH]1]

To a solution of 4-bromo-2-hydroxybenzaldehyde (5 g, 119 mmol) in methanol (100 mL) was added an aqueous solution of methylglyoxal (40 wt. %, 80 mL). Then aqueous ammonia (28 wt. %, 40 g) was slowly added dropwise in a water bath under stirring. The dropwise addition process lasted for 30 minutes, and the temperature of the solution was controlled not to exceed 40° C. Then the reaction solution was stirred at 75° C. for 2 hours, then cooled to room temperature to precipitate a solid, which was filtered to obtain the title compound 5-bromo-2-(5-methyl-1H-imidazol-2-yl)phenol (3.6 g, 57%).

MS m/z (ESI): 253.0 $[M+H]^+$.

Step 2: Preparation of 9-bromo-3-methyl-5,6-dihydrobenzo[f]imidazo[1,2-d][1,4]oxazepine

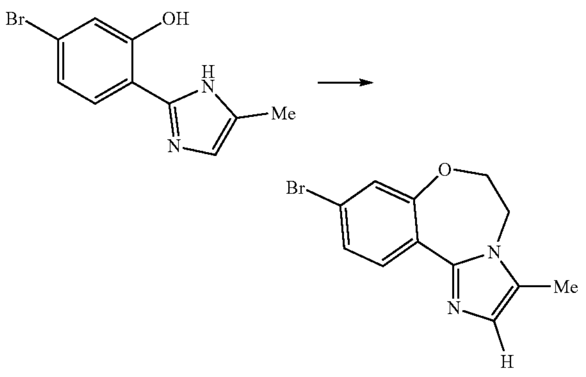

5-Bromo-2-(5-methyl-1H-imidazol-2-yl)phenol (2.5 g, 9.8 mmol), cesium carbonate (12.2 g, 37.5 mmol) and 1,2-dibromoethane (42.0 mL, 37.5 mmol) were mixed in DMF (30 mL), and the reaction solution was stirred at 85° C. overnight. The reaction solution was cooled to room temperature and diluted with a large amount of ethyl acetate. The organic phase was washed with saturated brine several times, then dried over sodium sulfate, concentrated, and subjected to column chromatography to obtain the title compound 9-bromo-3-methyl-5,6-dihydrobenzo[f]imidazo[1,2-d][1,4]oxazepine (0.92 g, 33%).

$^1$H NMR (400 MHz, $CDCl_3$) δ 2.25 (s, 3H), 4.12-4.29 (m, 2H), 4.40-4.53 (m, 2H), 6.94 (s, 1H), 7.14-7.18 (m, 1H), 7.20-7.22 (m, 1H), 8.37 (d, J=8.6 Hz, 1H);

MS m/z (ESI): 279.1 $[M+H]^+$.

Step 3: Preparation of 9-bromo-2-iodo-3-methyl-5,6-dihydrobenzo[f]imidazo[1,2-d][1,4]oxazepine

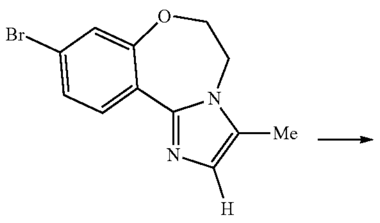

-continued

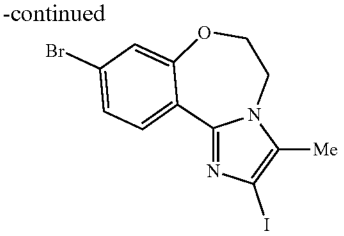

9-Bromo-2-iodo-3-methyl-5,6-dihydrobenzo[f]imidazo[1,2-d][1,4]oxazepine was prepared by referring to the method of Example 1.

MS m/z (ESI): 404.9 $[M+H]^+$.

Step 4: Preparation of (S)-3-(9-bromo-3-methyl-5,6-dihydrobenzo[f]imidazo[1,2-d][1,4]oxazepin-2-yl)-4-(difluoromethyl)oxazolidin-2-one

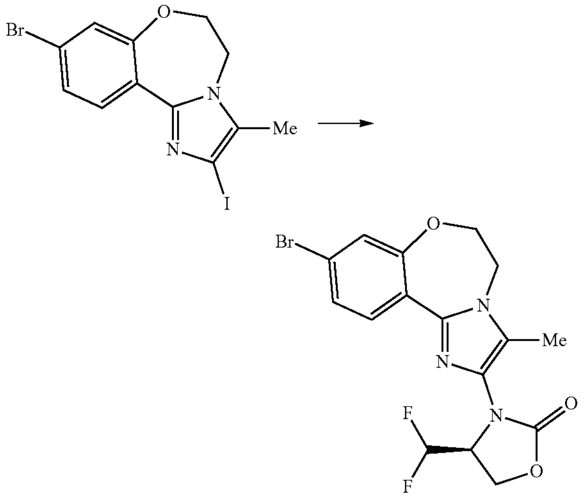

(S)-3-(9-Bromo-3-methyl-5,6-dihydrobenzo[f]imidazo[1,2-d][1,4]oxazepin-2-yl)-4-(di fluoromethyl)oxazolidin-2-one was prepared by referring to the method of Example 1.

MS m/z (ESI): 414.0 $[M+H]^+$.

Step 5: Preparation of (2-((S)-4-(difluoromethyl)-2-oxooxazolidin-3-yl)-3-methyl-5,6-dihydrobenzo[f]imidazo[1, 2-d][1,4]oxazepin-9-yl)-L-alanine

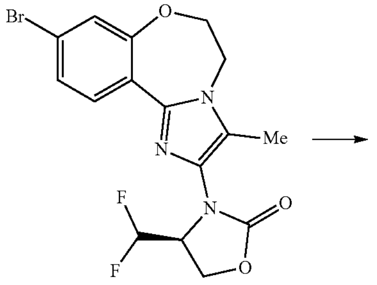

-continued

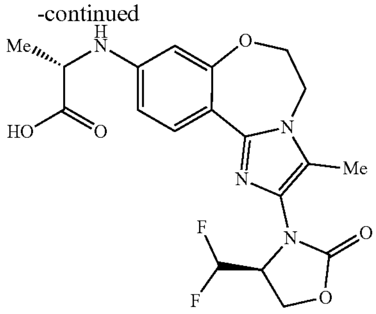

(2-((S)-4-(Difluoromethyl)-2-oxooxazolidin-3-yl)-3-methyl-5,6-dihydrobenzo[f]imidazo[1,2-d][1,4]oxazepin-9-yl)-L-alanine was prepared by referring to the method of Example 1.

MS m/z (ESI): 423.1 $[M+H]^+$.

Step 6: Synthesis of (S)-2-((2-((S)-4-(difluoromethyl)-2-oxooxazolidin-3-yl)-3-methyl-5,6-dihydrobenzo[f]imidazo[1,2-d][1,4]oxazepin-9-yl)amino) propionamide

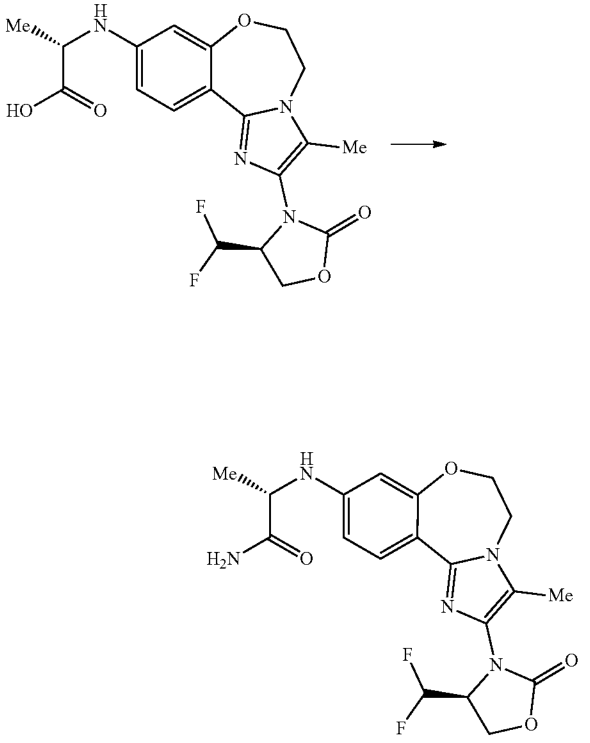

(S)-2-((2-((S)-4-(Difluoromethyl)-2-oxooxazolidin-3-yl)-3-methyl-5,6-dihydrobenzo[f]imidazo[1,2-d][1,4]oxazepin-9-yl)amino)propionamide was prepared by referring to the method of Example 1.

$^1H$ NMR (400 MHz, $CD_3OD$) δ 1.37 (d, J=7.0 Hz, 3H), 2.08 (s, 3H), 3.68-3.75 (m, 1H), 4.18-4.24 (m, 2H), 4.32-4.35 (m, 2H), 4.45-4.61 (m, 3H), 6.10 (m, 2H), 6.34 (d, J=8.8 Hz, 1H), 7.83 (d, J=8.8 Hz, 1H).

MS m/z (ESI): 422.2 $[M+H]^+$.

Example 5

Preparation of (S)-1-(2-((S)-4-(difluoromethyl)-2-oxooxazolidin-3-yl)-3-methyl-5,6-dihydrobenzo[f]imidazo[1,2-d][1,4]oxazepin-9-yl)pyrrolidine-2-carboxamide

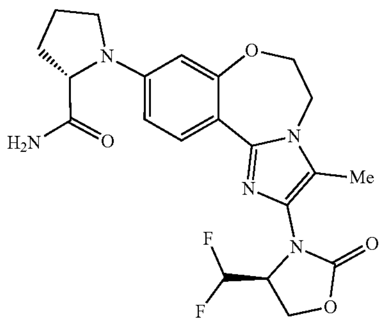 [SMILES: Cc1c(N2C(=O)OC[C@H]2C(F)F)nc2n1CCOc1cc(N3CCC[C@H]3C(N)=O)ccc1-2]

(S)-1-(2-((S)-4-(Difluoromethyl)-2-oxooxazolidin-3-yl)-3-methyl-5,6-dihydrobenzo[f]imidazo[1,2-d][1,4]oxazepin-9-yl)pyrrolidine-2-carboxamide was prepared by referring to the method of Example 4.

MS m/z (ESI): 448.2 $[M+H]^+$.

Example 6

Preparation of (S)-2-((2-((S)-4-(difluoromethyl)-2-oxooxazolidin-3-yl)-3-(trifluoro methyl)-5,6-dihydrobenzo[f]imidazo[1,2-d][1,4]oxazepin-9-yl)amino)propionamide

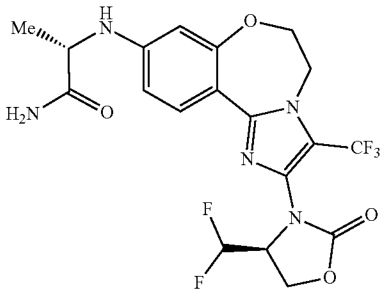 [SMILES: C[C@H](Nc1ccc2c(c1)OCCn1c-2nc(N2C(=O)OC[C@H]2C(F)F)c1C(F)(F)F)C(N)=O]

(S)-2-((2-((S)-4-(Difluoromethyl)-2-oxooxazolidin-3-yl)-3-(trifluoromethyl)-5,6-dihydrobenzo[f]imidazo[1,2-d][1,4]oxazepin-9-yl)amino)propionamide was prepared by referring to the method of Example 4.

MS m/z (ESI): 476.1 $[M+H]^+$.

Example 7

Preparation of (S)-2-((3-cyano-2-((S)-4-(difluoromethyl)-2-oxooxazolidin-3-yl)-5,6-dihydrobenzo[f]imidazo[1,2-d][1,4]oxazepin-9-yl)amino)propionamide

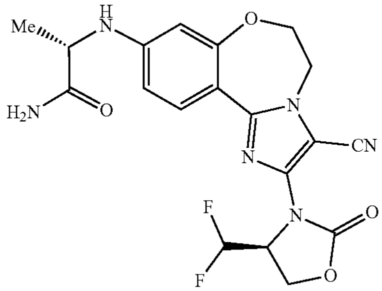

(S)-2-((3-Cyano-2-((S)-4-(difluoromethyl)-2-oxooxazolidin-3-yl)-5,6-dihydrobenzo[f]imidazo[1,2-d][1,4]oxazepin-9-yl)amino)propionamide was prepared by referring to the method of Example 4.

MS m/z (ESI): 433.1 $[M+H]^+$.

Example 8

Preparation of (S)-1-(3-cyano-2-((S)-4-(difluoromethyl)-2-oxooxazolidin-3-yl)-5,6-dihydrobenzo[f]imidazo[1,2-d][1,4]oxazepin-9-yl)pyrrolidine-2-carboxamide

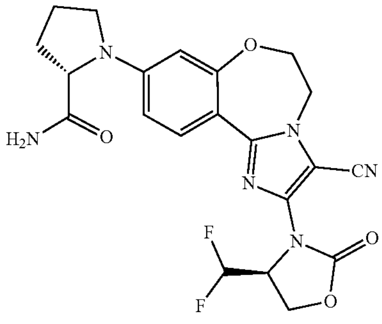 [SMILES: N#Cc1c(N2C(=O)OC[C@H]2C(F)F)nc2n1CCOc1cc(N3CCC[C@H]3C(N)=O)ccc1-2]

(S)-1-(3-Cyano-2-((S)-4-(difluoromethyl)-2-oxooxazolidin-3-yl)-5,6-dihydrobenzo[f]imidazo[1,2-d][1,4]oxazepin-9-yl)pyrrolidine-2-carboxamide was prepared by referring to the method of Example 4.

MS m/z (ESI): 459.2 $[M+H]^+$.

Example 9

Preparation of (S)-2-((3-cyclopropyl-2-((S)-4-(difluoromethyl)-2-oxooxazolidin-3-yl)-5,6-dihydrobenzo[f]imidazo[1,2-d][1,4]oxazepin-9-yl)amino)propionamide

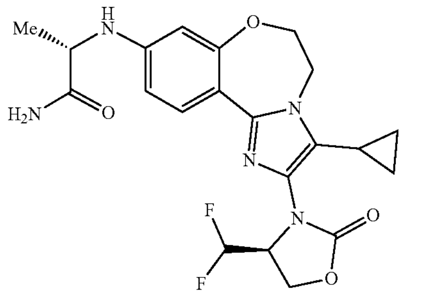 [SMILES: C[C@H](Nc1ccc2c(c1)OCCn1c-2nc(N2C(=O)OC[C@H]2C(F)F)c1C1CC1)C(N)=O]

(S)-2-((3-Cyclopropyl-2-((S)-4-(difluoromethyl)-2-oxooxazolidin-3-yl)-5,6-dihydrobenzo[f]imidazo[1,2-d][1,4]oxazepin-9-yl)amino)propionamide was prepared by referring to the method of Example 4.

MS m/z (ESI): 448.2 $[M+H]^+$.

Example 10

Preparation of (S)-2-((2-((S)-4-(difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)propionamide

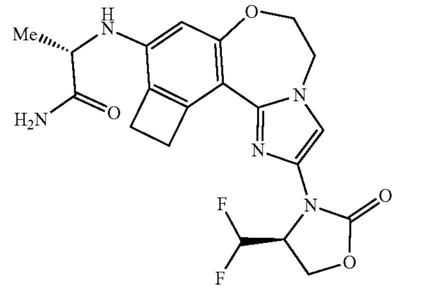 [SMILES: C[C@H](Nc1cc2c(c3c1CC3)-c1nc(N3C(=O)OC[C@H]3C(F)F)cn1CCO2)C(N)=O]

Step 1: Preparation of 1-(bicyclo[4.2.0]oct-1(6),2,4-trien-3-yl)ethan-1-one

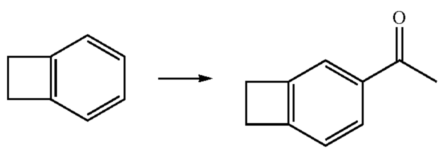

$AlCl_3$ (3.33 g, 25 mmol) was suspended in nitromethane (25 mL). A solution of bicyclo[4.2.0]octa-1(6),2,4-triene (2.08 g, 20 mmol) and acetyl chloride (1.73 g, 22 mmol) in nitromethane (25 mL) was added dropwise under a $N_2$ atmosphere in an ice bath. The reaction solution was naturally warmed up to room temperature and the reaction was carried out overnight. The reaction solution was added to 200 mL of ice water and extracted with DCM (200 mL×2). The organic phases were combined, concentrated under reduced pressure, and subjected to column chromatography to obtain the title compound 1-(bicyclo[4.2.0]oct-1(6),2,4-trien-3-yl)ethan-1-one (800 mg, 27%).

Step 2: Preparation of 1-(5-bromobicyclo[4.2.0]oct-1(6),2,4-trien-3-yl)ethan-1-one

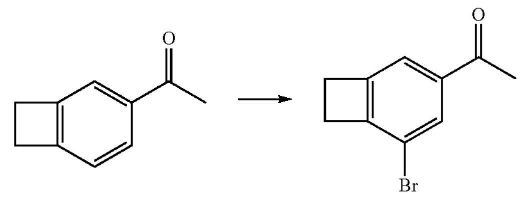

1-(Bicyclo[4.2.0]oct-1(6),2,4-trien-3-yl)ethan-1-one (731 mg, 5 mmol) was dissolved in acetic acid (20 mL). Bromine (878.9 mg, 5.5 mmol) was added dropwise under a $N_2$ atmosphere, and the reaction was carried out at room temperature for 3 h. The reaction solution was concentrated, DCM and saturated aqueous sodium bicarbonate solution were added to the concentrate, and two phases were separated. The organic phase was concentrated under reduced pressure and then subjected to column chromatography to obtain the title compound 1-(5-bromobicyclo[4.2.0]oct-1(6),2,4-trien-3-yl)ethan-1-one (900 mg, 80%).

Step 3: Preparation of 5-bromobicyclo[4.2.0]oct-1(6),2,4-trien-3-yl acetate

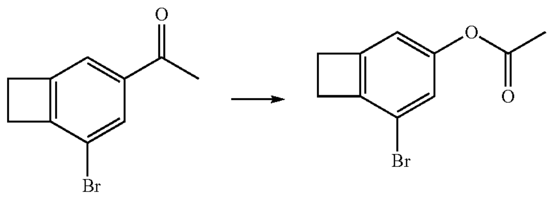

1-(5-Bromobicyclo[4.2.0]oct-1(6),2,4-trien-3-yl)ethan-1-one (900 mg, 4 mmol) and m-CPBA (75%, 2.30 g, 10 mmol) were mixed in DCM (20 mL), and the reaction solution was refluxed and reacted under a $N_2$ atmosphere overnight. After cooling to room temperature, the reaction solution was filtered to remove the insolubles and washed with saturated aqueous sodium bicarbonate solution. The organic phase was concentrated under reduced pressure and then subjected to column chromatography to obtain the title compound 5-bromobicyclo[4.2.0]oct-1(6),2,4-trien-3-yl acetate (723 mg, 75%).

Step 4: Preparation of 5-bromobicyclo[4.2.0]oct-1(6),2,4-trien-3-ol

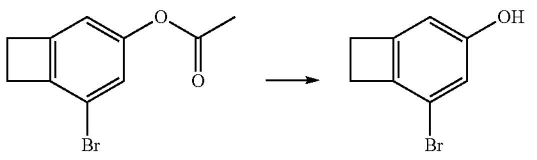

5-Bromobicyclo[4.2.0]oct-1(6),2,4-trien-3-yl acetate (723 mg, 3 mmol) was dissolved in methanol (20 mL). 5 N aqueous sodium hydroxide solution (3 mL) was added, and the reaction was carried out at room temperature overnight. 50 mL of water was added, and the pH of the reaction solution was adjusted to 5 with 1N hydrochloric acid. The reaction solution was extracted with DCM (50 mL×2). The organic phases were combined, concentrated under reduced pressure and subjected to column chromatography to obtain the title compound 5-bromobicyclo[4.2.0]oct-1(6),2,4-trien-3-ol (567 mg, 95%).

Step 5: Preparation of 5-bromo-3-hydroxybicyclo[4.2.0]octa-1(6),2,4-triene-2-carbaldehyde

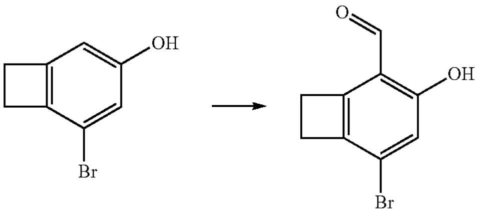 [SMILES: Oc1cc(Br)c2c(c1)CC2 ; O=Cc1c(O)cc(Br)c2c1CC2]

5-Bromobicyclo[4.2.0]oct-1(6),2,4-trien-3-ol (567.2 mg, 2.85 mmol), magnesium chloride (407 mg, 4.28 mmol) and TEA (1.15 g, 11.4 mmol) were added to acetonitrile (5 mL). The reaction solution was warmed up to 40° C. and reacted for 30 min. Paraformaldehyde (770 mg, 8.55 mmol) was added, and the reaction was carried out at 80° C. overnight. After cooling to room temperature, 50 mL of water was added, and the pH of the reaction solution was adjusted to 5 with 4 N hydrochloric acid. The reaction solution was extracted with DCM (50 mL×2). The organic phases were combined, concentrated under reduced pressure, and subjected to column chromatography to obtain the title compound 5-bromo-3-hydroxybicycle[4.2.0]octa-1(6),2,4-triene-2-carbaldehyde (517.6 mg, 80%).

Step 6: Preparation of (S)-2-((2-((S)-4-(difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)propionamide

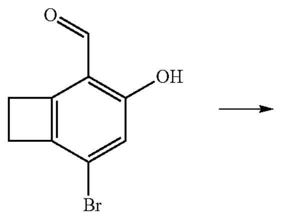

-continued

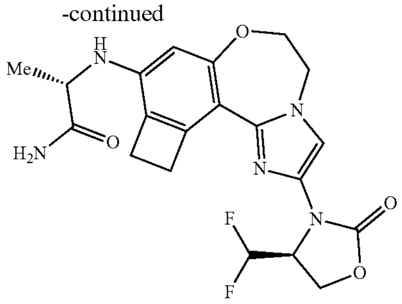

(S)-2-((2-((S)-4-(Difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)propionamide was prepared by referring to the method of Example 1.

MS m/z (ESI): 434.2 $[M+H]^+$.

Example 11

Preparation of (S)-2-((2-((S)-4-(difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)-2-methoxyacetamide

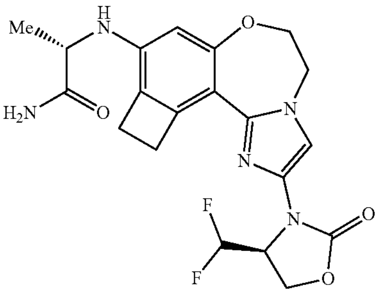 [SMILES: C[C@H](Nc1cc2c(c3c1CC3)-c1nc(N3C(=O)OC[C@H]3C(F)F)cn1CCO2)C(N)=O]

(S)-2-((2-((S)-4-(Difluoromethyl)-2-oxooxazolidin-3-yl)-5,6,10,11-tetrahydrocyclobuta[5,6]benzo[1,2-f]imidazo[1,2-d][1,4]oxazepin-9-yl)amino)-2-methoxyacetamide was prepared by referring to the method of Example 10.

MS m/z (ESI): 450.1 $[M+H]^+$.

Example 12

Preparation of (S)-2-((2-((S)-4-(difluoromethyl)-2-oxooxazolidin-3-yl)-5,6,11, 12-tetrahydro-10H-imidazo[1,2-d]indeno[4,5-f][1,4]oxazepin-9-yl)amino)propionamide

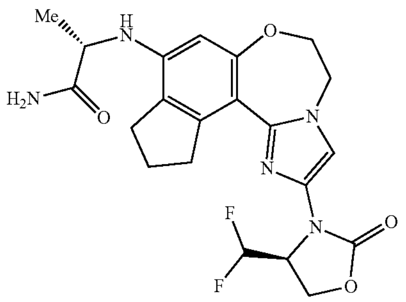 [SMILES: C[C@H](Nc1cc2c(c3c1CCC3)-c1nc(N3C(=O)OC[C@H]3C(F)F)cn1CCO2)C(N)=O]

(S)-2-((2-((S)-4-(Difluoromethyl)-2-oxooxazolidin-3-yl)-5,6,11,12-tetrahydro-10H-imidazo[1,2-d]indeno[4,5-f][1,4]oxazepin-9-yl)amino)propionamide was prepared by referring to the method of Example 10.

MS m/z (ESI): 448.1 [M+H]$^+$.

Example 13

Preparation of (S)-2-((11-((S)-4-(difluoromethyl)-2-oxooxazolidin-3-yl)-7,8-dihydro-[1,3]dioxazolo[4',5': 5,6]benzo[1,2-f]imidazo[1,2-d][1,4]oxazepin-4-yl)amino)propionamide

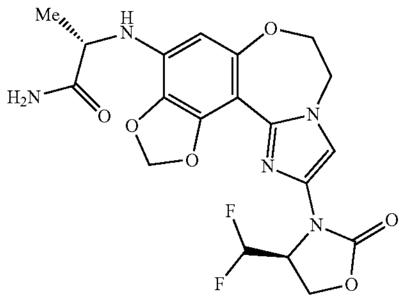 [SMILES: C[C@H](Nc1cc2c(c3c1OCO3)-c1nc(N3C(=O)OC[C@H]3C(F)F)cn1CCO2)C(N)=O]

(S)-2-((11-((S)-4-(Difluoromethyl)-2-oxooxazolidin-3-yl)-7,8-dihydro-[1,3]dioxazolo[4',5':5,6]benzo[1,2-f]imidazo[1,2-d][1,4]oxazepin-4-yl)amino)propionamide was prepared by referring to the method of Example 10.

MS m/z (ESI): 452.1 [M+H]$^+$.

Example 14

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-3-methylbutanamide

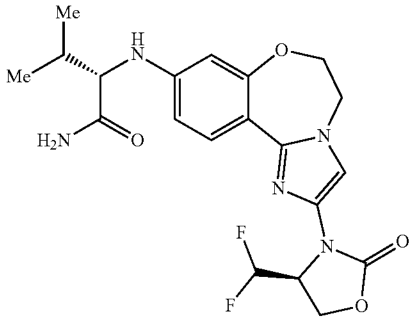 [SMILES: CC(C)[C@H](Nc1ccc2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-5,6-dihydrobenzo[f]imidazo[1,2-d][1,4]oxazepin-9-yl)amino)-3-methylbutanamide was prepared by referring to the method of Example 1.

$^1$H NMR (400 MHz, $CD_3OD$) δ 1.09 (t, J=6.1 Hz, 6H), 2.13 (d, J=7.0 Hz, 1H), 3.60 (d, J=6.4 Hz, 1H), 4.38 (d, J=19.3 Hz, 4H), 4.68-4.60 (m, 3H), 6.27 (s, 1H), 6.43-6.78 (m, 2H), 7.17 (s, 1H), 8.06 (d, J=8.7 Hz, 1H);

MS m/z (ESI): 436.1 [M+H]$^+$.

Example 15

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-2-methoxyacetamide

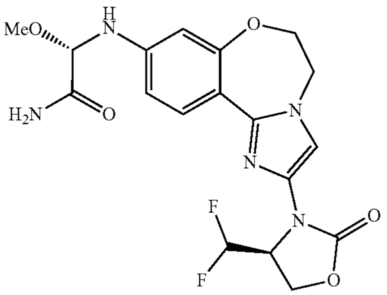 [SMILES: CO[C@H](Nc1ccc2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-5,6-dihydrobenzo[f]imidazo[1,2-d][1,4]oxazepin-9-yl)amino)-2-methoxyacetamide was prepared by referring to the method of Example 1.

MS m/z (ESI): 424.1 [M+H]$^+$.

Example 16

Preparation of (R)-2-((2-((S)-4-(difluoromethyl)-2-oxooxazolidin-3-yl)-5,6-dihydrobenzo[f]imidazo[1,2-d][1,4]oxazepin-9-yl)amino)-3-fluoropropionamide

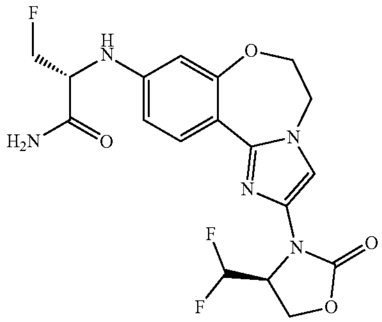 [SMILES: NC(=O)[C@H](CF)Nc1ccc2c(c1)OCCn1cc(N3C(=O)OC[C@H]3C(F)F)nc1-2]

(R)-2-((2-((S)-4-(Difluoromethyl)-2-oxooxazolidin-3-yl)-5,6-dihydrobenzo[f]imidazo[1,2-d][1,4]oxazepin-9-yl)amino)-3-fluoropropionamide was prepared by referring to the method of Example 1.

MS m/z (ESI): 426.1 [M+H]$^+$.

Example 17

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-2-(oxetan-3-yl)acetamide

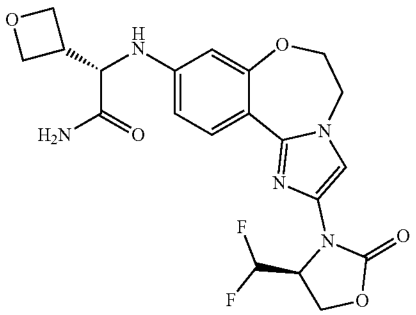 [SMILES: NC(=O)[C@@H](Nc1ccc2c(c1)OCCn1cc(N3C(=O)OC[C@H]3C(F)F)nc1-2)C1COC1]

(S)-2-((2-((S)-4-(Difluoromethyl)-2-oxooxazolidin-3-yl)-5,6-dihydrobenzo[f]imidazo[1,2-d][1,4]oxazepin-9-yl)amino)-2-(oxetan-3-yl) acetamide was prepared by referring to the method of Example 1.

$^{1}$H NMR (400 MHz, $CD_3OD$) δ 3.26-3.33 (m, 2H), 4.08 (d, J=9.6 Hz, 1H), 4.22-4.25 (m, 2H), 4.29-4.31 (m, 2H), 4.40-4.50 (m, 5H), 4.61-4.69 (m, 1H), 6.18 (d, J=2.2 Hz, 1H), 6.44-6.50 (m, 2H), 7.06 (s, 1H), 7.97 (d, J=8.8 Hz, 1H);

MS m/z (ESI): 450.1 $[M+H]^+$.

Example 18

Preparation of (S)-2-((2-(4-(difluoromethyl)-2-oxooxazolidin-3-yl)-5,6-dihydrobenzo[f]imidazo[1,2-d][1, 4]oxazepin-9-yl)amino)-2-methylpropionamide

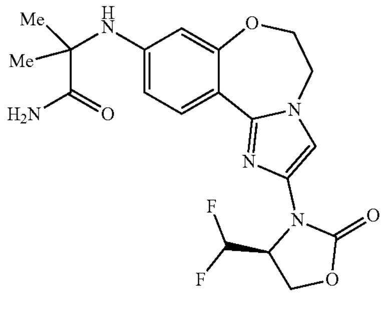 [SMILES: CC(C)(Nc1ccc2c(c1)OCCn1cc(N3C(=O)OC[C@H]3C(F)F)nc1-2)C(N)=O]

(S)-2-((2-(4-(Difluoromethyl)-2-oxooxazolidin-3-yl)-5,6-dihydrobenzo[f]imidazo[1,2-d][1,4]oxazepin-9-yl)amino)-2-methylpropionamide was prepared by referring to the method of Example 1.

$^{1}$H NMR (400 MHz, $CD_3OD$) δ 1.50 (s, 6H), 4.31-4.36 (m, 2H), 4.38-4.43 (m, 2H), 4.61-4.65 (m, 2H), 4.95 (d, J=10.6 Hz, 1H), 6.19 (d, J=2.2 Hz, 1H), 6.64-6.81 (m, 2H), 7.17 (s, 1H), 8.05 (d, J=8.8 Hz, 1H);

MS m/z (ESI): 422.1 $[M+H]^+$.

Example 19

Preparation of (S)-2-((2-((S)-4-(difluoromethyl)-2-oxooxazolidin-3-yl)-5,6-dihydrobenzo[f]imidazo[1,2-d][1,4]oxazepin-9-yl)(methyl)amino)propionamide

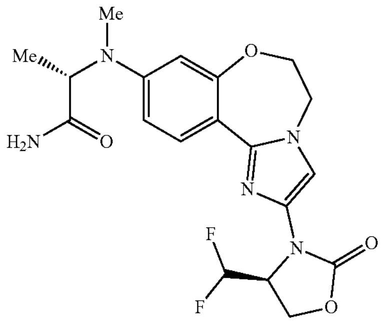 [SMILES: C[C@@H](C(N)=O)N(C)c1ccc2c(c1)OCCn1cc(N3C(=O)OC[C@H]3C(F)F)nc1-2]

(S)-2-((2-((S)-4-(Difluoromethyl)-2-oxooxazolidin-3-yl)-5,6-dihydrobenzo[f]imidazo[1,2-d][1,4]oxazepin-9-yl)(methyl)amino)propionamide was prepared by referring to the method of Example 1.

$^{1}$H NMR (400 MHz, $CD_3OD$): δ 1.40 (d, J=6.8 Hz, 3H), 2.90 (s, 3H), 4.37-4.64 (m, 7H), 4.96 (m, 1H), 6.41 (s, 1H), 6.46-6.74 (m, 2H), 7.16 (s, 1H), 8.13 (d, J=9.2 Hz, 1H);

MS m/z (ESI): 422.1 $[M+H]^+$.

Example 20

Preparation of (S)-3-((2-(4-(difluoromethyl)-2-oxooxazolidin-3-yl)-5,6-dihydrobenzo[f]imidazo[1,2-d][1, 4]oxazepin-9-yl)amino)oxetane-3-carboxamide

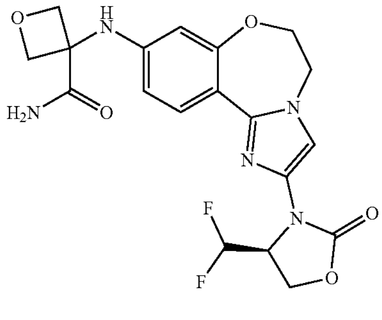 [SMILES: NC(=O)C1(Nc2ccc3c(c2)OCCn2cc(N4C(=O)OC[C@H]4C(F)F)nc2-3)COC1]

(S)-3-((2-(4-(Difluoromethyl)-2-oxooxazolidin-3-yl)-5,6-dihydrobenzo[f]imidazo[1,2-d][1,4]oxazepin-9-yl)amino)oxetane-3-carboxamide was prepared by referring to the method of Example 1.

$^{1}$H NMR (400 MHz, $CD_3OD$) δ 4.35 (m, 4H), 4.63 (m, 4H), 4.90 (m, 1H), 5.10 (d, J=8.0 Hz, 2H), 5.90 (s, 1H), 6.29 (d, J=8.0 Hz, 1H), 6.59 (t, J=56 Hz, 1H), 7.16 (s, 1H), 8.10 (d, J=8.0 Hz, 1H);

MS m/z (ESI): 436.1 $[M+H]^+$.

Example 21

Preparation of (S)-1-(2-((S)-4-(difluoromethyl)-2-oxooxazolidin-3-yl)-5,6-dihydrobenzo[f]imidazo[1,2-d][1,4]oxazepin-9-yl)azetidine-2-carboxamide

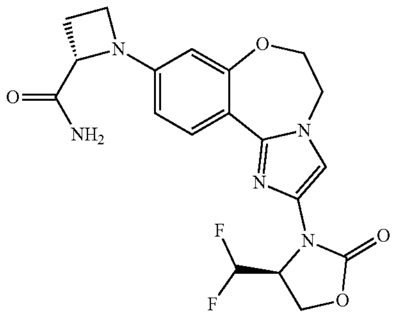 [SMILES: NC(=O)[C@@H]1CCN1c1ccc2c(c1)OCCn1cc(N3C(=O)OC[C@H]3C(F)F)nc1-2]

(S)-1-(2-((S)-4-(Difluoromethyl)-2-oxooxazolidin-3-yl)-5,6-dihydrobenzo[f]imidazo[1,2-d][1,4]oxazepin-9-yl)azetidine-2-carboxamide was prepared by referring to the method of Example 1.

$^1$H NMR (400 MHz, $CD_3OD$) δ 2.30-2.40 (m, 1H), 2.52-2.58 (m, 1H), 3.66-3.72 (m, 1H), 3.91-3.96 (m, 1H), 4.22-4.27 (m, 2H), 4.28-4.34 (m, 2H), 4.48-4.59 (m, 2H), 4.79-4.85 (m, 2H), 6.00 (d, J=2.2 Hz, 1H), 6.20-6.22 (m, 1H), 6.37-6.65 (m, 1H), 7.08 (s, 1H), 8.06 (d, J=8.7 Hz, 1H).

MS m/z (ESI): 420.1 $[M+H]^+$.

Example 22

Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide

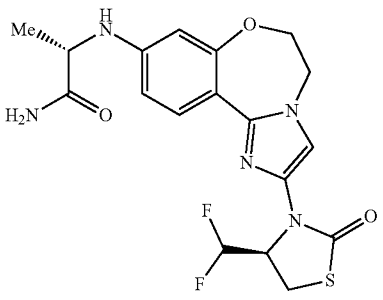 [SMILES: C[C@H](Nc1ccc2c(c1)OCCn1cc(N3C(=O)SC[C@H]3C(F)F)nc1-2)C(N)=O]

Step 1: Preparation of (S)-3-(9-bromo-5,6-dihydrobenzo[f]imidazo[1,2-d][1,4]oxazepin-2-yl)-4-(difluoromethyl)oxazolidine-2-thione

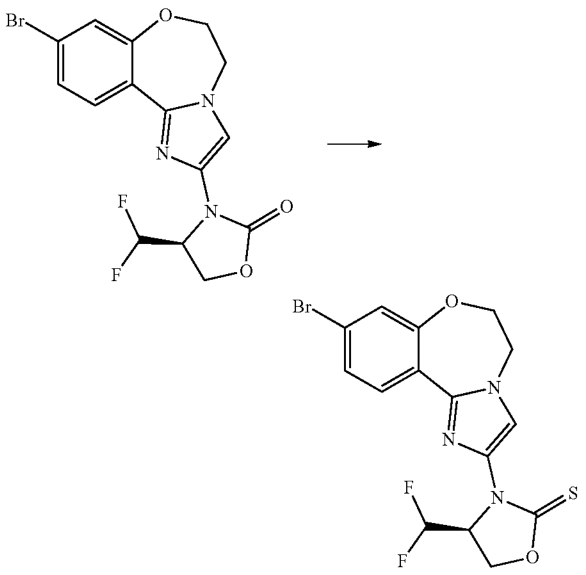

To a solution of (S)-3-(10-bromo-6,7-dihydro-5H-benzo[b]imidazo[2,1-d][1,5]oxazin-2-yl)-4-(difluoromethyl)oxazolidin-2-one (100 mg, 0.25 mmol) in toluene (10 mL) was added Lawesson's reagent (1.01 g, 2.5 mmol), and the reaction solution was microwaved at 140° C. and reacted for three hours. After cooling to room temperature, the reaction solution was filtered. The filter cake was washed with EtOAc (20 mL). The filtrate was dried over anhydrous sodium sulfate, concentrated under reduced pressure, and subjected to column chromatography to obtain the title compound (S)-3-(9-bromo-5,6-dihydrobenzo[f]imidazo[1,2-d][1,4]oxazepin-2-yl)-4-(difluoromethyl)oxazolidine-2-thione (42 mg, 40%).

$^1$H NMR (400 MHz, DMSO-$d_6$) δ 4.43-4.52 (m, 4H), 4.79-4.86 (m, 2H), 5.24-5.35 (m, 1H), 6.57-6.85 (m, 1H), 7.23-7.38 (m, 2H), 8.10 (s, 1H), 8.26 (d, J=8.6 Hz, 1H);

MS m/z (ESI): 416.1 $[M+H]^+$.

Step 2: Preparation of (R)-3-(9-bromo-5,6-dihydrobenzo[f]imidazo[1,2-d][1,4]oxazepin-2-yl)-4-(difluoromethyl)thiazolidin-2-one

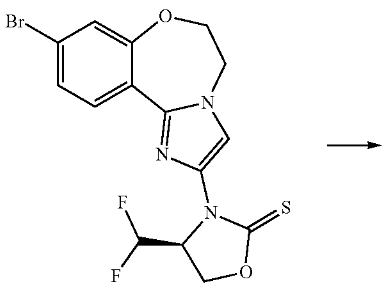

-continued

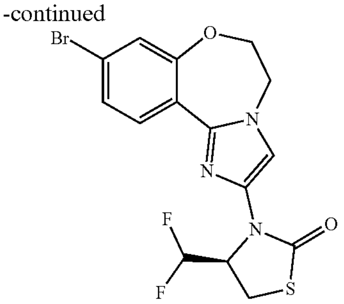

To a solution of (S)-3-(10-bromo-6,7-dihydro-5H-benzo[b]imidazo[2,1-d][1,5]oxazin-2-yl)-4-(difluoromethyl)oxazolidine-2-thione (33 mg, 0.079 mmol) in toluene (1 mL) was added dichloro(p-methylisopropylphenyl)ruthenium(II) dimer (14.7 mg, 0.024 mmol) and 2-dicyclohexylphosphine-2',6'-dimethoxybiphenyl (9.7 mg, 0.024 mmol), and the reaction was carried out under air atmosphere at 110° C. for 12 hours. The reaction solution was cooled to room temperature and diluted with EtOAc. The organic phase was washed with saturated aqueous sodium chloride solution, dried over anhydrous sodium sulfate, concentrated under reduced pressure and subjected to column chromatography to obtain the title compound (R)-3-(9-bromo-5,6-dihydrobenzo[f]imidazo[1,2-d][1,4]oxazepin-2-yl)-4-(difluoromethyl)thiazolidin-2-one (26 mg, 79%).

$^1$H NMR (400 MHz, $CDCl_3$) δ 3.57-3.72 (m, 2H), 4.28-4.41 (m, 2H), 4.44-4.47 (m, 2H) 5.14-5.24 (m, 1H), 6.29-6.67 (m, 1H), 7.14-7.25 (m, 2H), 7.42 (s, 1H), 8.21 (d, J=8.8 Hz, 1H);

MS m/z (ESI): 416.1 [M+H]$^+$.

Step 3: Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide

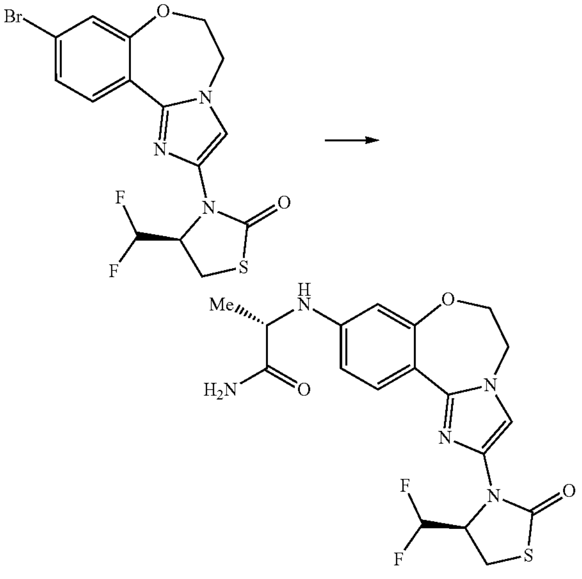

(R)-3-(9-bromo-5,6-dihydrobenzo[f]imidazo[1,2-d][1,4]oxazepin-2-yl)-4-(difluoromethyl)thiazolidin-2-one (26 mg, 0.062 mmol), L-alanine (19.5 mg, 0.22 mmol), cuprous iodide (6 mg, 0.03 mmol) and potassium phosphate (40 mg, 0.19 mmol) were mixed in dimethyl sulfoxide (3 mL). The reaction system was purged with nitrogen three times, and the reaction was carried out at 100° C. for 12 hours. The reaction solution was cooled to room temperature, then ammonium chloride (20 mg, 0.37 mmol) and triethylamine (95 mg, 0.94 mmol) were added. The reaction solution was stirred for 5 minutes, and O-(7-azabenzotriazol-1-yl)-N,N,N',N'-tetramethyluronium hexafluorophosphate (212 mg, 0.56 mmol) was added. The reaction solution was stirred at room temperature for 2 hours and filtered. Saturated aqueous sodium bicarbonate solution was added, and the reaction solution was extracted with ethyl acetate three times. The organic phases were combined, dried over anhydrous sodium sulfate, concentrated under reduced pressure, and subjected to column chromatography to obtain the title compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide (15 mg, 56%).

$^1$H NMR (400 MHz, $CD_3OD$) δ 1.37 (d, J=7.2 Hz, 3H), 3.57-3.61 (m, 1H), 3.83-3.87 (m, 2H), 4.33-4.41 (m, 4H), 5.12-5.19 (m, 1H), 6.15-6.17 (m, 1H), 6.47-6.52 (m, 2H), 7.28 (s, 1H), 8.10 (d, J=8.8 Hz, 1H);

MS m/z (ESI): 424.1 [M+H]$^+$.

Example 23

Preparation of (S)-2-((2-((S)-5-(difluoromethyl)-2-oxoimidazolidin-1-yl)-5,6-dihydrobenzo[f]imidazo[1,2-d][1,4]oxazepin-9-yl)amino)propionamide

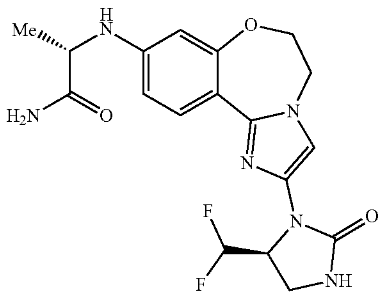 [SMILES: C[C@H](Nc1ccc2c(c1)OCCn1cc(N3C(=O)NC[C@H]3C(F)F)nc1-2)C(N)=O]

(S)-2-((2-((S)-5-(Difluoromethyl)-2-oxoimidazolidin-1-yl)-5,6-dihydrobenzo[f]imidazo[1,2-d][1,4]oxazepin-9-yl)amino)propionamide was prepared by referring to the method of Example 22.

MS m/z (ESI): 407.2 [M+H]$^+$.

Example 24

Preparation of (S)-2-((2-((S)-5-(difluoromethyl)-3-methyl-2-oxoimidazolidin-1-yl)-5,6-dihydrobenzo[f]imidazo[1,2-d][1,4]oxazepin-9-yl)amino)propionamide

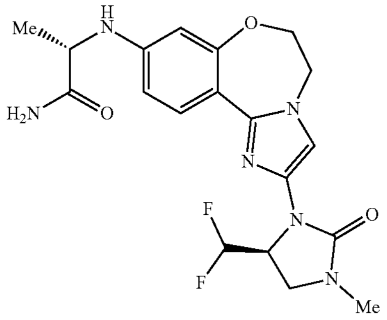 [SMILES: C[C@H](Nc1ccc2c(c1)OCCn1cc(N3C(=O)N(C)C[C@H]3C(F)F)nc1-2)C(N)=O]

(S)-2-((2-((S)-5-(Difluoromethyl)-3-methyl-2-oxoimidazolidin-1-yl)-5,6-dihydrobenzo[f]imidazo[1,2-d][1,4]oxazepin-9-yl)amino)propionamide was in accordance with Example 22.

$^1$H NMR (400 MHz, $CD_3OD$) δ 1.46 (d, J=7.0 Hz, 3H), 2.85 (s, 3H), 3.62-3.68 (m, 2H), 3.79-3.85 (m, 1H), 4.27-4.30 (m, 2H), 4.35-4.37 (m, 2H), 4.63-4.69 (m, 1H), 6.17 (d, J=2.0 Hz, 1H), 6.34-6.62 (m, 2H), 7.05 (s, 1H), 8.01 (d, J=8.8 Hz, 1H);

MS m/z (ESI): 421.2 [M+H]$^+$.

Example 25

Preparation of (S)-2-((2-((4S,5R)-4-(difluoromethyl)-5-methyl-2-oxooxazolidin-3-yl)-5,6-dihydrobenzo[f]imidazo[1,2-d][1,4]oxazepin-9-yl)amino)propionamide

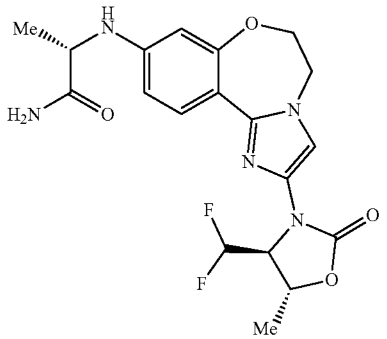 [SMILES: C[C@H](Nc1ccc2c(c1)OCCn1cc(N3C(=O)O[C@H](C)[C@H]3C(F)F)nc1-2)C(N)=O]

Step 1: Preparation of methyl (4S,5R)-5-methyl-2-oxooxazolidine-4-carboxylate

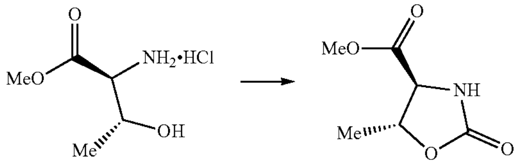

Methyl L-threoninate hydrochloride (500 mg, 2.95 mmol) was dissolved in dichloromethane (15 mL), and the resulting solution was cooled to 0° C. in an ice water bath. Triphosgene (289 mg, 0.97 mmol) was added, and a solution of ethylamine (895 mg, 8.84 mmol) in dichloromethane (2 mL) was added dropwise. After completion of addition, the reaction was carried out at 0° C. for 1 hour. Water was added, and the reaction solution extracted with dichloromethane. The organic phase was dried over anhydrous sodium sulfate, concentrated under reduced pressure to remove the organic solvent, and then the crude product was purified by column chromatography to obtain the title compound methyl (4S,5R)-5-methyl-2-oxooxazolidine-4-carboxylate (251 mg, 53%).

MS m/z (ESI): 160.1 [M+H]$^+$.

Step 2: Preparation of methyl (4S,5R)-3-benzyl-5-methyl-2-oxooxazolidine-4-carboxylate

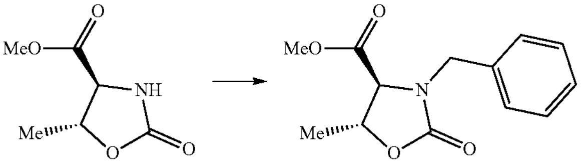 [SMILES: COC(=O)[C@H]1NC(=O)O[C@@H]1C ; COC(=O)[C@@H]1[C@@H](C)OC(=O)N1Cc1ccccc1]

Methyl (4S,5R)-5-methyl-2-oxooxazolidine-4-carboxylate (200 mg, 1.26 mmol) was dissolved in DMF (5 mL), and the resulting solution was cooled to −15° C. NaH (60% in kerosene, 50 mg, 1.26 mmol) was added, and the reaction solution was stirred at this temperature for one hour. Benzyl bromide (322 mg, 1.89 mmol) was added, and the reaction solution was stirred for 2 hours. The reaction was quenched by adding water, and the reaction solution was extracted with dichloromethane. The organic phase was dried over anhydrous sodium sulfate, concentrated under reduced pressure to remove the organic solvent, and then the crude product was purified by column chromatography to obtain the title compound methyl (4S,5R)-3-benzyl-5-methyl-2-oxooxazolidine-4-carboxylate (260 mg, 83%).

MS m/z (ESI): 250.1 [M+H]$^+$.

Step 3: Preparation of (4R,5R)-3-benzyl-4-(hydroxymethyl)-5-methyloxazolidin-2-one

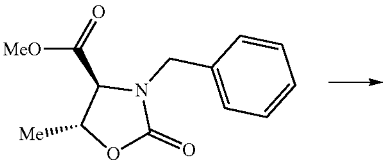

-continued

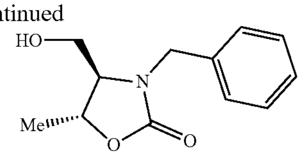

(4S,5R)-3-benzyl-5-methyl-2-oxooxazolidine-4-carboxylate (260 mg, 1.0 mmol) was dissolved in methanol (5 mL), and the resulting solution was cooled to 0° C. in an ice water bath. Sodium borohydride (11 mg, 3.1 mmol) was added in batches. The reaction solution was gradually warmed up to room temperature, and the reaction was carried out for 2 hours. The reaction solution was concentrated, and then the crude product was purified by column chromatography to obtain the title compound (4R,5R)-3-benzyl-4-(hydroxymethyl)-5-methyloxazolidin-2-one (180 mg, 78%).

MS m/z (ESI): 222.1 [M+H]$^+$.

Step 4: Preparation of (4S,5R)-3-benzyl-5-methyl-2-oxooxazolidine-4-carbaldehyde

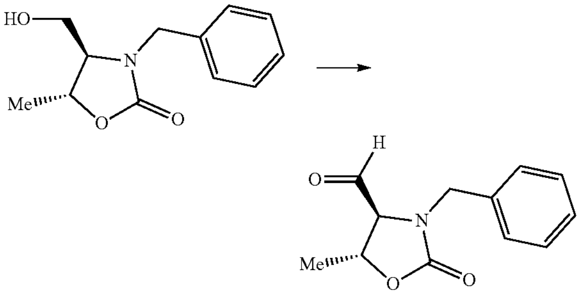

(4R,5R)-3-benzyl-4-(hydroxymethyl)-5-methyloxazolidin-2-one (180 mg, 0.81 mmol) and IBX (683 mg, 2.44 mmol) were mixed in ethyl acetate (10 mL), and the reaction was carried out under a nitrogen atmosphere at 85° C. for 3 h. After cooling, the reaction solution was filtered and concentrated under reduced pressure to obtain 178 mg of the crude product (4S,5R)-3-benzyl-5-methyl-2-oxooxazolidine-4-carbaldehyde, which was directly used in the next step.

MS m/z (ESI): 220.2 [M+H]$^+$.

Step 5: Preparation of (4S,5R)-3-benzyl-4-(difluoromethyl)-5-methyloxazolidin-2-one

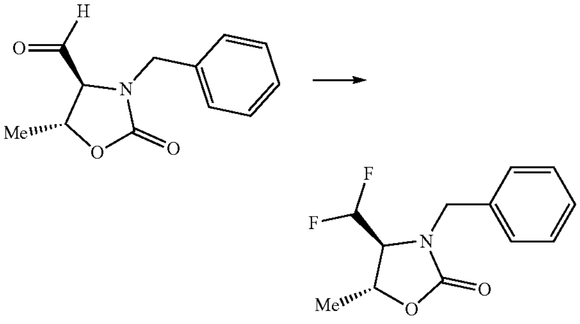

(4S,5R)-3-benzyl-5-methyl-2-oxooxazolidine-4-carbaldehyde (178 mg, 0.81 mmol) was dissolved in dichloromethane (10 mL), and the resulting solution was cooled to 0° C. under a nitrogen atmosphere in an ice water bath. DAST (262 mg, 1.62 mmol) was added dropwise, and the reaction solution was naturally warmed up to room temperature and reacted for 3 h. The reaction solution was slowly added dropwise to a pre-cooled saturated aqueous sodium bicarbonate solution, and extracted with dichloromethane (20 mL×2). The organic phases were combined, dried over anhydrous sodium sulfate, concentrated under reduced pressure to remove the organic solvent, and then subjected to column chromatography separation to obtain the title compound (4S,5R)-3-benzyl-4-(difluoromethyl)-5-methyloxazolidin-2-one (110 mg, two-step yield: 56%).

$^1$H NMR (400 MHz, $CDCl_3$) δ 1.33 (d, J=6.4 Hz, 3H), 3.27-3.33 (m, 1H), 4.16-4.20 (m, 1H), 4.41-4.64 (m, 1H), 4.91 (d, J=15.0 Hz, 1H), 5.56-5.88 (m, 1H), 7.27-7.44 (m, 5H);

MS m/z (ESI): 242.1 [M+H]$^+$.

Step 6: Preparation of (4S,5R)-4-(difluoromethyl)-5-methyloxazolidin-2-one

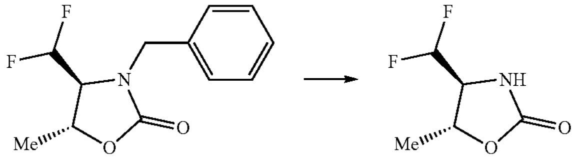 [SMILES: C[C@H]1OC(=O)N(Cc2ccccc2)[C@@H]1C(F)F ; C[C@H]1OC(=O)N[C@@H]1C(F)F]

(4S,5R)-3-benzyl-4-(difluoromethyl)-5-methyloxazolidin-2-one (110 mg, 0.46 mmol) was dissolved in mesitylene (2 mL), followed by the addition of methanesulfonic acid (438 mg, 4.56 mmol). The reaction solution was heated to 135° C., and the reaction was carried out for 5 hours. The reaction solution was cooled to room temperature, slowly added dropwise to a pre-cooled saturated aqueous sodium bicarbonate solution, and extracted with dichloromethane (20 mL×2). The organic phases were combined, dried over anhydrous sodium sulfate, concentrated under reduced pressure to remove the organic solvent, and subjected to column chromatography separation to obtain 68 mg of the crude title compound (4S,5R)-4-(difluoromethyl)-5-methyloxazolidin-2-one, which was directly used in the next step.

MS m/z (ESI): 152.1 [M+H]$^+$.

Step 7: Preparation of (4S,5R)-3-(9-bromo-5,6-dihydrobenzo[f]imidazo[1,2-d][1,4]oxazepin-2-yl)-4-(difluoromethyl)-5-methyloxazolidin-2-one

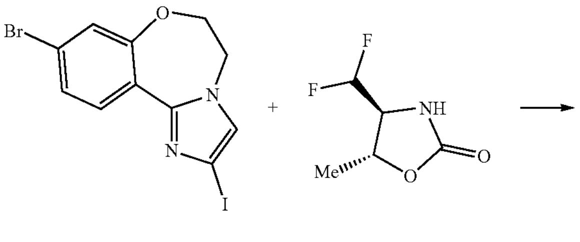

-continued

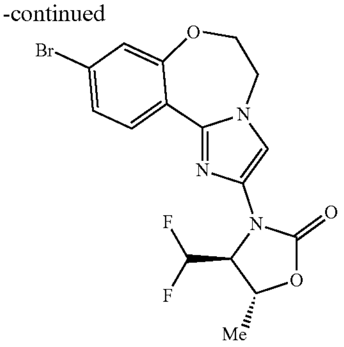

9-Bromo-2-iodo-5,6-dihydrobenzo[f]imidazo[1,2-d][1,4]oxazepine (100 mg, 0.25 mmol), (4S,5R)-4-(difluoromethyl)-5-methyloxazolidin-2-one (38.5 mg, 0.25 mmol), (1R,2R)—$N^1$,$N^2$-dimethylcyclohexane-1,2-diamine (22 mg, 0.15 mmol), cuprous iodide (14 mg, 0.08 mmol) and potassium phosphate (108 mg, 051 mmol) were mixed in dimethyl sulfoxide (3 mL), and the reaction was carried out at 130° C. for 3 hours. The reaction solution was cooled to room temperature, and 15% aqueous ammonia (5 mL) was added. The reaction solution was stirred for 5 minutes and extracted with ethyl acetate three times. The organic phases were combined, washed with saturated sodium chloride, dried over anhydrous sodium sulfate, concentrated under reduced pressure to remove the organic solvent, and then subjected to column chromatography to obtain the title compound (S)-3-(9-bromo-3-fluoro-5,6-dihydrobenzo[f]imidazo[1,2-d][1,4]oxazepin-2-yl)-4-(difluoro methyl)oxazolidin-2-one (61 mg, 57%).

MS m/z (ESI): 414.2 $[M+H]^+$.

Step 8: Preparation of (S)-2-((2-((4S,5R)-4-(difluoromethyl)-5-methyl-2-oxooxazolidin-3-yl)-5,6-dihydrobenzo[f]imidazo[1,2-d][1,4]oxazepin-9-yl)amino)propionamide

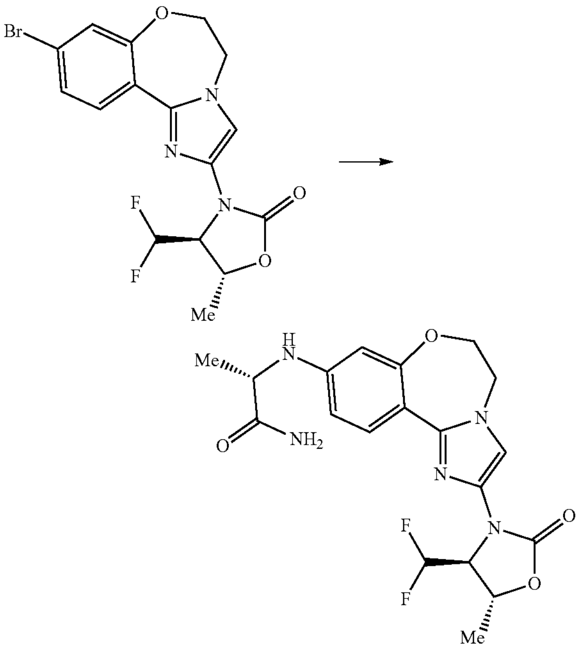

(4S,5R)-3-(9-Bromo-5,6-dihydrobenzo[f]imidazo[1,2-d][1,4]oxazepin-2-yl)-4-(difluoromethyl)-5-methyloxazolidin-2-one (61 mg, 0.15 mmol), L-alanine (39 mg, 0.44 mmol), cuprous iodide (14 mg, 0.07 mmol) and potassium phosphate (94 mg, 0.44 mmol) were mixed in dimethyl sulfoxide (5 mL). The reaction system was purged with nitrogen three times, and the reaction was carried out at 100° C. for 5 hours. The reaction solution was cooled to room temperature, then ammonium chloride (47 mg, 0.88 mmol) and triethylamine (223 mg, 2.21 mmol) were added. The reaction solution was stirred for 5 minutes, and O-(7-azabenzotriazol-1-yl)-N,N,N',N'-tetramethyluronium hexafluorophosphate (505 mg, 1.33 mmol) was added. The reaction solution was stirred at room temperature for 2 hours and filtered. Saturated aqueous sodium bicarbonate solution was added, and the reaction solution was extracted with ethyl acetate three times. The organic phases were combined, dried over anhydrous sodium sulfate, concentrated under reduced pressure to remove the organic solvent and then subjected to column chromatography separation to obtain the title compound (S)-2-((2-((S)-4-(difluoromethyl)-2-oxooxazolidin-3-yl)-6,7-dihydro-5H-benzo[b]imidazo[2,1-d][1,5]oxazin-10-yl)amino)propionamide (33 mg, 53%).

$^1H$ NMR (400 MHz, $CD_3OD$) δ 1.46 (d, J=6.8 Hz, 3H), 1.53 (d, J=6.2 Hz, 3H), 3.79-3.85 (m, 1H), 4.32-4.39 (m, 4H), 4.46-4.55 (m, 1H), 4.93-4.95 (m, 1H), 6.17 (s, 1H), 6.39-6.72 (m, 2H), 7.14 (s, 1H), 8.03 (d, J=8.6 Hz, 1H);

MS m/z (ESI): 422.1 $[M+H]^+$.

Example 26

Preparation of (R)-2-((2-((4S,5R)-4-(difluoromethyl)-5-methyl-2-oxooxazolidin-3-yl)-5,6-dihydrobenzo[f]imidazo[1,2-d][1,4]oxazepin-9-yl)amino)propionamide

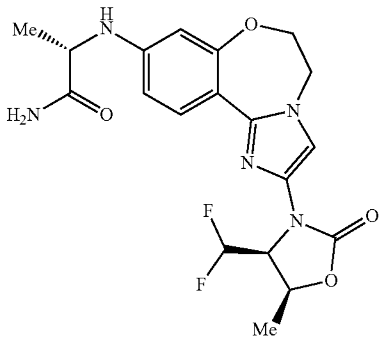 [SMILES: C[C@H](Nc1ccc2c(c1)OCCn1cc(N3C(=O)O[C@@H](C)[C@H]3C(F)F)nc1-2)C(N)=O]

(R)-2-((2-((4S,5R)-4-(Difluoromethyl)-5-methyl-2-oxooxazolidin-3-yl)-5,6-dihydrobenzo[f]imidazo[1,2-d][1,4]oxazepin-9-yl)amino)propionamide was prepared by referring to the method of Example 25.

MS m/z (ESI): 422.2 $[M+H]^+$.

Example 27

Preparation of (S)-2-((2-((S)-4-(difluoromethyl)-5,5-dimethyl-2-oxooxazolidin-3-yl)-5,6-dihydrobenzo[f]imidazo[1,2-d][1,4]oxazepin-9-yl)amino)propionamide

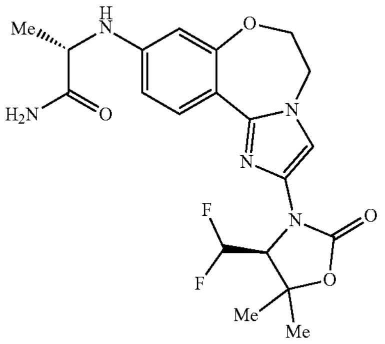 [SMILES: C[C@H](Nc1ccc2c(c1)OCCn1cc(N3C(=O)OC(C)(C)[C@H]3C(F)F)nc1-2)C(N)=O]

(S)-2-((2-((S)-4-(Difluoromethyl)-5,5-dimethyl-2-oxooxazolidin-3-yl)-5,6-dihydrobenzo[f]imidazo[1,2-d][1,4]oxazepin-9-yl)amino)propionamide was prepared by referring to the method of Example 25.

MS m/z (ESI): 436.2 [M+H]$^+$.

Example 28

Preparation of (S)-2-((2-((S)-7-(difluoromethyl)-5-oxo-4-oxa-6-azaspiro[2.4]heptan-6-yl)-5,6-dihydrobenzo[f]imidazo[1,2-d][1,4]oxazepin-9-yl)amino)propionamide

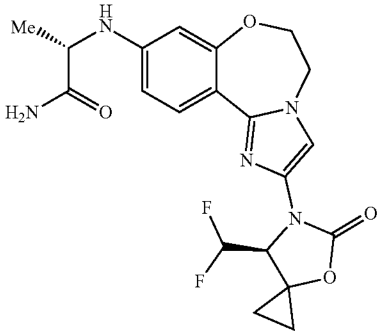 [SMILES: C[C@H](Nc1ccc2c(c1)OCCn1cc(N3C(=O)OC4(CC4)[C@H]3C(F)F)nc1-2)C(N)=O]

(S)-2-((2-((S)-7-(Difluoromethyl)-5-oxo-4-oxa-6-azaspiro[2.4]heptan-6-yl)-5,6-dihydrobenzo[f]imidazo[1,2-d][1,4]oxazepin-9-yl)amino)propionamide was prepared by referring to the method of Example 25.

MS m/z (ESI): 434.2 [M+H]$^+$.

Example 29

Preparation of (S)-2-((2-((S)-8-(difluoromethyl)-6-oxo-2,5-dioxa-7-azaspiro[3.4]octan-7-yl)-5,6-dihydrobenzo[f]imidazo[1,2-d][1,4]oxazepin-9-yl)amino)propionamide

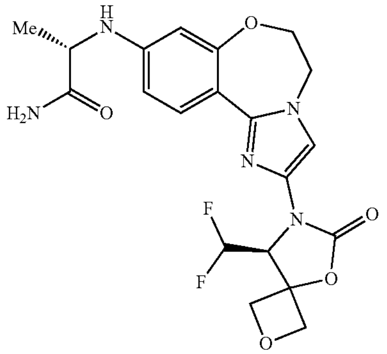 [SMILES: C[C@H](Nc1ccc2c(c1)OCCn1cc(N3C(=O)OC4(COC4)[C@H]3C(F)F)nc1-2)C(N)=O]

(S)-2-((2-((S)-8-(Difluoromethyl)-6-oxo-2,5-dioxa-7-azaspiro[3.4]octan-7-yl)-5,6-dihydrobenzo[f]imidazo[1,2-d][1,4]oxazepin-9-yl)amino)propionamide was prepared by referring to the method of Example 25.

MS m/z (ESI): 450.2 [M+H]$^+$.

Example 30

Preparation of (S)-2-((2-((S)-5-(difluoromethyl)-3-methyl-2,4-dioxoimidazolidin-1-yl)-5,6-dihydrobenzo[f]imidazo[1,2-d][1,4]oxazepin-9-yl)amino)propionamide

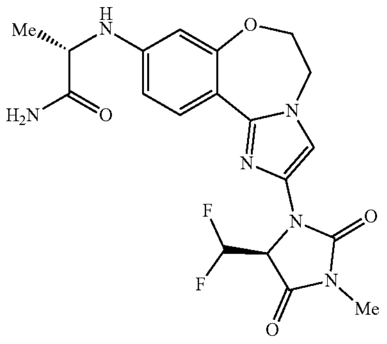 [SMILES: C[C@H](Nc1ccc2c(c1)OCCn1cc(N3C(=O)N(C)C(=O)[C@H]3C(F)F)nc1-2)C(N)=O]

(S)-2-((2-((S)-5-(Difluoromethyl)-3-methyl-2,4-dioxoimidazolidin-1-yl)-5,6-dihydrobenzo[f]imidazo[1,2-d][1,4]oxazepin-9-yl)amino)propionamide was prepared by referring to the method of Example 1.

MS m/z (ESI): 435.2 [M+H]$^+$.

Example 31

Preparation of (S)-2-((2-((S)-4-(difluoromethyl)-2-oxooxazolidin-3-yl)-8-fluoro-5,6-dihydrobenzo[f]imidazo[1,2-d][1,4]oxazepin-9-yl)amino)propionamide

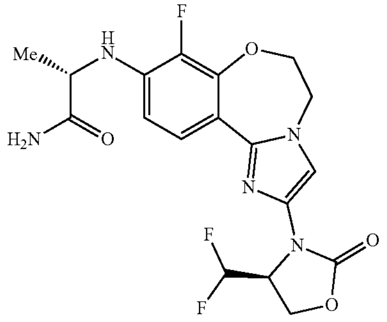 [SMILES: C[C@H](Nc1ccc2c(c1F)OCCn1cc(N3C(=O)OC[C@H]3C(F)F)nc1-2)C(N)=O]

Step 1: Preparation of 4-bromo-3-fluoro-2-methoxybenzaldehyde

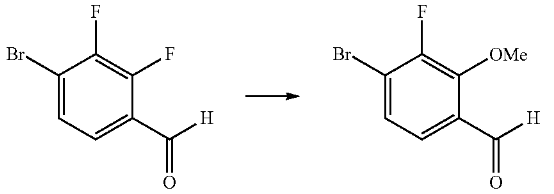 [SMILES: O=Cc1ccc(Br)c(F)c1F ; COc1c(C=O)ccc(Br)c1F]

To a solution of 4-bromo-2,3-difluorobenzaldehyde (2.0 g, 9.05 mmol) in methanol (25 mL) was added sodium methoxide (733 mg, 13.56 mmol) at room temperature, and the reaction was carried out at 65° C. for 2 h. The reaction solution was concentrated and purified by column chromatography to obtain 4-bromo-3-fluoro-2-methoxybenzaldehyde (1.78 g, 85%).

MS m/z (ESI): 233.0 $[M+H]^+$.

Step 2: Preparation of 4-bromo-3-fluoro-2-hydroxybenzaldehyde

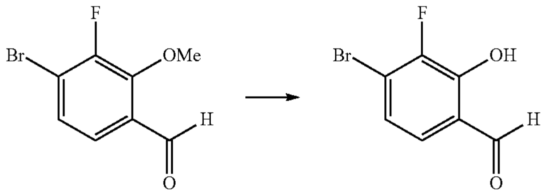 [SMILES: COc1c(C=O)ccc(Br)c1F ; O=Cc1ccc(Br)c(F)c1O]

To a solution of 4-bromo-3-fluoro-2-methoxybenzaldehyde (1.78 g, 7.67 mmol) in acetic acid (15 mL) was added hydrobromic acid (8.7 mL, 48%) at room temperature, and the reaction was carried out at 120° C. for 16 h. The reaction solution was cooled and concentrated under reduced pressure. Then water and ethyl acetate were added to the reaction flask, and then two phases were separated. The organic phase was dried over anhydrous sodium sulfate, concentrated under reduced pressure to remove the organic solvent, and then purified by column chromatography separation to obtain 4-bromo-3-fluoro-2-hydroxybenzaldehyde (1.12 g, 67%).

MS m/z (ESI): 219.0 $[M+H]^+$.

Step 3: Preparation of 3-bromo-2-fluoro-6-(1H-imidazol-2-yl)phenol

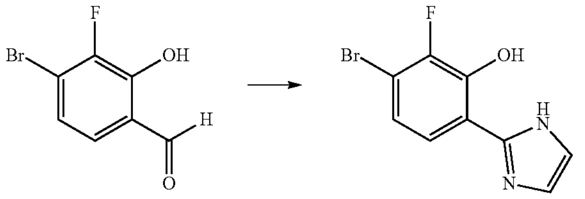 [SMILES: O=Cc1ccc(Br)c(F)c1O ; Oc1c(-c2ncc[nH]2)ccc(Br)c1F]

To a methanol solution (12 mL) of 4-bromo-3-fluoro-2-hydroxybenzaldehyde (1.12 g, 5.14 mmol) was added an aqueous glyoxal solution (40 wt. %, 3.73 g, 25.7 mmol). Then aqueous ammonia (28 wt. %, 5.14 g, 51.4 mmol) was slowly added dropwise in a water bath under stirring. The dropwise addition process lasted for 30 minutes, and the temperature of the reaction solution was controlled not to exceed 40° C. Then the mixture was stirred at 35° C. for two days, cooled, concentrated under reduced pressure to remove the organic solvent, and purified by column chromatography to obtain 3-bromo-2-fluoro-6-(1H-imidazol-2-yl)phenol (1.31 g, 100%).

MS m/z (ESI): 257.0 $[M+H]^+$.

Step 4: Preparation of 9-bromo-8-fluoro-5,6-dihydrobenzo[f]imidazo[1,2-d][1,4]oxazepine

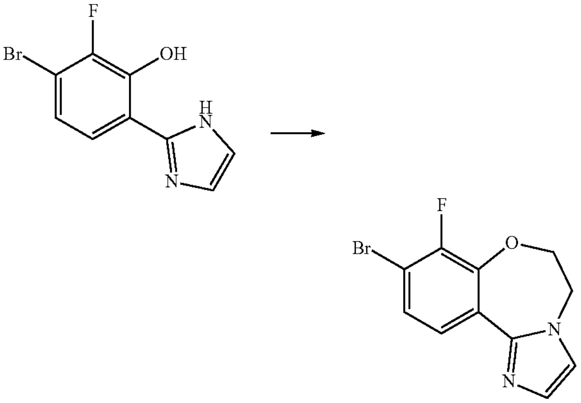

3-Bromo-2-fluoro-6-(1H-imidazol-2-yl)phenol (1.31 g, 5.14 mmol), cesium carbonate (6.3 g, 19.53 mmol) and 1,2-dibromoethane (3.6 g, 19.12 mmol) were mixed in DMF (12 mL), and the reaction solution was stirred at 85° C. overnight. The reaction solution was cooled and diluted with ethyl acetate. The organic phase was washed with saturated brine several times, then dried over anhydrous sodium sulfate, concentrated under reduced pressure to remove the organic solvent, and purified by column chromatography to obtain the title compound 9-bromo-8-fluoro-5,6-dihydrobenzo[f]imidazo[1,2-d][1,4]oxazepine (995 mg, 69%).

MS m/z (ESI): 283.0 $[M+H]^+$.

Step 5: Preparation of 9-bromo-8-fluoro-2,3-diiodo-5,6-dihydrobenzo[f]imidazo[1,2-d][1,4]oxazepine

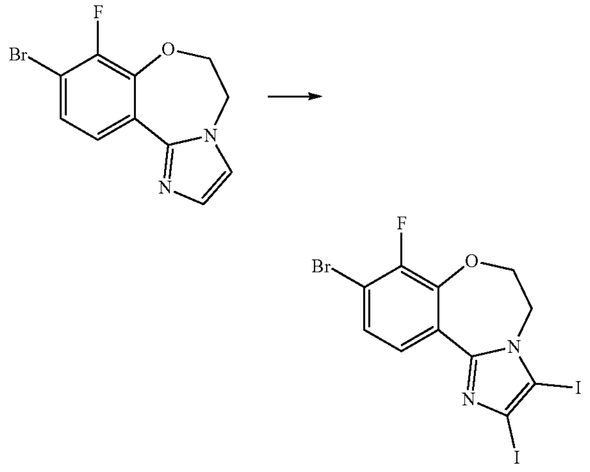

To a solution of 9-bromo-8-fluoro-5,6-dihydrobenzo[f]imidazo[1,2-d][1,4]oxazepine (995 mg, 3.53 mmol) in DMF (8 mL) was added NIS (2.23 g, 9.88 mmol) at room temperature, and the reaction solution was stirred at 60° C. overnight. The reaction solution was cooled, and water was added to precipitate a solid. After filtration, the solid was dissolved in ethyl acetate, washed with 1 M NaOH aqueous solution and saturated brine successively, dried over anhydrous sodium sulfate, and concentrated to obtain the title compound 9-bromo-8-fluoro-2,3-diiodo-5,6-dihydrobenzo[f]imidazo[1,2-d][1,4]oxazepine (1.79 g, 94%).

MS m/z (ESI): 534.7 $[M+H]^+$.

Step 6: Preparation of 9-bromo-8-fluoro-2-iodo-5,6-dihydrobenzo[f]imidazo[1,2-d][1,4]oxazepine

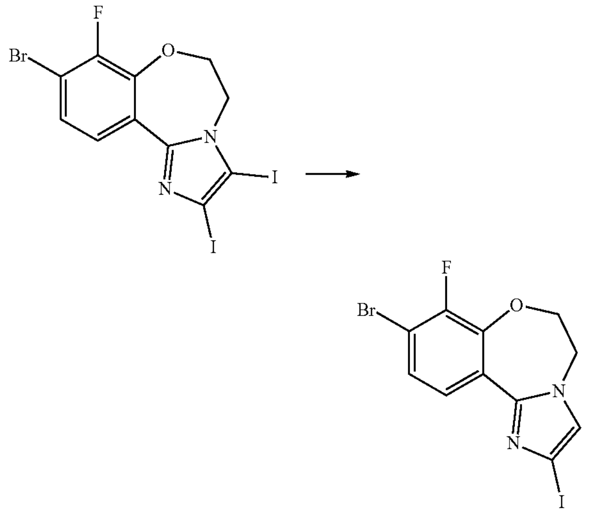

To a solution of 9-bromo-8-fluoro-2,3-diiodo-5,6-dihydrobenzo[f]imidazo[1,2-d][1,4]oxazepine (1.79 g, 3.35 mmol) in THE (10 mL) was slowly added dropwise EtMgBr (1.0 M solution in THF, 1.23 mL, 3.69 mmol) at −20° C. After completion of the dropwise addition, the reaction solution was stirred at −15° C. for 3 hours and slowly warmed up to room temperature. Then a saturated aqueous ammonium chloride solution was added dropwise. The reaction solution was stirred for 15 minutes and extracted with ethyl acetate several times. The organic phases were combined and then washed with saturated brine. The organic phase was separated and dried over anhydrous sodium sulfate, concentrated under reduced pressure to remove the organic solvent, and subjected to column chromatography separation to obtain the title compound 9-bromo-8-fluoro-2-iodo-5,6-dihydrobenzo[f]imidazo[1,2-d][1,4]oxazepine (610 mg, 45%).

MS m/z (ESI): 408.9 $[M+H]^+$.

Step 7: Preparation of (S)-4-(difluoromethyl)-3-(8-fluoro-9-iodo-5,6-dihydrobenzo[f]imidazo[1,2-d][1,4]oxazepin-2-yl)oxazolidin-2-one

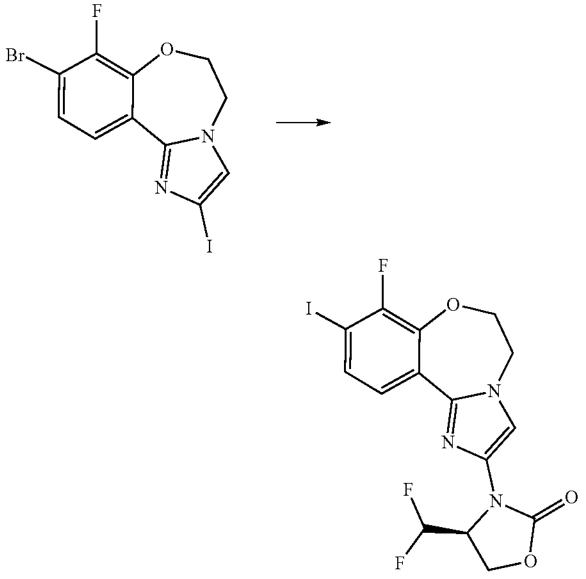

9-Bromo-8-fluoro-2-iodo-5,6-dihydrobenzo[f]imidazo[1,2-d][1,4]oxazepine (300 mg, 0.74 mmol), (S)-4-(difluoromethyl)oxazolidin-2-one (102 mg, 0.74 mmol), (1R,2R)—$N^1$,$N^2$-dimethylcyclohexane-1,2-diamine (42 mg, 0.30 mmol), cuprous iodide (28 mg, 0.15 mmol) and potassium carbonate (205 mg, 1.5 mmol) were mixed in 1,4-dioxane (6 mL). The reaction system was purged with nitrogen three times, and the reaction was carried out at 105° C. for 5 hours. The reaction solution was cooled to room temperature, and 15% aqueous ammonia was added. The reaction solution was stirred for 5 minutes and extracted with EtOAc three times. The organic phases were combined, washed with saturated aqueous sodium chloride solution, dried over anhydrous sodium sulfate, concentrated under reduced pressure, and then subjected to column chromatography to obtain the title compound (S)-4-(difluoromethyl)-3-(8-fluoro)-9-iodo-5,6-dihydrobenzo[f]imidazo[1,2-d][1,4]oxazepin-2-yl)oxazolidin-2-one (225 mg, 65%).

MS m/z (ESI): 466.0 $[M+H]^+$.

(S)-2-((2-((S)-4-(difluoromethyl)-2-oxooxazolidin-3-yl)-8-fluoro-5,6-dihydrobenzo[f]imidazo[1,2-d][1,4]oxazepin- 9-yl)amino)propionamide was prepared subsequently by referring to the method of Example 1.

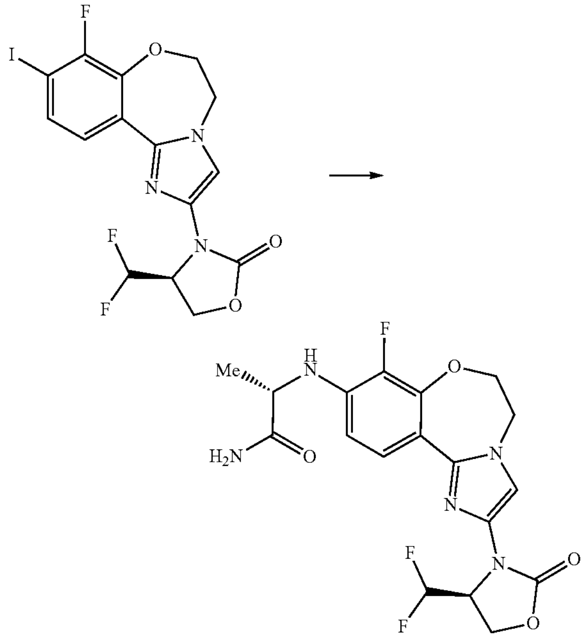

$^1$H NMR (400 MHz, $CD_3OD$) δ 1.50 (d, J=7.0 Hz, 3H), 3.95-4.01 (m, 1H), 4.36-4.41 (m, 2H), 4.47-4.53 (m, 2H), 4.57-4.67 (m, 2H), 4.93-4.98 (m, 1H), 6.37-6.42 (m, 1H), 6.44-6.73 (m, 1H), 7.20 (s, 1H), 7.87-7.91 (m, 1H);

MS m/z (ESI): 426.1 $[M+H]^+$.

Example 32

Preparation of (S)-2-((2-((S)-4-(difluoromethyl)-2-oxooxazolidin-3-yl)-11-fluoro-5,6-dihydrobenzo[f]imidazo[1,2-d][1,4]oxazepin-9-yl)amino)propionamide

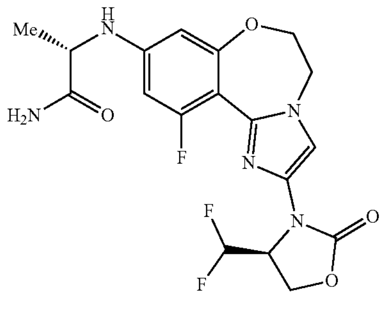 [SMILES: C[C@H](Nc1cc(F)c2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-11-fluoro-5,6-dihydrobenzo[f]imidazo[1,2-d][1,4]oxazepin-9-yl)amino)propionamide was prepared by referring to the method of Example 31.

$^1$H NMR (400 MHz, $CD_3OD$) δ 1.46 (d, J=4.0 Hz, 3H), 3.84 (m, 1H), 4.24 (m, 2H), 4.49 (m, 2H), 4.60 (m, 3H), 6.19 (s, 1H), 6.28 (d, J=8.0 Hz, 1H), 6.49 (t, J=56 Hz, 1H), 7.30 (s, 1H);

MS m/z (ESI): 426.1 $[M+H]^+$.

Example 33

Preparation of (S)-2-((2-((S)-4-(difluoromethyl)-2-oxooxazolidin-3-yl)-10-fluoro-5,6-dihydrobenzo[f]imidazo[1,2-d][1,4]oxazepin-9-yl)amino)propionamide

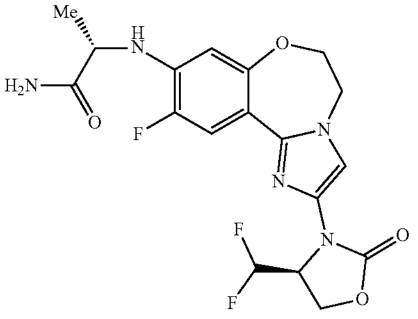 [SMILES: C[C@H](Nc1cc2c(cc1F)-c1nc(N3C(=O)OC[C@H]3C(F)F)cn1CCO2)C(N)=O]

(S)-2-((2-((S)-4-(Difluoromethyl)-2-oxooxazolidin-3-yl)-10-fluoro-5,6-dihydrobenzo[f]imidazo[1,2-d][1,4]oxazepin-9-yl)amino)propionamide was prepared by referring to the method of Example 31.

$^1$H NMR (400 MHz, $CD_3OD$): δ 1.52 (d, J=6.8 Hz, 3H), 3.86-3.96 (m, 1H), 4.30-4.42 (m, 4H), 4.60-4.69 (m, 3H), 4.91-5.00 (m, 1H), 6.19-6.25 (m, 1H), 6.46-6.76 (m, 1H), 7.18 (s, 1H), 8.04 (d, J=13.4 Hz, 1H).

MS m/z (ESI): 426.1 $[M+H]^+$.

Example 34

Preparation of (S)-2-((2-((S)-4-(difluoromethyl)-2-oxooxazolidin-3-yl)-8-methyl-5,6-dihydrobenzo[f]imidazo[1,2-d][1,4]oxazepin-9-yl)amino)propionamide

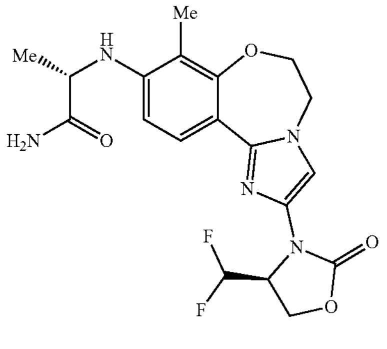 [SMILES: Cc1c(N[C@@H](C)C(N)=O)ccc2c1OCCn1cc(N3C(=O)OC[C@H]3C(F)F)nc1-2]

(S)-2-((2-((S)-4-(Difluoromethyl)-2-oxooxazolidin-3-yl)-8-methyl-5,6-dihydrobenzo[f]imidazo[1,2-d][1,4]oxazepin-9-yl)amino)propionamide was prepared by referring to the method of Example 31.

$^1$H NMR (400 MHz, $CD_3OD$) δ 1.51 (d, J=6.9 Hz, 3H), 2.15 (s, 3H), 3.99-4.02 (m, 1H), 4.33-4.37 (m, 2H), 4.43-4.47 (m, 2H), 4.55-4.68 (m, 2H), 4.93-4.97 (m, 1H), 6.36 (d, J=8.9 Hz, 1H), 6.43-6.71 (m, 1H), 7.19 (s, 1H), 7.94 (d, J=8.8 Hz, 1H);

MS m/z (ESI): 422.1 $[M+H]^+$.

Example 35

Preparation of (S)-2-((2-((S)-4-(difluoromethyl)-2-oxooxazolidin-3-yl)-11-methyl-5,6-dihydrobenzo[f]imidazo[1,2-d][1,4]oxazepin-9-yl)amino)propionamide

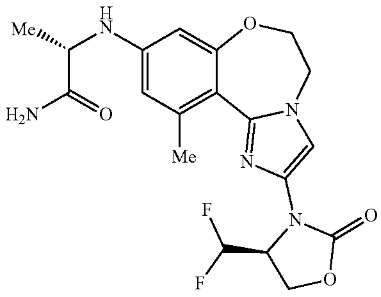 [SMILES: Cc1cc(N[C@@H](C)C(N)=O)cc2c1-c1nc(N3C(=O)OC[C@H]3C(F)F)cn1CCO2]

(S)-2-((2-((S)-4-(Difluoromethyl)-2-oxooxazolidin-3-yl)-11-methyl-5,6-dihydrobenzo[f]imidazo[1,2-d][1,4]oxazepin-9-yl)amino)propionamide was prepared by referring to the method of Example 31.

MS m/z (ESI): 422.1 $[M+H]^+$.

Example 36

Preparation of (S)-2-((2-((S)-4-(difluoromethyl)-2-oxooxazolidin-3-yl)-10-methyl-5,6-dihydrobenzo[f]imidazo[1,2-d][1,4]oxazepin-9-yl)amino)propionamide

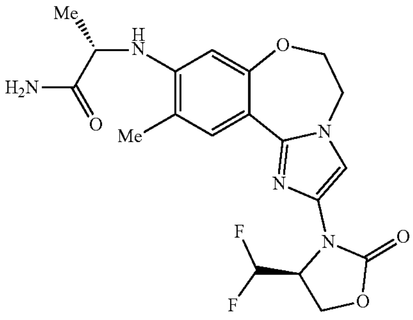 [SMILES: Cc1cc2c(cc1N[C@@H](C)C(N)=O)OCCn1cc(N3C(=O)OC[C@H]3C(F)F)nc1-2]

(S)-2-((2-((S)-4-(Difluoromethyl)-2-oxooxazolidin-3-yl)-10-methyl-5,6-dihydrobenzo [f]imidazo[1,2-d][1,4]oxazepin-9-yl)amino)propionamide was prepared by referring to the method of Example 31.

$^1H$ NMR (400 MHz, $CD_3OD$): δ 1.52 (d, J=6.9 Hz, 3H), 2.19 (s, 3H), 3.85-3.93 (m, 1H), 4.25-4.36 (m, 4H), 4.55-4.67 (m, 2H), 4.92-4.96 (m, 1H), 6.09 (s, 1H), 6.43-6.71 (m, 1H), 7.12 (s, 1H), 7.90 (s, 1H).

MS m/z (ESI): 422.1 $[M+H]^+$.

Example 37

Preparation of (S)-2-((2-((S)-4-(difluoromethyl)-2-oxooxazolidin-3-yl)-8-methoxy-5,6-dihydrobenzo[f]imidazo[1,2-d][1,4]oxazepin-9-yl)amino)propionamide

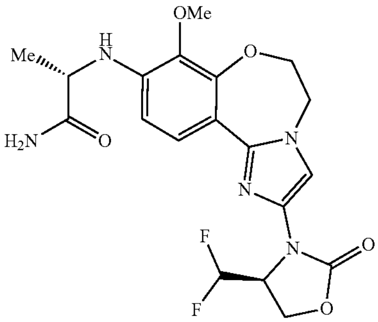

(S)-2-((2-((S)-4-(Difluoromethyl)-2-oxooxazolidin-3-yl)-8-methoxy-5,6-dihydrobenzo [f]imidazo[1,2-d][1,4]oxazepin-9-yl)amino)propionamide was prepared by referring to the method of Example 31.

MS m/z (ESI): 438.1 $[M+H]^+$.

Example 38

Preparation of (S)-2-((2-((S)-4-(difluoromethyl)-2-oxooxazolidin-3-yl)-11-methoxy-5,6-dihydrobenzo[f]imidazo[1,2-d][1,4]oxazepin-9-yl)amino)propionamide

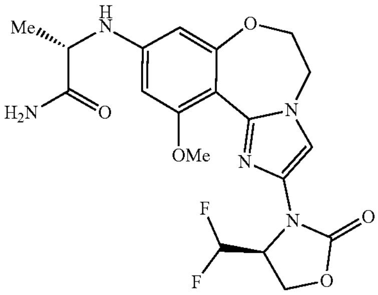 [SMILES: COc1cc(N[C@@H](C)C(N)=O)cc2c1-c1nc(N3C(=O)OC[C@H]3C(F)F)cn1CCO2]

(S)-2-((2-((S)-4-(Difluoromethyl)-2-oxooxazolidin-3-yl)-11-methoxy-5,6-dihydrobenzo[f]imidazo[1,2-d][1,4]oxazepin-9-yl)amino)propionamide was prepared by referring to the method of Example 31.

MS m/z (ESI): 438.1 $[M+H]^+$.

Example 39

Preparation of (S)-2-((2-((S)-4-(difluoromethyl)-2-oxooxazolidin-3-yl)-10-methoxy-5,6-dihydrobenzo[f]imidazo[1,2-d][1,4]oxazepin-9-yl)amino)propionamide

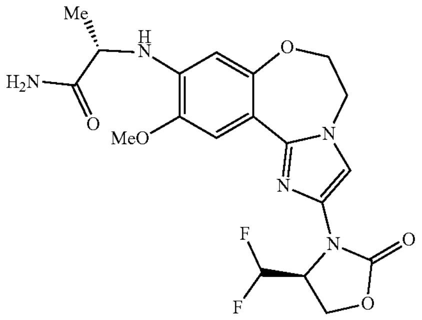 [SMILES: COc1cc2c(cc1N[C@@H](C)C(N)=O)OCCn1cc(N3C(=O)OC[C@H]3C(F)F)nc1-2]

(S)-2-((2-((S)-4-(Difluoromethyl)-2-oxooxazolidin-3-yl)-10-methoxy-5,6-dihydrobenzo[f]imidazo[1,2-d][1,4]oxazepin-9-yl)amino)propionamide was prepared by referring to the method of Example 31.

MS m/z (ESI): 438.1 $[M+H]^+$.

Example 40

Preparation of (S)-2-((8-cyano-2-((S)-4-(difluoromethyl)-2-oxooxazolidin-3-yl)-5,6-dihydrobenzo[f]imidazo[1,2-d][1,4]oxazepin-9-yl)amino)propionamide

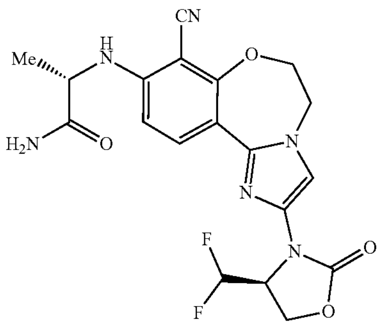 [SMILES: C[C@H](Nc1ccc2c(c1C#N)OCCn1cc(N3C(=O)OC[C@H]3C(F)F)nc1-2)C(N)=O]

(S)-2-((8-Cyano-2-((S)-4-(difluoromethyl)-2-oxooxazolidin-3-yl)-5,6-dihydrobenzo[f]imidazo[1,2-d][1,4]oxazepin-9-yl)amino)propionamide was prepared by referring to the method of Example 31.

MS m/z (ESI): 433.1 $[M+H]^+$.

Example 41

Preparation of (S)-2-((11-cyano-2-((S)-4-(difluoromethyl)-2-oxooxazolidin-3-yl)-5,6-dihydrobenzo[f]imidazo[1,2-d][1,4]oxazepin-9-yl)amino)propionamide

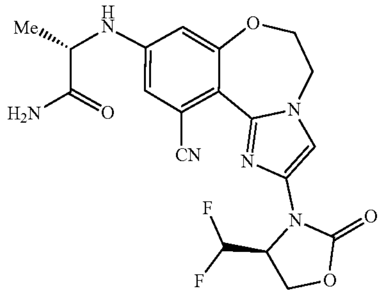 [SMILES: C[C@H](Nc1cc(C#N)c2c(c1)OCCn1cc(N3C(=O)OC[C@H]3C(F)F)nc1-2)C(N)=O]

(S)-2-((11-Cyano-2-((S)-4-(difluoromethyl)-2-oxooxazolidin-3-yl)-5,6-dihydrobenzo[f]imidazo[1,2-d][1,4]oxazepin-9-yl)amino)propionamide was prepared by referring to the method of Example 31.

MS m/z (ESI): 433.1 $[M+H]^+$.

Example 42

Preparation of (S)-2-((10-cyano-2-((S)-4-(difluoromethyl)-2-oxooxazolidin-3-yl)-5,6-dihydrobenzo[f]imidazo[1,2-d][1,4]oxazepin-9-yl)amino)propionamide

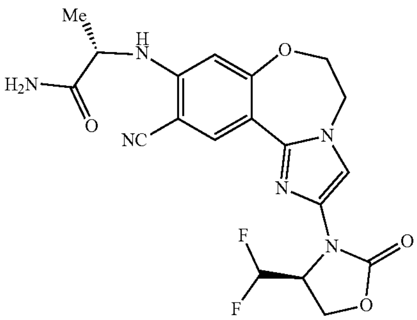 [SMILES: C[C@H](Nc1cc2c(cc1C#N)-c1nc(N3C(=O)OC[C@H]3C(F)F)cn1CCO2)C(N)=O]

(S)-2-((10-Cyano-2-((S)-4-(difluoromethyl)-2-oxooxazolidin-3-yl)-5,6-dihydrobenzo[f]imidazo[1,2-d][1,4]oxazepin-9-yl)amino)propionamide was prepared by referring to the method of Example 31.

MS m/z (ESI): 433.1 $[M+H]^+$.

Example 43

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-3-methoxypropionamide

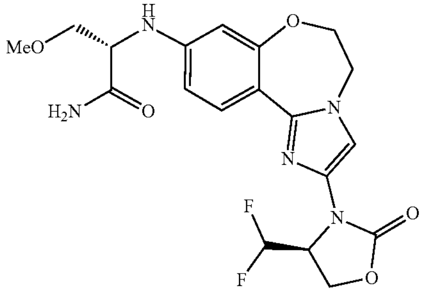 [SMILES: COC[C@H](Nc1ccc2c(c1)OCCn1cc(N3C(=O)OC[C@H]3C(F)F)nc1-2)C(N)=O]

(S)-2-((2-((S)-4-(Difluoromethyl)-2-oxooxazolidin-3-yl)-5,6-dihydrobenzo[f]imidazo[1,2-d][1,4]oxazepin-9-yl)amino)-3-methoxypropionamide was prepared by referring to the method of Example 1.

$^1$H NMR (400 MHz, $CD_3OD$) δ 3.39 (s, 3H), 3.67-3.76 (m, 2H), 3.94-3.98 (m, 1H), 4.30-4.34 (m, 2H), 4.37-4.41 (m, 2H), 4.57-4.66 (m, 2H), 4.91-4.96 (m, 1H), 6.21-6.25 (m, 1H), 6.43-6.46 (m, 1H), 6.48-6.73 (m, 1H), 7.15 (s, 1H), 8.06 (d, J=8.8 Hz, 1H);

MS m/z (ESI): 438.2 $[M+H]^+$.

Example 44

Preparation of (2S,3R)-2-((2-((S)-4-(difluoromethyl)-2-oxooxazolidin-3-yl)-5,6-dihydrobenzo[f]imidazo[1,2-d][1,4]oxazepin-9-yl)amino)-3-methoxybutanamide

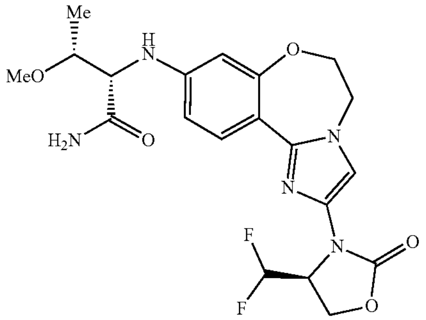 [SMILES: CO[C@H](C)[C@H](Nc1ccc2c(c1)OCCn1cc(N3C(=O)OC[C@H]3C(F)F)nc1-2)C(N)=O]

(2S,3R)-2-((2-((S)-4-(Difluoromethyl)-2-oxooxazolidin-3-yl)-5,6-dihydrobenzo[f]imidazo[1,2-d][1,4]oxazepin-9-yl)amino)-3-methoxybutanamide was prepared by referring to the method of Example 1.

$^1$H NMR (400 MHz, $CD_3OD$): δ 1.23-1.27 (d, J=6.9 Hz, 3H), 3.39 (s, 3H), 3.75-3.80 (m, 1H), 3.88-3.93 (m, 1H), 4.29-4.43 (m, 4H), 4.56-4.68 (m, 2H), 4.89-4.98 (m, 1H), 6.22-6.25 (m, 1H), 6.43-6.74 (m, 2H), 7.15 (s, 1H), 8.03-8.08 (d, J=8.8 Hz, 1H);

MS m/z (ESI): 452.2 $[M+H]^+$.

Example 45

Preparation of (2S,3S)-2-((2-((S)-4-(difluoromethyl)-2-oxooxazolidin-3-yl)-5,6-dihydrobenzo[f]imidazo[1,2-d][1,4]oxazepin-9-yl)amino)-3-methoxybutanamide

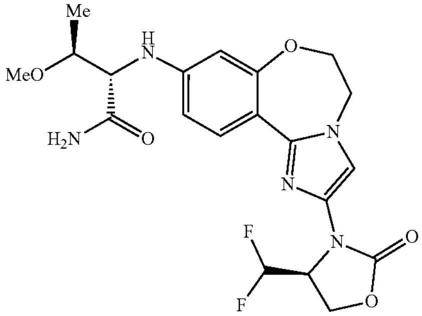 [SMILES: CO[C@@H](C)[C@H](Nc1ccc2c(c1)OCCn1cc(N3C(=O)OC[C@H]3C(F)F)nc1-2)C(N)=O]

(2S,3S)-2-((2-((S)-4-(Difluoromethyl)-2-oxooxazolidin-3-yl)-5,6-dihydrobenzo[f]imidazo[1,2-d][1,4]oxazepin-9-yl)amino)-3-methoxybutanamide was prepared by referring to the method of Example 1.

MS m/z (ESI): 452.2 $[M+H]^+$.

Example 46

Preparation of (S)-2-((2-((S)-2-(difluoromethyl)-5-oxopyrrolidin-1-yl)-5,6-dihydrobenzo[f]imidazo[1,2-d][1,4]oxazepin-9-yl)amino)propionamide

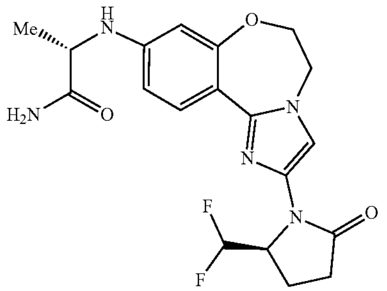 [SMILES: C[C@H](Nc1ccc2c(c1)OCCn1cc(N3C(=O)CC[C@H]3C(F)F)nc1-2)C(N)=O]

(S)-2-((2-((S)-2-(Difluoromethyl)-5-oxopyrrolidin-1-yl)-5,6-dihydrobenzo[f]imidazo[1,2-d][1,4]oxazepin-9-yl)amino)propionamide was prepared by referring to the method of Example 1.

$^1$H NMR (400 MHz, DMSO-$d_6$) δ 1.30 (d, J=8.0 Hz, 3H), 2.20-2.45 (m, 3H), 3.31 (d, J=8.0 Hz, 1H), 3.76 (t, J=7.6 Hz, 1H), 4.32-4.36 (m, 4H), 4.69-4.78 (m, 1H), 6.08 (s, 1H), 6.15 (d, J=8.0 Hz, 1H), 6.41 (d, J=8.0 Hz, 1H), 6.66 (t, J=56 Hz, 1H), 7.00 (s, 1H), 7.38 (d, J=8.0 Hz, 1H), 7.40 (s, 1H), 8.00 (d, J=8.0 Hz, 1H);

MS m/z (ESI): 406.2 $[M+H]^+$.

Example 47

Preparation of (S)-2-((2-((3S,5S)-5-(difluoromethyl)-3-methoxy-2-oxopyrrolidin-1-yl)-5,6-dihydrobenzo[f]imidazo[1,2-d][1,4]oxazepin-9-yl)amino) propionamide

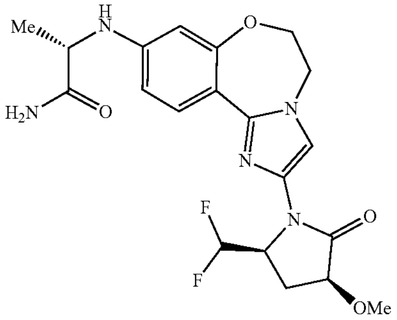 [SMILES: CO[C@H]1C[C@@H](C(F)F)N(c2cn3c(n2)-c2ccc(N[C@@H](C)C(N)=O)cc2OCC3)C1=O]

(S)-2-((2-((3S,5S)-5-(Difluoromethyl)-3-methoxy-2-oxopyrrolidin-1-yl)-5,6-dihydrobenzo[f]imidazo[1,2-d][1,4]oxazepin-9-yl)amino)propionamide was prepared by referring to the method of Example 1.

$^1$H NMR (400 MHz, $CD_3OD$) δ 1.46 (d, J=7.0 Hz, 3H), 2.10-2.20 (m, 1H), 2.74-2.84 (m, 1H), 3.57 (s, 3H), 3.81 (q, J=7.0 Hz, 1H), 4.25-4.40 (m, 5H), 4.71-4.84 (m, 1H), 6.13-6.18 (m, 1H), 6.37-6.70 (m, 2H), 7.38 (s, 1H), 8.04 (d, J=8.8 Hz, 1H);

MS m/z (ESI): 436.2 $[M+H]^+$.

Example 48

Preparation of (S)-2-((2-((3R,5S)-5-(difluoromethyl)-3-methoxy-2-oxopyrrolidin-1-yl)-5,6-dihydrobenzo[f]imidazo[1,2-d][1,4]oxazepin-9-yl)amino) propionamide

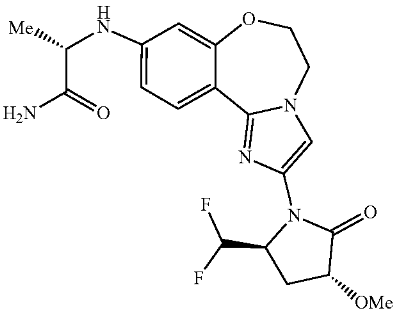 [SMILES: CO[C@@H]1C[C@@H](C(F)F)N(c2cn3c(n2)-c2ccc(N[C@@H](C)C(N)=O)cc2OCC3)C1=O]

(S)-2-((2-((3R,5S)-5-(Difluoromethyl)-3-methoxy-2-oxopyrrolidin-1-yl)-5,6-dihydrobenzo[f]imidazo[1,2-d][1,4]oxazepin-9-yl)amino)propionamide was prepared by referring to the method of Example 1.

MS m/z (ESI): 436.2 $[M+H]^+$.

Example 49

Preparation of (S)-2-((2-((S)-4-(difluoromethyl)-2-oxooxazolidin-3-yl)-5,6-dihydrobenzo[f]imidazo[1,2-d][1,4]oxazepin-9-yl)amino)-3-hydroxypropionamide

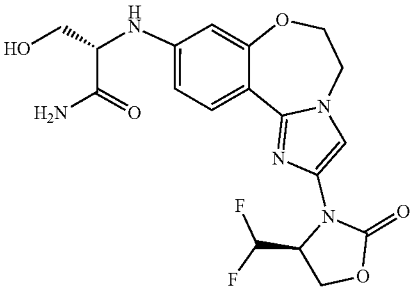 [SMILES: NC(=O)[C@H](CO)Nc1ccc2c(c1)OCCn1cc(N3C(=O)OC[C@H]3C(F)F)nc1-2]

(S)-2-((2-((S)-4-(Difluoromethyl)-2-oxooxazolidin-3-yl)-5,6-dihydrobenzo[f]imidazo[1,2-d][1,4]oxazepin-9-yl)amino)-3-hydroxypropionamide was prepared by referring to the method of Example 1.

$^1$H NMR (400 MHz, $CD_3OD$) δ 3.87 (s, 2H), 4.34 (d, J=4.3 Hz, 2H), 4.37-4.43 (m, 2H), 4.62 (m, 4H), 6.23 (d, J=2.6 Hz, 1H), 6.41-6.62 (m, 2H), 7.16 (s, 1H), 8.06 (d, J=8.8 Hz, 1H);

MS m/z (ESI): 424.1$[M+H]^+$.

Example 50

Preparation of (S)-2-((2-((R)-4-(difluoromethyl)-2-oxothiazolidin-3-yl)-8-fluoro-5,6-dihydrobenzo[f]imidazo[1,2-d][1,4]oxazepin-9-yl)amino)propionamide

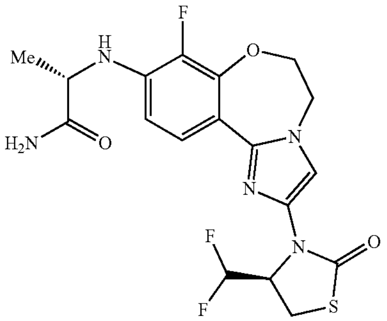 [SMILES: C[C@H](Nc1ccc2c(c1F)OCCn1cc(N3C(=O)SC[C@H]3C(F)F)nc1-2)C(N)=O]

Step 1: Preparation of 4-bromo-3-fluoro-2-methoxybenzaldehyde

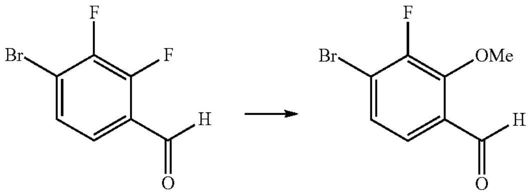 [SMILES: O=Cc1ccc(Br)c(F)c1F ; COc1c(C=O)ccc(Br)c1F]

To a solution of 4-bromo-2,3-difluorobenzaldehyde (2.0 g, 9.05 mmol) in methanol (25 mL) was added sodium methoxide (733 mg, 13.56 mmol) at room temperature. The reaction solution was warmed up to 65° C. and reacted for 2 h. The reaction solution was concentrated and purified by column chromatography to obtain 4-bromo-3-fluoro-2-methoxybenzaldehyde (1.78 g, 85%).

MS m/z (ESI): 233.0 $[M+H]^+$.

Step 2: Preparation of 4-bromo-3-fluoro-2-hydroxybenzaldehyde

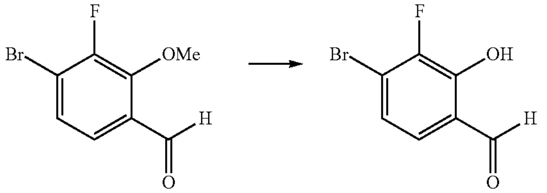 [SMILES: COc1c(C=O)ccc(Br)c1F ; O=Cc1ccc(Br)c(F)c1O]

To a solution of 4-bromo-3-fluoro-2-methoxybenzaldehyde (1.78 g, 7.67 mmol) in acetic acid (15 mL) was added hydrobromic acid (8.7 mL, 48%) at room temperature. The reaction solution was warmed up to 120° C. and reacted for 16 h. The reaction solution was cooled and then concentrated under reduced pressure. Then water and ethyl acetate were added to the reaction flask, and then two phases were separated. The organic phase was dried over anhydrous sodium sulfate, concentrated under reduced pressure to remove the organic solvent, and purified by column chromatography separation to obtain 4-bromo-3-fluoro-2-hydroxybenzaldehyde (1.12 g, 67%).

MS m/z (ESI): 219.0 $[M+H]^+$.

Step 3: Preparation of 3-bromo-2-fluoro-6-(1H-imidazol-2-yl)phenol

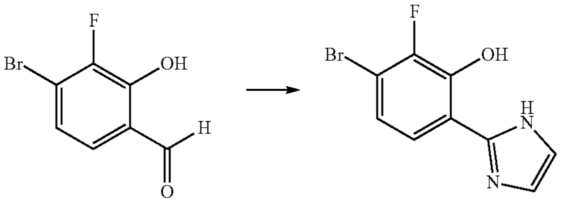 [SMILES: O=Cc1ccc(Br)c(F)c1O ; Oc1c(-c2ncc[nH]2)ccc(Br)c1F]

To a solution of 4-bromo-3-fluoro-2-hydroxybenzaldehyde (1.12 g, 5.14 mmol) in methanol (12 mL) was added an aqueous glyoxal solution (40 wt. %, 3.73 g, 25.7 mmol). Then aqueous ammonia (28 wt. %, 5.14 g, 51.4 mmol) was slowly added dropwise in a water bath under stirring. The dropwise addition process lasted for 30 minutes, and the temperature of the reaction solution was controlled not to exceed 40° C. Then the mixture was stirred at 35° C. for two days, cooled, and purified by column chromatography after removing the organic solvent under reduced pressure to obtain 3-bromo-2-fluoro-6-(1H-imidazol-2-yl)phenol (1.31 g, 100%).

MS m/z (ESI): 257.0 $[M+H]^+$.

Step 4: Preparation of 9-bromo-8-fluoro-5,6-dihydrobenzo[f]imidazo[1,2-d][1,4]oxazepine

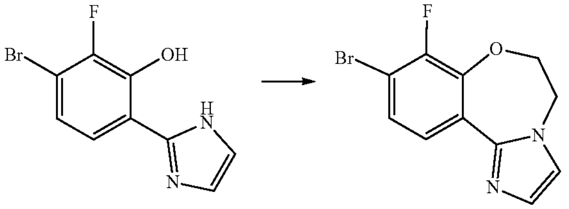 [SMILES: Oc1c(-c2ncc[nH]2)ccc(Br)c1F ; Fc1c(Br)ccc2c1OCCn1ccnc1-2]

3-Bromo-2-fluoro-6-(1H-imidazol-2-yl)phenol (1.31 g, 5.14 mmol), cesium carbonate (6.3 g, 19.53 mmol) and 1,2-dibromoethane (3.6 g, 19.12 mmol) were mixed in DMF (12 mL) and stirred at 85° C. overnight. The reaction solution was cooled and diluted with ethyl acetate. The organic phase was washed with saturated brine several times, then dried over anhydrous sodium sulfate, concentrated under reduced pressure to remove the organic solvent, and then purified by column chromatography to obtain the title compound 9-bromo-8-fluoro-5,6-dihydrobenzo[f]imidazo[1,2-d][1,4]oxazepine (995 mg, 69%).

MS m/z (ESI): 283.0 $[M+H]^+$.

Step 5: Preparation of 9-bromo-8-fluoro-2,3-diiodo-5,6-dihydrobenzo[f]imidazo[1,2-d][1,4]oxazepine

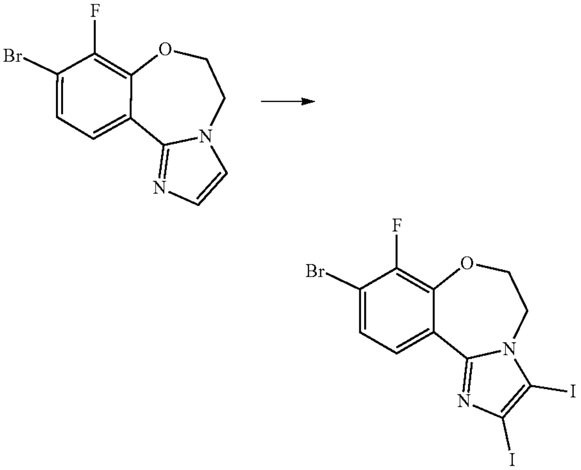

To a solution of 9-bromo-8-fluoro-5,6-dihydrobenzo[f]imidazo[1,2-d][1,4]oxazepine (995 mg, 3.53 mmol) in DMF (8 mL) was added NIS (2.23 g, 9.88 mmol) at room temperature, followed by stirring at 60° C. overnight. After cooling, water was added to precipitate a solid. After filtration, the solid was dissolved in ethyl acetate, washed with 1 M NaOH aqueous solution and saturated brine successively, dried over anhydrous sodium sulfate, and concentrated to obtain the title compound 9-bromo-8-fluoro-2,3-diiodo-5,6-dihydrobenzo[f]imidazo[1,2-d][1,4]oxazepine (1.79 g, 94%).

MS m/z (ESI): 534.7 $[M+H]^+$.

Step 6: Preparation of 9-bromo-8-fluoro-2-iodo-5,6-dihydrobenzo[f]imidazo[1,2-d][1,4]oxazepine

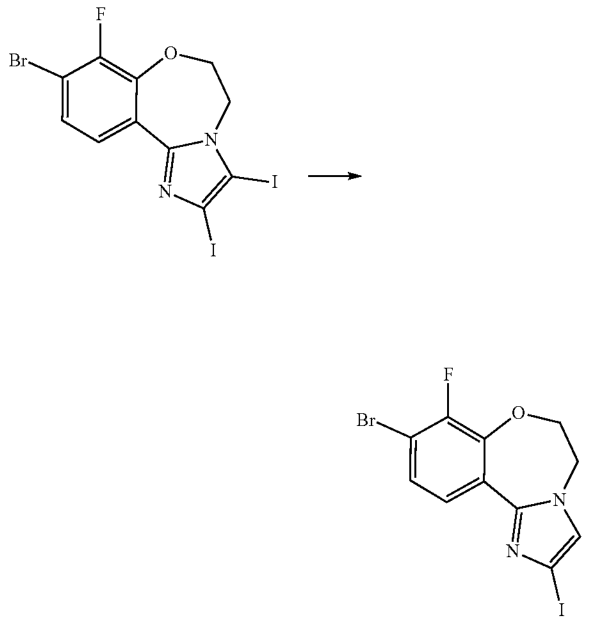

To a solution of 9-bromo-8-fluoro-2,3-diiodo-5,6-dihydrobenzo[f]imidazo[1,2-d][1,4]oxazepine (1.79 g, 3.35 mmol) in THE (10 mL) was slowly added dropwise EtMgBr (1.0 M solution in THF, 1.23 mL, 3.69 mmol) at −20° C. After completion of the dropwise addition, the mixture was stirred at −15° C. for 3 hours and slowly warmed up to room temperature. Then a saturated aqueous ammonium chloride solution was added dropwise. The reaction solution was stirred for 15 minutes and extracted with ethyl acetate several times. The organic phases were combined and then washed with saturated brine. The organic phase was separated and dried over anhydrous sodium sulfate, concentrated under reduced pressure to remove the organic solvent, and subjected to column chromatography to obtain the title compound 9-bromo-8-fluoro-2-iodo-5,6-dihydrobenzo[f]imidazo[1,2-d][1,4]oxazepine (610 mg, 45%).

MS m/z (ESI): 408.9 [M+H]$^+$.

Step 7: Preparation of (S)-4-(difluoromethyl)-3-(8-fluoro-9-iodo-5,6-dihydrobenzo[f]imidazo[1,2-d][1,4]oxazepin-2-yl)oxazolidin-2-one

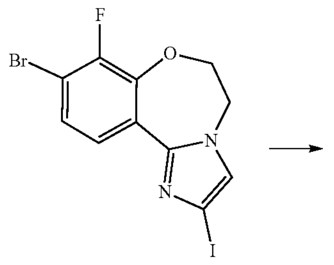

-continued

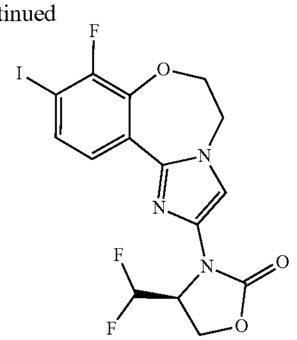

9-Bromo-8-fluoro-2-iodo-5,6-dihydrobenzo[f]imidazo[1,2-d][1,4]oxazepine (300 mg, 0.74 mmol), (S)-4-(difluoromethyl)oxazolidin-2-one (102 mg, 0.74 mmol), (1R,2R)—N$^1$,N$^2$-dimethylcyclohexane-1,2-diamine (42 mg, 0.30 mmol), cuprous iodide (28 mg, 0.15 mmol) and potassium carbonate (205 mg, 1.5 mmol) were mixed in 1,4-dioxane (6 mL). The reaction system was purged with nitrogen three times, and the reaction was carried out at 105° C. for 5 hours. The reaction solution was cooled to room temperature, and 15% aqueous ammonia was added. The reaction solution was stirred for 5 minutes and extracted with EtOAc three times. The organic phases were combined, washed with saturated aqueous sodium chloride solution, dried over anhydrous sodium sulfate, concentrated under reduced pressure, and subjected to column chromatography to obtain the title compound (S)-4-(difluoromethyl)-3-(8-fluoro)-9-iodo-5,6-dihydrobenzo[f]imidazo[1,2-d][1,4]oxazepin-2-yl)oxazolidin-2-one (225 mg, 65%).

MS m/z (ESI): 466.0 [M+H]$^+$.

Step 8: Preparation of (S)-4-(difluoromethyl)-3-(8-fluoro-9-iodo-5,6-dihydrobenzo[f]imidazo[1,2-d][1,4]oxazepin-2-yl)oxazolidine-2-thione

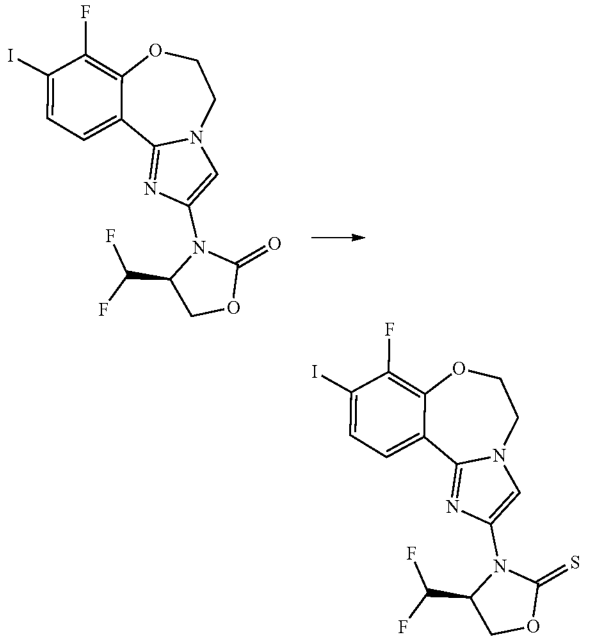

To a solution of (S)-4-(difluoromethyl)-3-(8-fluoro-9-iodo-5,6-dihydrobenzo[f]imidazo[1,2-d][1,4]oxazin-2-yl) oxazolidin-2-one (220 mg, 0.47 mmol) in toluene (20 mL) was added Lawesson's reagent (1.92 g, 4.73 mmol). The reaction solution was warmed up to 145° C., and the reaction was carried out for 6 hours. After cooling to room temperature, the reaction solution was filtered. The filter cake was washed with EtOAc (20 mL). The filtrate was dried over anhydrous sodium sulfate, concentrated under reduced pressure, and subjected to column chromatography to obtain the title compound (S)-3-(9-bromo-8-fluoro-5,6-dihydrobenzo [f]imidazo[1,2-d][1,4]oxazepin-2-yl)-4-(difluoro methyl) oxazolidine-2-thione (105 mg, 46%).

MS m/z (ESI): 482.1[M+H]$^+$.

Step 9: Preparation of (R)-4-(difluoromethyl)-3-(8-fluoro-9-iodo-5,6-dihydrobenzo[f]imidazo[1,2-d][1,4]oxazepin-2-yl)thiazolidin-2-one

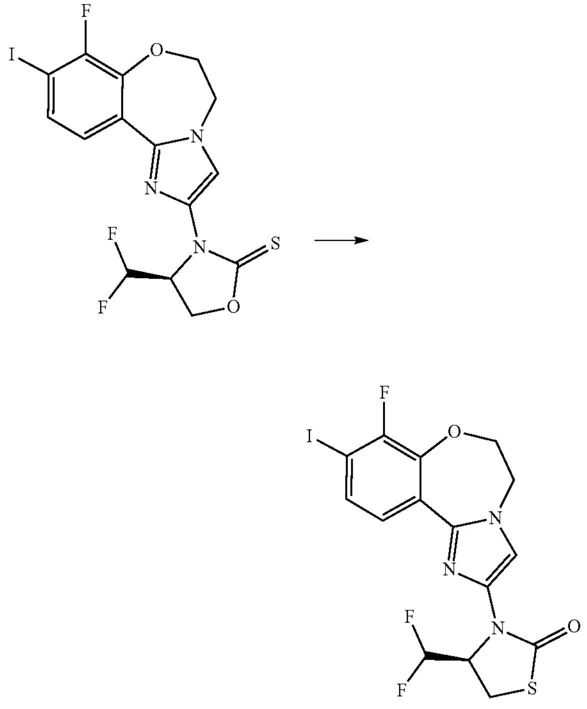 [SMILES: Fc1c(I)ccc2c1OCCn1cc(N3C(=S)OC[C@H]3C(F)F)nc1-2 ; O=C1SC[C@@H](C(F)F)N1c1cn2c(n1)-c1ccc(I)c(F)c1OCC2]

To a solution of (S)-3-(9-bromo-8-fluoro-5,6-dihydrobenzo[f]imidazo[1,2-d][1,4]oxazepin-2-yl)-4-(difluoro methyl)oxazolidine-2-thione (105 mg, 0.22 mmol) in toluene (3 mL) was added dichloro(p-methylisopropylphenyl) ruthenium(II) dipolymer (27 mg, 0.045 mmol) and 2-dicyclohexylphosphine-2',6'-dimethoxybiphenyl (27 mg, 0.065 mmol). The reaction was carried out under an air atmosphere at 115° C. for 16 hours. The reaction solution was cooled to room temperature and diluted with EtOAc. The organic phase was washed with saturated aqueous sodium chloride solution, dried over anhydrous sodium sulfate, concentrated under reduced pressure and subjected to column chromatography to obtain the title compound (R)-4-(difluoromethyl)-3-(8-fluoro-9-iodo-5,6-dihydrobenzo[f]imidazo[1,2-d][1,4]oxazepin-2-yl)thiazolidin-2-one (55 mg, 52%).

MS m/z (ESI): 482.1 [M+H]$^+$.

Step 10: Preparation of (S)-2-((2-((R)-4-(difluoromethyl)-2-oxothiazolidin-3-yl)-8-fluoro-5,6-dihydrobenzo[f]imidazo[1,2-d][1,4]oxazepin-9-yl)amino) propionamide

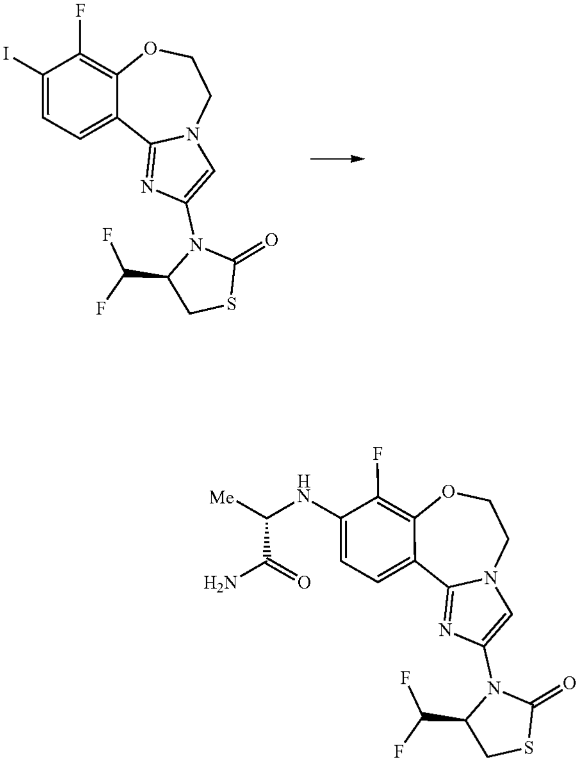 [SMILES: O=C1SC[C@@H](C(F)F)N1c1cn2c(n1)-c1ccc(I)c(F)c1OCC2 ; C[C@H](Nc1ccc2c(c1F)OCCn1cc(N3C(=O)SC[C@H]3C(F)F)nc1-2)C(N)=O]

(R)-4-(difluoromethyl)-3-(8-fluoro-9-iodo-5,6-dihydrobenzo[f]imidazo[1,2-d][1,4]oxazepin-2-yl)thiazolidin-2-one (40 mg, 0.083 mmol), L-alanine (15 mg, 0.17 mmol), cuprous iodide (6.3 mg, 0.033 mmol) and potassium phosphate (53 mg, 0.25 mmol) were mixed in dimethyl sulfoxide (3 mL). The reaction system was purged with nitrogen three times, and the reaction was carried out at 125° C. for 1.5 hours. The reaction solution was cooled to room temperature, then ammonium chloride (27 mg, 0.5 mmol) and DMAP (161 mg, 1.25 mmol) were added, The reaction solution was stirred for 5 minutes, and O-(7-azabenzotriazol-1-yl)-N,N,N',N'-tetramethyluronium hexafluorophosphate (284 mg, 0.75 mmol) was added. The reaction solution was stirred at room temperature for 2 hours and filtered. Saturated aqueous sodium bicarbonate solution was added, and the reaction solution was extracted with ethyl acetate three times. The organic phases were combined, dried over anhydrous sodium sulfate, concentrated under reduced pressure, and then subjected to column chromatography to obtain the title compound (S)-2-((2-((R)-4-(difluoromethyl)-2-oxothiazolidin-3-yl)-8-fluoro-5,6-dihydrobenzo[f] imidazo[1,2-d][1,4]oxazepin-9-yl)amino)propionamide (7.9 mg, 22%).

$^1$H NMR (400 MHz, $CD_3OD$) δ 1.49 (d, J=7.0 Hz, 3H), 3.54-3.60 (m, 1H), 3.76-3.93 (m, 1H), 3.95-4.00 (m, 1H), 4.36-4.40 (m, 2H), 4.47-4.52 (m, 2H), 5.10-5.20 (m, 1H), 6.32-6.62 (m, 2H), 7.32 (s, 1H), 7.85-7.91 (m, 1H);

MS m/z (ESI): 442.1 [M+H]$^+$.

Example 51

Preparation of (S)-2-((2-((R)-4(difluoromethyl)-2-oxothiazolidin-3-yl)-8-fluoro-5,6-dihydrobenzo[f]imidazo[1,2-d][1,4]oxazepin-9-yl)amino)-3-methoxypropionamide

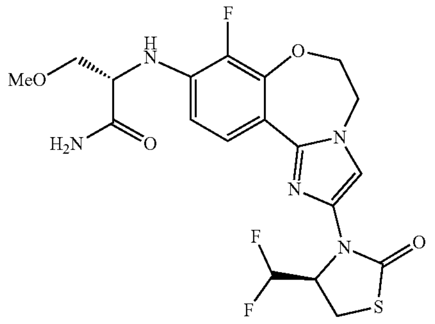 [SMILES: COC[C@H](Nc1ccc2c(c1F)OCCn1cc(N3C(=O)SC[C@H]3C(F)F)nc1-2)C(N)=O]

(S)-2-((2-((R)-4(Difluoromethyl)-2-oxothiazolidin-3-yl)-8-fluoro-5,6-dihydrobenzo[f]imidazo[1,2-d][1,4]oxazepin-9-yl)amino)-3-methoxypropionamide was prepared by referring to the method of Example 50.

$^1$H NMR (400 MHz, $CD_3OD$) δ 3.40 (s, 3H), 3.53-3.60 (m, 1H), 3.69-3.83 (m, 3H), 4.06-4.13 (m, 1H), 4.35-4.41 (m, 2H), 4.47-4.52 (m, 2H), 5.10-5.21 (m, 1H), 6.30-6.60 (m, 2H), 7.32 (s, 1H), 7.89 (d, J=8.5 Hz, 1H);

MS m/z (ESI): 472.1 $[M+H]^+$.

Example 52

Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)-3-methoxypropionamide

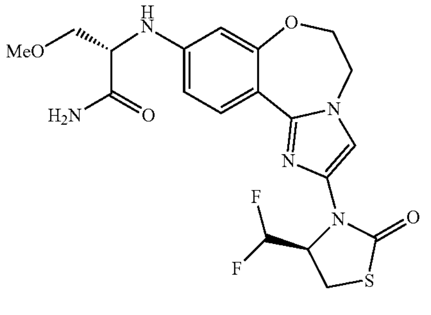 [SMILES: COC[C@H](Nc1ccc2c(c1)OCCn1cc(N3C(=O)SC[C@H]3C(F)F)nc1-2)C(N)=O]

Step 1: Preparation of (S)-2-((2-((R)-4-(difluoromethyl)-2-oxothiazolidin-3-yl)-5,6-dihydrobenzo[f]imidazo[1,2-d][1,4]oxazepin-9-yl)amino)-3-methoxypropionamide

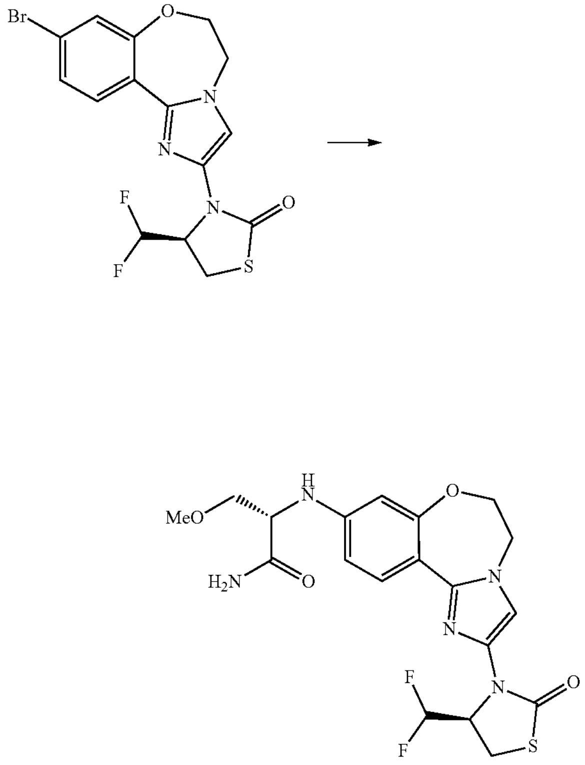 [SMILES: O=C1SC[C@@H](C(F)F)N1c1cn2c(n1)-c1ccc(Br)cc1OCC2 ; COC[C@H](Nc1ccc2c(c1)OCCn1cc(N3C(=O)SC[C@H]3C(F)F)nc1-2)C(N)=O]

(R)-3-(9-bromo-5,6-dihydrobenzo[f]imidazo[1,2-d][1,4]oxazepin-2-yl)-4-(difluoromethyl)thiazolidin-2-one (26 mg, 0.062 mmol), O-methyl-L-serine (22 mg, 0.18 mmol), cuprous iodide (6.0 mg, 0.03 mmol) and potassium phosphate (40 mg, 0.19 mmol) were mixed in dimethyl sulfoxide (3 mL). The reaction system was purged with nitrogen three times, and the reaction was carried out at 100° C. for 12 hours. The reaction solution was cooled to room temperature, then ammonium chloride (20 mg, 0.37 mmol) and triethylamine (95 mg, 0.94 mmol) were added. The reaction solution was stirred for 5 minutes, and O-(7-azabenzotriazol-1-yl)-N,N,N',N'-tetramethyluronium hexafluorophosphate (212 mg, 0.56 mmol) was added. The reaction solution was stirred at room temperature for 2 hours and filtered. Saturated aqueous sodium bicarbonate solution, and the reaction solution was extracted with ethyl acetate three times. The organic phases were combined, dried over anhydrous sodium sulfate, was concentrated under reduced pressure to remove the organic solvent, and subjected to column chromatography separation to obtain the title compound (S)-2-((2-((R)-4-(difluoromethyl)-2-oxothiazolidin-3-yl)-5,6-dihydrobenzo[f]imidazo[1,2-d][1,4]oxazepin-9-yl)amino)-3-methoxypropionamide (13 mg, 46%).

$^1$H NMR (400 MHz, $CD_3OD$) δ 3.39 (s, 3H), 3.53-3.57 (m, 1H), 3.62-3.76 (m, 3H), 3.93-3.98 (m, 1H), 4.16-4.30 (m, 4H), 5.06-5.16 (m, 1H), 6.21-6.23 (m, 1H), 6.28-6.52 (m, 2H), 7.23 (s, 1H), 8.02 (d, J=8.8 Hz, 1H);

MS m/z (ESI): 454.1 $[M+H]^+$.

Example 53

Preparation of (S)-1-(2-((R)-4-(difluoromethyl)-2-oxothiazolidin-3-yl)-5,6-dihydrobenzo[f]imidazo[1,2-d][1,4]oxazepin-9-yl)pyrrolidine-2-carboxamide

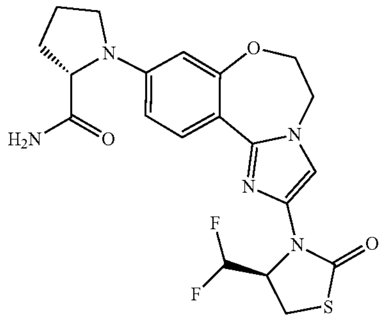 [SMILES: NC(=O)[C@@H]1CCCN1c1ccc2c(c1)OCCn1cc(N3C(=O)SC[C@H]3C(F)F)nc1-2]

(S)-1-(2-((R)-4-(Difluoromethyl)-2-oxothiazolidin-3-yl)-5,6-dihydrobenzo[f]imidazo[1,2-d][1,4]oxazepin-9-yl)pyrrolidine-2-carboxamide was prepared by referring to the method of Example 22.

$^1$H NMR (400 MHz, DMSO-$d_6$) δ 1.83-1.92 (m, 2H), 2.09-2.15 (m, 1H), 3.72-3.81 (m, 4H), 4.25-4.32 (m, 4H), 5.07-5.15 (m, 1H), 5.93-5.97 (m, 1H), 6.22-6.28 (m, 1H), 6.35-6.65 (s, 1H), 7.00 (s, 1H), 7.26 (s, 1H), 7.35 (s, 1H), 7.99 (d, J=8.6 Hz, 1H);

MS m/z (ESI): 450.1 [M+H]$^+$.

Example 54

Preparation of (S)-2-((2-((R)-4-(difluoromethyl)-2-oxothiazolidin-3-yl)-5,6-dihydrobenzo[f]imidazo[1,2-d][1,4]oxazepin-9-yl)(methyl)amino)propionamide

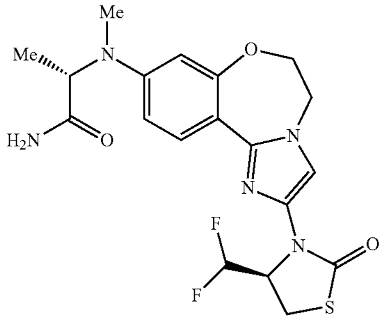 [SMILES: C[C@@H](C(N)=O)N(C)c1ccc2c(c1)OCCn1cc(N3C(=O)SC[C@H]3C(F)F)nc1-2]

(S)-2-((2-((R)-4-(Difluoromethyl)-2-oxothiazolidin-3-yl)-5,6-dihydrobenzo[f]imidazo[1,2-d][1,4]oxazepin-9-yl)(methyl)amino)propionamide was prepared by referring to the method of Example 22.

$^1$H NMR (400 MHz, $CD_3OD$) δ 1.40 (d, J=7.0 Hz, 3H), 2.90 (s, 3H), 3.53-3.58 (m, 1H), 3.75-3.80 (m, 1H), 4.30-4.44 (m, 4H), 4.46-4.51 (m, 1H), 5.08-5.18 (m, 1H), 6.22-6.41 (m, 2H), 6.51-6.73 (m, 1H), 7.28 (s, 1H), 8.11 (d, J=9.0 Hz, 1H);

MS m/z (ESI): 438.1[M+H]$^+$.

Example 55

Preparation of (2S,3R)-1-(2-((S)-4-(difluoromethyl)-2-oxooxazolidin-3-yl)-5,6-dihydrobenzo[f]imidazo[1, 2-d][1,4]oxazepin-9-yl)-3-methylpyrrolidine-2-carboxamide

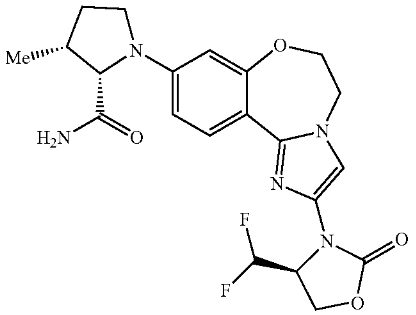 [SMILES: C[C@@H]1CCN(c2ccc3c(c2)OCCn2cc(N4C(=O)OC[C@H]4C(F)F)nc2-3)[C@@H]1C(N)=O]

(2S,3R)-1-(2-((S)-4-(Difluoromethyl)-2-oxooxazolidin-3-yl)-5,6-dihydrobenzo[f]imidazo[1,2-d][1,4]oxazepin-9-yl)-3-methylpyrrolidine-2-carboxamide was prepared by referring to the method of Example 1.

MS m/z (ESI): 448.1 [M+H]$^+$.

Example 56

Preparation of (S)-2-((2-((S)-4-(difluoromethyl)-2-oxooxazolidin-3-yl)-7-methyl-6,7-dihydro-5H-benzo[f]imidazo[1,2-d][1,4]diazoheptin-9-yl)amino)propionamide

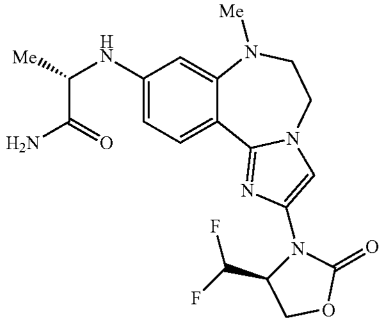 [SMILES: C[C@H](Nc1ccc2c(c1)N(C)CCn1cc(N3C(=O)OC[C@H]3C(F)F)nc1-2)C(N)=O]

Step 1: Preparation of 5-bromo-2-(1H-imidazol-2-yl)aniline

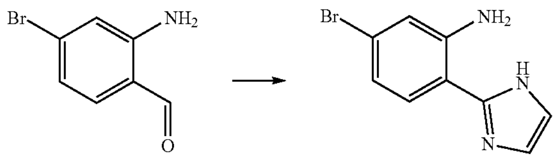 [SMILES: Nc1cc(Br)ccc1C=O ; Nc1cc(Br)ccc1-c1ncc[nH]1]

To a solution of 2-amino-4-bromobenzaldehyde (4.9 g, 24.6 mmol) in methanol (50 mL) was added an aqueous glyoxal solution (40 wt. %, 18 g, 124 mmol). Then aqueous ammonia (28 wt. %, 24 g, 172 mmol) was slowly added dropwise in a water bath under stirring. The dropwise addition process lasted for 30 minutes, and the temperature of the reaction solution was controlled not to exceed 40° C. Then the mixture was stirred at 35° C. overnight, cooled, concentrated under reduced pressure, and subjected to column chromatography to obtain the title compound 5-bromo-2-(1H-imidazol-2-yl)aniline (3.5 g, yield: 60%).

MS m/z (ESI): 238.0 $[M+H]^+$.

Step 2: Preparation of 10-bromo-5,6,7,8-tetrahydrobenzo[c]imidazo[1,2-a][1,5]diazine

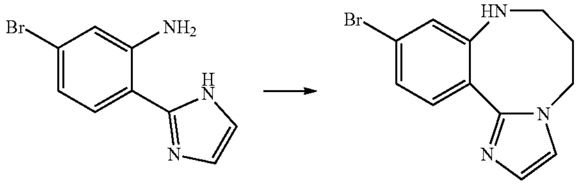 [SMILES: Nc1cc(Br)ccc1-c1ncc[nH]1 ; Brc1ccc2c(c1)NCCCn1ccnc1-2]

5-Bromo-2-(1H-imidazol-2-yl)aniline (3.3 g, 14 mmol), 1,2-dibromoethane (1.38 mL, 15.9 mmol) and cesium carbonate (10.4 g, 31.8 mmol) were mixed in N,N-dimethylformamide (50 mL), and the reaction solution was stirred at room temperature for 1.5 hours. Water was added, and the reaction solution was stirred for 5 minutes and extracted with EtOAc three times. The organic phases were combined, dried over anhydrous sodium sulfate, concentrated under reduced pressure, and then subjected to column chromatography to obtain the title compound 10-bromo-5,6,7,8-tetrahydrobenzo[c]imidazo[1,2-a][1,5]diazine (1.55 g, yield: 40%).

MS m/z (ESI): 278.0$[M+H]^+$.

Step 3: Preparation of 9-bromo-2,3-diiodo-6,7-dihydro-5H-benzo[f]imidazo[1,2-d][1,4]diazepine

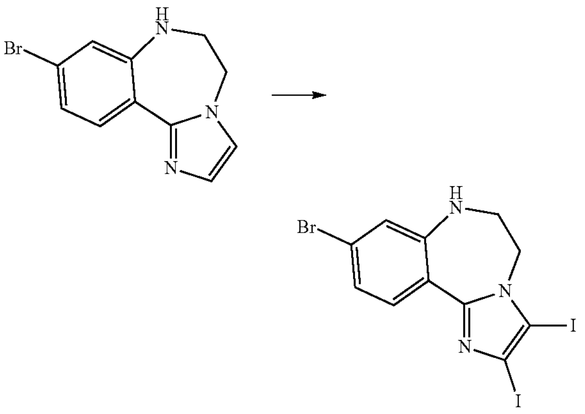

To a solution of 10-bromo-5,6,7,8-tetrahydrobenzo[c]imidazo[1,2-a][1,5]diazepine (1.55 g, 5.6 mmol) in DMF (30 mL) was added NIS (3.8 g, 16.8 mmol) in batches at room temperature, followed by stirring at 60° C. overnight. After cooling, water was added to precipitate a solid. After filtration, the solid was dissolved in ethyl acetate, washed with 1 M NaOH aqueous solution and saturated brine successively, dried over anhydrous sodium sulfate, and concentrated to obtain the title compound 9-bromo-2,3-diiodo-6,7-dihydro-5H-benzo[f]imidazo[1,2-d][1,4]diazepine (2.6 g, yield: 90.2%).

MS m/z (ESI): 515.8 $[M+H]^+$.

Step 4: Preparation of 9-bromo-2-iodo-6,7-dihydro-5H-benzo[f]imidazo[1,2-d][1,4]diazepine

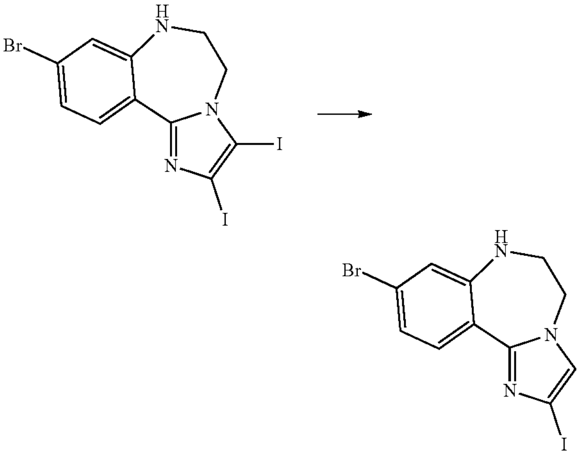

To a solution of 9-bromo-2,3-diiodo-6,7-dihydro-5H-benzo[f]imidazo[1,2-d][1,4]diazepine (2.52 g, 4.9 mmol) in THF (20 mL) was slowly added dropwise EtMgBr (1.0 M solution in THF, 10 mL, 10 mmol) at −20° C. After completion of the dropwise addition, the reaction solution was stirred at −15° C. for 3 hours and slowly warmed up to room temperature. A saturated aqueous ammonium chloride solution was added dropwise. The reaction solution was stirred for 15 minutes and extracted with ethyl acetate three times. The organic phases were combined, washed with saturated brine, dried over anhydrous sodium sulfate, concentrated and then subjected to column chromatography to obtain the title compound 9-bromo-2-iodo-6,7-dihydro-5H-benzo[f]imidazo[1,2-d][1,4]diazepine (1.52 g, yield: 80%).

MS m/z (ESI): 389.9 $[M+H]^+$.

Step 5: Preparation of (S)-3-(9-bromo-6,7-dihydro-5H-benzo[f]imidazo[1,2-d][1,4]diazoheptin-2-yl)-4-(difluoromethyl)oxazolidin-2-one

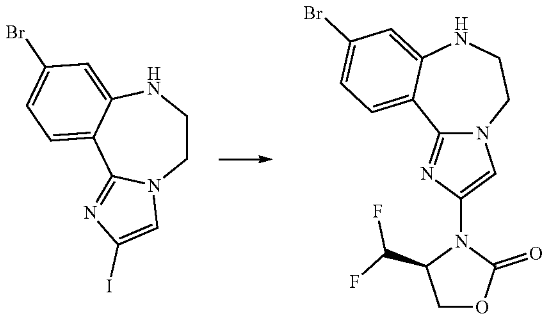 [SMILES: Brc1ccc2c(c1)NCCn1cc(I)nc1-2 ; O=C1OC[C@@H](C(F)F)N1c1cn2c(n1)-c1ccc(Br)cc1NCC2]

9-Bromo-2-iodo-6,7-dihydro-5H-benzo[f]imidazo[1,2-d][1,4]diazepine (179 mg, 0.46 mmol), (S)-4-(difluoromethyl)

oxazolidin-2-one (63 mg, 0.46 mmol), (1R,2R)—$N^1$,$N^2$-dimethylcyclohexane-1,2-diamine (28.4 mg, 0.2 mmol), cuprous iodide (19.0 mg, 0.1 mmol) and potassium carbonate (138 mg, 1.0 mmol) were mixed in 1,4-dioxane (4 mL). The reaction solution was heated to 100° C., and the reaction was carried out for 5 hours. The reaction solution was cooled to room temperature, and 14% aqueous ammonia was added. The reaction solution was stirred for 5 minutes and extracted with EtOAc three times. The organic phases were combined, washed with saturated aqueous sodium chloride solution, dried over anhydrous sodium sulfate, concentrated under reduced pressure, and then subjected to column chromatography to obtain the title compound (S)-3-(9-bromo-6,7-dihydro-5H-benzo[f]imidazo[1,2-d][1,4]diazoheptin-2-yl)-4-(difluoromethyl)oxazolidin-2-one (111 mg, yield: 60%).

MS m/z (ESI): 399.1 $[M+H]^+$.

Step 6: Preparation of (S)-3-(9-bromo-7-methyl-6,7-dihydro-5H-benzo[f]imidazo[1,2-d][1,4]diazoheptin-2-yl)-4-(difluoromethyl)oxazolidin-2-one

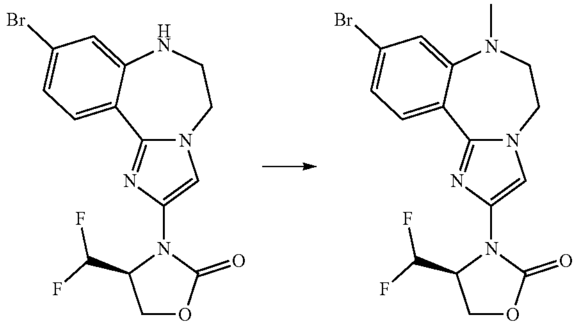 [SMILES: O=C1OC[C@@H](C(F)F)N1c1cn2c(n1)-c1ccc(Br)cc1NCC2 ; CN1CCn2cc(N3C(=O)OC[C@H]3C(F)F)nc2-c2ccc(Br)cc21]

(S)-3-(9-bromo-6,7-dihydro-5H-benzo[f]imidazo[1,2-d][1,4]diazoheptin-2-yl)-4-(difluoromethyl)oxazolidin-2-one (111 mg, 0.28 mmol) was dissolved in methanol (5 mL). A catalytic amount of acetic acid and aqueous formaldehyde (37% aqueous solution, 50 mg, 0.62 mmol) were added, and the reaction solution was stirred at room temperature for 30 minutes. Sodium cyanoborohydride (39 mg, 0.62 mmol) was added. The reaction was carried out at room temperature for 3 hours and quenched with saturated aqueous ammonium chloride solution. The reaction solution was extracted with EtOAc three times. The organic phases were combined, washed with saturated aqueous sodium chloride solution, dried over anhydrous sodium sulfate, concentrated under reduced pressure, and then subjected to column chromatography to obtain the title compound (S)-3-(9-bromo-7-methyl-6,7-dihydro-5H-benzo[f]imidazo[1,2-d][1,4]diazoheptin-2-yl)-4-(difluoromethyl)oxazolidin-2-one (81 mg, yield: 70%).

MS m/z (ESI): 413.1 $[M+H]^+$.

Step 7: Preparation of (S)-2-((2-((S)-4-(difluoromethyl)-2-oxooxazolidin-3-yl)-7-methyl-6,7-dihydro-5H-benzo[f]imidazo[1,2-d][1,4]diazoheptin-9-yl)amino)propionamide

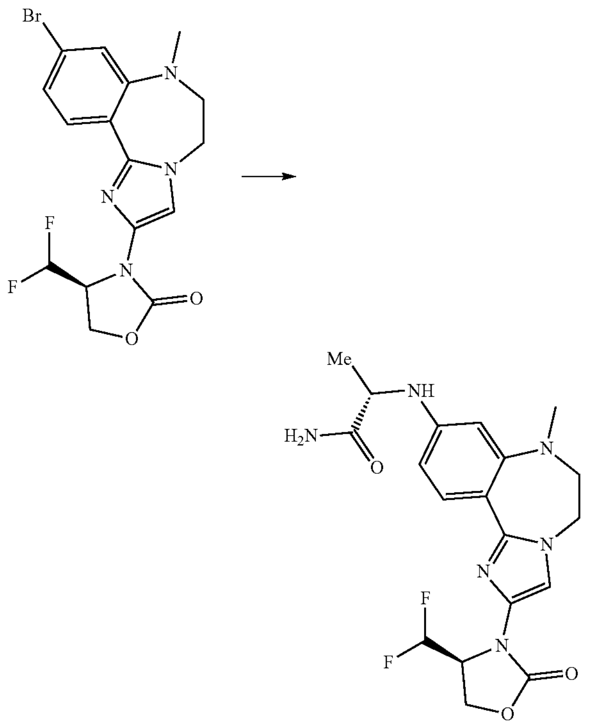

(S)-3-(9-bromo-7-methyl-6,7-dihydro-5H-benzo[f]imidazo[1,2-d][1,4]diazoheptin-2-yl)-4-(difluoromethyl)oxazolidin-2-one (49.4 mg, 0.12 mmol), L-alanine (21.4 mg, 0.24 mmol), cuprous iodide (4.6 mg, 0.024 mmol) and potassium phosphate (51.5 mg, 0.24 mmol) were mixed in dimethyl sulfoxide (2 mL), and the reaction was carried out at 100° C. for 5 hours. The reaction solution was cooled to room temperature, then ammonium chloride (39 mg, 0.72 mmol) and triethylamine (184 mg, 1.8 mmol) were added. The reaction solution was stirred for 5 minutes, and O-(7-azabenzotriazol-1-yl)-N,N,N',N'-tetramethyluronium hexafluorophosphate (418 mg, 1.1 mmol) was added. The reaction solution was stirred at room temperature for 2 hours and filtered. Saturated aqueous sodium bicarbonate solution was added, and the reaction solution was extracted with ethyl acetate three times. The organic phases were combined, dried over anhydrous sodium sulfate, concentrated under reduced pressure, and subjected to column chromatography to obtain the title compound (S)-2-((2-((S)-4-(difluoromethyl)-2-oxooxazolidin-3-yl)-7-methyl-6,7-dihydro-5H-benzo[f]imidazo[1,2-d][1,4]diazoheptin-9-yl)amino)propionamide (20 mg, yield: 40%).

$^1H$ NMR (400 MHz, $CD_3OD$) δ 1.47 (d, J=7.0 Hz, 3H), 2.95 (s, 3H), 3.43-3.50 (m, 2H), 3.86 (q, J=7.0 Hz, 1H), 4.15 (t, J=5.2 Hz, 2H), 4.54-4.67 (m, 2H), 4.90-4.95 (m, 1H), 6.18 (d, J=2.2 Hz, 1H), 6.27 (dd, J=8.7, 2.2 Hz, 1H), 6.35-6.68 (m, 1H), 7.16 (s, 1H), 7.84 (d, J=8.7 Hz, 1H);

MS m/z (ESI): 421.1 $[M+H]^+$.

Example 57

Preparation of (S)-2-((2-((S)-4-(difluoromethyl)-2-oxooxazolidin-3-yl)-6,7-dihydro-5H-benzo[f]imidazo[1,2-d][1,4]diazoheptin-9-yl)amino)propionamide

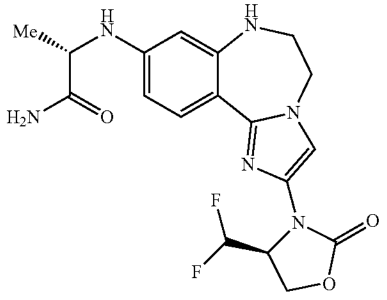 [SMILES: C[C@H](Nc1ccc2c(c1)NCCn1cc(N3C(=O)OC[C@H]3C(F)F)nc1-2)C(N)=O]

(S)-2-((2-((S)-4-(Difluoromethyl)-2-oxooxazolidin-3-yl)-6,7-dihydro-5H-benzo[f]imidazo[1,2-d][1,4]diazoheptin-9-yl)amino)propionamide was prepared by referring to the method of Example 56.

$^1$H NMR (400 MHz, $CD_3OD$) δ 1.45 (d, J=7.0 Hz, 3H), 3.42-3.49 (m, 2H), 3.78 (q, J=7.0 Hz, 1H), 4.12-4.18 (m, 2H), 4.54-4.67 (m, 2H), 4.90-4.96 (m, 1H), 5.86 (d, J=2.3 Hz, 1H), 6.17 (dd, J=8.8, 2.3 Hz, 1H), 6.32-6.62 (m, 1H), 7.05 (s, 1H), 7.91 (d, J=8.8 Hz, 1H);

MS m/z (ESI): 407.1 $[M+H]^+$.

Example 58

Preparation of (S)-2-((2-((S)-4-(difluoromethyl)-2-oxooxazolidin-3-yl)-7-ethyl-6,7-dihydro-5H-benzo[f]imidazo[1,2-d][1,4]diazoheptin-9-yl)amino)propionamide

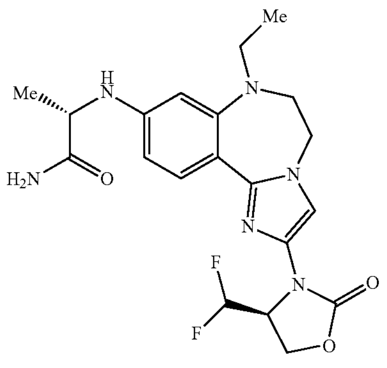 [SMILES: CCN1CCn2cc(N3C(=O)OC[C@H]3C(F)F)nc2-c2ccc(N[C@@H](C)C(N)=O)cc21]

(S)-2-((2-((S)-4-(Difluoromethyl)-2-oxooxazolidin-3-yl)-7-ethyl-6,7-dihydro-5H-benzo[f]imidazo[1,2-d][1,4]diazoheptin-9-yl)amino)propionamide was prepared by referring to the method of Example 56.

MS m/z (ESI): 435.1 $[M+H]^+$.

Example 59

Preparation of (S)-2-((2-((S)-4-(difluoromethyl)-2-oxooxazolidin-3-yl)-7-isopropyl-6,7-dihydro-5H-benzo [f]imidazo[1,2-d][1,4]diazoheptin-9-yl) amino)propionamide

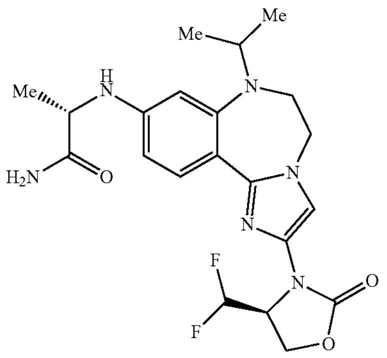 [SMILES: CC(C)N1CCn2cc(N3C(=O)OC[C@H]3C(F)F)nc2-c2ccc(N[C@@H](C)C(N)=O)cc21]

(S)-2-((2-((S)-4-(Difluoromethyl)-2-oxooxazolidin-3-yl)-7-isopropyl-6,7-dihydro-5H-benzo[f]imidazo[1,2-d][1,4]diazoheptin-9-yl)amino)propionamide was prepared by referring to the method of Example 56.

MS m/z (ESI): 449.1 $[M+H]^+$.

Example 60

Preparation of (S)-2-((7-cyclopropyl-2-((S)-4-(difluoromethyl)-2-oxooxazolidin-3-yl)-6,7-dihydro-5H-benzo[f]imidazo[1,2-d][1,4]diazoheptin-9-yl)amino) propionamide

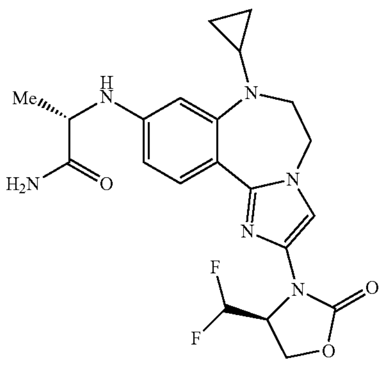 [SMILES: C[C@H](Nc1ccc2c(c1)N(C1CC1)CCn1cc(N3C(=O)OC[C@H]3C(F)F)nc1-2)C(N)=O]

(S)-2-((7-Cyclopropyl-2-((S)-4-(difluoromethyl)-2-oxooxazolidin-3-yl)-6,7-dihydro-5H-benzo[f]imidazo[1,2-d][1,4]diazoheptin-9-yl)amino)propionamide was prepared by referring to the method of Example 56.

MS m/z (ESI): 447.1 $[M+H]^+$.

Example 61

Preparation of (S)-2-((2-((S)-4-(difluoromethyl)-2-oxooxazolidin-3-yl)-7-(oxbutan-3-yl)-6,7-dihydro-5H-benzo[f]imidazo[1,2-d][1,4]diazoheptin-9-yl) amino)propionamide

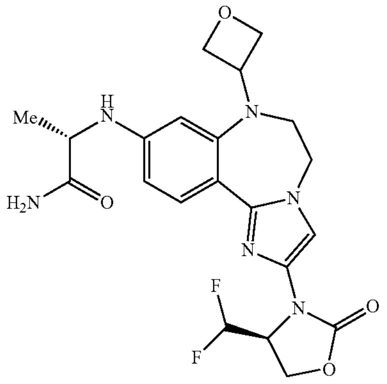 [SMILES: C[C@H](Nc1ccc2c(c1)N(C1COC1)CCn1cc(N3C(=O)OC[C@H]3C(F)F)nc1-2)C(N)=O]

(S)-2-((2-((S)-4-(Difluoromethyl)-2-oxooxazolidin-3-yl)-7-(oxbutan-3-yl)-6,7-dihydro-5H-benzo[f]imidazo[1,2-d][1,4]diazoheptin-9-yl)amino)propionamide was prepared by referring to the method of Example 56.

MS m/z (ESI): 463.1 $[M+H]^+$.

Example 62

Preparation of (S)-2-((2-((S)-4-(difluoromethyl)-2-oxooxazolidin-3-yl)-5,6-dihydrobenzo[f]imidazo[1,2-d][1,4]thiazepin-9-yl)amino)propionamide

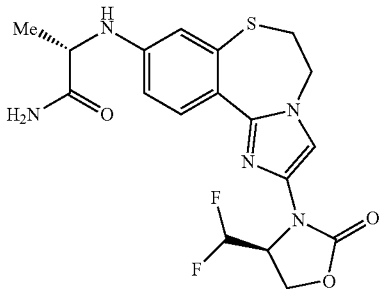 [SMILES: C[C@H](Nc1ccc2c(c1)SCCn1cc(N3C(=O)OC[C@H]3C(F)F)nc1-2)C(N)=O]

Step 1: Preparation of 2-(5-bromo-2-fluorophenyl)-1H-imidazole

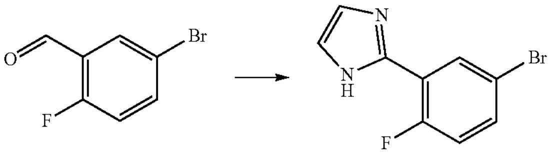 [SMILES: O=Cc1cc(Br)ccc1F ; Fc1ccc(Br)cc1-c1ncc[nH]1]

5-Bromo-2-fluorobenzaldehyde (5.0 g, 24.6 mmol) was dissolved in isopropanol/water (25 mL/25 mL) at room temperature, followed by the addition of ammonium acetate (17.6 g, 221.7 mmol) and the dropwise addition of glyoxal (4.5 mL, 221.7 mmol), and the reaction solution was stirred overnight. The reaction solution was diluted with isopropanol, filtered and then concentrated under reduced pressure. Dichloromethane and water were added to the concentrate, and two phases were separated. The organic phases were combined, and then dried over anhydrous sodium sulfate, concentrated under reduced pressure and subjected to column chromatography to obtain the title compound 2-(5-bromo-2-fluorophenyl)-1H-imidazole (3.3 g, yield: 56%).

$^1H$ NMR (400 MHz, DMSO-$d_6$) δ 8.16-8.10 (m, 1H), 7.60-7.56 (m, 1H), 7.38-7.33 (m, 1H), 7.27-7.18 (m, 2H).

MS m/z (ESI): 241.0$[M+H]^+$.

Step 2: Preparation of 9-bromo-5,6-dihydrobenzo[f]imidazo[1,2-d][1,4]thiazepine

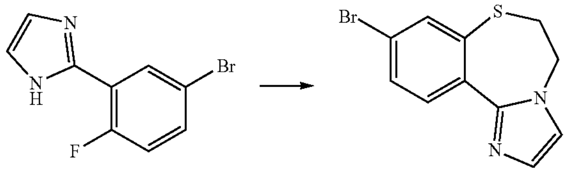 [SMILES: Fc1ccc(Br)cc1-c1ncc[nH]1 ; Brc1ccc2c(c1)SCCn1ccnc1-2]

2-(5-Bromo-2-fluorophenyl)-1H-imidazole (2.0 g, 8.4 mmol) was dissolved in N,N-dimethylformamide (10 mL), followed by the addition of sodium hydride (442 mg, 9.2 mmol) in an ice water bath, and the reaction solution was stirred for 10 minutes. Ethylene sulfide (612 mg, 10.2 mmol) was added. The reaction solution was warmed up to 95° C. and stirred for 6 hours. After cooling to room temperature, a saturated aqueous ammonium chloride solution was added to the reaction flask. The reaction solution was extracted with dichloromethane three times. The organic phases were combined, then dried over anhydrous sodium sulfate, concentrated under reduced pressure, and subjected to column chromatography to obtain the title compound 9-bromo-5,6-dihydrobenzo[f]imidazo[1,2-d][1,4]thiazepine (1.0 g, yield: 43%).

MS m/z (ESI): 281.0 $[M+H]^+$.

Step 3: Preparation of 9-bromo-2,3-diiodo-5,6-dihydrobenzo[f]imidazo[1,2-d][1,4]thiazepine

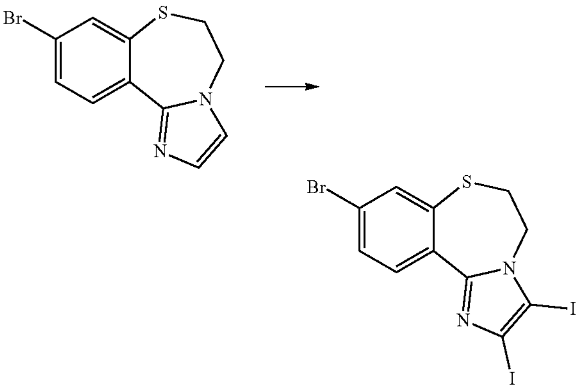

To a solution of 9-bromo-5,6-dihydrobenzo[f]imidazo[1,2-d][1,4]thiazepine (980 mg, 3.5 mmol) in DMF (20 mL)

was added NIS (2.4 g, 10.5 mmol) in batches at room temperature, followed by stirring at 60° C. overnight. After cooling, water was added to precipitate a solid. After filtration, the solid was dissolved in ethyl acetate, washed with 1 M NaOH aqueous solution and saturated brine successively, dried over anhydrous sodium sulfate, and concentrated to obtain the title compound 9-bromo-2,3-diiodo-5,6-dihydrobenzene[f]imidazo[1,2-d][1,4]thiazepine (1.6 g, yield: 86%).

MS m/z (ESI): 532.8 $[M+H]^+$.

Step 4: Preparation of 9-bromo-2-iodo-5,6-dihydrobenzo[f]imidazo[1,2-d][1,4]thiazepine

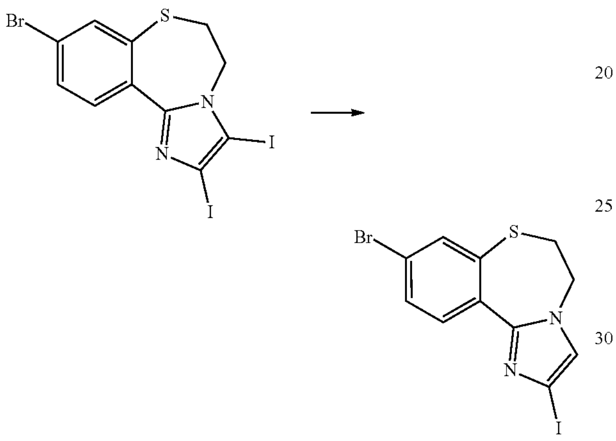

To a solution of 9-bromo-2,3-diiodo-5,6-dihydrobenzo[f]imidazo[1,2-d][1,4]thiazepine (1.6 g, 3.0 mmol) in THE (10 mL) was slowly dropwise added EtMgBr (1.0 M solution in THF, 3.3 mL, 3.3 mmol) at −20° C. After completion of the dropwise addition, the reaction solution was stirred at −15° C. for 3 hours and slowly warmed up to room temperature. A saturated aqueous ammonium chloride solution was added dropwise. The reaction solution was stirred for 15 minutes and extracted with ethyl acetate three times. The organic phases were combined, washed with saturated brine, dried over anhydrous sodium sulfate, concentrated and then subjected to column chromatography to obtain the title compound 9-bromo-2-iodo-5,6-dihydrobenzo[f]imidazo[1,2-d][1,4]thiazepine (1.03 g, yield: 85%).

MS m/z (ESI): 406.9 $[M+H]^+$.

Step 5: Preparation of (S)-3-(9-bromo-5,6-dihydrobenzo[f]imidazo[1,2-d][1,4]thiazepin-2-yl)-4-(difluoromethyl)oxazolidin-2-one

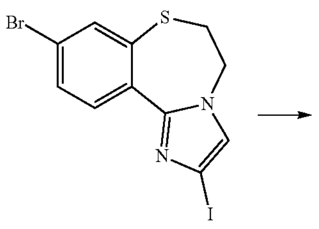

-continued

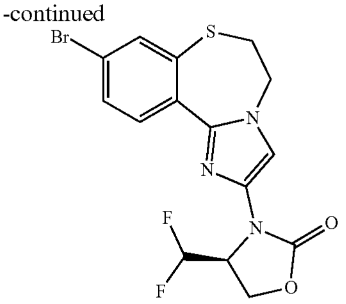

9-Bromo-2-iodo-5,6-dihydrobenzo[f]imidazo[1,2-d][1,4]thiazepine (186.7 mg, 0.46 mmol), (S)-4-(difluoromethyl)oxazolidin-2-one (63 mg, 0.46 mmol), (1R,2R)—$N^1$,$N^2$-dimethylcyclohexane-1,2-diamine (28.4 mg, 0.2 mmol), cuprous iodide (19.0 mg, 0.1 mmol) and potassium carbonate (138 mg, 1.0 mmol) were mixed in 1,4-dioxane (4 mL), and the reaction was carried out at 100° C. for 5 hours. The reaction solution was cooled to room temperature, and 14% aqueous ammonia was added. The reaction solution was stirred for 5 minutes and extracted with EtOAc three times. The organic phases were combined, washed with saturated aqueous sodium chloride solution, dried over anhydrous sodium sulfate, concentrated under reduced pressure, and then subjected to column chromatography to obtain the title compound (S)-3-(9-bromo-5,6-dihydrobenzo[f]imidazo[1,2-d][1,4]thiazepin-2-yl)-4-(difluoromethyl)oxazolidin-2-one (124 mg, yield: 65%).

MS m/z (ESI): 416.0 $[M+H]^+$.

Step 6: Preparation of (S)-2-((2-((S)-4-(difluoromethyl)-2-oxooxazolidin-3-yl)-5,6-dihydrobenzo[f]imidazo[1,2-d][1,4]thiazepin-9-yl)amino)propionamide

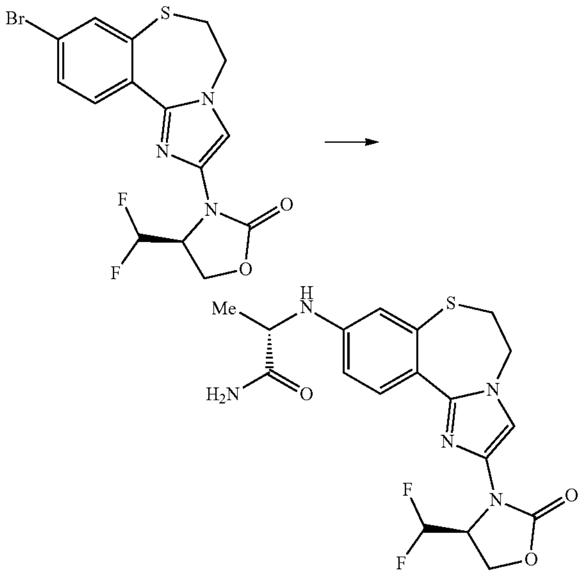

(S)-3-(9-bromo-5,6-dihydrobenzo[f]imidazo[1,2-d][1,4]thiazepin-2-yl)-4-(difluoromethyl)oxazolidin-2-one (49.8 mg, 0.12 mmol), L-alanine (21.4 mg, 0.24 mmol), cuprous iodide (4.6 mg, 0.024 mmol) and potassium phosphate (51.5 mg, 0.24 mmol) were mixed in dimethyl sulfoxide (2 mL), and the reaction was carried out at 100° C. for 5 hours. The reaction solution was cooled to room temperature, then ammonium chloride (39 mg, 0.72 mmol) and triethylamine (184 mg, 1.8 mmol) were added. The reaction solution was stirred for 5 minutes, and O-(7-azabenzotriazol-1-yl)-N,N,N',N'-tetramethyluronium hexafluorophosphate (418 mg, 1.1 mmol) was added. The reaction solution was stirred at room temperature for 2 hours and filtered. Saturated aqueous sodium bicarbonate solution was added, and the reaction solution was extracted with ethyl acetate three times. The organic phases were combined, dried over anhydrous sodium sulfate, concentrated under reduced pressure, and then subjected to column chromatography to obtain the title compound (S)-2-((2-((S)-4-(difluoromethyl)-2-oxooxazolidin-3-yl)-5,6-dihydrobenzo[f]imidazo[1,2-d][1,4]thiazepin-9-yl)amino)propanamide (18 mg, yield: 35%).

$^1$H NMR (400 MHz, $CDCl_3$) δ 1.56 (d, J=7.0 Hz, 3H), 3.44-3.52 (m, 2H), 3.84-3.92 (m, 1H), 4.12-4.21 (m, 2H), 4.48-4.56 (m, 1H), 4.68-4.74 (m, 1H), 4.88-5.02 (m, 1H), 5.36 (s, 1H), 6.40 (s, 1H), 6.45-6.77 (m, 2H), 6.83-6.88 (m, 1H), 7.33 (s, 1H), 7.61 (d, J=8.4 Hz, 1H);

MS m/z (ESI): 424.1 $[M+H]^+$.

II. Biological Assay and Evaluation of the Compounds

The present invention will be further described with reference to the following test examples, but these examples do not limit the scope of the present invention.

1. Determination of the Inhibitory Effect of the Compounds of the Examples of the Present Invention on PI3Kα/β/γ/δ Kinase Activity 1.1 Experimental Objective:

The objective of this test example was to test the inhibitory activity of the compounds of the examples on PI3Kα/β/γ/δ kinase activity.

1.2 Experimental Instruments:

The centrifuge (5810R) was purchased from Eppendorf.

The pipettes were purchased from Eppendorf or Rainin.

The microplate reader was purchased from BioTek, USA, model: SynergyH1 Hybrid Multi-Mode Microplate Reader.

1.3 Experimental Method:

In this experiment, ADP-Glo Lipid Kinase Assay (Promega #V9102) from Promega was used. The lipid kinases PI3Kα/β/γ/δ catalyzed the ATP-to-ADP reaction in the presence of the substrate PIP2:3PS and ATP. The lipid kinase activity was characterized by measuring the ADP content in the reaction, and the half inhibition concentrations $IC_{50}$ of the compounds on PI3Kα/β/γ/δ kinase activity were obtained.

The specific experimental process was as follows:

Kinase reactions were carried out in white 384-well plates (Perkin Elmer #6007299). 2 μL of the compound of various concentrations diluted with $ddH_2O$ containing 1% DMSO was added to each well, and 2 μL of $ddH_2O$ containing 1% DMSO was added to positive control wells. Then 2 μL of 0.1 to 2 nM PI3K kinase solution diluted with 5× kinase buffer (HEPES 250 mM, $MgCl_2$ 15 mM, NaCl 250 mM, BSA 0.05%) was added to each well, and 2 μL of 5× kinase buffer was added to the negative control wells. 4 μL of 50 μM substrate PIP2:3PS (Promega #V1701) prepared with 10× Dilution buffer and $ddH_2O$ was added to all wells. Finally, 2 μL of 50 to 100 μM ATP solution diluted with water was added to start the reaction. After the reaction was carried out at room temperature for 90 to 120 minutes, 10 L of ADP-Glo Reagent (containing 10 mM $MgCl_2$) was added to each well, and the reaction was carried out at room temperature for 60 minutes to eliminate excess adenosine triphosphate (ATP) in the reaction. Then 20 μL of Kinase Detection Reagent was added to each well. After the reaction was carried out for 20 minutes at room temperature in the dark, the chemiluminescence was measured by BioTek Synergy H1 microplate reader.

| Name of enzyme | Catalog No. | Enzyme reaction concentration | Enzyme reaction time | ATP concentration |
|---|---|---|---|---|
| PI3Kα | Promega #V1721 | 0.1 nM | 120 min | 50 μM |
| PI3Kβ | Carna #11-102 | 0.4 nM | 90 min | 100 μM |
| PI3Kγ | Thermofisher #PV4786 | 0.4 nM | 120 min | 50 μM |
| PI3Kδ | Carna #11-103 | 0.1 nM | 90 min | 100 μM |

Experimental Data Processing Method:

The percentage inhibition data of the compound-treated well was calculated from positive control wells (DMSO control wells) and negative control wells (no kinase added) on the plate {% inhibition=100−[(test compound value−negative control value)]/(positive control value-negative control value)×100}. $IC_{50}$ values were calculated using GraphPad prism and using a four-parameter nonlinear logistic formula to fit the data of different concentrations and corresponding percent inhibition.

1.4 Experimental Conclusion:

According to the above scheme, the compounds of the examples of the present invention showed biological activities in the PI3Kα/β/γ/δ kinase activity test as shown in Table 7 below.

TABLE 7

| Example | PI3Kα, $IC_{50}$ (nM) | PI3Kβ, $IC_{50}$ (nM) | PI3Kγ, $IC_{50}$ (nM) | PI3Kδ, $IC_{50}$ (nM) | Selectivity of PI3Kα vs PI3Kβ | Selectivity ofPI3Kα vs PI3Kγ | Selectivity of PI3Kα vs PI3Kδ |
|---|---|---|---|---|---|---|---|
| Example 1 | 7.9 | >10000 | 1788 | 1398 | >1266 | 226 | 177 |
| Example 14 | 4 | 1432 | 447 | 410 | 358 | 112 | 103 |
| Example 19 | 0.86 | 283 | 557 | 25 | 329 | 648 | 29 |
| Example 22 | 0.2 | 168 | 90 | 49 | 840 | 450 | 245 |
| Example 24 | 5 | 6190 | 402 | 373 | 1238 | 80 | 75 |
| Example 25 | 1.2 | 1799 | 481 | 336 | 1499 | 401 | 280 |
| Example 26 | 1.7 | 1872 | 363 | 213 | 1101 | 214 | 125 |
| Example 31 | 5.2 | 924 | 450 | 306 | 178 | 87 | 59 |
| Example 32 | 5.2 | 2786 | 510 | 459 | 536 | 98 | 88 |
| Example 46 | 2.1 | 1649 | 510 | 190 | 785 | 243 | 90 |
| Example 50 | 2.4 | 472 | 247 | 194 | 197 | 103 | 81 |
| Example 51 | 6.8 | 1069 | 1154 | 348 | 157 | 170 | 51 |
| Example 52 | 1 | 754 | 376 | 139 | 754 | 376 | 139 |

TABLE 7-continued

| Example | PI3Kα, $IC_{50}$ (nM) | PI3Kβ, $IC_{50}$ (nM) | PI3Kγ, $IC_{50}$ (nM) | PI3Kδ, $IC_{50}$ (nM) | Selectivity of PI3Kα vs PI3Kβ | Selectivity ofPI3Kα vs PI3Kγ | Selectivity of PI3Kα vs PI3Kδ |
|---|---|---|---|---|---|---|---|
| Example 53 | 2.9 | 1227 | 736 | 125 | 423 | 254 | 43 |
| Example 54 | 2.2 | 523 | 478 | 69 | 238 | 217 | 31 |
| Example 56 | 0.5 | 168 | 90 | 49 | 336 | 180 | 98 |
| Example 62 | 0.1 | 102 | 50 | 28 | 1020 | 500 | 280 |

The above data show that the compounds of the examples of the present invention have good activity and selectivity in terms of PI3Kα/β/γ/δ kinase activity.

2. Determination of the Proliferation Inhibitory Effect of the Compounds of the Examples of the Present Invention on the PI3Kα Mutant Cancer Cells 2.1 Experimental Objective:

The objective of this test example was to test the proliferation inhibitory activity of the example compounds on PI3Kα mutant cancer cells HCC1954 (H1047R), HGC-27 (E542K) and MKN1 (E545K).

2.2 Experimental Instruments:

The centrifuge (5702R) was purchased from Eppendorf.

The carbon dioxide incubator was purchased from Thermo.

The biological safety cabinet was purchased from Shanghai Boxun.

The pipettes were purchased from Eppendorf or Rainin.

The microplate reader was purchased from BioTek, USA, model: SynergyH1 Hybrid Multi-Mode Microplate Reader.

2.3 Experimental Method:

The proliferation inhibitory effect of the compounds of the examples on the PI3Kα mutant cancer cell lines (HCC1954, HGC-27 and MKN1) was detected by Cell Titer-Glo method. Cell lines were cultured in RPMI 1640 medium (Gibco #22400089) containing 10% FBS (Gibco #10091148) and 1% P/S (Hyclone #SV30010) under the condition of 37° C. and 5% $CO_2$. The cells were collected before the experiment, and the cell density was adjusted after cell counting. The cells were seeded in a white 96-well plate (Corning #3610) at a density of 1000 to 10000 cells/well, and incubated in an incubator at 37° C. and 5% $CO_2$ overnight. The prepared compound solutions of different concentrations and the corresponding solvent controls were added to the plate. The plate was again incubated in an incubator at 37° C. and 5% $CO_2$ for 48 to 96 hours. Then the cell plate and its contents were equilibrated to room temperature. 20 to 100 μL of Cell Titer-Glo solution (Promega #G7573) was added to each well, and the plate was shaken and mixed well, then incubated at room temperature for 5 to 30 minutes in the dark. The chemiluminescence was measured by a SynergyH1 microplate reader from BioTek.

2.4 Experimental Data Processing Method:

The percentage inhibition data of the compound-treated well was calculated from solvent control wells on the plate {% inhibition=100−(test compound value−solvent control value)×100}. $IC_{50}$ values were calculated using GraphPad prism and using a four-parameter nonlinear logistic formula to fit the data of different concentrations and corresponding percent inhibition.

2.5 Experimental Conclusion of the Experiment:

According to the above scheme, the compounds of the examples of the present invention showed biological activities in the test of the proliferation inhibitory activity on the PI3Kα mutant cancer cells HCC1954 (H1047R), HGC-27 (E542K) and MKN1 (E545K), as shown in Table 8 below.

TABLE 8

| Example | HCC1954 (H1047R) $IC_{50}$ (nM) | MKN1 (E545K) $IC_{50}$ (nM) | HGC-27(E542K) $IC_{50}$ (nM) |
|---|---|---|---|
| Example 14 | 204 | 615 | 417 |
| Example 19 | 112 | 214 | 169 |
| Example 21 | 205 | 399 | 396 |
| Example 22 | 21 | 60 | 40 |
| Example 25 | 79 | 84 | 93 |
| Example 26 | 160 | 508 | 325 |
| Example 31 | 226 | 653 | 499 |
| Example 43 | 222 | 368 | 531 |
| Example 46 | 184 | 268 | 186 |
| Example 50 | 98 | 118 | 233 |
| Example 51 | 243 | 426 | 455 |
| Example 52 | 57 | 109 | 137 |
| Example 53 | 40 | 66 | 77 |
| Example 54 | 29 | 42 | 32 |
| Example 56 | 50 | 104 | 110 |
| Example 62 | 13 | 25 | 22 |

The above data show that the compounds of the examples of the present invention have good activity in terms of the proliferation inhibitory activity on the PI3Kα mutant cancer cells HCC1954 (H1047R), HGC-27 (E542K) and MKN1 (E545K).

3. Toxicity Test of a 7-Day Repeatedly Intragastric Administration in SD Rats 3.1 Experimental Objective The objective of this study was to investigate the possible toxic reactions of GDC-0077, the compounds of Example 22 and Example 62 in SD rats after a 7-day repeatedly intragastric administration, and to compare the differences in the toxicity of GDC-0077, the compounds of Example 22 and Example 62.

3.2 Experimental Materials and Instruments 3.2.1 Test Compounds

Test compound 1: GDC-0077

Test compound 2: the compounds of Example 22 and Example 62

3.2.2 Vehicle

Name: 20% aqueousSBE-β-CD (Captisol) solution 3.2.3 Animal Information

Species & strains: Sprague-Dawley (SD) rat

Animal grade: SPF grade

Number and sex of animals: 160 rats, half male and half female.

3.2.4 Instruments

The ADVIA®2120 series Hematology System with Autoslide was used for blood cell counting;

The SYSMEX CA-500 Coagulation Analyzer was used for the detection of coagulation function indicators;

The TBA-120FR Automated Biochemical Analyzer was used for the detection of blood biochemical indicators;

The Easylyte Electrolyte Analyzer was used for the detection of electrolytes;

The liquid mass spectrometry detector model API4000;

The electron spray ionization (ESI) positive ion mode and column type Agilent ZORBAX XDB-C18 (3.5 μm, 2.1×50 mm) were used for bioanalytical detection of plasma samples.

3.3 Experimental Method

1) In the experiment, 160 rats (80 rats/sex) were divided into 20 groups according to their sex and body weight, wherein 100 rats were used for toxicology study (groups 1 to 10, 5 rats/sex/group) and 60 rats were used for toxicokinetic study (groups 11 to 20, 3 rats/sex/group);
2) As the vehicle control group, the animals in groups 1 and 11 were intragastrically administered 20% aqueous SBE-β-CD (Captisol) solution;
3) The animals in groups 2 and 12, groups 3 and 13, and groups 4 and 14 were intragastrically administered 10, 30 and 60 mg/kg of GDC-0077, respectively;
4) The animals in groups 5 and 15, groups 6 and 16, and groups 7 and 17 were intragastrically administered 10, 30 and 60 mg/kg of the compound of Example 22, respectively;
5) The animals in groups 8 and 18, groups 9 and 19, groups 10 and 20 were intragastrically administered 10, 30 and 60 mg/kg of the compound of Example 62, respectively;
5) The animals were administered once a day for 7 consecutive days (the animals in groups 7, 17, 10 and 20 were administered for 6 consecutive days).
6) The administration volume was 10 mL/kg.
7) During the experiment, items such as clinical observation, body weight, food intake, clinicopathological indicators (blood cell count, coagulation function, blood biochemistry), toxicokinetics and the like were studied.
8) All animals were euthanized on Day 8 (the animals in groups 7, 10, 17 and 20 were euthanized after administration on Day 6).
9) During the experiment, gross anatomical observation was performed on the animals in groups 1 to 10, animals in groups 17 and 20, and dead animals (including animals in toxicological study). Histopathological examination was performed on abnormal tissues, gastrointestinal tissues (such as colon, cecum) and immune tissues (such as thymus).

3.4 Experimental Conclusion

At the dose of 30 mg, the average systemic exposure AUC of the compound of Example 22 after the last administration (male: 11400 h*ng/mL, female: 15900 h*ng/mL) was about 2.4 to 3.8 times that of GDC-0077 at the same dose (male: 3000 h*ng/mL, female: 6510 h*ng/mL), and was similar to that of GDC-0077 at the dose of 60 mg/kg after the first administration (male: 15400 h*ng/mL, female: 22800 h*ng/mL).

At the dose of 10 mg, the average systemic exposure AUC of the compound of Example 22 after the last administration (male: 2110 h*ng/mL, female: 3170 h*ng/mL) was about 1.4 to 2.5 times that of GDC-0077 (male: 845 h*ng/mL, female: 2250 h*ng/mL).

Therefore, the systemic exposure of the compound of Example 22 was significantly higher than that of GDC-0077 at the same dose.

Under the conditions of this experiment, the test compounds GDC-0077 and Example 22 were administered repeatedly intragastrically to SD rats for 7 days at the doses of 10, 30 and 60 mg/kg (once/day). The lethal dose of GDC-0077 and the compound of Example 22 was 60 mg/kg, and the maximum tolerated dose (MTD) was 30 mg/kg. At the dose of 30 mg/kg, the $C_{max}$ and $AUC_{(0-24\ h)}$ of the compound of Example 22 were significantly higher than those of GDC-0077. The tolerance of the compound of Example 22 was better than that of GDC-0077.

Under the conditions of this experiment, the test compounds GDC-0077, Example 22 and Example 62 were administered repeatedly intragastrically to SD rats for 7 days at the doses of 10, 30 and 60 mg/kg for 7 days (once/day). The $C_{max}$ and $AUC_{(0-24\ h)}$ of the compounds of Example 22 and Example 62 were significantly higher than those of GDC-0077. The tolerance of the compound of Example 22 and Example 62 were better than that of GDC-0077.

4. In Vivo Efficacy Test of the Compounds of the Examples of the Present Invention 4.1 Experimental Objective The objective is to screen the compounds with more significant efficacy and less toxic and side effects through in vivo efficacy experiments.

4.2 Main Experimental Instruments and Materials 4.2.1 Instruments:

1. Biological safety cabinet (BSC-130011 A2, Shanghai Boxun Medical Biological Instrument Corp.)
2. Ultra-clean workbench (CJ-2F, Suzhou Fengshi Laboratory Animal Equipment Co., Ltd.)
3. $CO_2$ incubator (Thermo-311)
4. Centrifuge (Centrifuge 5702R, Eppendorf)
5. Automatic cell counter (Countess II, Life)
6. Pipettes (10-20 μL, Eppendorf)
7. Microscope (TS2, Nikon)
8. Vernier caliper (CD-6" AX, Mitutoyo, Japan)
9. Cell culture flasks (T75/T225, Corning)
10. Electronic balance (CPA2202S, Sartorius)

4.2.2 Reagents:

1. RPMI-1640 medium (22400-089, Gibco)
2. Fetal bovine serum (FBS) (10091-148, Gibco)
3. 0.25% Trypsin (25200-056, Gibco)
4. Penicillin-streptomycin double antibiotics (15140-122, Gibco)
5. Phosphate buffered saline (PBS) (10010-023, Gibco)
6. Matrigel Matrix (356234, Corning)

4.2.3 Animals:

BALB/c nude mice (6 to 8 weeks old, ♀) were purchased from Shanghai Xipuer-Bikai Laboratory Animal Co., Ltd.

4.3 Experimental Process 4.3.1 Cell Culture and Preparation of Cell Suspension a. A strain of HCC1954 cell was taken from the cell bank, recovered with RPMI-1640 medium (RPMI-1640+10% FBS+1% SP), plated in a cell culture flask (cell type, date, name of the experimenter and the like were labeled on the wall of the flask) and cultured in a $CO_2$ incubator (the temperature was 37° C. and the $CO_2$ concentration was 5% in the incubator).
b. Cells were passaged when they covered 80 to 90% of the bottom of the culture flask. After passage, the cells continued to be cultured in the $CO_2$ incubator. This process was repeated until the number of cells was sufficient for the in vivo efficacy test.
c. The cultured cells were collected and counted with an automatic cell counter, and then resuspended with PBS and Matrigel Matrix according to the counting results to prepare a cell suspension (density $5\times10^7$/mL), which was placed in an ice box for use.

4.3.2 Cell Inoculation a. The nude mice were labeled with disposable universal ear tags for rats and mice before inoculation.
b. During the inoculation, the cell suspension was mixed well. 0.1 to 1 mL of the cell suspension was drawn with a 1 mL syringe, air bubbles were removed, and then the syringe was placed on an ice pack for use.

c. The nude mouse was bound with the left hand. The position on the right side of the back close to the right shoulder of the nude mouse (inoculation site) was disinfected with 75% alcohol. Inoculation started after 30 seconds.

d. The test nude mice were successively inoculated (each mouse was inoculated with 0.1 mL of cell suspension).

4.3.3 Tumor Measurement, Grouping and Administration of Tumor-Bearing Mice a. According to the tumor growth, the tumors was measured on 14 to 18 days after inoculation, and the tumor size was calculated.

Calculation of tumor volume: tumor volume ($mm^3$)= length (mm)×width (mm)×width (mm)/2 b. The tumor-bearing mice were grouped according to their body weight and tumor size by random grouping.

c. The test compounds were administered according to the grouping results (administration route: oral administration; administration dose: 10 mg/kg; administration volume: 10 mL/kg; administration frequency: once/day; administration cycle: 21 days; vehicle: 0.5% CMC/1% Tween 80).

d. Tumors were measured and weighed twice a week after the administration of test compounds began.

e. Animals were euthanized at the end of the experiment.

f. Data were processed by using softwares such as Excel. Calculation of the tumor growth inhibition rate TGI (%) of the compound: when the tumor does not regress, TGI (%)=[(1−(average tumor volume of the treatment group at the end of the administration−average tumor volume of the treatment group at the beginning of the administration))/(average tumor volume of the vehicle control group at the end of the treatment−average tumor volume of the vehicle control group at the beginning of the treatment)]×100%. When the tumor regress, TGI (%)=[1−(average tumor volume of the treatment group at the end of the administration−average tumor volume of the treatment group at the beginning of the administration)/average tumor volume of the treatment group at the beginning of the administration]×100%.

4.4 The Test Data were as Follows in Table 9:

TABLE 9

| Group | Number of animals | Administration days (days) | Tumor growth inhibition rate |
|---|---|---|---|
| Blank control | 5 | 21 | — |
| Example 22 | 5 | 19 | 132% |

TABLE 9-continued

| Group | Number of animals | Administration days (days) | Tumor growth inhibition rate |
|---|---|---|---|
| Example 25 | 5 | 21 | 120% |
| Example 50 | 5 | 21 | 96% |
| Example 52 | 5 | 21 | 98% |
| Example 56 | 5 | 21 | 122% |
| Example 62 | 5 | 21 | 147% |

4.5 Experimental Results

It can be seen from the above results that the above compounds of the present invention have good tumor growth inhibition rates.

5. Pharmacokinetic (PK) Assay of the Compounds of the Examples of the Present Invention in Mice The pharmacokinetic assay of the preferred compounds of the examples of the present invention in mice was carried out in Balb/c male mice (Shanghai Jiesijie Laboratory Animal Co., Ltd.).

5.1 Administration route: single intragastric administration.

5.2 Administration dose: 5 mg/10 ml/kg (body weight).

5.3 Formulation: the compound was dissolved in 0.5% CMC-Na by ultrasound to obtain a clear solution or a homogeneous suspension.

5.4 Sampling points: 0.5, 1, 2, 4, 6, 8 and 24 hours after administration.

5.5 Sample Processing:

1) 0.1 mL of orbital blood was collected and placed in a $K_2$-EDTA test tube, centrifuged at 1000 to 3000×g at room temperature for 5 to 20 min to separate the plasma, which was then stored at −80° C.

2) 160 uL of acetonitrile was added to 40 uL of plasma sample for precipitation. After mixing, the sample was centrifuged at 500 to 2000×g for 5 to 20 minutes.

3) 100 uL of the supernatant after processing was taken and analyzed by LC/MS/MS assay to determine the concentrations of the example compound.

5.6 LC-MS/MS Assay:

Liquid chromatography condition: Shimadzu LC-20AD pump

Mass spectrometry condition: AB Sciex API 4000 mass spectrometer

Chromatographic column: phenomenex Gemiu 5 μm C18 50×4.6 mm

Mobile phase: solution A was 0.1% aqueous formic acid solution, and solution B was acetonitrile Flow rate: 0.8 mL/min Elution time: 0 to 4 minutes, gradient elution 5.7 Pharmacokinetics:

The main parameters were calculated with WinNonlin 6.1, and the experimental results of the pharmacokinetic assay in mice are shown in Table 10 below:

TABLE 10

| | Pharmacokinetic assay (5 mg/kg) | | | | | |
|---|---|---|---|---|---|---|
| Example No. | Peak time $t_{max}$ (h) | Plasma concentration $C_{max}$ (ng/mL) | Area under the curve $AUC_{0-t}$ (ng/mL × h) | Area under the curve $AUC_{0-\infty}$ (ng/mL × h) | Half life $t_{1/2}$ (h) | Mean residence time MRT (h) |
| 19 | 0.5 | 2060 | 3442 | 3499 | 1.0 | 1.8 |
| 22 | 0.5 | 1057 | 2185 | 2274 | 1.6 | 2.2 |
| 24 | 0.5 | 1088 | 1283 | 1289 | 0.8 | 1.2 |
| 25 | 1.0 | 832 | 1560 | 1615 | 1.8 | 2.0 |
| 31 | 0.5 | 2300 | 4089 | 4116 | 1.2 | 1.7 |
| 43 | 0.5 | 1287 | 2072 | 2086 | 1.0 | 1.6 |
| 50 | 0.5 | 1227 | 4238 | 4241 | 2.0 | 3.4 |
| 52 | 0.5 | 4020 | 13703 | 13712 | 2.8 | 3.7 |

TABLE 10-continued

| | Pharmacokinetic assay (5 mg/kg) | | | | | |
|---|---|---|---|---|---|---|
| Example No. | Peak time $t_{max}$ (h) | Plasma concentration $C_{max}$ (ng/mL) | Area under the curve $AUC_{0-t}$ (ng/mL × h) | Area under the curve $AUC_{0-\infty}$ (ng/mL × h) | Half life $t_{1/2}$ (h) | Mean residence time MRT (h) |
| 53 | 0.5 | 466 | 1742 | 1744 | 2.8 | 3.9 |
| 56 | 0.5 | 985 | 1350 | 1360 | 1.6 | 2.2 |
| 62 | 0.5 | 1254 | 3440 | 3470 | 1.5 | 2.8 |

It can be seen from the results of the pharmacokinetic assay in mice in the table that the compounds of the examples of the present invention showed good metabolic properties, and both the plasma exposure AUC and the maximum plasma concentration $C_{max}$ were good.

III. Study on the Salts and Crystal Forms of (S)-2-((2-((R)-4-(difluoromethyl)-2-oxothiazolidin-3-yl)-5,6-dihydrobenzo[f]imidazo[1, 2-d][1,4]oxazepin-9-yl)amino)propionamide 1. Screening of Salts and Crystal Forms of the Compound 1.1 Screening of Salts of the Compound 1.1.1 Experimental Objective:

The objective is to identify the counter ion acids that can form salts with the compound by selecting different counter ion acids and by suitable crystallization methods.

1.1.2 Experimental Steps:

1) Instruments and Equipments

| Name | Model | Source |
|---|---|---|
| Analytical Balance | BSA224S-CW | Sartorius |
| Ultrasonic cleaner | SK5200LHC | Shanghai Kudos Ultrasonic Instrument |
| Pipettes | Eppendorf (50 mL, 1000 μL) | Eppendorf |

2) Operating Procedures (1) THF was Used as Solvent in the Liquid-Liquid Reaction for Crystallization 300 mg of free base was weighed, 15 mL of THE was added, and the mixture was heated to 50° C. to dissolve completely. The solution of the free base in THE was divided into 8 equal parts, and a certain amount of acid was added to each part (molar reaction ratio of base:acid=1:1.2), detailed as follows:

| No. | Acid | Phenomenon after adding acid | Results |
|---|---|---|---|
| 1 | 1M hydrochloric acid in ethanol | Cloudy, oil was formed and adhered to the wall | No solids were precipitated |
| 2 | 1M sulfuric acid in ethanol | Cloudy, oil was formed and adhered to the wall | No solids were precipitated |
| 3 | 1M methanesulfonic acid in ethanol | Precipitate was formed | Mesylate salt was obtained |
| 4 | 1M p-toluenesulfonic acid in ethanol | Still clear | Oil was obtained by evaporating solvent |
| 5 | 1M benzenesulfonic acid in ethanol | Still clear | Oil was obtained by evaporating solvent |
| 6 | 1M phosphoric acid in ethanol | Still clear | Oil was obtained by evaporating solvent |
| 7 | 1M oxalic acid in ethanol | Still clear | Oil was obtained by evaporating solvent |
| 8 | 1M maleic acid in ethanol | Still clear | Oil was obtained by evaporating solvent |

(2) Acetone was Used as Solvent in the Solid-Liquid Reaction for Crystallization 20 mg of free base was weighed, 0.2 mL of acetone was added, and the mixture was stirred and suspended at room temperature. Acid (molar reaction ratio of base:acid=1:1.2) was added to the suspension system for reaction, detailed as follows:

| No. | Acid | Phenomenon after adding acid | Results |
|---|---|---|---|
| 1 | 1M hydrochloric acid in ethanol | Turned clear | No solids were precipitated under stirring, then oil was formed by evaporating solvent |
| 2 | 1M sulfuric acid in ethanol | Turned clear | No solids were precipitated under stirring, then oil was formed by evaporating solvent |
| 3 | 1M methanesulfonic acid in ethanol | Turned viscous | Mesylate was obtained |
| 4 | 1M p-toluenesulfonic acid in ethanol | Turned clear | No solids were precipitated under stirring, then oil was formed by evaporating solvent |
| 5 | 1M benzenesulfonic acid in ethanol | Turned clear | No solids were precipitated under stirring, then oil was formed by evaporating solvent |
| 6 | 1M phosphoric acid in ethanol | No obvious phenomenon, still suspended | No reaction, free base remained |
| 7 | 1M oxalic acid in ethanol | No obvious phenomenon, still suspended | No reaction, free base remained |
| 8 | 1M maleic acid in ethanol | No obvious phenomenon, still suspended | No reaction, free base remained |

(3) Acetone was Used as Solvent in the Reaction for Crystallization

About 20 mg of free base was weighed and suspended in 400 μl of acetone at room temperature. The following acids were added for reaction:

| No. | Acid | Phenomenon after adding acid | Post-treatment |
|---|---|---|---|
| 1 | 1M hydrochloric acid in ethanol | Clear | No solids were precipitated after prolonged stirring |
| 2 | 1M oxalic acid in ethanol | Suspended | No reaction, being cystal form B of free base |
| 3 | 1M HBr in ethanol | Clear | No solids were precipitated after prolonged stirring |
| 4 | 1M p-toluenesulfonic acid in ethanol | Clear | No solids were precipitated after prolonged stirring |
| 5 | 0.25M 1,5-naphthalenedisulfonic acid in ethanol | Clear | No solids were precipitated after prolonged stirring |
| 6 | 1M benzenesulfonic acid in methanol | Clear | No solids were precipitated after prolonged stirring |
| 7 | 1M isethionic acid in methanol | Clear | Oil was formed and solution turned slightly cloudy after stirring |
| 8 | 1M ethanesulfonic acid in methanol | Clear | Ethanesulfonate salt was obtained after stirring for 10 min to precipitate a solid |

(4) DMF was Used as Solvent for Crystallization

About 20 mg of free base was weighed and dissolved in 200 μl of DMF to form a clear solution at room temperature. The following acids were added for reaction:

| No. | Acid | Phenomenon after adding acid | Post-treatment |
|---|---|---|---|
| 1 | 1M hydrochloric acid in ethanol | Still clear | Oil was formed by adding anti-solvent MTBE, then no solids were precipitated by stirring |
| 2 | 1M oxalic acid in ethanol | Still clear | Oil was formed by adding anti-solvent MTBE, then no solids were precipitated by stirring |
| 3 | 1M HBr in ethanol | Still clear | Oil was formed by adding anti-solvent MTBE, then no solids were precipitated by stirring |
| 4 | 1M p-toluenesulfonic acid in ethanol | Still clear | Oil was formed by adding anti-solvent MTBE, then no solids were precipitated by stirring |
| 5 | 0.25M 1,5-naphthalenedisulfonic acid in ethanol | Still clear | Oil was formed by adding anti-solvent MTBE, then no solids were precipitated by stirring |

-continued

| No. | Acid | Phenomenon after adding acid | Post-treatment |
|---|---|---|---|
| 6 | 1M benzenesulfonic acid in methanol | Still clear | Oil was formed by adding anti-solvent MTBE, then no solids were precipitated by stirring |
| 7 | 1M isethionic acid in methanol | Still clear | Oil was formed by adding anti-solvent MTBE, then no solids were precipitated by stirring |
| 8 | 1M ethanesulfonic acid in methanol | Still clear | Oil was formed by adding anti-solvent MTBE, then no solids were precipitated by stirring |

(5) Methanol was Used as a Solvent for Crystallization 20 mg of free base was weighed, 0.2 mL of methanol was added, and the mixture was stirred and suspended at 50° C. Acid (molar reaction ratio of base:acid=1:1.2) was added to the suspension system for reaction, detailed as follows:

| No. | Acid | Phenomenon after adding acid | Post-treatment |
|---|---|---|---|
| 1 | 1M hydrochloric acid in ethanol | Clear solution | Oil was formed by adding anti-solvent MTBE, then no solids were precipitated by stirring |
| 2 | 1M sulfuric acid in ethanol | Clear solution | Oil was formed by adding anti-solvent MTBE, then sulfate salt was obtained by stirring to precipitate a solid |
| 3 | 1M maleic acid in methanol | Still suspended | No reaction, free base remained |
| 4 | 1M phosphoric acid in ethanol | Still suspended | No reaction, free base remained |
| 5 | 1M oxalic acid in ethanol | Still suspended | No reaction, free base remained |

(6) The Method of Natural Evaporation was Used to Prepare Salts

THF was used as solvent in No. 1 to 10, and the free base was dissolved in THE to form a clear solution and then acid was added. Ethanol was used as solvent in No. 11 to 14, the free base was suspended in ethanol, and a clear solution formed after adding an acid. The clear solution formed in No. 1-14 was placed at room temperature without sealing the container to evaporate the solvent.

| No. | Acid | Phenomenon after adding acid | Post-treatment | Experimental results |
|---|---|---|---|---|
| 1 | Maleic acid | Still clear | Solvent was evaporated at room temperature | Oil formed |
| 2 | Oxalic acid | Still clear | Solvent was evaporated at room temperature | Oil formed |
| 3 | Phosphoric acid | Still clear | Solvent was evaporated at room temperature | Oil formed |
| 4 | Tartaric acid | Still clear | Solvent was evaporated at room temperature | Oil formed |
| 5 | Fumaric acid | Still clear | Solvent was evaporated at room temperature | Oil formed |
| 6 | Citric acid | Still clear | Solvent was evaporated at room temperature | Oil formed |
| 7 | Glycolic acid | Still clear | Solvent was evaporated at room temperature | Oil formed |
| 8 | Succinic acid | Still clear | Solvent was evaporated at room temperature | Oil formed |
| 9 | Adipic acid | Still clear | Solvent was evaporated at room temperature | Oil formed |
| 10 | Malic acid | Still clear | Solvent was evaporated at room temperature | Oil formed |
| 11 | p-Toluenesulfonic acid | Clear solution was formed after adding acid | Solvent was evaporated at room temperature | Amorphous |

-continued

| No. | Acid | Phenomenon after adding acid | Post-treatment | Experimental results |
|---|---|---|---|---|
| 12 | Hydrochloric acid | Clear solution was formed after adding acid | Solvent was evaporated at room temperature | Amorphous |
| 13 | Benzenesulfonic acid | Clear solution was formed after adding acid | Solvent was evaporated at room temperature | Amorphous |
| 14 | Isethionic acid | Clear solution was formed after adding acid | Solvent was evaporated at room temperature | Amorphous |

1.1.3 Experimental Results

Through the screening experiment of salt forms, the salt forms obtained with crystal forms were ethanesulfonate, methanesulfonate and sulfate salts.

2 Screening of Crystal Forms of Salts of the Compound

According to the results of salt form screening, suitable crystallization methods were selected to screen different crystal forms of ethanesulfonate, methanesulfonate and sulfate salts.

2.1 Experimental Instruments 2.1.1 Some Parameters of Physical and Chemical Testing Instruments

| | | |
|---|---|---|
| XRPD | Instrument model | BRUKER D8 ADVANCE |
| | Diffraction ray | CuK (40 kV, 25 mA) |
| | Scan rate | 0.02°/S (2θ value) |
| | Scan range | 4° to 40° (2θ value) |
| DSC | Instrument model | NETZSCH DSC 214 polyma |
| | Purge gas | Nitrogen |
| | Purge speed | 40 mL/min |
| | Heating rate | 10° C./min |
| | Temperature range | 25 to 350° C. |
| | Plate type | Aluminum plate |
| TGA | Instrument model | NETZSCH TG 209 Tarsus |
| | Purge gas | Nitrogen |
| | Purge speed | 40 mL/min |
| | Heating rate | 10° C./min |
| | Temperature range | Room temperature~400° C. |
| | Plate type | $Al_2O_3$ |

2.2 Instruments and Liquid Phase Analysis Conditions 2.2.1 Instruments and Devices

| Instrument name | Model |
|---|---|
| Analytical Balance | Sartorius BSA224S-CW |
| Water purifier | Milli-Q Plus, Millipore |
| High performance liquid chromatograph | Agilent1260 |
| Pump | Agilent G1311B |
| Injector | G1329B |
| Column oven | G1316A |
| Detector | G1315D |
| Ultrasonic cleaner | SK5200LHC |
| Pipettes | Eppendorf (50 mL, 1000 μL) |

2.2.2 Chromatography Conditions

Chromatographic column: ZORBAX (SB-C8, 3.5 μm, 4.6*75 mm)

Flow rate: 1 mL/min

Column temperature: 40° C.

Detection wavelength: 220/328 nm

Injection volume: 5.0 μL

Running time: 12 min

Diluent: ACN-water (v/v, 1:1)

Mobile phase: A: water (0.05% trifluoroacetic acid); B: acetonitrile (0.05% trifluoroacetic acid)

| T(min) | A(%) | B(%) |
|---|---|---|
| 0.00 | 90 | 10 |
| 8.00 | 10 | 90 |
| 10.00 | 10 | 90 |
| 10.10 | 90 | 10 |
| 12.00 | 90 | 10 |

Figure 2:
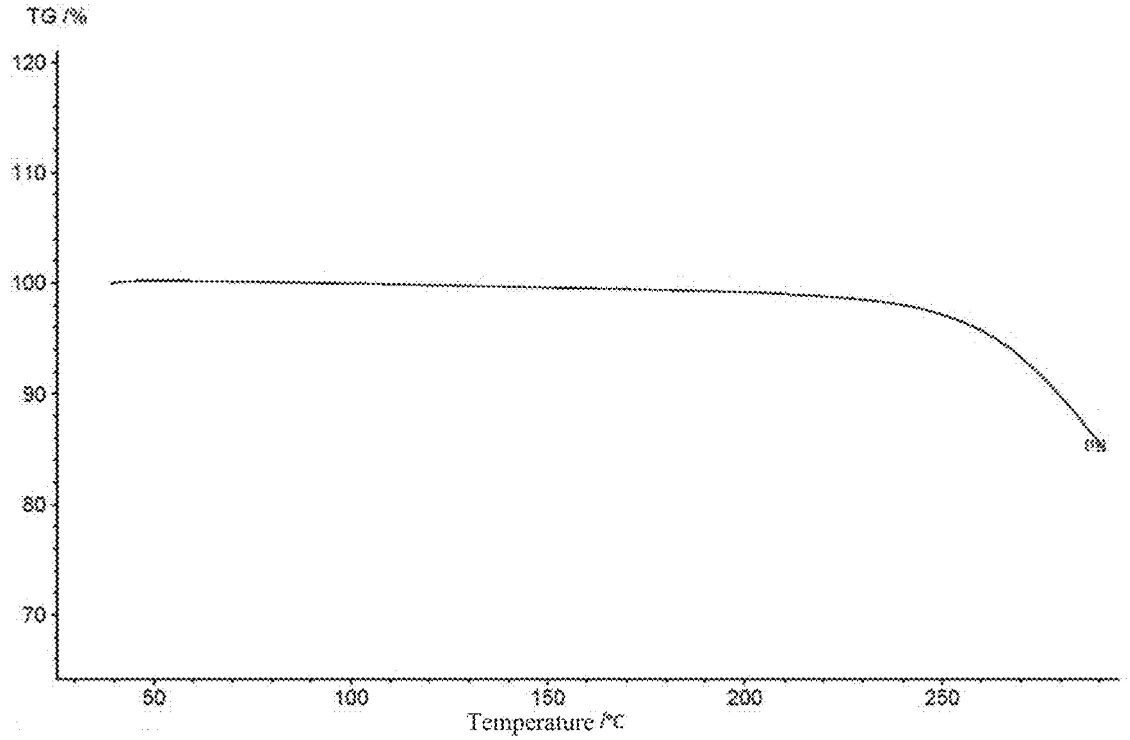
FIG. 2 is the TGA spectrum of crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.
Figure 3:
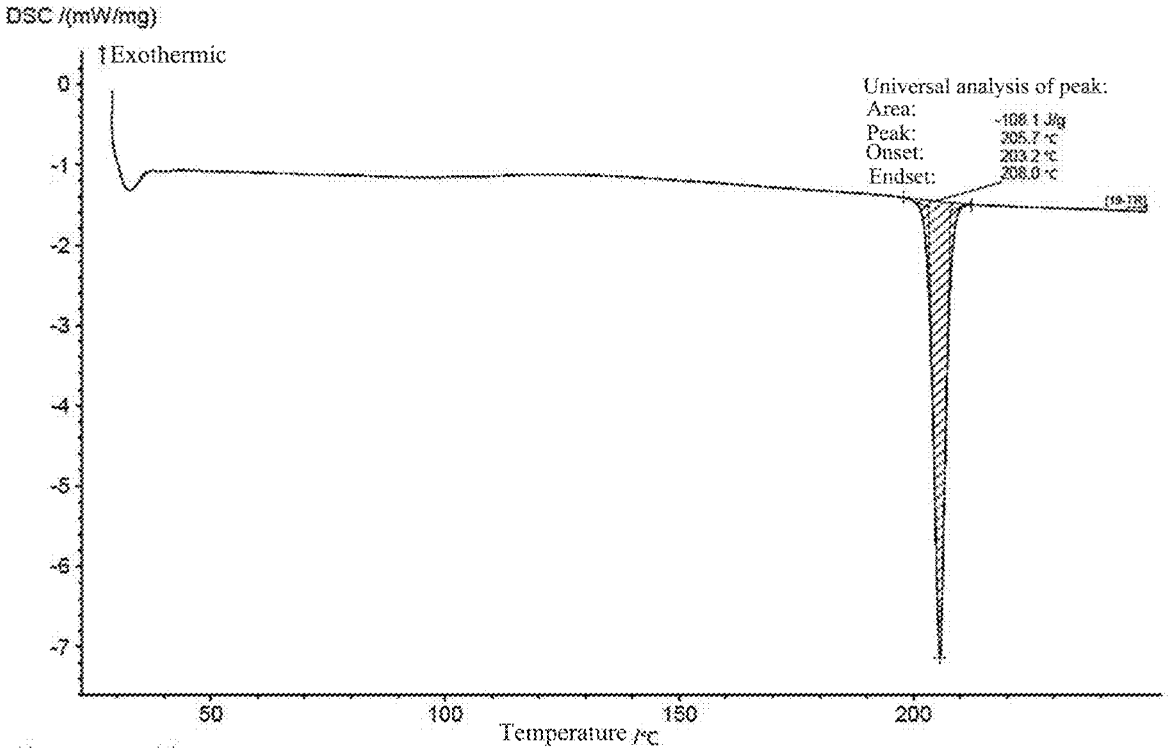
FIG. 3 is the DSC spectrum of crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

2.3 Operating Procedures (1) Preparation of Crystal Form A of ethanesulfonate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 60 mg of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed 1.2 mL of acetone was added, and the mixture was stirred at 50° C. to form a suspension. 0.18 mL of 1 M ethanesulfonic acid in methanol was added to the system to form a clear solution, which was stirred to precipitate a large amount of solid. Finally, the reaction solution was stirred and reacted at 50° C. for 2 h, then cooled, filtered and dried to finally obtain crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 1, the TGA spectrum as shown in FIG. 2 and the DSC spectrum as shown in FIG. 3.

Figure 4:
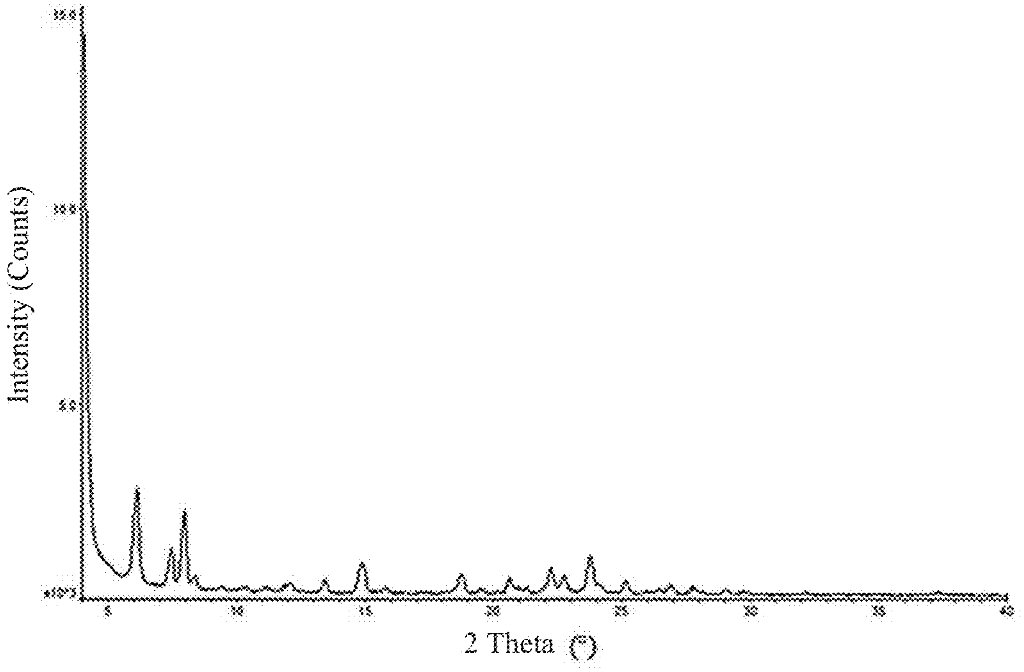
FIG. 4 is the XRPD pattern of crystal form A of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(2) Preparation of Crystal Form A of mesylate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 60 mg of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed, 3 mL of ethanol was added, and the mixture was stirred at 50° C. to form a suspension. 0.18 mL of 1 M methanesulfonic acid in methanol was added to the system to form a clear solution, and a large amount of solid was rapidly precipitated. Then 0.6 mL of ethanol was added, and the reaction solution was stirred and reacted at 50° C. for 2 h, then cooled, filtered and dried to finally obtain crystal form A of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 4.

Figure 5:
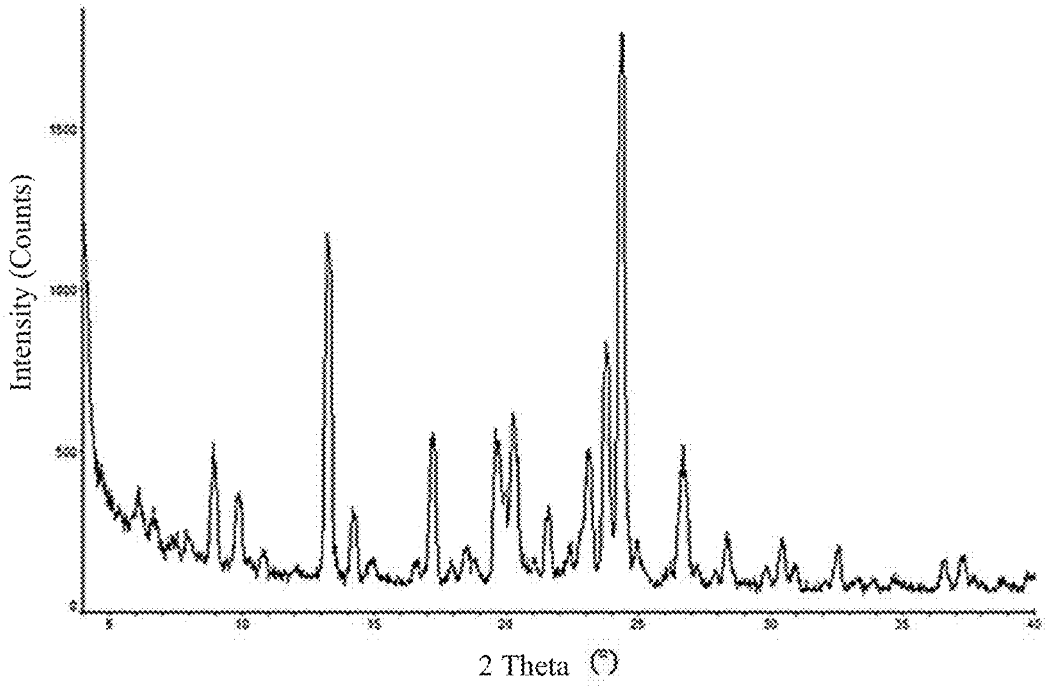
FIG. 5 is the XRPD pattern of crystal form B of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(3) Preparation of Crystal Form B of mesylate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 30 mg of crystal form A of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed, 200 μL of methanol was added, and the mixture was slurried at room temperature for 10 d. Finally, the solid was centrifuged and the supernatant was removed. The solid was then dried in a vacuum drying oven at 40° C. to constant weight to obtain crystal form B of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 5.

Figure 6:
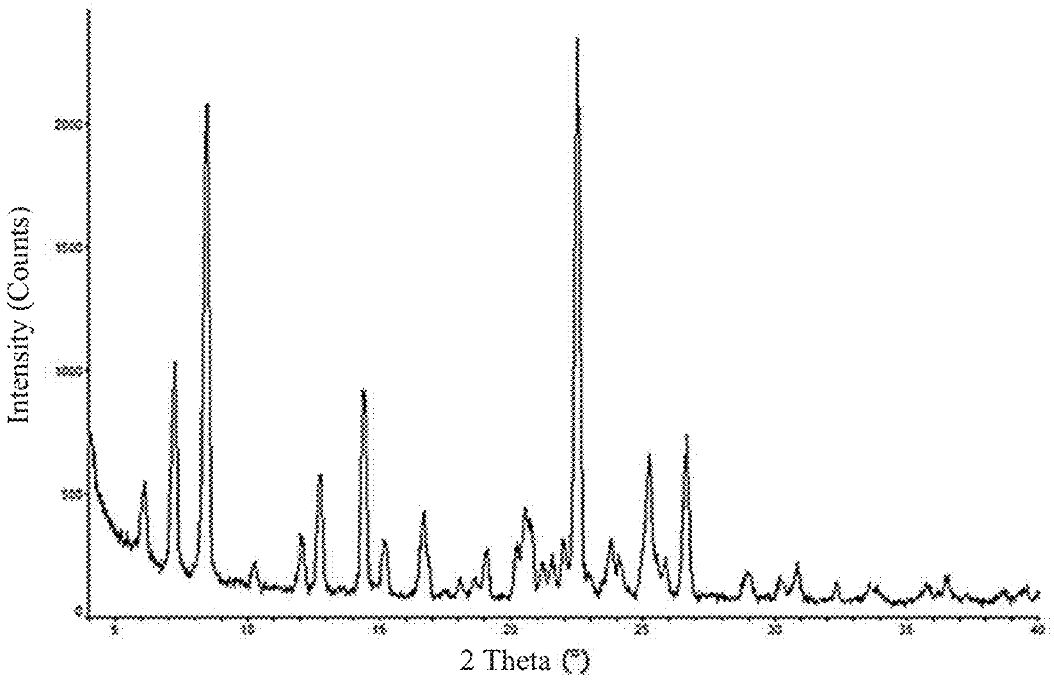
FIG. 6 is the XRPD pattern of crystal form C of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(4) Preparation of Crystal Form C of mesylate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 30 mg of crystal form A of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed and left to stand at room temperature under a relative humidity of 92.5% for 3 h to obtain crystal form C of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 6.

Figure 7:
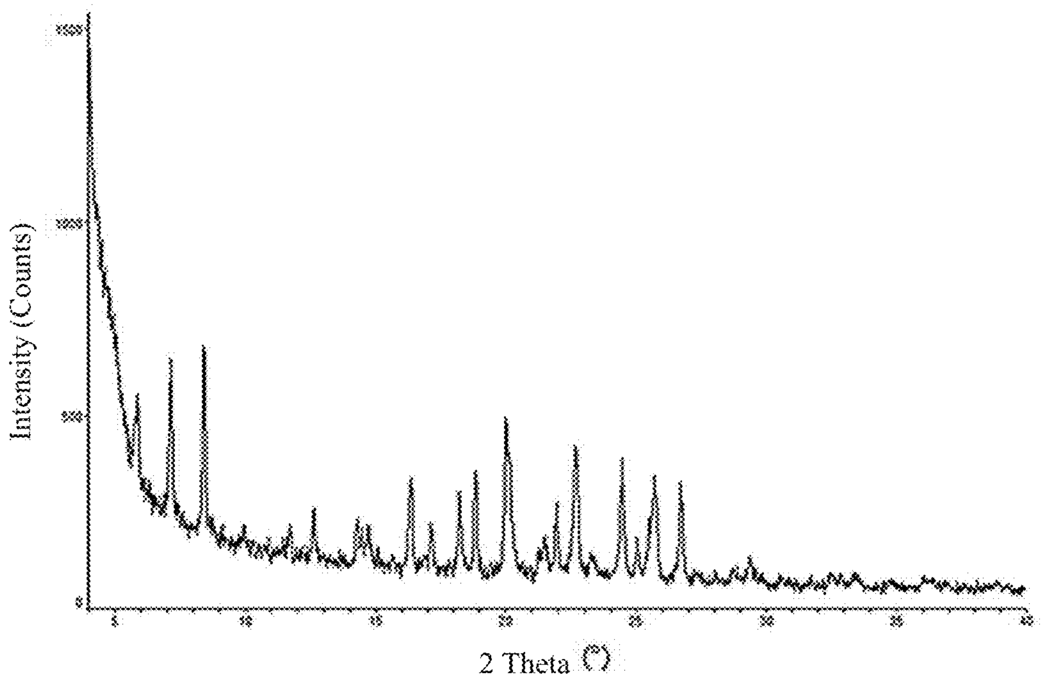
FIG. 7 is the XRPD pattern of crystal form A of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(5) Preparation of Crystal Form A of sulfate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 14 mg of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed, 280 μL of isopropanol was added, and the mixture was suspended at 40° C. 39 μL of 1 M $H_2SO_4$ in ethanol was added, and an oil was formed and adhered to the wall. Then the reaction system was stirred to precipitate a large amount of solid, which was characterized as amorphous after centrifugation. 200 μL of ethyl acetate was added to the obtained amorphous solid, and there was still no obvious crystal after slurrying the mixture at room temperature. Then 100 μL of ethanol was added, and the system was completely dissolved to form a clear solution. A small amount of methyl tert-butyl ether was added at room temperature, and the solution turned cloudy. After stirring, the finally precipitated solid was crystal form A of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 7.

Figure 8:
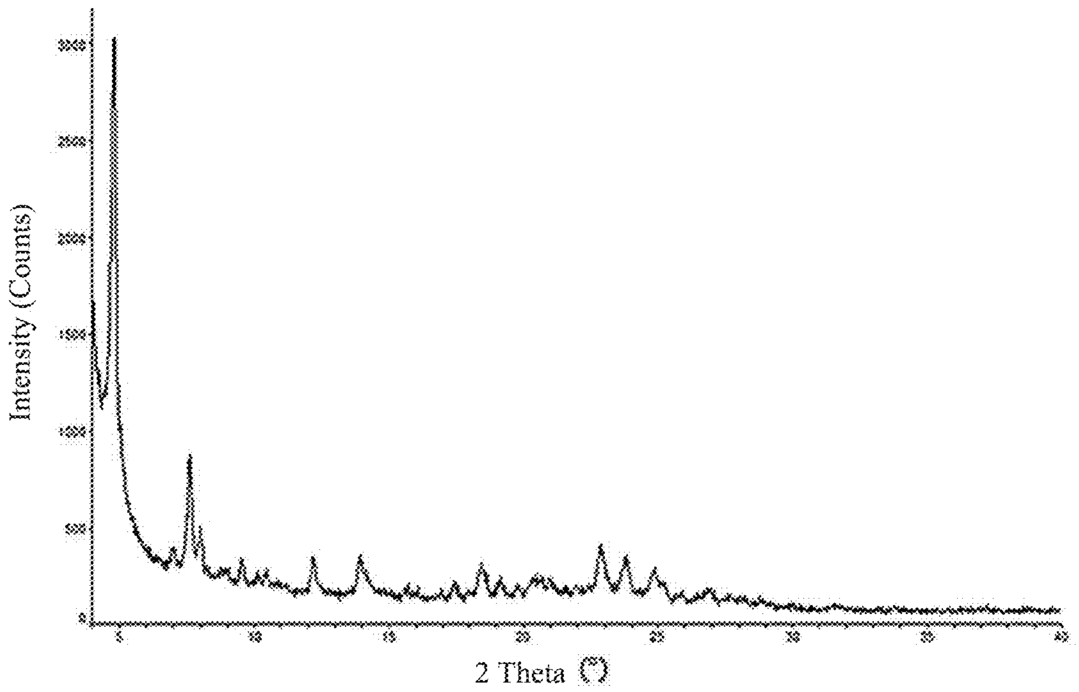
FIG. 8 is the XRPD pattern of crystal form B of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(6) Preparation of Crystal Form B of sulfate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 15 mg of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed, 300 μL of isopropanol was added, and the mixture was suspended at room temperature. 42 μL of 1 M $H_2SO_4$ in ethanol was added, there was no reaction and the free base remained. After the mixture was warmed up to 50° C., stirred for 1 h and left to stand at room temperature overnight, there was still no obvious crystals. 100 μL of methanol was added, and a small amount of oil was formed and adhered to the wall. The mixture was stirred at 50° C. to form a clear solution. A small amount of methyl tert-butyl ether was added, and the solution turned cloudy, stirred at room temperature for 48 hours and then at 50° C. 200 μL methanol and 400 μL methyl tert-butyl ether were added, and the mixture was finally turned cloudy to precipitate a large amount of solid, which was crystal form B of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 8.

Figure 9:
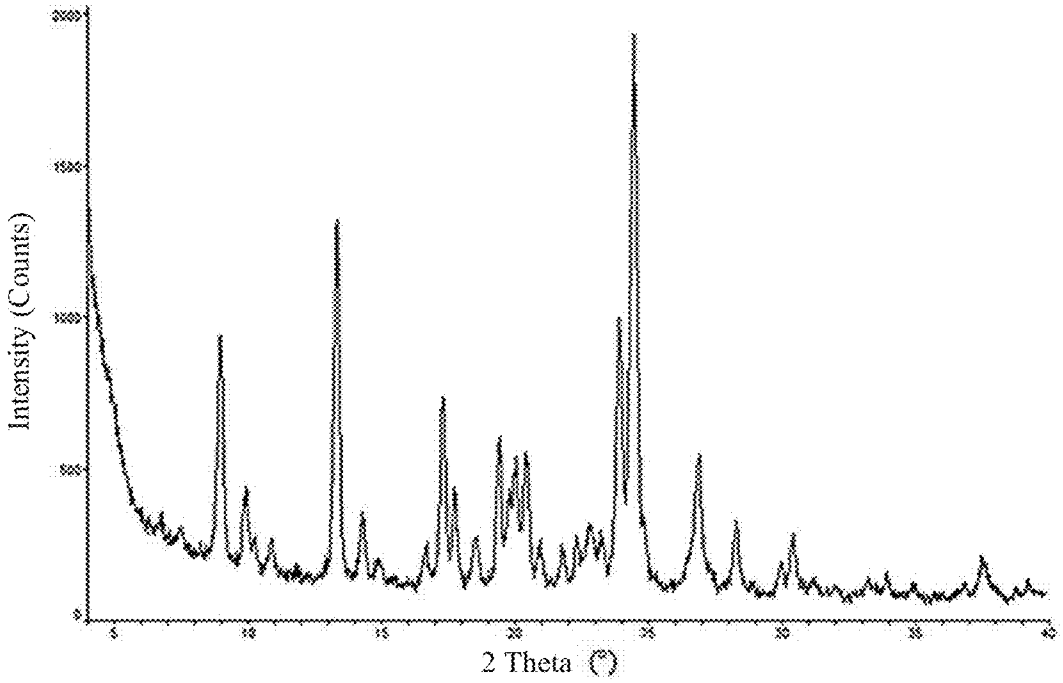
FIG. 9 is the XRPD pattern of crystal form C of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(7) Preparation of Crystal Form C of sulfate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 23.5 mg of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed, 235 μL of methanol was added, and the mixture was suspended at 50° C. 66 μL of 1 M $H_2SO_4$ in ethanol was added, and the reaction solution turned clear. 300 μL of methyl tert-butyl ether was added, and the reaction solution turned cloudy. Then a small amount of crystal form A of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was added, and a large amount of solid was precipitated. Finally, 400 μL methanol was added, and the solid did not dissolve. After 1 h of reaction, 400 μL of methyl tert-butyl ether was added. Finally, the solid was centrifuged and dried to obtain crystal form C of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 9.

Figure 10:
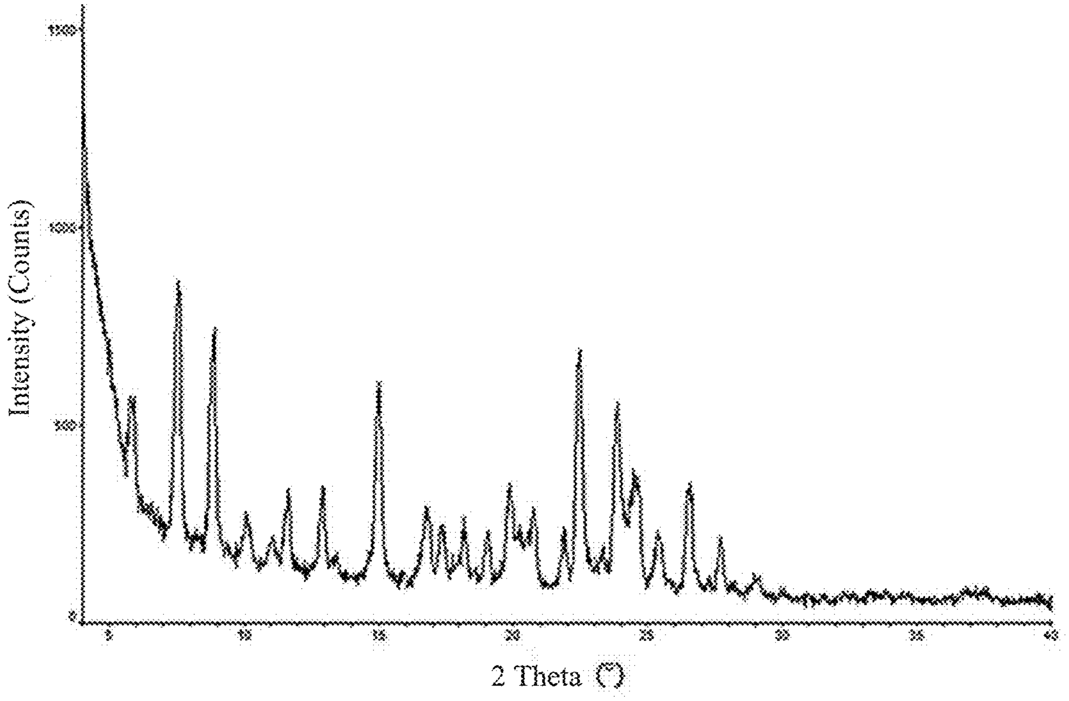
FIG. 10 is the XRPD pattern of crystal form D of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(8) Preparation of Crystal Form D of sulfate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 60 mg of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed, 1.2 mL of methanol was added, and the mixture was stirred at 50° C. to form a suspension. 0.18 mL of 1 M $H_2SO_4$ in ethanol was added to the system to form a clear solution. Then 2.4 mL of methyl tert-butyl ether was added, and the solution was slightly cloudy. Then a small amount of crystal form C of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was added as crystal seeds. A large amount of solid was precipitated after stirring. Finally, the reaction solution was stirred and reacted at 50° C. for 2 h, then cooled, filtered and dried to finally obtain crystal form D of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 10.

Figure 11:
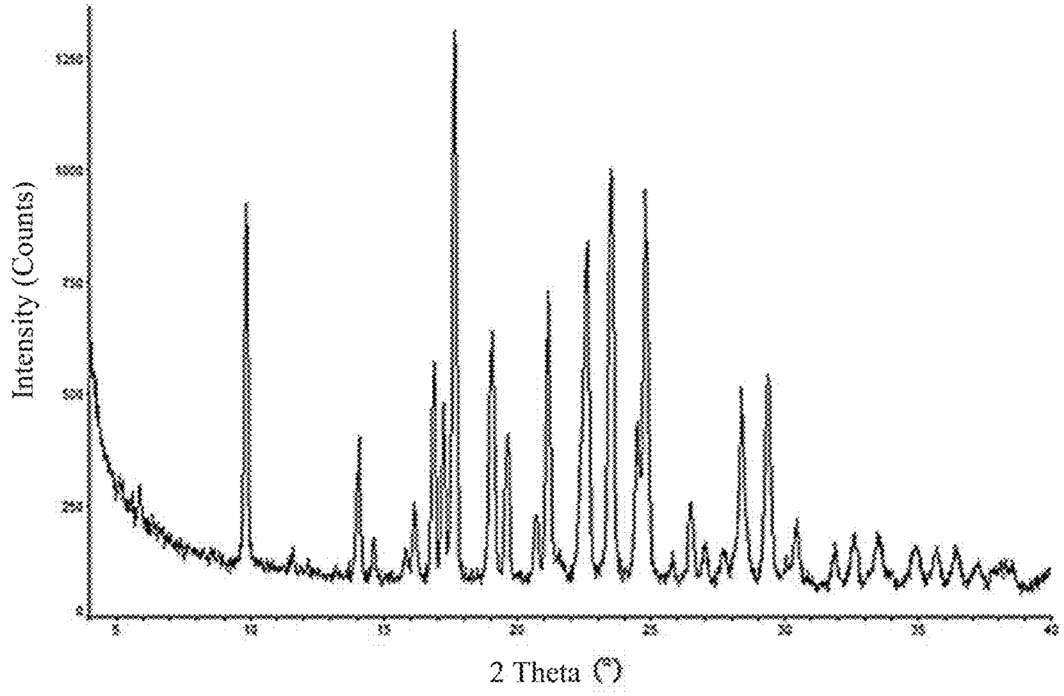
FIG. 11 is the XRPD pattern of crystal form E of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

(9) Preparation of Crystal Form E of sulfate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 30 mg of crystal form D of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was weighed, 200 μL of acetone was added, and the mixture was slurried at room temperature for 10 d. Finally, the solid was centrifuged, and the supernatant was removed. The solid was then dried in a vacuum drying oven at 40° C. to constant weight to obtain crystal form E of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide. After detection and analysis, it had the XRPD pattern as shown in FIG. 11.

3. Stability Experiment of the Solids 3.1 Experimental Objective:

The objective is to investigate the physicochemical stability of crystal form A of mesylate salt, crystal form C of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide under accelerated conditions or influencing factors, and to provide a basis for screening salt forms and storage of salts of the compound.

3.2 Experimental Scheme:

About 2 mg of crystal form A of mesylate salt, crystal form C of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide was placed in a sealed oven at 60° C., in an unsealed container at room temperature under RH 95% (saturated aqueous $KNO_3$ solution) and in a light box (5000 lx±500 lx) and observed for 5 days and 10 days. The content of salt was determined by HPLC using the external standard method. Changes of related substance of salt in substances related to the salts were calculated by normalization of chromatography peak area.

3.3 Experimental Results:

By comparing the liquid chromatograms, it was found that as for crystal form A of mesylate salt, 1 new impurity appeared with an increase of 0.523% under the light condition for 10 days compared with 0 days, and the impurity increase was less than 0.05% both at 60° C. and at room temperature under RH 95% for 10 days compared with 0 days; as for crystal form C of sulfate salt, 1 new impurity appeared with an increase of 0.172% under the light condition for 10 days compared with 0 days, and the impurity increase was less than 0.05% both at 60° C. and at room temperature under RH95% for 10 days compared with 0 days; as for crystal form A of ethanesulfonate salt, 1 new impurity appeared with an increase of 0.134% under the light condition for 10 days compared with 0 days, and the impurity increase was less than 0.05% both at 60° C. and at room temperature under RH 95% for 10 days compared with 0 days.

3.4 Experimental Conclusion

The crystal forms of the salts of the compound are unstable under light condition, and needs to be protected from light in the later storage process. However, relatively speaking, the salts of the compound and the crystal forms thereof are relatively stable under light condition. Moreover, the salts of the compound and the crystal forms thereof are more stable at 60° C. and at room temperature under RH 95%.

4. Hygroscopicity Experiment 4.1 Experimental Objective

The objective is to investigate the hygroscopicity of crystal form A of mesylate salt, crystal form D of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide under different relative humidity conditions, and to provide a basis for the screening and storage of the salts of the compound.

4.2 Experimental Scheme:

Crystal form A of mesylate salt, crystal form D of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide were placed in saturated water vapor with different relative humidity, so that the compound and water vapor reached a dynamic equilibrium, and the percentage of hygroscopic weight gain of the compound after the equilibrium was calculated.

4.3 Experimental Results:

4.3.1 the Hygroscopicity of Crystal Form A of mesylate Salt, Crystal Form D of sulfate Salt and Crystal Form A of ethanesulfonate Salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide 1) Crystal form A of mesylate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide had a hygroscopic weight gain of 3.6% under RH 80%, and had hygroscopicity. After 1 cycle of humidification and dehumidification under 0 to 95% relative humidity, the XRPD pattern of crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide changed, i.e. the crystal form changed, and the changed crystal form was crystal form C of mesylate salt.
2) Crystal form D of sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide had a hygroscopic weight gain of 1.256% under RH 80%, and had hygroscopicity.
3) Crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide had a hygroscopic weight gain of 0.207% under RH 80%, had slight hygroscopicity, and no obvious changes in hygroscopicity. After 1 cycle of humidification and dehumidification under 0 to 95% relative humidity, the XRPD pattern of crystal form A of ethanesulfonate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide did not change, i.e. the crystal form did not change.

5. Solubility Experiment in Different Media 5.1 Experimental Objective

The objective is to compare the solubility of crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide in media with different pH values, water, simulated gastric fluid (SGF), fasted-state simulated intestinal fluid (FaSSIF) and fed-state simulated intestinal fluid (FeSSIF), and to provide a basis for the evaluation of druggability of the salts.

5.2 Experimental Scheme:

About 2 mg of crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)

propionamide was suspended in different media for 24 hours. The thermodynamic solubility of the compound at 37° C. was determined by HPLC using the external standard method.

5.3 Experimental Results:

As shown in Table 15.

TABLE 15

| Sample name<br>Media | Crystal form A of ethanesulfonate salt<br>Solubility (mg/mL) |
|---|---|
| pH 1 | 9.37 |
| pH 2 | 0.974 |
| pH 3 | 0.268 |
| pH 4 | 0.049 |
| pH 5 | 0.020 |
| pH 6 | 0.005 |
| pH 7 | 0.012 |
| pH 8 | 0.014 |
| Fa | 0.044 |
| Fe | 0.163 |
| SGF | 1.151 |
| water | 0.608 |

5.4 Experimental Conclusion

From the solubility results of crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide in the above different media, it can be seen that (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide after salt formation had slightly lower solubility in the media of pH4 to 8 buffer, but salt formation increased the solubility of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide in other media, most obviously in water.

6. Polymorphic Screening Experiment 6.1 Experimental Objective:

The objective is to find more stable crystal forms by polymorphic screening.

6.2 Experimental Scheme:

Organic solvents and water with a certain solubility was chosen to suspend the compound in the solvent system, and the mixture was stirred and slurried at room temperature for 1 week, and then centrifuged. The supernatant was discarded, and the solid was dried in vacuum (−0.1 Mpa) at 40° C. overnight. Then the XRPD of the solid was measured and compared with the XRPD of salt of the compound.

6.3 Experimental Results:

Through slurrying, changing the solvent for crystallization, the crystallization model and the like, only ethanesulfonate salt of (S)-2-(((2-((R)-4-(difluoromethyl)-2-oxothiazolidin-3-yl)-5,6-dihydrobenzo[f]imidazo[1,2-d][1,4]oxazepin-9-yl)amino)propionamide in crystal form A was obtained.

7. PK Studies in Animals 7.1 Experimental Objective:

7.1.1 The objective is to compare the exposure differences of crystal form A of mesylate salt, crystal form D of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide in animals in vivo by PK studies in animals.

7.2 Experimental Scheme:

7.2.1 Crystal form A of mesylate salt, crystal form D of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide were evenly suspended in an aqueous solution containing 0.5% HPMC (hydroxypropyl methylcellulose) K4M, and then intragastrically administered to rats in duplicate at a dose of 30 mg/kg. The amount of the compound was all converted into the amount of the same compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

7.3 Experimental Results:

7.3.1 The experimental results of the PK experiment of crystal form A of mesylate salt, crystal form D of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide were shown in Table 16 below:

TABLE 16

| Parameters | Crystal form D of sulfate salt | Crystal form A of mesylate salt | Crystal form A of ethanesulfonate salt |
|---|---|---|---|
| $t_{max}$ (h) | 1.0 | 1.0 | 1.0 |
| $C_{max}$ (ng/mL) | 1365.0 | 1180.0 | 1465.0 |
| $AUC_{0-t}$ (ng/mL*h) | 9423.2 | 9836.9 | 10000.7 |
| $AUC_{0-\infty}$ (ng/mL*h) | 9601.2 | 10152.2 | 10427.8 |
| $t_{1/2}$ (h) | 3.30 | 3.54 | 3.01 |
| $MRT_{0-\infty}$ (h) | 5.77 | 6.52 | 6.98 |
| Formulation | | 0.5% HPMC K4M | |

The PK results in rats showed that crystal form A of mesylate salt, crystal form D of sulfate salt and crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide all had higher exposures.

7.4 Experimental Conclusion

The exposure of the drug in rats can be increased by salt formation.

What is claimed is:

1. An acid addition salt of a compound, wherein the specific structure of the compound is as follows:

22

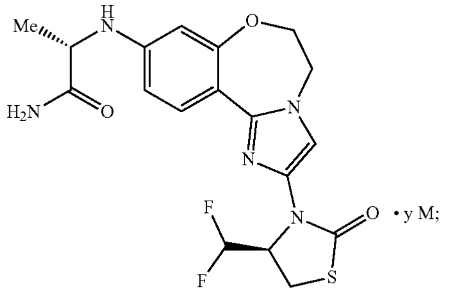

wherein, M is an inorganic acid or an organic acid, wherein the inorganic acid is selected from the group consisting of hydrochloric acid, sulfuric acid, nitric acid, hydrobromic acid, hydrofluoric acid, hydroiodic acid and phosphoric acid; the organic acid is selected from the group consisting of 2,5-dihydroxybenzoic acid, 1-hydroxy-2-naphthoic acid, acetic acid, dichloroacetic acid, trichloroacetic acid, acetohydroxamic acid, adipic acid, benzenesulfonic acid, 4-chlorobenzenesulfonic acid, benzoic acid, 4-acetamidobenzoic acid, 4-aminobenzoic acid, capric acid, caproic acid, caprylic acid, cinnamic acid, citric acid, cyclamic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecyl sulfuric acid, dibenzoyl tartaric acid, ethane-1,2-disulfonic acid, ethanesulfonic acid, formic acid, fumaric acid, galactonic acid, gentisic acid, glutaric acid, 2-ketoglutaric acid, glycolic acid, hippuric acid, isethionic acid, lactobionic acid, ascorbic acid, aspartic acid, lauric acid, camphoric acid, maleic acid, malonic acid, methanesulfonic acid, 1,5-naphthalenedisulfonic acid, naphthalene-2-sulfonic acid, nicotinic acid, oleic acid, orotic acid, oxalic acid, palmitic acid, embonic acid, propionic acid, salicylic acid, 4-aminosalicylic acid, sebacic acid, stearic acid, succinic acid, thiocyanic acid, undecylenic acid, trifluoroacetic acid, benzenesulfonic acid, p-toluenesulfonic acid and L-malic acid; and y is an integer from 1 to 5.

2. The acid addition salt according to claim 1, wherein the acid addition salt is an ethanesulfonate, mesylate or sulfate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide.

3. The acid addition salt according to claim 2, wherein the acid addition salt is

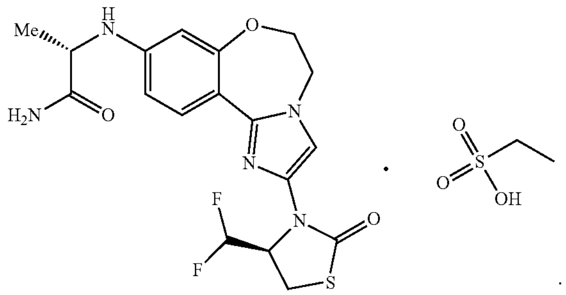

4. A method for preparing the acid addition salt according to claim 1, specifically comprising the following steps of:

1) weighing free base of the compound and adding an organic solvent to obtain a clear or suspended stock solution;
2) adding acid M into an organic solvent or water to obtain a counter ion acid solution;
3) adding the counter ion acid solution to the stock solution to obtain a salt solution, stirring the salt solution to precipitate a solid, and drying the solid.

5. A crystal form of the acid addition salt according to claim 1, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 6.8±0.2°, 13.4±0.2°, 14.7±0.2°, 19.5±0.2°, 20.1±0.2°, 23.9±0.2°, 24.4±0.2°, 25.0±0.2°, 23.0±0.2°, 23.6±0.2°, 9.3±0.2° and 17.3±0.2°;

or, wherein the crystal form is crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 6.1±0.2°, 7.5±0.2°, 8.0±0.2°, 14.9±0.2°, 23.8±0.2°, 8.4±0.2°, 18.8±0.2°, 20.7±0.2°, 22.3±0.2° and 22.8±0.2°;

or, wherein the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 24.4±0.2°, 13.3±0.2°, 23.8±0.2°, 20.3±0.2° 19.7±0.2°, 17.2±0.2°, 26.7±0.2°, 9.0±0.2°, 23.1±0.2°, 9.9±0.2°, 14.3±0.2° and 21.6±0.2°;

or, wherein the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 22.5±0.2°, 8.5±0.2°, 7.2±0.2°, 14.4±0.2°, 26.7±0.2°, 25.3±0.2°, 12.8±0.2°, 16.7±0.2°, 6.1±0.2°, 12.1±0.2°, 15.2±0.2° and 22.0±0.2°;

or, wherein the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 8.4±0.2°, 7.2±0.2°, 20.1±0.2°, 22.7±0.2°, 24.5±0.2°, 25.7±0.2°, 18.9±0.2°, 26.7±0.2°, 16.4±0.2°, 18.2±0.2°, 22.0±0.2° and 12.6±0.2°;

or, wherein the crystal form is crystal form B of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 4.8±0.2°, 7.6±0.2°, 12.2±0.2°, 14.0±0.2°, 18.5±0.2°, 22.9±0.2°, 23.8±0.2° and 24.9±0.2°:

or, wherein the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 24.5±0.2°, 13.3±0.2°, 23.9±0.2°, 9.0±0.2°, 17.3±0.2° 19.4±0.2°, 26.9±0.2°, 20.4±0.2°, 17.7±0.2°, 9.9±0.2°, 20.0±0.2° and 28.3±0.2°;

or, wherein the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 7.6±0.2°, 22.5±0.2°, 8.9±0.2°, 15.0±0.2°, 23.9±0.2°, 26.6±0.2°, 24.6±0.2°, 5.8±0.2°, 12.9±0.2°, 19.9±0.2°, 20.7±0.2° and 11.6±0.2°;

or, wherein the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises one or more diffraction peaks at 2θ of 17.7±0.2°, 23.5±0.2°, 24.8±0.2°, 9.9±0.2°, 22.6±0.2°, 21.2±0.2°, 19.1±0.2°, 29.4±0.2°, 16.9±0.2°, 28.4±0.2°, 17.3±0.2° and 24.5±0.2°.

6. The acid addition salt according to claim 1, wherein the acid addition salt is a hydrate or an anhydrate.

7. The crystal form according to claim 5, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino) propionamide, the X-ray powder diffraction pattern thereof comprises two or three diffraction peaks at 2θ of 6.8±0.2°, 13.4±0.2°, 14.7±0.2° and 19.5±0.2°, optionally further comprises one or more diffraction peaks at 2θ of 20.1±0.2°, 23.9±0.2°, 24.4±0.2°, 25.0±0.2°, 23.0±0.2° and 23.6±0.2°;

or, the X-ray powder diffraction pattern thereof has characteristic peaks at 13.4±0.2°, 14.7±0.2°, 19.5±0.2°, 20.1±0.2°, 23.0±0.2°, 23.9±0.2°, 24.4±0.2° and 25.0=0.2;

or, the X-ray powder diffraction pattern thereof has characteristic peaks at 6.8±0.2°, 13.4±0.2°, 14.7±0.2°, 19.5±0.2°, 20.1±0.2°, 23.9±0.2°, 23.0±0.2° and 23.6±0.2°;

or, the X-ray powder diffraction pattern thereof has characteristic peaks at 6.8±0.2°, 13.4±0.2°, 14.7±0.2°, 19.5±0.2°, 20.1±0.2°, 23.9±0.2°, 24.4±0.2° and 25.0±0.2°;

or, the X-ray powder diffraction pattern thereof has characteristic peaks at 6.8±0.2°, 13.4±0.2°, 14.7±0.2°, 19.5±0.2°, 20.1±0.2°, 23.9±0.2°, 24.4±0.2°, 25.0±0.2°, 23.0±0.2° and 23.6±0.2°;

or, wherein the crystal form is crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises two or three diffraction peaks at 2θ of 6.1±0.2°, 7.5±0.2° and 8.0±0.2°, optionally further comprises one or more diffraction peaks at 2θ of 14.9±0.2°, 18.8±0.2°, 20.7±0.2°, 22.3±0.2°, 22.8±0.2° and 23.8±0.2°;

or, the X-ray powder diffraction pattern thereof has characteristic peaks at 6.1±0.2°, 7.5±0.2°, 8.0±0.2°, 14.9±0.2°, 18.8±0.2°, 22.3±0.2°, 22.8±0.2° and 23.8±0.2°;

or, wherein the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises two or three diffraction peaks at 24.4±0.2°, 13.3±0.2° and 23.8±0.2°, optionally further comprises one or more diffraction peaks at 2θ of 9.0±0.2°, 9.9±0.2°, 26.7±0.2°, 17.2±0.2° and 23.1±0.2°;

or, the X-ray powder diffraction pattern thereof has characteristic peaks at 24.4±0.2°, 13.3±0.2°, 23.8±0.2°, 9.0±0.2°, 9.9±0.2°, 26.7±0.2°, 17.2±0.2° and 23.1±0.2°;

or, wherein the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises two or three diffraction peaks at 2θ of 22.5±0.2°, 8.5±0.2° and 7.2±0.2°, optionally further comprises one or more diffraction peaks at 2θ of 14.4±0.2°, 26.7±0.2°, 12.8±0.2°, 16.7±0.2° and 6.1±0.2°;

or, the X-ray powder diffraction pattern thereof has characteristic peaks at 2θ of 22.5±0.2°, 8.5±0.2°, 7.2±0.2°, 14.4±0.2°, 26.7±0.2°, 12.8±0.2°, 16.7±0.2° and 6.1±0.2°;

or, wherein the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises two or three diffraction peaks at 2θ of 8.4±0.2°, 7.2±0.2° and 20.1±0.2°, optionally further comprises one or more diffraction peaks at 2θ of 22.7±0.2°, 24.5±0.2°, 25.7±0.2°, 18.9±0.2° and 16.4±0.2°;

or, the X-ray powder diffraction pattern thereof has diffraction peaks at 2θ of 8.4±0.2°, 7.2±0.2°, 20.1±0.2°, 22.7±0.2°, 24.5±0.2°, 25.7±0.2°, 18.9±0.2° and 16.4±0.2°;

or, wherein the crystal form is crystal form B of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, for example, the X-ray powder diffraction pattern thereof has diffraction peaks at 2θ of 4.8±0.2°, 7.6±0.2°, 12.2±0.2°, 14.0±0.2°, 18.5±0.2°, 22.9±0.2°, 23.8±0.2° and 24.9±0.2°;

or, wherein the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises two or three diffraction peaks at 2θ of 24.5±0.2°, 13.3±0.2° and 23.9±0.2°, optionally further comprises one or more diffraction peaks at 2θ of 9.0±0.2°, 17.3±0.2°, 19.4±0.2°, 17.7±0.2° and 9.9±0.2°;

or, the X-ray powder diffraction pattern thereof has diffraction peaks at 2θ of 24.5±0.2°, 13.3±0.2°, 23.9±0.2°, 9.0±0.2°, 17.3±0.2°, 19.4±0.2°, 17.7±0.2° and 9.9±0.2°;

or, wherein the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises two or three diffraction peaks at 2θ of 7.6±0.2°, 22.5±0.2° and 8.9±0.2°, optionally further comprises one or more diffraction peaks at 2θ of 15.0±0.2°, 26.6±0.2°, 5.8±0.2°, 12.9±0.2° and 11.6±0.2°;

or, the X-ray powder diffraction pattern thereof has diffraction peaks at 2θ of 7.6±0.2°, 22.5±0.2°, 8.9±0.2°, 15.0±0.2°, 26.6±0.2°, 5.8±0.2°, 12.9±0.2° and 11.6±0.2°;

or, wherein the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof comprises two or three diffraction peaks at 2θ of 17.7±0.2°, 23.5±0.2° and 24.8±0.2°, optionally further comprises one or more diffraction peaks at 2θ of 9.9±0.2°, 22.6±0.2°, 21.2±0.2°, 19.1±0.2° and 29.4±0.2°;

or, the X-ray powder diffraction pattern thereof has diffraction peaks at 2θ of 17.7±0.2°, 23.5±0.2°, 24.8±0.2°, 9.9±0.2°, 22.6±0.2°, 21.2±0.2°, 19.1±0.2° and 29.4±0.2°.

8. The crystal form according to claim 5, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino) propionamide, the X-ray powder diffraction pattern thereof has diffraction peaks at 2θ of 6.8±0.2°, 9.3±0.2°, 13.4±0.2° and 14.7±0.2°;

or, the X-ray powder diffraction pattern thereof has diffraction peaks at 2θ of 6.8±0.2° and 13.4±0.2°;

the crystal form is crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 6.1±0.2° and 8.0±0.2°;

the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 13.3±0.2° and 23.1±0.2°;

the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 7.2±0.2° and 22.5±0.2°;

the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 8.4±0.2° and 20.1±0.2°;

the crystal form is crystal form B of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 4.8±0.2° and 7.6±0.2°;

the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 13.3±0.2° and 24.5±0.2°;

the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 7.6±0.2° and 15.0±0.2°;

the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 9.9±0.2° and 22.6±0.2°.

9. A method for preparing the crystal form according to claim 5, comprising:

1) weighing an appropriate amount of free base and suspending it with a poor solvent;
2) weighing an appropriate amount of acid M and dissolving it with an organic solvent;
3) adding the solution in step 2) to the suspension in step 1), and stirring the resulting mixture to precipitate a solid;
4) optionally, adding an organic solvent to the solid obtained in step 3), and stirring the resulting mixture to precipitate a crystal;
5) stirring and cooling the mixture, followed by precipitating a crystal to obtain the target product;

wherein, the poor solvent is one or more selected from the group consisting of alcohols, esters, ketones, ethers, benzenes, amides and nitriles;

wherein, the organic solvent in step 2) is one or more selected from the group consisting of alcohols, esters, hydrocarbons, ketones, ethers, benzenes, amides and nitriles;

wherein the organic solvent in step 4) is one or more selected from the group consisting of alcohols, esters and ethers.

10. A method for preparing the crystal form according to claim 5, comprising:

1) weighing an appropriate amount of salt of the compound and suspending it with a poor solvent;
2) shaking the suspension obtained above;
3) centrifuging the above suspension, removing the supernatant, and vacuum-drying the remaining solid to obtain the target product;

wherein, the poor solvent is one or more selected from the group consisting of alcohols, ketones, esters, ethers, benzenes, amides and nitriles.

11. A method for preparing the crystal form according to claim 5, comprising:

weighing an appropriate amount of salt of the compound, and exposing the salt of the compound to a certain humidity for a certain period of time;

wherein, the humidity is RH=70% to 95%.

12. A method for preparing the crystal form according to claim 5, comprising:

1) weighing an appropriate amount of free base and suspending it with a poor solvent;
2) weighing an appropriate amount of acid M and dissolving it with an organic solvent;
3) adding the solution in step 2) to the suspension in step 1), and heating the reaction;
4) optionally, adding an organic solvent to the solution in step 3);
5) optionally, adding a salt of the compound to the solution in step 4);
6) cooling the mixture to precipitate a crystal;

wherein, the poor solvent is one or more selected from the group consisting of alcohols, ketones, esters, ethers, benzenes, amides and acetonitrile;

wherein, the organic solvent in step 2) is selected from alcoholic solvents;

wherein, the heating temperature in step 3) is 30 to 80° C.;

wherein, the organic solvent in step 4) is one or more selected from the group consisting of alcohols, esters and ethers.

13. A pharmaceutical composition, comprising a therapeutically effective amount of the acid addition salt according to claim 1 and or more pharmaceutically acceptable carriers or excipients.

14. The pharmaceutical composition according to claim 13, wherein the acid addition salt is

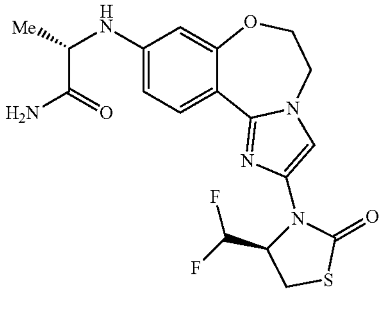

•M, wherein, M is selected from the group consisting of sulfuric acid, tartaric acid, ethane-1,2-disulfonic acid, ethanesulfonic acid, fumaric acid and methanesulfonic acid.

15. The crystal form according to claim 8, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino) propionamide, the X-ray powder diffraction pattern thereof also has diffraction peaks at 2θ of 17.3±0.2°, 19.5±0.2°, 20.8±0.2°, 23.9±0.2° and 25.0±0.2°;

or, the X-ray powder diffraction pattern thereof also has one or two diffraction peaks at 2θ of 14.7±0.2° and 19.5±0.2°;

the crystal form is crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 6.1±0.2°, 7.5±0.2°, 8.0±0.2°, 14.9±0.2° and 23.8±0.2°;

the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 9.0±0.2°, 13.3±0.2°, 19.7±0.2° and 23.1±0.2°;

the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 7.2±0.2°, 14.4±0.2°, 22.5±0.2° and 26.7±0.2°;

the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 7.2±0.2°, 8.4±0.2°, 20.1±0.2° and 22.7±0.2°;

the crystal form is crystal form B of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 12.2±0.2°, 14.0±0.2°, 18.5±0.2°, 22.9±0.2° and 23.8±0.2°;

the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 9.0±0.2°, 13.3±0.2°, 17.3±0.2° and 24.5±0.2°;

the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 7.6±0.2°, 15.0±0.2°, 22.5±0.2° and 23.9±0.2°;

the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof has diffraction peaks at 2θ of 9.9±0.2°, 17.7±0.2°, 22.6±0.2° and 24.8±0.2°.

16. The crystal form according to claim 15, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino) propionamide, the X-ray powder diffraction pattern thereof also has diffraction peaks at 2θ of 9.8±0.2°, 18.4±0.2°, 19.1±0.2°, 20.1±0.2°, 23.0±0.2°, 23.6±0.2°, 24.4±0.2°, 27.3±0.2° and 30.7±0.2°;

or, the X-ray powder diffraction pattern thereof also has one or more diffraction peaks at 20) (±0.2° of 20.1±0.2°, 23.9±0.2°, 24.4±0.2° and 25.0±0.2°;

the crystal form is crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 8.4±0.2°, 18.8±0.2°, 20.7±0.2°, 22.3±0.2° and 22.8±0.2°;

the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 9.9±0.2°, 17.2±0.2°, 20.3±0.2° and 26.7±0.2°;

the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 6.1±0.2°, 12.8±0.2°, 16.7±0.2° and 20.8±0.2°;

the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 5.8±0.2°, 16.4±0.2°, 18.9±0.2° and 26.7±0.2°;

the crystal form is crystal form B of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern is substantially as shown in FIG. 8;

the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 9.9±0.2°, 17.7±0.2°, 19.4±0.2° and 26.9±0.2°;

the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 5.8±0.2°, 12.9±0.2°, 19.9±0.2° and 26.6±0.2°;

the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 16.9±0.2°, 21.2±0.2°, 23.5±0.2° and 29.4±0.2°.

17. The crystal form according to claim 16, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino) propionamide, the X-ray powder diffraction pattern thereof also has diffraction peaks at 2θ of 10.5±0.2°, 17.5±0.2°, 26.9±0.2°, 27.7±0.2°, 28.6±0.2°, 29.6±0.2°, 35.7±0.2° and 37.6±0.2°;

or, the X-ray powder diffraction pattern thereof also has one or two diffraction peaks at 23.0±0.2° and 23.6±0.2°;

the crystal form is crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 13.5±0.2° and 25.2±0.2°;

the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 14.3±0.2°, 21.6±0.2°, 23.8±0.2° and 28.4±0.2°;

the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 8.5±0.2°, 15.2±0.2°, 22.0±0.2° and 25.3±0.2°;

the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 12.6±0.2°, 14.7±0.2°, 17.2±0.2° and 25.1±0.2°;

the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 14.3±0.2°, 18.6±0.2°, 28.3±0.2° and 37.5±0.2°;

the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 8.9±0.2°, 16.8±0.2°, 20.7±0.2° and 24.6±0.2°;

the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 17.3±0.2°, 19.1±0.2°, 28.4±0.2° and 30.5±0.2°.

18. The crystal form according to claim 17, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has one or two diffraction peaks at 9.3±0.2° and 17.3±0.2°;

the crystal form is crystal form A of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 4;

the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 24.4±0.2°, 30.5±0.2° and 32.6±0.2°;

the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 12.1±0.2°, 19.1±0.2° and 23.8±0.2°;

the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 14.4±0.2°, 18.2±0.2°, 24.5±0.2° and 25.7±0.2°;

the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 16.7±0.2°, 20.0±0.2°, 20.4±0.2°, 24.0±0.2° and 30.4±0.2°;

the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 10.1±0.2°, 11.6±0.2°, 17.4±0.2°, 18.2±0.2°, 19.1±0.2°, 21.9±0.2°, 25.4±0.2° and 27.7±0.2°;

the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 14.1±0.2°, 16.2±0.2°, 19.6±0.2°, 20.7±0.2°, 24.5±0.2° and 26.5±0.2°.

19. The crystal form according to claim 18, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 9.8±0.2°, 18.4±0.2°, 19.1±0.2°, 23.6±0.2°, 27.3±0.2° and 30.7±0.2°;

the crystal form is crystal form B of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 5;

the crystal form is crystal form C of mesylate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 6;

the crystal form is crystal form A of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 7;

the crystal form is crystal form C of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 9;

the crystal form is crystal form D of sulfate salt of the compound (S)-2-((2-((R)-4-(difluoromethyl)-2-oxothiazolidin-3-yl)-5,6-dihydrobenzo[f]imidazo[1,2-d][1,4]

oxazepin-9-yl)amino)propionamide, the X-ray powder diffraction pattern thereof is substantially as shown in FIG. 10;

the crystal form is crystal form E of sulfate salt of the compound (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 11.

20. The crystal form according to claim 19, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof also has diffraction peaks at 2θ of 10.5±0.2°, 17.5±0.2°, 26.9±0.2°, 27.7±0.2°, 28.6±0.2°, 29.6±0.2°, 35.7±0.2° and 37.6±0.2°.

21. The crystal form according to claim 20, wherein the crystal form is crystal form A of ethanesulfonate salt of (S)-2-((2-((R)-4-(difluoromethyl)-2-oxothiazolidin-3-yl)-5,6-dihydrobenzo[f]imidazo[1,2-d][1,4]oxazepin-9-yl)amino)propionamide, the X-ray powder diffraction pattern thereof is substantially as shown in FIG. 1;

the TGA spectrum thereof is substantially as shown in FIG. 2;

the DSC spectrum thereof is substantially as shown in FIG. 3.

22. A method for the prevention and/or treatment of a condition mediated by PI3Kα, comprising administering to a patient a therapeutically effective dose of the crystal form according to claim 5.

* * * * *